(12) United States Patent
Gasior et al.

(10) Patent No.: US 11,332,752 B2
(45) Date of Patent: May 17, 2022

(54) USE OF MORPHOGENIC FACTORS FOR THE IMPROVEMENT OF GENE EDITING

(71) Applicant: PIONEER HI-BRED INTERNATIONAL, INC., Johnston, IA (US)

(72) Inventors: Stephen Lawrence Gasior, Johnston, IA (US); William James Gordon-Kamm, Urbandale, IA (US); Keith S Lowe, Johnston, IA (US); David J Peterson, Ames, IA (US); Sergei Svitashev, Johnston, IA (US); Joshua K Young, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 16/979,917

(22) PCT Filed: Mar. 11, 2019

(86) PCT No.: PCT/US2019/021631
§ 371 (c)(1),
(2) Date: Sep. 11, 2020

(87) PCT Pub. No.: WO2019/177978
PCT Pub. Date: Sep. 19, 2019

(65) Prior Publication Data
US 2021/0010012 A1 Jan. 14, 2021

Related U.S. Application Data

(60) Provisional application No. 62/641,733, filed on Mar. 12, 2018, provisional application No. 62/641,725, filed on Mar. 12, 2018.

(51) Int. Cl.
*C12N 15/82* (2006.01)

(52) U.S. Cl.
CPC ..... *C12N 15/8213* (2013.01); *C12N 15/8205* (2013.01); *C12N 15/8207* (2013.01); *C12N 15/8216* (2013.01)

(58) Field of Classification Search
None
See application file for complete search history.

(56) References Cited

U.S. PATENT DOCUMENTS

| 2011/0165679 A1 | 7/2011 | Gordon-Kamm et al. |
| 2017/0183677 A1 | 6/2017 | Gao et al. |

FOREIGN PATENT DOCUMENTS

| WO | WO-2016007948 A1 * | 1/2016 | ......... C12N 15/8271 |
| WO | 2016149352 A1 | 9/2016 | |

OTHER PUBLICATIONS

Ziemienowicz et al 2015 (Cell-Penetrating Peptides: Methods and Protocols, Methods in Molecular Biology 1324) (Year: 2015).*
International Search Report and Written Opinion for PCT/US19/21631 dated May 29, 2019.
Ramakrishna, et al; "Gene Disruption by Cell-Penetrating Peptide-Mediated Delivery of Cas9 Protein and Guide RNA"; Genome Research (2014) 24(6):1020-1027.

* cited by examiner

*Primary Examiner* — Matthew R Keogh

(57) ABSTRACT

Methods and compositions are provided for the improvement of double-strand-break-inducing agent activity in eukaryotic cells, through the usage of one or more morphogenic factors or developmental genes. The morphogenic factor may be provided to the same cell or to a different cell than that comprising or receiving the double-strand-break-inducing agent. The morphogenic factor may be provided to a cell as a polynucleotide composition on a recombinant vector, and may be placed on the vector outside of a T-DNA border. The morphogenic factor may be provided via an upregulation of an endogenous gene. The morphogenic factor, or the double-strand-break-inducing agent, may further comprise a cell penetrating peptide. The morphogenic factor may be co-introduced with a vector comprising RepA.

13 Claims, 8 Drawing Sheets
Specification includes a Sequence Listing.

FIG. 2E

|  | SEQ ID NO: | 1 | 50 |
|---|---|---|---|
| Translation of WUS2_B73 | 50 | (1) | MAANAGGGGAGGGSGSGSVAAPAVCRPSGSRWTPTPEQIRMLKELYYGCG |
| Translation: WUS2_Artificial | 49 | (1) | MAANAGGGGAGGGSGSGSVAAPAVCRPSGSRWTPTPEQIRMLKELYYGCG |
| Translation of WUS2_Var1 | 51 | (1) | MAANAGGGAGGGSG--SVAAPAVCRPSGSRWTPTPEQIRMLKELYYGCG |
| Consensus | 106 | (1) | MAANAGGGGAGGGSGSGSVAAPAVCRPSGSRWTPTPEQIRMLKELYYGCG |

|  |  | 51 | 100 |
|---|---|---|---|
| Translation of WUS2_B73 |  | (51) | IRSPSSEQIQRITAMLRQHGKIEGKNVFYWFQNHKARERQKRRLTSLDVN |
| Translation: WUS2_Artificial |  | (51) | IRSPSSEQIQRITAMLRQHGKIEGKNVFYWFQNHKARERQKRRLTSLDVN |
| Translation of WUS2_Var1 |  | (49) | IRSPSSEQIQRITAMLRQHGKIEGKNVFYWFQNHKARERQKRRLTSLDVN |
| Consensus |  | (51) | IRSPSSEQIQRITAMLRQHGKIEGKNVFYWFQNHKARERQKRRLTSLDVN |

|  |  | 101 | 150 |
|---|---|---|---|
| Translation of WUS2_B73 |  | (101) | VPAAGAADATTSQLGVLSLSSPP-SGAAPPSPTLGFYAAGNGGGSAGLLD |
| Translation: WUS2_Artificial |  | (101) | VPAAGAADATTSQLGVLSLSSP--SGAAPPSPTLGFYAAGNGGGSAVLLD |
| Translation of WUS2_Var1 |  | (99) | VPAAGAADATTSQLGVLSLSSPPFSGAAPPSPTLGFYAAGNGGGSAVLLD |
| Consensus |  | (101) | VPAAGAADATTSQLGVLSLSSPP SGAAPPSPTLGFYAAGNGGGSAVLLD |

|  |  | 151 | 200 |
|---|---|---|---|
| Translation of WUS2_B73 |  | (150) | TSSDWGSSGAAMATETCFLQD----------------------------- |
| Translation: WUS2_Artificial |  | (149) | TSSDWGSSGAAMATETCFLQVGAVVRSFLGHCAQFHVRTYELIAASFHPP |
| Translation of WUS2_Var1 |  | (149) | TSSDWGSSGAAMATETCFLQD----------------------------- |
| Consensus |  | (151) | TSSDWGSSGAAMATETCFLQD |

|  |  | 201 | 250 |
|---|---|---|---|
| Translation of WUS2_B73 |  | (171) | ----------------YMGVTDTGSSSQWPCFSSSDTIMAAAAAARVATTR |
| Translation: WUS2_Artificial |  | (199) | VYITVRYGGARPQDYMGVTDTGSSSQWPRFSSSDTIMAAAARA----ATTR |
| Translation of WUS2_Var1 |  | (170) | ----------------YMGVTDTGSSSQWPRFSSSDTIMAAAARA--ATTR |
| Consensus |  | (201) | YMGVTDTGSSSQWPRFSSSDTIMAAAARA  ATTR |

|  |  | 251 | 300 |
|---|---|---|---|
| Translation of WUS2_B73 |  | (207) | APETLPLFPTCGDDDDDSQPPPRPRHAVPVPAGETIRGGGGSSSSYLPF |
| Translation: WUS2_Artificial |  | (247) | APETLPLFPTCGDDGSGS-----------------------------SSYLPF |
| Translation of WUS2_Var1 |  | (204) | APETLPLFPTCGDDGSGS-----------------------------SSYLPF |
| Consensus |  | (251) | APETLPLFPTCGDDGSGS                              SSYLPF |

|  |  | 301 | 350 |
|---|---|---|---|
| Translation of WUS2_B73 |  | (257) | WGAGAASTTAGATSSVAIQQQHQLQEQYSFYSN--STQLAGTGSQDVSAS |
| Translation: WUS2_Artificial |  | (272) | WG--AASTTAGATSSVAIQQQHQLQEQYSFYSNSNSTQLAGTGNQDVSAT |
| Translation of WUS2_Var1 |  | (229) | WG--AASTTAGATSSVAIQQQHQLQEQYSFYSNSNSTQLAGTGNQDVSAT |
| Consensus |  | (301) | WG  AASTTAGATSSVAIQQQHQLQEQYSFYSNSNSTQLAGTGNQDVSAT |

|  |  | 351 | 375 |
|---|---|---|---|
| Translation of WUS2_B73 |  | (305) | ---AAALELSLSSWCSPYPAAGSM- |
| Translation: WUS2_Artificial |  | (320) | AAAAAALELSLSSWCSPYPAAGSM- |
| Translation of WUS2_Var1 |  | (277) | AAAAAALELSLSSWCSPYPAAGSM- |
| Consensus |  | (351) | AAAAAALELSLSSWCSPYPAAGSM |

SEQUENCE LISTING

```
<160> NUMBER OF SEQ ID NOS: 110

<210> SEQ ID NO 1
<211> LENGTH: 2040
<212> TYPE: DNA
<213> ORGANISM: Zea mays

<400> SEQUENCE: 1
atggcttcag cgaacaactg gctgggcttc tcgctctcgg gccaggataa cccgcagcct      60
aaccaggaca gctcgcctgc cgccggtatc gacatctccg gcgccagcga cttctatggc     120
ctgcccacgc agcagggctc cgacgggcat ctcggcgtgc cgggcctgcg ggacgatcac     180
gcttcttatg gtatcatgga ggcctacaac agggttcctc aagaaaccca agattggaac    240
```

```
atgagggget tggactacaa cggcggtggc tcggagctct cgatgcttgt ggggtccagc    300
ggcggcggcg ggggcaacgg caagagggcc gtggaagaca gcgagcccaa gctcgaagat    360
ttcctcggcg caactcgtt cgtctccgat caagatcagt ccggcggtta cctgttctct     420
ggagtcccga tagccagcag cgccaatagc aacagcggga gcaacaccat ggagctctcc    480
atgatcaaga cctggctacg gaacaaccag gtggcccagc cccagccgcc agctccacat    540
cagccgcagc ctgaggaaat gagcaccgac gccagcggca gctttgg atgctcggat      600 tcgatgggaa ggaacagcat ggtggcggct ggtgggagct cgcagagcct ggcgctctcg    660
atgagcacgg gctcgcacct gcccatggtt gtgcccagcg cgccgccag cggagcggcc     720 tcggagagca tcgtcgga gaacaagcga gcgagcggtg ccatggattc gcccggcagc     780
gcggtagaag ccgtaccgag gaagtccatc gacacgttcg gcaaaggac ctctatatat     840 cgaggtgtaa caaggcatag atggacaggg cggtatgagg ctcatctatg gataatagt    900 tgtagaaggg aagggcagag tcgcaagggt aggcaagttt accttggtgg ctatgacaag    960
gaggacaagg cagcaagggc ttacgatttg gcagctctca gtattgggg cactacgaca    1020 acaacaaatt tccctataag caactacgaa aaagagctag aagaaatgaa acatatgact    1080
agacaggagt acattgcata cctaagaaga aatagcagtg gattttctcg tggggcatca    1140
aagtatcgtg gagtaactag acatcatcag catgggagat ggcaagcaag gataggagga    1200
gttgcaggaa acaaggatct ttacttgggc acattcagca ccgaggagga ggcggcggag    1260
gcctacgaca tcgccgcgat caagttccgc ggtctcaacg ccgtcaccaa cttcgacatg    1320
agccgctacg acgtgaagag catcctcgag agcagcacac tgcctgtcgg cggtgcggcc    1380
aggcgcctca aggacgccgt ggaccacgtg gaggccggcg ccaccatctg gcgcgccgac    1440
atggacggcg ccgtgatctc ccagctggcc gaagccggga tgggcggcta cgcctcgtac    1500
ggccaccacg gctggccgac catcgcgttc cagcagccgt cgccgctctc cgtccactac    1560
ccgtacggcc agccgtcccg cgggtggtgc aaacccgagc aggacgcggc cgccgccgcg    1620
gcgcacagcc tgcaggacct ccagcagctg cacctcggca gcgcggccca caacttcttc    1680
caggcgtcgt cgagctccac agtctacaac ggcggcgccg cgccagtgg tgggtaccag     1740 ggcctcggtg gtggcagctc tttcctcatg ccgtcgagca ctgtcgtggc ggcggccgac    1800 cagggggcaca gcagcacggc caaccagggg agcacgtgca gctacgggga cgaccaccag    1860
gaggggaagc tcatcggtta cgacgccgcc atggtggcga ccgcagctgg tggagacccg    1920
tacgctgcgg cgaggaacgg gtaccagttc tcgcagggct cgggatccac ggtgagcatc    1980
gcgagggcga acgggtacgc taacaactgg agctctcctt tcaacaacgg catggggtga    2040
```

<210> SEQ ID NO 2
<211> LENGTH: 1680
<212> TYPE: DNA
<213> ORGANISM: Oryza sativa

<400> SEQUENCE: 2

```
atggcctcca tcaccaactg gctcggcttc tcctcctcct ccttctccgg cgccggcgcc     60
gaccccgtcc tgccccaccc gccgctgcaa gagtggggga gcgcttatga gggcggcggc    120
acggtggcgg ccgccggcgg ggaggagacg gcggcgccga agctggagga cttcctcggc    180
atgcaggtgc agcaggagac ggccgccgcg gggcggggc acggccgtgg aggcagctcg    240
tcggtcgttg ggctgtccat gatcaagaac tggctacgca gccagccgcc gcccgcggtg    300
```

```
gttgggggag aagacgctat gatggcgctc gcggtgtcga cgtcggcgtc gccgccggtg      360
gacgcgacgg tgccggcctg catttcgccg gatgggatgg ggtcgaaggc ggccgacggc      420
ggcggcgcgg ccgaggcggc ggcggcggcg gcggcgcaga ggatgaaggc ggccatggac      480
acgttcgggc agcggacgtc catctaccgg ggtgtcacca agcacaggtg gacaggaagg      540
tatgaagccc atctttggga taacagctgc agaagagaag gtcagactcg caaaggcaga      600
caagtcaatg caggaggata tgataaggaa gaaaaagctg ctagggctta tgatttggct      660
gcccttaaat actgggcac tacaacgacg acgaattttc cggtaagcaa ctacgaaaaa       720
gagttggatg aaatgaagca catgaatagg caggaatttg ttgcatccct tagaagaaaa      780
agcagtggat tttcacgtgg tgcttccata tatcgtggtg ttacaagaca ccatcagcat      840
ggaaggtggc aagcaaggat aggacgggtg gcaggaaaca aggatctgta tttgggcaca      900
tttggcaccc aagaggaagc tgcagaggca tatgatatcg ctgcaatcaa attccgtggt      960
ctcaatgctg tgacaaactt tgacatgagc cggtacgatg tcaagagcat cattgaaagc     1020
agcaatctcc caattggtac tggaaccacc cggcgattga aggactcctc tgatcacact     1080
gataatgtca tggacatcaa tgtcaatacc gaacccaata atgtggtatc atcccacttc     1140
accaatgggg ttggcaacta tggttcgcag cattatggtt acaatggatg gtcgccaatt     1200
agcatgcagc cgatcccctc gcagtacgcc aacggccagc ccagggcatg gttgaaacaa     1260
gagcaggaca gctctgtggt tacagcgcg cagaacctgc acaatctaca tcattttagt      1320
tccttgggct acacccacaa cttcttccag caatctgatg ttccagacgt cacaggtttc     1380
gttgatcgcg cttcgaggtc cagtgactca tactccttca ggtacaatgg aacaaatggc     1440
tttcatggtc tcccgggtgg aatcagctat gctatgccgg ttgcgacagc ggtggaccaa     1500
ggtcaggca tccatggcta tggagaagat ggtgtggcag gcattgacac cacacatgac      1560
ctgtatggca gccgtaatgt gtactacctt tccgagggtt cgcttcttgc cgatgtcgaa     1620
aaagaaggcg actatggcca atctgtgggg ggcaacagct gggttttgcc gacaccgtag     1680
```

<210> SEQ ID NO 3
<211> LENGTH: 2104
<212> TYPE: DNA
<213> ORGANISM: Oryza sativa

<400> SEQUENCE: 3

```
atggcttctg caaacaactg gctgggcttc tcgctctccg gccaagagaa tccgcagcct       60
caccaggata gctcgcctcc ggcagccatc gacgtctccg gcgccggcga cttctatggc      120
ctgccgacgt cgcagccgac ggcggccgac gcgcacctcg gcgtggcggg gcatcatcac      180
aacgcctcgt atggcatcat ggaggccttc aataggggag ctcaagaggc acaagattgg      240
aacatgaggg ggctggacta caacggcggc gcctcggagc tgtcgatgct cgtcggctcc      300
agcggcggca agagggcggc ggcggtggag gagaccgagc cgaagctgga ggacttcctc      360
ggcggcaact cgttcgtctc cgagcaagat catcacgcgg cggggggctt cctcttctcc      420
ggcgtcccga tggccagcag caccaacagc aacagcggga gcaacactat ggagctctcc      480
atgatcaaga cctggctccg gaacaacggc caggtgcccg ccggccacca gccgcagcag      540
cagcagccgg cggccgcggc cgccgccgcg cagcagcagg cgcacgaggc ggcggagatg      600
agcaccgacg cgagcgcgag cagcttcggg tgctcctccg acgcgatggg gaggagtaac      660
aacgcggcc cggtctcggc ggcggccggc gggacgagct cgcagagcct ggcgctctcg      720
atgagcacgg gctcgcactc gcacctgcct atcgtcgtcg ccggcggcgg gaacgccagc      780
```

```
ggcggagcgg ccgagagcac atcgtcggag aacaagcggg ccagcggcgc catggattcg      840
ccgggcggtg gcgcgataga ggccgtgccg aggaagtcca tcgacacgtt cgggcaaagg      900
acctcgatat atcgaggtgt aacaaggcat agatggacag ggcgatatga ggctcatctc      960
tgggataata gctgtagaag agaagggcag agtcgcaagg gtaggcaagg tggctatgac     1020
aaggaggata aagcagcgag agcttatgat ttggcagctc tgaagtattg gggcacaaca     1080
acaacaacaa atttcccaat aagtaactat gaaaaagagc tagatgaaat gaaacatatg     1140
accaggcagg agtatattgc atacctaaga aggaatagca gtggattttc tcgtggtgca     1200
tcgaaatatc gtggtgtaac caggcaccat cagcatggga gatggcaagc aaggatagggg     1260 agggttgcag gaaacaagga cctctactta ggcaccttca gcaccgagga ggaggcggcg     1320
gaggcgtacg acatcgcggc gatcaagttc cggggggctca acgccgtcac caactttgac     1380
atgagccgct acgacgtcaa gagcatcctg gagagcagca cgctgccggt gggcggcgcg     1440
gcgaggcggc tgaaggaggc ggcggaccac gcggaggcgg ccggcgccac catctggcgc     1500
gccgccgaca tggacggcgc cggcgtcatc tccggcctgg ccgacgtcgg gatgggcgcc     1560
tacgccgcct cgtaccacca ccaccaccac acggcctggc cgaccatcgc gttccagcag     1620
ccgccgccgc tcgccgtgca ctacccgtac ggccaggcgc cggcggcgcc gtcgcgcggg     1680
tggtgcaagc ccgagcagga cgccgccgtc gctgccgccg cgcacagcct ccaggacctc     1740
cagcagctgc acctcggcag cgccgccgcc cacaacttct tccaggcgtc gtcgagctcg     1800
acggtctaca acggcggcgg cggcgggtac caggggcctcg gtggcaacgc cttcttgatg     1860
ccggcgagca ccgtcgtggc cgaccagggg cacagcagca cggccaccaa ccatggaaac     1920
acctgcagct acggcaacga ggagcagggg aagctcatcg ggtacgacgc catggcgatg     1980
gcgagcggcg ccgccggcgg cgggtaccag ctgtcgcagg gctcggcgtc gacggtgagc     2040
atcgcgaggg cgaacggcta ctcggccaac tggagctcgc ctttcaatgg cgccatggga     2100
tgat                                                                 2104

<210> SEQ ID NO 4
<211> LENGTH: 1977
<212> TYPE: DNA
<213> ORGANISM: Oryza sativa

<400> SEQUENCE: 4
atggcttctg cagataactg gctaggcttc tcgctctccg ccaaggcaa cccacagcat       60 caccagaacg gctcgccgtc tgccgccggc gacgccgcca tcgacatctc cggctcaggc      120
gacttctatg gtctgccaac gccggacgca caccacatcg gcatggcggg cgaagacgcg      180
ccctatggcg tcatggatgc tttcaacaga ggcacccatg aaacccaaga ttgggcgatg      240
aggggtttgg actacggcgg cggctcctcc gacctctcga tgctcgtcgg ctcgagcggc      300
ggcgggagga ggacggtggc cggcgacggc gtcggcgagg cgccgaagct ggagaacttc      360
ctcgacggca actcattctc cgacgtgcac ggccaagccg ccggcgggta cctctactcc      420
ggaagcgctg tcggcggcgc cggtggttac agtaacggcg gatgcggcgg cggaaccata      480
gagctgtcca tgatcaagac gtggctccgg agcaaccagt cgcagcagca gccatcgccg      540
ccgcagcacg ctgatcaggg catgagcacc gacgccagcg cgagcagcta cgcgtgctcc      600
gacgtgctgg tggggagctg cggcggcggc ggcgccgggg gcacggcgag ctcgcatggg      660
cagggcctgg cgctgtcgat gagcacgggg tcggtggccg ccgccggagg gggcggcgcc      720
```

```
gtcgtcgcgg ccgagagctc gtcgtcggag aacaagcggg tggattcgcc gggcggcgcc      780
gtggacggcg ccgtcccgag gaaatccatc gacaccttcg gcaaaggac gtctatatac       840 cgaggtgtaa caaggcatag atggacagga agatatgaag ctcatctgtg ggataatagc      900
tgtaggagag aaggccaaag tcgcaagggg agacaggttt gtgtaggcgg ttatgacaaa      960
gaagataagg cggctcgggc ttatgatttg gcagctctaa atactgggg cacgaccaca      1020 acaacaaatt tcccaatgag taattatgaa aaggagctag aggaaatgaa acacatgacc     1080
aggcaggagt acattgcaca tcttagaagg aatagcagtg gattttctcg tggtgcatcc     1140
aaatatcgtg gtgttactag gcatcatcag catgggagat ggcaggcaag gatagggcga     1200
gttgcaggca acaaggatat ctacctaggc accttcagca ccgaggagga ggccgccgag     1260
gcgtacgaca tcgccgccat caagttccgc gggctcaacg ccgtcaccaa cttcgacatg     1320
agccggtacg acgtcaagag catcctggac agcagcacgc tgccggtcgg cggcgcggcg     1380
cggcggctca aggaggcgga ggtcgccgcc gccgccgcgg gcggcggcgt gatcgtctcc     1440
cacctggccg acggcggtgt gggtgggtac tactacgggt gcggcccgac catcgcgttc     1500
ggcggcggcg ccagcagcc ggcgccgctc gccgtgcact accgtcgta cggccaggcc      1560 agcgggtggt gcaagccgga gcaggacgcg gtgatcgcgg ccgggcactg cgcgacggac     1620
ctccagcacc tgcacctcgg gagcggcggc gccgccgcca cccacaactt cttccagcag     1680
ccggcgtcaa gctcggccgt ctacggcaac ggcggcggcg gcggcggcaa cgcgttcatg     1740
atgccgatgg gcgccgtggt ggccgccgcc gatcacggcg gcagagcag cgcctacggc      1800 ggtggcgacg agagcgggag gctcgtcgtg gggtacgacg gcgtcgtcga cccgtacgcg     1860
gccatgagaa gcgcgtacga gctctcgcag ggctcgtcgt cgtcgtcggt gagcgtcgcg     1920
aaggcggcga acgggtaccc ggacaactgg agctcgccgt tcaacggcat gggatga       1977

<210> SEQ ID NO 5
<211> LENGTH: 2082
<212> TYPE: DNA
<213> ORGANISM: Sorghum bicolor

<400> SEQUENCE: 5
atggcttcga cgaacaacca ctggctgggt ttctcgctct cgggccagga taacccgcag       60
cctaatcatc aggacagctc gcctgccgcc gccggcatcg acatctccgg cgccagcgac      120
ttctatggct tgcccacgca gcagggctcc gacgggaatc tcggcgtgcc gggcctgcgg      180
gacgatcacg cttcttatgg catcatggag gccttcaaca gggttcctca agaaacccaa      240
gattggaaca tgagggattt ggactacaac ggcggtggct cggaactctc gatgcttgtg      300
gggtccagcg gcggcggcgg gggcggcggc aagagggccg tggaagacag cgagcccaag      360
ctcgaagatt tcctcggcgg caactcgttc gtctccgagc atgatcagtc cggcggttac      420
ctgttctctg gagtcccgat ggccagcagc accaacagca acagcgggag caacaccatg      480
gagctctcca tgatcaagac ctggctccgg aacaaccagg tgcccagcc gcagccgcca      540 gcagctccgc atcaggcgcc gcagactgag gagatgagca ccgacgccaa cgccagcgcc      600
agcagctttg gctgctcgga ttcgatgggg aggaacggca cggtggcggc tgctgggagc      660
tcccagagcc tggcgctctc gatgagcacg ggctcgcacc tgccgatggt tgtggccggc      720
ggcggcgcca gcggagcggc ctcggagagc acgtcatcgg agaacaagcg agcgagcggc      780
gccatggatt cgcccggcag cgcggtagaa gccgtcccga ggaagtccat cgacacgttc      840
gggcaaagga cctctatata tcgaggtgta acaagacata gatggacagg gcgatatgag      900
```

```
gctcatctat gggataatag ttgtagaaga gaagggcaga gtcgcaaggg taggcaagtt      960
taccttggtg gctatgacaa ggaagacaag gcagcaaggg cttatgattt ggcagctctc     1020
aagtattggg gcactactac aacaacaaat ttccctataa gcaactatga aaaggagcta     1080
gaggaaatga acatatgac taggcaggag tatattgcat acctaagaag aaatagcagt      1140 ggatttctc gtggcgcatc aaaatatcgt ggagtaacta gacatcatca gcatgggaga      1200 tgcaagcaa ggataggag agttgcagga aacaaggatc tctacttggg cacattcagc       1260
accgaggagg aggcggcgga ggcctacgac atcgccgcga tcaagttccg cggtctgaac     1320
gccgtcacca acttcgacat gagccgctac gacgtcaaga gcatcctcga gagcagcacg     1380
ctgcctgtcg gcggcgcggc caggcgcctc aaggatgccg tggaccacgt ggaggccggc     1440
gccaccatct ggcgcgccga catggacggc ggcgtgatct cccagctcgc cgaagccggg     1500
atgggcggct acgcctcgta cgggcaccac gcctggccga ccatcgcgtt ccagcagccg     1560
tcgccgctct ccgtccacta cccgtacggg cagccgccgt cccgcgggtg gtgcaagccc     1620
gagcaggacg cggccgtcgc cgccgccgcg cacagcctgc aggacctcca gcagctgcac     1680
ctcggcagcg cggcacacaa cttcttccag gcgtcgtcga gctcggcagt ctacaacagc     1740
ggcggcggcg cgctagcgg cgggtaccac cagggcctcg gtggcggcag cagctccttc      1800
ctcatgccgt cgagcactgt cgtggcgggg gccgaccagg ggcacagcag cagcacggcc     1860
aaccagggga gcacgtgcag ctacggggac gatcaccagg aagggaagct catcgggtac     1920
gacgccatgg tggcggcgac cgcagccggc ggggacccgt acgccgcggc gaggagcggg     1980
taccagttct cgtcgcaggg ctcgggatcc acggtgagca tcgcgagggc gaacgggtac     2040
tctaacaact ggagctctcc tttcaacggc ggcatggggt ga                       2082
```

<210> SEQ ID NO 6
<211> LENGTH: 679
<212> TYPE: PRT
<213> ORGANISM: Zea mays

<400> SEQUENCE: 6

```
Met Ala Ser Ala Asn Asn Trp Leu Gly Phe Ser Leu Ser Gly Gln Asp
1               5                  10                  15

Asn Pro Gln Pro Asn Gln Asp Ser Ser Pro Ala Ala Gly Ile Asp Ile
            20                  25                  30

Ser Gly Ala Ser Asp Phe Tyr Gly Leu Pro Thr Gln Gln Gly Ser Asp
        35                  40                  45

Gly His Leu Gly Val Pro Gly Leu Arg Asp Asp His Ala Ser Tyr Gly
    50                  55                  60

Ile Met Glu Ala Tyr Asn Arg Val Pro Gln Glu Thr Gln Asp Trp Asn
65                  70                  75                  80

Met Arg Gly Leu Asp Tyr Asn Gly Gly Ser Glu Leu Ser Met Leu
                85                  90                  95

Val Gly Ser Ser Gly Gly Gly Gly Asn Gly Lys Arg Ala Val Glu
            100                 105                 110

Asp Ser Glu Pro Lys Leu Glu Asp Phe Leu Gly Asn Ser Phe Val
        115                 120                 125

Ser Asp Gln Asp Gln Ser Gly Gly Tyr Leu Phe Ser Gly Val Pro Ile
    130                 135                 140

Ala Ser Ser Ala Asn Ser Asn Ser Gly Ser Asn Thr Met Glu Leu Ser
145                 150                 155                 160
```

```
Met Ile Lys Thr Trp Leu Arg Asn Asn Gln Val Ala Gln Pro Gln Pro
                165                 170                 175

Pro Ala Pro His Gln Pro Gln Pro Glu Glu Met Ser Thr Asp Ala Ser
            180                 185                 190

Gly Ser Ser Phe Gly Cys Ser Asp Ser Met Gly Arg Asn Ser Met Val
        195                 200                 205

Ala Ala Gly Gly Ser Ser Gln Ser Leu Ala Leu Ser Met Ser Thr Gly
    210                 215                 220

Ser His Leu Pro Met Val Val Pro Ser Gly Ala Ala Ser Gly Ala Ala
225                 230                 235                 240

Ser Glu Ser Thr Ser Ser Glu Asn Lys Arg Ala Ser Gly Ala Met Asp
                245                 250                 255

Ser Pro Gly Ser Ala Val Glu Ala Val Pro Arg Lys Ser Ile Asp Thr
            260                 265                 270

Phe Gly Gln Arg Thr Ser Ile Tyr Arg Gly Val Thr Arg His Arg Trp
        275                 280                 285

Thr Gly Arg Tyr Glu Ala His Leu Trp Asp Asn Ser Cys Arg Arg Glu
    290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
                325                 330                 335

Gly Thr Thr Thr Thr Thr Asn Phe Pro Ile Ser Asn Tyr Glu Lys Glu
            340                 345                 350

Leu Glu Glu Met Lys His Met Thr Arg Gln Glu Tyr Ile Ala Tyr Leu
        355                 360                 365

Arg Arg Asn Ser Ser Gly Phe Ser Arg Gly Ala Ser Lys Tyr Arg Gly
    370                 375                 380

Val Thr Arg His His Gln His Gly Arg Trp Gln Ala Arg Ile Gly Arg
385                 390                 395                 400

Val Ala Gly Asn Lys Asp Leu Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
        435                 440                 445

Leu Glu Ser Ser Thr Leu Pro Val Gly Gly Ala Ala Arg Arg Leu Lys
    450                 455                 460

Asp Ala Val Asp His Val Glu Ala Gly Ala Thr Ile Trp Arg Ala Asp
465                 470                 475                 480

Met Asp Gly Ala Val Ile Ser Gln Leu Ala Glu Ala Gly Met Gly Gly
                485                 490                 495

Tyr Ala Ser Tyr Gly His His Gly Trp Pro Thr Ile Ala Phe Gln Gln
            500                 505                 510

Pro Ser Pro Leu Ser Val His Tyr Pro Tyr Gly Gln Pro Ser Arg Gly
        515                 520                 525

Trp Cys Lys Pro Glu Gln Asp Ala Ala Ala Ala Ala His Ser Leu
    530                 535                 540

Gln Asp Leu Gln Gln Leu His Leu Gly Ser Ala Ala His Asn Phe Phe
545                 550                 555                 560

Gln Ala Ser Ser Ser Thr Val Tyr Asn Gly Gly Ala Gly Ala Ser
                565                 570                 575

Gly Gly Tyr Gln Gly Leu Gly Gly Gly Ser Ser Phe Leu Met Pro Ser
```

```
              580                 585                 590
Ser Thr Val Val Ala Ala Asp Gln Gly His Ser Ser Thr Ala Asn
            595                 600                 605

Gln Gly Ser Thr Cys Ser Tyr Gly Asp Asp His Gln Glu Gly Lys Leu
            610                 615                 620

Ile Gly Tyr Asp Ala Ala Met Val Ala Thr Ala Ala Gly Gly Asp Pro
625                 630                 635                 640

Tyr Ala Ala Arg Asn Gly Tyr Gln Phe Ser Gln Gly Ser Gly Ser
                645                 650                 655

Thr Val Ser Ile Ala Arg Ala Asn Gly Tyr Ala Asn Asn Trp Ser Ser
            660                 665                 670

Pro Phe Asn Asn Gly Met Gly
                675

<210> SEQ ID NO 7
<211> LENGTH: 559
<212> TYPE: PRT
<213> ORGANISM: Oryza sativa

<400> SEQUENCE: 7

Met Ala Ser Ile Thr Asn Trp Leu Gly Phe Ser Ser Ser Phe Ser
1               5                   10                  15

Gly Ala Gly Ala Asp Pro Val Leu Pro His Pro Pro Leu Gln Glu Trp
                20                  25                  30

Gly Ser Ala Tyr Glu Gly Gly Thr Val Ala Ala Ala Gly Gly Glu
            35                  40                  45

Glu Thr Ala Ala Pro Lys Leu Glu Asp Phe Leu Gly Met Gln Val Gln
    50                  55                  60

Gln Glu Thr Ala Ala Ala Ala Gly His Gly Arg Gly Gly Ser Ser
65                  70                  75                  80

Ser Val Val Gly Leu Ser Met Ile Lys Asn Trp Leu Arg Ser Gln Pro
                85                  90                  95

Pro Pro Ala Val Val Gly Gly Glu Asp Ala Met Met Ala Leu Ala Val
            100                 105                 110

Ser Thr Ser Ala Ser Pro Pro Val Asp Ala Thr Val Pro Ala Cys Ile
        115                 120                 125

Ser Pro Asp Gly Met Gly Ser Lys Ala Ala Asp Gly Gly Ala Ala
    130                 135                 140

Glu Ala Ala Ala Ala Ala Ala Gln Arg Met Lys Ala Ala Met Asp
145                 150                 155                 160

Thr Phe Gly Gln Arg Thr Ser Ile Tyr Arg Gly Val Thr Lys His Arg
                165                 170                 175

Trp Thr Gly Arg Tyr Glu Ala His Leu Trp Asp Asn Ser Cys Arg Arg
            180                 185                 190

Glu Gly Gln Thr Arg Lys Gly Arg Gln Val Asn Ala Gly Gly Tyr Asp
        195                 200                 205

Lys Glu Glu Lys Ala Ala Arg Ala Tyr Asp Leu Ala Ala Leu Lys Tyr
    210                 215                 220

Trp Gly Thr Thr Thr Thr Thr Asn Phe Pro Val Ser Asn Tyr Glu Lys
225                 230                 235                 240

Glu Leu Asp Glu Met Lys His Met Asn Arg Gln Glu Phe Val Ala Ser
                245                 250                 255

Leu Arg Arg Lys Ser Ser Gly Phe Ser Arg Gly Ala Ser Ile Tyr Arg
            260                 265                 270
```

```
Gly Val Thr Arg His His Gln His Gly Arg Trp Gln Ala Arg Ile Gly
            275                 280                 285

Arg Val Ala Gly Asn Lys Asp Leu Tyr Leu Gly Thr Phe Gly Thr Gln
        290                 295                 300

Glu Ala Ala Glu Ala Tyr Asp Ile Ala Ala Ile Lys Phe Arg Gly
305                 310                 315                 320

Leu Asn Ala Val Thr Asn Phe Asp Met Ser Arg Tyr Asp Val Lys Ser
                325                 330                 335

Ile Ile Glu Ser Ser Asn Leu Pro Ile Gly Thr Gly Thr Thr Arg Arg
            340                 345                 350

Leu Lys Asp Ser Ser Asp His Thr Asp Asn Val Met Asp Ile Asn Val
        355                 360                 365

Asn Thr Glu Pro Asn Asn Val Val Ser Ser His Phe Thr Asn Gly Val
    370                 375                 380

Gly Asn Tyr Gly Ser Gln His Tyr Gly Tyr Asn Gly Trp Ser Pro Ile
385                 390                 395                 400

Ser Met Gln Pro Ile Pro Ser Gln Tyr Ala Asn Gly Gln Pro Arg Ala
                405                 410                 415

Trp Leu Lys Gln Glu Gln Asp Ser Ser Val Val Thr Ala Ala Gln Asn
            420                 425                 430

Leu His Asn Leu His His Phe Ser Ser Leu Gly Tyr Thr His Asn Phe
        435                 440                 445

Phe Gln Gln Ser Asp Val Pro Asp Val Thr Gly Phe Val Asp Ala Pro
    450                 455                 460

Ser Arg Ser Ser Asp Ser Tyr Ser Phe Arg Tyr Asn Gly Thr Asn Gly
465                 470                 475                 480

Phe His Gly Leu Pro Gly Gly Ile Ser Tyr Ala Met Pro Val Ala Thr
                485                 490                 495

Ala Val Asp Gln Gly Gln Gly Ile His Gly Tyr Gly Glu Asp Gly Val
            500                 505                 510

Ala Gly Ile Asp Thr Thr His Asp Leu Tyr Gly Ser Arg Asn Val Tyr
        515                 520                 525

Tyr Leu Ser Glu Gly Ser Leu Leu Ala Asp Val Glu Lys Glu Gly Asp
    530                 535                 540

Tyr Gly Gln Ser Val Gly Gly Asn Ser Trp Val Leu Pro Thr Pro
545                 550                 555
```

<210> SEQ ID NO 8
<211> LENGTH: 700
<212> TYPE: PRT
<213> ORGANISM: Oryza sativa

<400> SEQUENCE: 8

```
Met Ala Ser Ala Asn Asn Trp Leu Gly Phe Ser Leu Ser Gly Gln Glu
1               5                   10                  15

Asn Pro Gln Pro His Gln Asp Ser Ser Pro Ala Ala Ile Asp Val
            20                  25                  30

Ser Gly Ala Gly Asp Phe Tyr Gly Leu Pro Thr Ser Gln Pro Thr Ala
        35                  40                  45

Ala Asp Ala His Leu Gly Val Ala Gly His His Asn Ala Ser Tyr
    50                  55                  60

Gly Ile Met Glu Ala Phe Asn Arg Gly Ala Gln Glu Ala Gln Asp Trp
65                  70                  75                  80

Asn Met Arg Gly Leu Asp Tyr Asn Gly Gly Ala Ser Glu Leu Ser Met
                85                  90                  95
```

Leu Val Gly Ser Ser Gly Gly Lys Arg Ala Ala Val Glu Glu Thr
            100                 105             110

Glu Pro Lys Leu Glu Asp Phe Leu Gly Gly Asn Ser Phe Val Ser Glu
        115                 120             125

Gln Asp His His Ala Ala Gly Gly Phe Leu Phe Ser Gly Val Pro Met
    130                 135             140

Ala Ser Ser Thr Asn Ser Asn Ser Gly Ser Asn Thr Met Glu Leu Ser
145             150              155                 160

Met Ile Lys Thr Trp Leu Arg Asn Asn Gly Gln Val Pro Ala Gly His
                165             170              175

Gln Pro Gln Gln Gln Pro Ala Ala Ala Ala Ala Ala Gln Gln
        180              185              190

Gln Ala His Glu Ala Ala Glu Met Ser Thr Asp Ala Ser Ala Ser Ser
    195              200              205

Phe Gly Cys Ser Ser Asp Ala Met Gly Arg Ser Asn Asn Gly Gly Ala
    210              215              220

Val Ser Ala Ala Ala Gly Gly Thr Ser Ser Gln Ser Leu Ala Leu Ser
225             230              235                 240

Met Ser Thr Gly Ser His Ser His Leu Pro Ile Val Ala Gly Gly
                245             250              255

Gly Asn Ala Ser Gly Gly Ala Ala Glu Ser Thr Ser Ser Glu Asn Lys
        260              265              270

Arg Ala Ser Gly Ala Met Asp Ser Pro Gly Gly Ala Ile Glu Ala
        275              280              285

Val Pro Arg Lys Ser Ile Asp Thr Phe Gly Gln Arg Thr Ser Ile Tyr
        290              295              300

Arg Gly Val Thr Arg His Arg Trp Thr Gly Arg Tyr Glu Ala His Leu
305             310              315                 320

Trp Asp Asn Ser Cys Arg Arg Glu Gly Gln Ser Arg Lys Gly Arg Gln
                325             330              335

Gly Gly Tyr Asp Lys Glu Asp Lys Ala Ala Arg Ala Tyr Asp Leu Ala
            340             345              350

Ala Leu Lys Tyr Trp Gly Thr Thr Thr Thr Asn Phe Pro Ile Ser
            355             360              365

Asn Tyr Glu Lys Glu Leu Asp Glu Met Lys His Met Thr Arg Gln Glu
    370              375              380

Tyr Ile Ala Tyr Leu Arg Arg Asn Ser Ser Gly Phe Ser Arg Gly Ala
385             390              395                 400

Ser Lys Tyr Arg Gly Val Thr Arg His His Gln His Gly Arg Trp Gln
            405             410              415

Ala Arg Ile Gly Arg Val Ala Gly Asn Lys Asp Leu Tyr Leu Gly Thr
            420             425              430

Phe Ser Thr Glu Glu Glu Ala Glu Ala Tyr Asp Ile Ala Ala Ile
    435              440              445

Lys Phe Arg Gly Leu Asn Ala Val Thr Asn Phe Asp Met Ser Arg Tyr
    450              455              460

Asp Val Lys Ser Ile Leu Glu Ser Ser Thr Leu Pro Val Gly Gly Ala
465             470              475                 480

Ala Arg Arg Leu Lys Glu Ala Ala Asp His Ala Glu Ala Ala Gly Ala
            485             490              495

Thr Ile Trp Arg Ala Ala Asp Met Asp Gly Ala Gly Val Ile Ser Gly
            500             505              510

-continued

```
Leu Ala Asp Val Gly Met Gly Ala Tyr Ala Ala Ser Tyr His His His
        515                 520                 525

His His His Gly Trp Pro Thr Ile Ala Phe Gln Gln Pro Pro Pro Leu
    530                 535                 540

Ala Val His Tyr Pro Tyr Gly Gln Ala Pro Ala Ala Pro Ser Arg Gly
545                 550                 555                 560

Trp Cys Lys Pro Glu Gln Asp Ala Ala Val Ala Ala Ala His Ser
                565                 570                 575

Leu Gln Asp Leu Gln Gln Leu His Leu Gly Ser Ala Ala His Asn
            580                 585                 590

Phe Phe Gln Ala Ser Ser Ser Thr Val Tyr Asn Gly Gly Gly
        595                 600                 605

Gly Tyr Gln Gly Leu Gly Gly Asn Ala Phe Leu Met Pro Ala Ser Thr
        610                 615                 620

Val Val Ala Asp Gln Gly His Ser Ser Thr Ala Thr Asn His Gly Asn
625                 630                 635                 640

Thr Cys Ser Tyr Gly Asn Glu Glu Gln Gly Lys Leu Ile Gly Tyr Asp
                645                 650                 655

Ala Met Ala Met Ala Ser Gly Ala Ala Gly Gly Tyr Gln Leu Ser
            660                 665                 670

Gln Gly Ser Ala Ser Thr Val Ser Ile Ala Arg Ala Asn Gly Tyr Ser
        675                 680                 685

Ala Asn Trp Ser Ser Pro Phe Asn Gly Ala Met Gly
        690                 695                 700

<210> SEQ ID NO 9
<211> LENGTH: 658
<212> TYPE: PRT
<213> ORGANISM: Oryza sativa

<400> SEQUENCE: 9

Met Ala Ser Ala Asp Asn Trp Leu Gly Phe Ser Leu Ser Gly Gln Gly
1               5                   10                  15

Asn Pro Gln His His Gln Asn Gly Ser Pro Ser Ala Ala Gly Asp Ala
            20                  25                  30

Ala Ile Asp Ile Ser Gly Ser Gly Asp Phe Gly Leu Pro Thr Pro
        35                  40                  45

Asp Ala His His Ile Gly Met Ala Gly Glu Asp Ala Pro Tyr Gly Val
    50                  55                  60

Met Asp Ala Phe Asn Arg Gly Thr His Glu Thr Gln Asp Trp Ala Met
65                  70                  75                  80

Arg Gly Leu Asp Tyr Gly Gly Gly Ser Ser Asp Leu Ser Met Leu Val
                85                  90                  95

Gly Ser Ser Gly Gly Gly Arg Arg Thr Val Ala Gly Asp Gly Val Gly
            100                 105                 110

Glu Ala Pro Lys Leu Glu Asn Phe Leu Asp Gly Asn Ser Phe Ser Asp
        115                 120                 125

Val His Gly Gln Ala Ala Gly Gly Tyr Leu Tyr Ser Gly Ser Ala Val
    130                 135                 140

Gly Gly Ala Gly Gly Tyr Ser Asn Gly Cys Gly Gly Gly Thr Ile
145                 150                 155                 160

Glu Leu Ser Met Ile Lys Thr Trp Leu Arg Ser Asn Gln Ser Gln
                165                 170                 175

Gln Pro Ser Pro Pro Gln His Ala Asp Gln Gly Met Ser Thr Asp Ala
            180                 185                 190
```

Ser Ala Ser Ser Tyr Ala Cys Ser Asp Val Leu Val Gly Ser Cys Gly
        195                 200                 205

Gly Gly Gly Ala Gly Gly Thr Ala Ser Ser His Gln Gly Leu Ala
210                 215                 220

Leu Ser Met Ser Thr Gly Ser Val Ala Ala Gly Gly Gly Ala
225                 230                 235                 240

Val Val Ala Ala Glu Ser Ser Ser Glu Asn Lys Arg Val Asp Ser
                245                 250                 255

Pro Gly Gly Ala Val Asp Gly Ala Val Pro Arg Lys Ser Ile Asp Thr
            260                 265                 270

Phe Gly Gln Arg Thr Ser Ile Tyr Arg Gly Val Thr Arg His Arg Trp
        275                 280                 285

Thr Gly Arg Tyr Glu Ala His Leu Trp Asp Asn Ser Cys Arg Arg Glu
    290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
                325                 330                 335

Gly Thr Thr Thr Thr Thr Asn Phe Pro Met Ser Asn Tyr Glu Lys Glu
            340                 345                 350

Leu Glu Glu Met Lys His Met Thr Arg Gln Glu Tyr Ile Ala His Leu
        355                 360                 365

Arg Arg Asn Ser Ser Gly Phe Ser Arg Gly Ala Ser Lys Tyr Arg Gly
    370                 375                 380

Val Thr Arg His His Gln His Gly Arg Trp Gln Ala Arg Ile Gly Arg
385                 390                 395                 400

Val Ala Gly Asn Lys Asp Ile Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
        435                 440                 445

Leu Asp Ser Ser Thr Leu Pro Val Gly Ala Ala Arg Arg Leu Lys
    450                 455                 460

Glu Ala Glu Val Ala Ala Ala Ala Gly Gly Gly Val Ile Val Ser
465                 470                 475                 480

His Leu Ala Asp Gly Val Gly Gly Tyr Tyr Tyr Gly Cys Gly Pro
                485                 490                 495

Thr Ile Ala Phe Gly Gly Gly Gln Gln Pro Ala Pro Leu Ala Val
            500                 505                 510

His Tyr Pro Ser Tyr Gly Gln Ala Ser Gly Trp Cys Lys Pro Glu Gln
        515                 520                 525

Asp Ala Val Ile Ala Ala Gly His Cys Ala Thr Asp Leu Gln His Leu
    530                 535                 540

His Leu Gly Ser Gly Gly Ala Ala Ala Thr His Asn Phe Phe Gln Gln
545                 550                 555                 560

Pro Ala Ser Ser Ser Ala Val Tyr Gly Asn Gly Gly Gly Gly Gly
                565                 570                 575

Asn Ala Phe Met Met Pro Met Gly Ala Val Val Ala Ala Ala Asp His
            580                 585                 590

Gly Gly Gln Ser Ser Ala Tyr Gly Gly Gly Asp Glu Ser Gly Arg Leu
        595                 600                 605

Val Val Gly Tyr Asp Gly Val Val Asp Pro Tyr Ala Ala Met Arg Ser
610                 615                 620

Ala Tyr Glu Leu Ser Gln Gly Ser Ser Ser Ser Val Ser Val Ala
625                 630                 635                 640

Lys Ala Ala Asn Gly Tyr Pro Asp Asn Trp Ser Ser Pro Phe Asn Gly
                645                 650                 655

Met Gly

<210> SEQ ID NO 10
<211> LENGTH: 693
<212> TYPE: PRT
<213> ORGANISM: Sorghum bicolor

<400> SEQUENCE: 10

Met Ala Ser Thr Asn Asn His Trp Leu Gly Phe Ser Leu Ser Gly Gln
1               5                   10                  15

Asp Asn Pro Gln Pro Asn His Gln Asp Ser Ser Pro Ala Ala Ala Gly
            20                  25                  30

Ile Asp Ile Ser Gly Ala Ser Asp Phe Tyr Gly Leu Pro Thr Gln Gln
        35                  40                  45

Gly Ser Asp Gly Asn Leu Gly Val Pro Gly Leu Arg Asp Asp His Ala
50                  55                  60

Ser Tyr Gly Ile Met Glu Ala Phe Asn Arg Val Pro Gln Glu Thr Gln
65                  70                  75                  80

Asp Trp Asn Met Arg Gly Leu Asp Tyr Asn Gly Gly Ser Glu Leu
            85                  90                  95

Ser Met Leu Val Gly Ser Ser Gly Gly Gly Gly Gly Lys Arg
                100                 105                 110

Ala Val Glu Asp Ser Glu Pro Lys Leu Glu Asp Phe Leu Gly Gly Asn
            115                 120                 125

Ser Phe Val Ser Glu His Asp Gln Ser Gly Gly Tyr Leu Phe Ser Gly
        130                 135                 140

Val Pro Met Ala Ser Ser Thr Asn Ser Asn Ser Gly Ser Asn Thr Met
145                 150                 155                 160

Glu Leu Ser Met Ile Lys Thr Trp Leu Arg Asn Asn Gln Val Pro Gln
                165                 170                 175

Pro Gln Pro Pro Ala Ala Pro His Gln Ala Pro Gln Thr Glu Glu Met
            180                 185                 190

Ser Thr Asp Ala Asn Ala Ser Ala Ser Ser Phe Gly Cys Ser Asp Ser
        195                 200                 205

Met Gly Arg Asn Gly Thr Val Ala Ala Ala Gly Ser Ser Gln Ser Leu
210                 215                 220

Ala Leu Ser Met Ser Thr Gly Ser His Leu Pro Met Val Val Ala Gly
225                 230                 235                 240

Gly Gly Ala Ser Gly Ala Ala Ser Glu Ser Thr Ser Ser Glu Asn Lys
                245                 250                 255

Arg Ala Ser Gly Ala Met Asp Ser Pro Gly Ser Ala Val Glu Ala Val
            260                 265                 270

Pro Arg Lys Ser Ile Asp Thr Phe Gly Gln Arg Thr Ser Ile Tyr Arg
        275                 280                 285

Gly Val Thr Arg His Arg Trp Thr Gly Arg Tyr Glu Ala His Leu Trp
290                 295                 300

Asp Asn Ser Cys Arg Arg Glu Gly Gln Ser Arg Lys Gly Arg Gln Val
305                 310                 315                 320

Tyr Leu Gly Gly Tyr Asp Lys Glu Asp Lys Ala Ala Arg Ala Tyr Asp
             325                 330                 335

Leu Ala Ala Leu Lys Tyr Trp Gly Thr Thr Thr Thr Asn Phe Pro
        340                 345                 350

Ile Ser Asn Tyr Glu Lys Glu Leu Glu Glu Met Lys His Met Thr Arg
            355                 360                 365

Gln Glu Tyr Ile Ala Tyr Leu Arg Arg Asn Ser Ser Gly Phe Ser Arg
370                 375                 380

Gly Ala Ser Lys Tyr Arg Gly Val Thr Arg His His Gln His Gly Arg
385                 390                 395                 400

Trp Gln Ala Arg Ile Gly Arg Val Ala Gly Asn Lys Asp Leu Tyr Leu
                405                 410                 415

Gly Thr Phe Ser Thr Glu Glu Glu Ala Ala Glu Ala Tyr Asp Ile Ala
            420                 425                 430

Ala Ile Lys Phe Arg Gly Leu Asn Ala Val Thr Asn Phe Asp Met Ser
        435                 440                 445

Arg Tyr Asp Val Lys Ser Ile Leu Glu Ser Ser Thr Leu Pro Val Gly
    450                 455                 460

Gly Ala Ala Arg Arg Leu Lys Asp Ala Val Asp His Val Glu Ala Gly
465                 470                 475                 480

Ala Thr Ile Trp Arg Ala Asp Met Asp Gly Val Ile Ser Gln Leu
                485                 490                 495

Ala Glu Ala Gly Met Gly Tyr Ala Ser Tyr Gly His His Ala Trp
            500                 505                 510

Pro Thr Ile Ala Phe Gln Gln Pro Ser Pro Leu Ser Val His Tyr Pro
        515                 520                 525

Tyr Gly Gln Pro Pro Ser Arg Gly Trp Cys Lys Pro Glu Gln Asp Ala
    530                 535                 540

Ala Val Ala Ala Ala His Ser Leu Gln Asp Leu Gln Gln Leu His
545                 550                 555                 560

Leu Gly Ser Ala Ala His Asn Phe Phe Gln Ala Ser Ser Ser Ala
                565                 570                 575

Val Tyr Asn Ser Gly Gly Gly Gly Ala Ser Gly Gly Tyr His Gln Gly
            580                 585                 590

Leu Gly Gly Gly Ser Ser Ser Phe Leu Met Pro Ser Ser Thr Val Val
        595                 600                 605

Ala Gly Ala Asp Gln Gly His Ser Ser Ser Thr Ala Asn Gln Gly Ser
    610                 615                 620

Thr Cys Ser Tyr Gly Asp Asp His Gln Glu Gly Lys Leu Ile Gly Tyr
625                 630                 635                 640

Asp Ala Met Val Ala Ala Thr Ala Ala Gly Gly Asp Pro Tyr Ala Ala
                645                 650                 655

Ala Arg Ser Gly Tyr Gln Phe Ser Ser Gln Gly Ser Gly Ser Thr Val
            660                 665                 670

Ser Ile Ala Arg Ala Asn Gly Tyr Ser Asn Asn Trp Ser Ser Pro Phe
        675                 680                 685

Asn Gly Gly Met Gly
    690

<210> SEQ ID NO 11
<211> LENGTH: 2130
<212> TYPE: DNA
<213> ORGANISM: Zea mays

<400> SEQUENCE: 11

```
atggccactg tgaacaactg gctcgctttc tccctctccc cgcaggagct gccgccctcc    60
cagacgacgg actccacgct catctcggcc gccaccgccg accatgtctc cggcgatgtc   120
tgcttcaaca tcccccaaga ttggagcatg aggggatcag agctttcggc gctcgtcgcg   180
gagccgaagc tggaggactt cctcggcggc atctccttct ccgagcagca tcacaagtcc   240
aactgcaact tgatacccag cactagcagc acagtttgct acgcgagctc agctgctagc   300
accggctacc atcaccagct gtaccagccc accagctccg cgctccactt cgcggactcc   360
gtcatggtgg cctcctcggc cggtgtccac gacggcggtt ccatgctcag cgcggccgcc   420
gctaacggtg tcgctggcgc tgccagtgcc aacggcggcg catcgggct gtccatgatc    480
aagaactggc tgcggagcca accggcgccc atgcagccga gggcggcggc ggctgagggc   540
gcgcaggggc tctctttgtc catgaacatg gcggggacga cccaaggcgc tgctggcatg   600
ccacttctcg ctggagagcg cgcacgggcg cccgagagtg tatcgacgtc agcacagggt   660
ggtgccgtcg tcgtcacggc gccgaaggag gatagcggtg gcagcggtgt tgccggtgct   720
ctagtagccg tgagcacgga cacgggtggc agcggcggcg cgtcggctga caacacggca   780
aggaagacgg tggacacgtt cgggcagcgc acgtcgattt accgtggcgt gacaaggcat   840
agatggactg ggagatatga ggcacatctt tgggataaca gttgcagaag ggaaggacaa   900
actcgtaagg gtcgtcaagt ctatttaggt ggctatgata agaggagaa agctgctagg    960
gcttatgatc ttgctgctct gaagtactgg ggtgccacaa caacaacaaa ttttccagtg  1020
agtaactacg aaaaggagct cgaggacatg aagcacatga aaggcagga gtttgtagcg   1080
tctctgagaa ggaagagcag tggtttctcc agaggtgcat ccatttacag gggagtgact  1140
aggcatcacc aacatggaag atggcaagca cggattggac gagttgcagg gaacaaggat  1200
ctttacttgg gcaccttcag cacccaggag gaggcagcgg aggcgtacga catcgcggcg  1260
atcaagttcc gcggcctcaa cgccgtcacc aacttcgaca tgagccgcta cgacgtgaag  1320
agcatcctgg acagcagcgc cctccccatc ggcagcgccg ccaagcgtct caaggaggcc  1380
gaggccgcag cgtccgcgca gcaccaccac gccggcgtgg tgagctacga cgtcggccgc  1440
atcgcctcgc agctcggcga cggcggagcc ctagcggcg cgtacggcgc gcactaccac   1500
ggcgccgcct ggccgaccat cgcgttccag ccgggcgccg ccaccacagg cctgtaccac  1560
ccgtacgcgc agcagccaat gcgcggcggc gggtggtgca agcaggagca ggaccacgcg  1620
gtgatcgcgg ccgcgcacag cctgcaggac ctccaccact tgaacctggg cgcggccggc  1680
gcgcacgact ttttctcggc agggcagcag gccgccgccg cagctgcgat gcacggcctg  1740
gctagcatcg acagtgcgtc gctcgagcac agcaccggct ccaactccgt cgtctacaac  1800
ggcggggtcg gcgatagcaa cggcgccagc gccgttggca gcggcggtgg ctacatgatg  1860
ccgatgagcg ctgccggagc aaccactaca tcggcaatgg tgagccacga gcagatgcat  1920
gcacgggcct acgacgaagc caagcaggct gctcagatgg ggtacgagag ctacctggtg  1980
aacgcggaga acaatggtgg cggaaggatg tctgcatggg ggaccgtcgt ctctgcagcc  2040
gcggcggcag cagcaagcag caacgacaac attgccgccg acgtcggcca tggcggcgcg  2100
cagctcttca gtgtctggaa cgacacttaa                                   2130
```

<210> SEQ ID NO 12
<211> LENGTH: 2133
<212> TYPE: DNA
<213> ORGANISM: Zea mays

<400> SEQUENCE: 12

```
atggccactg tgaacaactg gctcgctttc tccctctccc cgcaggagct gccgccctcc     60
cagacgacgg actccacact catctcggcc gccaccgccg accatgtctc cggcgatgtc    120
tgcttcaaca tccccaaga ttggagcatg aggggatcag agctttcggc gctcgtcgcg    180
gagccgaagc tggaggactt cctcggcggc atctccttct ccgagcagca tcacaaggcc    240
aactgcaaca tgatacccag cactagcagc acagtttgct acgcgagctc aggtgctagc    300
accggctacc atcaccagct gtaccaccag cccaccagct cagcgctcca cttcgcggac    360
tccgtaatgg tggcctcctc ggccggtgtc cacgacggcg tgccatgct cagcgcggcc    420
gccgctaacg tgtcgctgg cgctgccagt gccaacggcg gcggcatcgg gctgtccatg    480
attaagaact ggctgcggag ccaaccggcg cccatgcagc cgaggtggc ggcggctgag    540
ggcgcgcagg ggctctcttt gtccatgaac atggcgggga cgacccaagg cgctgctggc    600
atgccacttc tcgctggaga gcgcacggg gcgcccgaga gtgtatcgac gtcagcacag    660
ggtggagccg tcgtcgtcac ggcgccgaag gaggatagcg tggcagcgg tgttgccggc    720
gctctagtag ccgtgagcac ggacacgggt ggcagcggcg gcgcgtcggc tgacaacacg    780
gcaaggaaga cggtggacac gttcgggcag cgcacgtcga tttaccgtgg cgtgacaagg    840
catagatgga ctgggagata tgaggcacat ctttgggata acagttgcag aaggggaaggg    900
caaactcgta agggtcgtca agtctattta ggtggctatg ataaagagga gaaagctgct    960
agggcttatg atcttgctgc tctgaagtac tggggtgcca acaacaac aaattttcca   1020
gtgagtaact acgaaaagga gctcgaggac atgaagcaca tgacaaggca ggagtttgta   1080
gcgtctctga aaggaagag cagtggtttc tccagaggtg catccattta caggggagtg   1140
actaggcatc accaacatgg aagatggcaa gcacggattg gacgagttgc agggaacaag   1200
gatctttact tgggcaccttt cagcacccag gaggaggcag cggaggcgta cgacatcgcg   1260
gcgatcaagt tccgcggcct caacgccgtc accaacttcg acatgagccg ctacgacgtg   1320
aagagcatcc tggacagcag cgccctcccc atcggcagcg ccgccaagcg cctcaaggag   1380
gccgaggccg cagcgtccgc gcagcaccac cacgccggcg tggtgagcta cgacgtcggc   1440
cgcatcgcct cgcagctcgg cgacggcgga gccctggcgg cggcgtacgg cgcgcactac   1500
cacggcgccg cctggccgac catcgcgttc cagccgggcg ccgccagcac aggcctgtac   1560
cacccgtacg cgcagcagcc aatgcgcggc ggcgggtggt gcaagcagga gcaggaccac   1620
gcggtgatcg cggccgcgca cagcctgcag gacctccacc acctgaacct gggcgcggcc   1680
ggcgcgcacg acttttctc ggcagggcag caggccgccg ccgctgcgat gcacggcctg   1740
ggtagcatcg acagtgcgtc gctcgagcac agcaccggct ccaactccgt cgtctacaac   1800
ggcggggtcg gcgacagcaa cggcgccagc gccgtcggcg gcagtggcgg tggctacatg   1860
atgccgatga cgctgccgg agcaaccact acatcggcaa tggtgagcca cgagcaggtg   1920
catgcacggg cctacgacga agccaagcag gctgctcaga tggggtacga gagctacctg   1980
gtgaacgcgg agaacaatgg tggcggaagg atgtctgcat ggggggactgt cgtgtctgca   2040
gccgcggcgc agcagcaag cagcaacgac aacatggccg ccgacgtcgg ccatggcggc   2100
gcgcagctct tcagtgtctg gaacgacact taa                                2133
```

<210> SEQ ID NO 13
<211> LENGTH: 2112
<212> TYPE: DNA
<213> ORGANISM: Sorghum bicolor

<400> SEQUENCE: 13

```
atggctactg tgaacaactg gctcgctttc tccctctccc cgcaggagct gccgcccacc      60
cagacggact ccaccctcat ctctgccgcc accaccgacg atgtctccgg cgatgtctgc     120
ttcaacatcc cccaagattg gagcatgagg ggatccgagc tttcggcgct cgtcgccgag     180
ccgaagctgg aggacttcct cggcggaatc tccttctccg agcagcacca caaggccaac     240
tgcaacatga tccccagcac tagcagcaca gcttgctacg cgagctcggg tgctaccgcc     300
ggctaccatc accagctgta ccaccagccc accagctccg cgctccactt cgctgactcc     360
gtcatggtgg cctcctcggc cggcggcgtc cacgacggag gtgccatgct cagcgcggcc     420
agcgctaatg gtagcgctgg cgctggcgct gccagtgcca atggcagcgg cagcatcggg     480
ctgtccatga tcaagaactg gctgcggagc caaccagctc ccatgcagcc gagggtggcg     540
gcggctgaga gcgtgcaggg gctctctttg tccatgaaca tggcgggggc gacgcaaggc     600
gccgctggca tgccacttct tgctggagag cgcggccggg cgcccgagag tgtctcgacg     660
tcggcacagg gtggagccgt cgtcacggct ccaaaggagg atagcggtgg cagcggtgtt     720
gccgccaccg gcgccctagt agccgtgagc acggacacgg gtggcagcgg cgcgtcggct     780
gacaacacgg caaggaagac ggtggacacg ttcgggcagc gcacgtcgat ttaccgtggc     840
gtgacaaggc atagatggac tgggagatat gaagcacatc tgtgggacaa cagttgcaga     900
agggaaggac aaactcgcaa gggtcgtcaa gtctatttag gtggctatga taaagaggag     960
aaagctgcta gggcttatga tctggctgct cttaagtact ggggtcccac gacaacaaca    1020
aattttccag tgaataacta cgaaaaggag ctggaggata tgaagcacat gacaaggcag    1080
gagtttgtag cgtctctgag aaggaagagc agtggtttct ccagaggtgc atccatttac    1140
aggggagtga ctaggcatca ccagcatgga agatggcaag cacggattgg acgagttgca    1200
gggaacaagg atctctactt gggcaccttc agcacgcagg aggaggcagc ggaggcatac    1260
gacattgcgg cgatcaagtt ccgcggcctc aacgccgtca caaacttcga catgagccgc    1320
tacgacgtca agagcatcct ggacagcagt gcgctcccca tcggcagcgc cgccaagcgt    1380
ctcaaggagg ccgaggccgc cgcgtccgca cagcaccatg ccggcgtggt gagctacgac    1440
gtcggccgca tagcctcaca gctcggcgac ggcggcgccc tggcggcggc gtacggcgcg    1500
cactaccatg gcgcctggcc gaccatcgcg ttccagccga gcgcggccac gggcctgtac    1560
cacccgtacg cgcagccgat gcgcgggtgg tgcaagcagg agcaggacca cgcggtgatc    1620
gcggccgcgc acagcctgca ggagctccac cacctgaacc tgggtgctgc cgccggcgcg    1680
cacgacttct tctcggcggg gcagcaggcg gcgatgcacg gcctgggtag catggacaat    1740
gcatcactcg agcacagcac cggctccaac tccgtcgtgt acaacggtgt tggtgatagc    1800
aacggcagca ccgtcgtcgg cagtggtggc tacatgatgc ctatgagcgc tgccacggcg    1860
acggctacca cggcaatggt gagccacgag caggtcatgc acgggcaca gggtgatcac    1920
cacgacgaag ccaagcaggc tgctcagatg gggtacgaga gctacctggt gaacgcagag    1980
aactatggcg gcgggaggat gtctgcggcc tgggcgactg tctcagcgcc accggcggca    2040
agcagcaacg ataacatggc ggacgtcggc catggcggcg cacagctctt cagtgtctgg    2100
aacgatactt aa                                                        2112
```

<210> SEQ ID NO 14
<211> LENGTH: 2112
<212> TYPE: DNA

<213> ORGANISM: Setaria italica

<400> SEQUENCE: 14

```
atggctactg tgaacaactg gctcgctttc tccctctccc cgcaggagct gccgcccacc      60
cagacggact ccaccctcat ctctgccgcc accaccgacg atgtctccgg cgatgtctgc     120
ttcaacatcc cccaagattg gagcatgagg ggatccgagc tttcggcgct cgtcgccgag     180
ccgaagctgg aggacttcct cggcggaatc tccttctccg agcagcacca caaggccaac     240
tgcaacatga tccccagcac tagcagcaca gcttgctacg cgagctcggg tgctaccgcc     300
ggctaccatc accagctgta ccaccagccc accagctccg cgctccactt cgctgactcc     360
gtcatggtgg cctcctcggc cggcggcgtc cacgacggag gtgccatgct cagcgcggcc     420
agcgctaatg gtagcgctgg cgctggcgct gccagtgcca atggcagcgg cagcatcggg     480
ctgtccatga tcaagaactg gctgcggagc caaccagctc ccatgcagcc gagggtggcg     540
gcggctgaga gcgtgcaggg gctctctttg tccatgaaca tggcggggc gacgcaaggc     600
gccgctggca tgccacttct tgctggagag cgcggccggg cgcccgagag tgtctcgacg     660
tcggcacagg gtggagccgt cgtcacggct ccaaaggagg atagcggtgg cagcggtgtt     720
gccgccaccg gcgccctagt agccgtgagc acggacacgg tggcagcgg cgcgtcggct     780
gacaacacgg caaggaagac ggtggacacg ttcgggcagc gcacgtcgat ttaccgtggc     840
gtgacaaggc atagatggac tgggagatat gaagcacatc tgtgggacaa cagttgcaga     900
agggaaggac aaactcgcaa gggtcgtcaa gtctatttag gtggctatga taagaggag     960
aaagctgcta gggcttatga tctggctgct cttaagtact ggggtcccac gacaacaaca    1020
aattttccag tgaataacta cgaaaaggag ctggaggata tgaagcacat gacaaggcag    1080
gagtttgtag cgtctctgag aaggaagagc agtggtttct ccagaggtgc atccatttac    1140
aggggagtga ctaggcatca ccagcatgga agatggcaag cacggattgg acgagttgca    1200
gggaacaagg atctctactt gggcaccttc agcacgcagg aggaggcagc ggaggcatac    1260
gacattgcgg cgatcaagtt ccgcggcctc aacgccgtca caaacttcga catgagccgc    1320
tacgacgtca agagcatcct ggacagcagt gcgctcccca tcggcagcgc cgccaagcgt    1380
ctcaaggagg ccgaggccgc cgcgtccgca cagcaccatg ccggcgtggt gagctacgac    1440
gtcgccgcca tagcctcaca gctcggcgac ggcggcgccc tggcggcggc gtacggcgcg    1500
cactaccatg gcgcctggcc gaccatcgcg ttccagccga gcgcggccac gggcctgtac    1560
cacccgtacg cgcagccgat gcgcgggtgg tgcaagcagg agcaggacca cgcggtgatc    1620
gcggccgcgc acagcctgca ggagctccac cacctgaacc tgggtgctgc cgccggcgcg    1680
cacgacttct tctcggcggg gcagcaggcg gcgatgcacg gcctgggtag catggacaat    1740
gcatcactcg agcacagcac cggctccaac tccgtcgtgt acaacggtgt tggtgatagc    1800
aacggcagca ccgtcgtcgg cagtggtggc tacatgatgc ctatgagcgc tgccacggcg    1860
acggctacca cggcaatggt gagccacgag caggtgcatg cacgggcaca gggtgatcac    1920
cacgacgaag ccaagcaggc tgctcagatg gggtacgaga gctacctggt gaacgcagag    1980
aactatggcg gcgggaggat gtctgcgcc tgggcgactg tctcagcgcc accgcggca     2040
agcagcaacg ataacatggc ggacgtcggc catggcggcg cacagctctt cagtgtctgg    2100
aacgatactt aa                                                         2112
```

<210> SEQ ID NO 15
<211> LENGTH: 2064

<212> TYPE: DNA
<213> ORGANISM: Brachypodium distachyum

<400> SEQUENCE: 15

```
atggctaccg tgaacaactg gctgggcttc tccctctccc cgcaggagct cccgtcctcc      60
gccgctgccg ccgccggcga cgtctccggc gccgacgtct gcttcaacat cccgcaagat     120
tggggcatga ggggatcgga gctgtcggcg ctggtggcgg agccgaagct ggaggacttc     180
ctcggcggca tctcttccta ctctgaccat cacaaggcag ccagaagcaa caacatgaac     240
atcaatggcg ccgccgcctg ctacgcgagc tccggcagca gcggctacca gctttaccac     300
gaccacccca actccctcca gttcgccgac tctgtcatgg tcgcttcctc cgctggcggc     360
gtccacaatg aacatggcat catggcaagc accactgcca atggtgcagg caccaatggc     420
ggcatcgggc tgtccatgat caagagctgg ctgcggagcc agccggcgcc ggcgcagcag     480
gagcagcaga gggcggaggg gctgtcgctg tccatgaaca tgccgctcct gcaggcggcg     540
gcggcggaga ctagcttgtc cacgtcggca gcgcagcagg atctcggaa ggagaataat      600
ggcagcagta gtgctggttc tggagccgtg gtgtcagccg gtactaccag cgccggcgcg     660
gtggtggtgg agtcgccggc agcggggagg aagaccgccg acacgttcgg gcagcggact     720
tcgatctacc gcggcgtcac caggcataga tggacaggga ggtatgaggc tcacctgtgg     780
gacaacagct gcagaagaga aggacaaact cgcaagggtc gtcaagtcta tctcggtggt     840
tatgacaaag aggagaaagc tgcaagagct tatgatttgg ctgctctcaa gtattgggc     900
cccaccacga cgacaaattt tccagtagat aactacgaga aggagctgga ggagatgaag     960
cacatgacaa ggcaggagtt tgtggcgtct ctccgaagga gagcagtgg tttttcaaga    1020
ggtgcatcca tttatcgtgg agtaactagg caccaccaac atgggagatg caagcaagg    1080
ataggagag ttgcagggaa caaggatctc tacttgggca ctttcagcac gcaggaggag    1140
gcggcggagg cgtacgacat cgcggcgatc aagttccggg ggctgaacgc cgtcactaac    1200
ttcgacatgt cccgctacga cgtcaagagc atcctcgaca gcaccgccgc gctgcctgtc    1260
ggcggcacca agcgcctcag ggacgcggct gccgccgatc agcactacca gcagcgcgcc    1320
gggggcgtcg tcagctacgc cgcgccgcag ctcgtggtg tcaacgagac cgcccttgcc    1380
tatggcgcgc cctactacca ccaccaaaacc tccgccgcag cgtggccgac catcgcgttc    1440
caggcggcgc cgcaagcgtc gtcggggcac gggcacatgc tgtaccaccc gtacgggcag    1500
ccattgatgc gcgggtggtg caagcaagag caggagcaag ggcaagggca gcaggagccg    1560
gaccacgcg tgatcgcggc cgcgcacagc ctgcaggacc tccaccacct caacctcggc    1620
gccggtgcgc acgacttctt ctcccagcat gcccacgcca tgcaccagca gcagcagcag    1680
cacggcggcc tcgcagcgt cgacaacaac ggcgcggcgt cgctggagca cagcactggc    1740
tccaactccg tcgtctacaa cggggccgct gccgccgggg acaccaacaa cagctacatg    1800
ctgccgccca tgagcgctgc agcagcagct ggcttcggcc tccgcgatca gcaggacgaa    1860
ggcgggaaga tggcgtacga gaacttcctc ctcggcgccg ccaccgacgg ctactgtggc    1920
cctggaagga tggcggccac ctggacaccg gtgtcggttt cggcggccca gccagtggcg    1980
gcaacgagca gcgcagcga catggccggt gccgtctgcc atggcggcgc gcagctcttc    2040
agcgtctgga acgacgacag ttag                                           2064
```

<210> SEQ ID NO 16
<211> LENGTH: 3769
<212> TYPE: DNA

<213> ORGANISM: Sorghum bicolor

<400> SEQUENCE: 16

| | | | | | |
|---|---|---|---|---|---|
| atggctactg | tgaacaactg | gctcgctttc | tccctctccc | cgcaggagct | gccgcccacc | 60 |
| cagacggact | ccaccctcat | ctctgccgcc | accaccgacg | atgtctccgg | cgatgtctgc | 120 |
| ttcaacatcc | cccaaggtat | gcatctatcg | atcgatatat | gtacgtacag | tgcgcatata | 180 |
| tatatatatc | tgcagtttgt | ggtacgaata | ctgattgaag | ctagcatgaa | atgtcgtttg | 240 |
| ttctttcaga | ttggagcatg | aggggatccg | agctttcggc | gctcgtcgcc | gagccgaagc | 300 |
| tggaggactt | cctcggcgga | atctccttct | ccgagcagca | ccacaaggcc | aactgcaaca | 360 |
| tgatccccag | cactagcagc | acagcttgct | acgcgagctc | gggtgctacc | gccggctacc | 420 |
| atcaccagct | gtaccaccag | cccaccagct | ccgcgctcca | cttcgctgac | tccgtcatgg | 480 |
| tggcctcctc | ggccggcggc | gtccacgacg | gaggtgccat | gctcagcgcg | ccagcgcta | 540 |
| atggtagcgc | tggcgctggc | gctgccagtg | ccaatggcag | cggcagcatc | gggctgtcca | 600 |
| tgatcaagaa | ctggctgcgg | agccaaccag | ctcccatgca | gccgagggtg | cgcggcggctg | 660 |
| agagcgtgca | ggggctctct | tgtccatga | acatggcggg | ggcgacgcaa | ggcgccgctg | 720 |
| gcatgccact | tcttgctgga | gagcgcggcc | gggcgcccga | gagtgtctcg | acgtcggcac | 780 |
| agggtggagc | cgtcgtcacg | gctccaaagg | aggatagcgg | tggcagcggt | gttgccgcca | 840 |
| ccggcgccct | agtagccgtg | agcacggaca | cgggtggcag | cggcgcgtcg | gctgacaaca | 900 |
| cggcaaggaa | gacggtggac | acgttcgggc | agcgcacgtc | gatttaccgt | ggcgtgacaa | 960 |
| ggtaataagg | gtccggtatt | acaatgaatc | gtcacttcgt | cagagaacta | aactagcaca | 1020 |
| aatcagcaat | gaatcaagta | atatcatgaa | atttagaaaa | gccgttagca | atgcaaggag | 1080 |
| ctatcattat | agatttgatt | gcatctagac | agttctgaat | taaatgagta | gggcaatgtg | 1140 |
| tagcctttga | tgatctcgct | gattattagg | agtgccattt | gtattggcta | tgattgtggt | 1200 |
| atatacagca | gtagacaatt | aacaaaaggc | taccactttc | gaattatttt | aggcatagat | 1260 |
| ggactgggag | atatgaagca | catctgtggg | acaacagttg | cagaagggaa | ggacaaactc | 1320 |
| gcaagggtcg | tcaaggtacc | aatataatgc | aatacaccgt | atttaaatat | atatgctttt | 1380 |
| ctgtaattaa | gtttatactt | tcacaaaact | gacattactt | cgcattatca | tttttggatt | 1440 |
| gtcgtcgtca | tgattggcgg | gattgaaatg | aactattgaa | tctacagtct | atttaggtaa | 1500 |
| gcgatttcac | ttggttatta | atttgggacc | aactacttaa | tccagtttgt | ttttcccta | 1560 |
| taaccattat | ttttcatct | gtgttctcaa | ctcttacttt | tccatcttgt | tccactgata | 1620 |
| ggtggctatg | ataaagagga | gaaagctgct | agggcttatg | atctggctgc | tcttaagtac | 1680 |
| tggggtccca | cgacaacaac | aaattttcca | gtatgtatat | gtagaatgca | gttttacttc | 1740 |
| actgaagatc | ataccctttgc | tatgtctcaa | atgccgttca | ttagttagtg | gatctgaagt | 1800 |
| gaaggttctg | taatttttgt | taactatgta | cattgctgga | attgtactta | aagtcatttg | 1860 |
| tttttgtata | tctaggtgaa | taactacgaa | aaggagctgg | aggatatgaa | gcacatgaca | 1920 |
| aggcaggagt | ttgtagcgtc | tctgagaagg | tcggtcgaac | agcattgatt | aatcaatgcc | 1980 |
| aactctattg | aataaacatc | tactctgtta | attgttaaag | tttgagagaa | agatctgcat | 2040 |
| gttagatctt | aatagaccac | tgtatatgaa | tgcaggaaga | gcagtggttt | ctccagaggt | 2100 |
| gcatccattt | acaggggagt | gactaggtat | gaattcatat | aatggcgtca | acaaacacac | 2160 |
| atacactttg | attgaggagg | cgaatgcacg | catggattga | atgtgaatgg | tgttttactt | 2220 |
| gaactatgta | attataggca | tcaccagcat | ggaagatggc | aagcacggat | tggacgagtt | 2280 |

```
gcagggaaca aggatctcta cttgggcacc ttcagtaagt atcagagatg ttttctcatt    2340
gtatatagag gagtacttct atatgtatat atacattcag ttattcacca cacaaaagca    2400
aattgcagtc aactaataac aatctcaacg caatgagaag caagtgttac agctgatagt    2460
acacatttgt agaccttctg catatggatg ttatatatga tgactattaa aaatgtgacc    2520
attgcatcaa gtcatgcaaa gttgcattgc agtagtacat acattactta gtgcatgctc    2580
ctcaagtggc ttttcaaac ctgatcccat gtctggcgct attgttgtct cccattcacc     2640
cgtgcatcag gtcaaaatag tactatgcct caataagaaa cacatgagca tgcactggca    2700
gcagcagact aatcaagttc tatcatttac taataaacta attaggctac agcatccaaa    2760
agattctacc cattaagcca caactgttca tgcatgcatt cataaaccag gataccacca    2820
tgcatgcgtg caccgtgttc gtgcttggaa tattgagctg agccgagtgc acccttgcgt    2880
ggatgcaggc acgcaggagg aggcagcgga ggcatacgac attgcggcga tcaagttccg    2940
cggcctcaac gccgtcacaa acttcgacat gagccgctac gacgtcaaga gcatcctgga    3000
cagcagtgcg ctccccatcg gcagcgccgc caagcgtctc aaggaggccg aggccgccgc    3060
gtccgcacag caccatgccg gcgtggtgag ctacgacgtc ggccgcatag cctcacagct    3120
cggcgacggc ggcgccctgg cggcggcgta cggcgcgcac taccatggcg cctggccgac    3180
catcgcgttc cagccgagcg cggccacggg cctgtaccac ccgtacgcgc agccgatgcg    3240
cgggtggtgc aagcaggagc aggaccacgc ggtgatcgcg gccgcgcaca gcctgcagga    3300
gctccaccac ctgaacctgg gtgctgccgc cggcgcgcac gacttcttct cggcggggca    3360
gcaggcggcg atgcacggcc tgggtagcat ggacaatgca tcactcgagc acagcaccgg    3420
ctccaactcc gtcgtgtaca acggtgttgg tgatagcaac ggcagcaccg tcgtcggcag    3480
tggtggctac atgatgccta tgagcgctgc cacggcgacg gctaccacgg caatggtgag    3540
ccacgagcag gtgcatgcac gggcacaggg tgatcaccac gacgaagcca agcaggctgc    3600
tcagatgggg tacgagagct acctggtgaa cgcagagaac tatggcggcg ggaggatgtc    3660
tgcggcctgg gcgactgtct cagcgccacc ggcggcaagc agcaacgata acatggcgga    3720
cgtcggccat ggcggcgcac agctcttcag tgtctggaac gatacttaa              3769
```

<210> SEQ ID NO 17
<211> LENGTH: 710
<212> TYPE: PRT
<213> ORGANISM: Zea mays

<400> SEQUENCE: 17

```
Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
                20                  25                  30

Ala Asp His Val Ser Gly Asp Val Cys Phe Asn Ile Pro Gln Asp Trp
            35                  40                  45

Ser Met Arg Gly Ser Glu Leu Ser Ala Leu Val Ala Glu Pro Lys Leu
        50                  55                  60

Glu Asp Phe Leu Gly Gly Ile Ser Phe Ser Gln His His Lys Ala
65                  70                  75                  80

Asn Cys Asn Met Ile Pro Ser Thr Ser Ser Thr Val Cys Tyr Ala Ser
                85                  90                  95

Ser Gly Ala Ser Thr Gly Tyr His His Gln Leu Tyr His Gln Pro Thr
            100                 105                 110
```

-continued

```
Ser Ser Ala Leu His Phe Ala Asp Ser Val Met Val Ala Ser Ser Ala
            115                 120                 125

Gly Val His Asp Gly Gly Ala Met Leu Ser Ala Ala Ala Asn Gly
130                 135                 140

Val Ala Gly Ala Ala Ser Ala Asn Gly Gly Ile Gly Leu Ser Met
145                 150                 155                 160

Ile Lys Asn Trp Leu Arg Ser Gln Pro Ala Pro Met Gln Pro Arg Val
                165                 170                 175

Ala Ala Ala Glu Gly Ala Gln Gly Leu Ser Leu Ser Met Asn Met Ala
            180                 185                 190

Gly Thr Thr Gln Gly Ala Ala Gly Met Pro Leu Leu Ala Gly Glu Arg
        195                 200                 205

Ala Arg Ala Pro Glu Ser Val Ser Thr Ser Ala Gln Gly Gly Ala Val
        210                 215                 220

Val Val Thr Ala Pro Lys Glu Asp Ser Gly Ser Gly Val Ala Gly
225                 230                 235                 240

Ala Leu Val Ala Val Ser Thr Asp Thr Gly Gly Ser Gly Gly Ala Ser
                245                 250                 255

Ala Asp Asn Thr Ala Arg Lys Thr Val Asp Thr Phe Gly Gln Arg Thr
            260                 265                 270

Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
        290                 295                 300

Gly Arg Gln Val Tyr Leu Gly Gly Tyr Asp Lys Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
        370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
450                 455                 460

Ala Ser Ala Gln His His Ala Gly Val Val Ser Tyr Asp Val Gly
465                 470                 475                 480

Arg Ile Ala Ser Gln Leu Gly Asp Gly Gly Ala Leu Ala Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525
```

-continued

Arg Gly Gly Gly Trp Cys Lys Gln Glu Gln Asp His Ala Val Ile Ala
    530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Gln Ala Ala Ala Ala Ala
                565                 570                 575

Met His Gly Leu Gly Ser Ile Asp Ser Ala Ser Leu Glu His Ser Thr
            580                 585                 590

Gly Ser Asn Ser Val Val Tyr Asn Gly Val Gly Asp Ser Asn Gly
        595                 600                 605

Ala Ser Ala Val Gly Gly Ser Gly Gly Tyr Met Met Pro Met Ser
610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Arg Met Ser
            660                 665                 670

Ala Trp Gly Thr Val Val Ser Ala Ala Ala Ala Ala Ala Ser Ser
            675                 680                 685

Asn Asp Asn Met Ala Ala Asp Val Gly Asn Gly Gly Ala Gln Leu Phe
690                 695                 700

Ser Val Trp Asn Asp Thr
705                 710

<210> SEQ ID NO 18
<211> LENGTH: 709
<212> TYPE: PRT
<213> ORGANISM: Zea mays

<400> SEQUENCE: 18

Met Ala Thr Val Asn Asn Trp Leu Ala Phe Ser Leu Ser Pro Gln Glu
1               5                   10                  15

Leu Pro Pro Ser Gln Thr Thr Asp Ser Thr Leu Ile Ser Ala Ala Thr
            20                  25                  30

Ala Asp His Val Ser Gly Asp Val Cys Phe Asn Ile Pro Gln Asp Trp
        35                  40                  45

Ser Met Arg Gly Ser Glu Leu Ser Ala Leu Val Ala Glu Pro Lys Leu
    50                  55                  60

Glu Asp Phe Leu Gly Gly Ile Ser Phe Ser Glu Gln His His Lys Ser
65                  70                  75                  80

Asn Cys Asn Leu Ile Pro Ser Thr Ser Ser Thr Val Cys Tyr Ala Ser
                85                  90                  95

Ser Ala Ala Ser Thr Gly Tyr His His Gln Leu Tyr Gln Pro Thr Ser
            100                 105                 110

Ser Ala Leu His Phe Ala Asp Ser Val Met Val Ala Ser Ser Ala Gly
        115                 120                 125

Val His Asp Gly Gly Ser Met Leu Ser Ala Ala Ala Asn Gly Val
    130                 135                 140

Ala Gly Ala Ala Ser Ala Asn Gly Gly Ile Gly Leu Ser Met Ile
145                 150                 155                 160

Lys Asn Trp Leu Arg Ser Gln Pro Ala Pro Met Gln Pro Arg Ala Ala
                165                 170                 175

Ala Ala Glu Gly Ala Gln Gly Leu Ser Leu Ser Met Asn Met Ala Gly
            180                 185                 190

```
Thr Thr Gln Gly Ala Ala Gly Met Pro Leu Leu Ala Gly Glu Arg Ala
    195                 200                 205

Arg Ala Pro Glu Ser Val Ser Thr Ser Ala Gln Gly Gly Ala Val Val
210                 215                 220

Val Thr Ala Pro Lys Glu Asp Ser Gly Gly Ser Gly Val Ala Gly Ala
225                 230                 235                 240

Leu Val Ala Val Ser Thr Asp Thr Gly Gly Ser Gly Gly Ala Ser Ala
                245                 250                 255

Asp Asn Thr Ala Arg Lys Thr Val Asp Thr Phe Gly Gln Arg Thr Ser
                260                 265                 270

Ile Tyr Arg Gly Val Thr Arg His Arg Trp Thr Gly Tyr Glu Ala
    275                 280                 285

His Leu Trp Asp Asn Ser Cys Arg Arg Glu Gly Gln Thr Arg Lys Gly
    290                 295                 300

Arg Gln Val Tyr Leu Gly Gly Tyr Asp Lys Glu Lys Ala Ala Arg
305                 310                 315                 320

Ala Tyr Asp Leu Ala Ala Leu Lys Tyr Trp Gly Ala Thr Thr Thr Thr
                325                 330                 335

Asn Phe Pro Val Ser Asn Tyr Glu Lys Glu Leu Glu Asp Met Lys His
                340                 345                 350

Met Thr Arg Gln Glu Phe Val Ala Ser Leu Arg Arg Lys Ser Ser Gly
            355                 360                 365

Phe Ser Arg Gly Ala Ser Ile Tyr Arg Gly Val Thr Arg His His Gln
        370                 375                 380

His Gly Arg Trp Gln Ala Arg Ile Gly Arg Val Ala Gly Asn Lys Asp
385                 390                 395                 400

Leu Tyr Leu Gly Thr Phe Ser Thr Gln Glu Glu Ala Ala Glu Ala Tyr
                405                 410                 415

Asp Ile Ala Ala Ile Lys Phe Arg Gly Leu Asn Ala Val Thr Asn Phe
                420                 425                 430

Asp Met Ser Arg Tyr Asp Val Lys Ser Ile Leu Asp Ser Ser Ala Leu
            435                 440                 445

Pro Ile Gly Ser Ala Ala Lys Arg Leu Lys Glu Ala Glu Ala Ala Ala
        450                 455                 460

Ser Ala Gln His His His Ala Gly Val Val Ser Tyr Asp Val Gly Arg
465                 470                 475                 480

Ile Ala Ser Gln Leu Gly Asp Gly Ala Leu Ala Ala Ala Tyr Gly
                485                 490                 495

Ala His Tyr His Gly Ala Ala Trp Pro Thr Ile Ala Phe Gln Pro Gly
            500                 505                 510

Ala Ala Thr Thr Gly Leu Tyr His Pro Tyr Ala Gln Gln Pro Met Arg
        515                 520                 525

Gly Gly Gly Trp Cys Lys Gln Glu Gln Asp His Ala Val Ile Ala Ala
530                 535                 540

Ala His Ser Leu Gln Asp Leu His His Leu Asn Leu Gly Ala Ala Gly
545                 550                 555                 560

Ala His Asp Phe Phe Ser Ala Gly Gln Gln Ala Ala Ala Ala Ala
                565                 570                 575

Met His Gly Leu Ala Ser Ile Asp Ser Ala Ser Leu Glu His Ser Thr
            580                 585                 590

Gly Ser Asn Ser Val Val Tyr Asn Gly Gly Val Gly Asp Ser Asn Gly
        595                 600                 605
```

```
Ala Ser Ala Val Gly Ser Gly Gly Tyr Met Met Pro Met Ser Ala
610                 615                 620

Ala Gly Ala Thr Thr Thr Ser Ala Met Val Ser His Glu Gln Met His
625                 630                 635                 640

Ala Arg Ala Tyr Asp Glu Ala Lys Gln Ala Ala Gln Met Gly Tyr Glu
                645                 650                 655

Ser Tyr Leu Val Asn Ala Glu Asn Asn Gly Gly Arg Met Ser Ala
            660                 665                 670

Trp Gly Thr Val Val Ser Ala Ala Ala Ala Ala Ser Ser Asn
            675                 680             685

Asp Asn Ile Ala Ala Asp Val Gly His Gly Ala Gln Leu Phe Ser
690                 695                 700

Val Trp Asn Asp Thr
705

<210> SEQ ID NO 19
<211> LENGTH: 703
<212> TYPE: PRT
<213> ORGANISM: Sorghum bicolor

<400> SEQUENCE: 19

Met Ala Thr Val Asn Asn Trp Leu Ala Phe Ser Leu Ser Pro Gln Glu
1               5                   10                  15

Leu Pro Pro Thr Gln Thr Asp Ser Thr Leu Ile Ser Ala Ala Thr Thr
                20                  25                  30

Asp Asp Val Ser Gly Asp Val Cys Phe Asn Ile Pro Gln Asp Trp Ser
            35                  40                  45

Met Arg Gly Ser Glu Leu Ser Ala Leu Val Ala Glu Pro Lys Leu Glu
50                  55                  60

Asp Phe Leu Gly Gly Ile Ser Phe Ser Glu Gln His His Lys Ala Asn
65                  70                  75                  80

Cys Asn Met Ile Pro Ser Thr Ser Ser Thr Ala Cys Tyr Ala Ser Ser
                85                  90                  95

Gly Ala Thr Ala Gly Tyr His His Gln Leu Tyr His Gln Pro Thr Ser
            100                 105                 110

Ser Ala Leu His Phe Ala Asp Ser Val Met Val Ala Ser Ser Ala Gly
        115                 120                 125

Gly Val His Asp Gly Gly Ala Met Leu Ser Ala Ala Ser Ala Asn Gly
    130                 135                 140

Ser Ala Gly Ala Gly Ala Ala Ser Ala Asn Gly Ser Gly Ser Ile Gly
145                 150                 155                 160

Leu Ser Met Ile Lys Asn Trp Leu Arg Ser Gln Pro Ala Pro Met Gln
                165                 170                 175

Pro Arg Val Ala Ala Ala Glu Ser Val Gln Gly Leu Ser Leu Ser Met
            180                 185                 190

Asn Met Ala Gly Ala Thr Gln Gly Ala Ala Gly Met Pro Leu Leu Ala
        195                 200                 205

Gly Glu Arg Gly Arg Ala Pro Glu Ser Val Ser Thr Ser Ala Gln Gly
    210                 215                 220

Gly Ala Val Val Thr Ala Pro Lys Glu Asp Ser Gly Gly Ser Gly Val
225                 230                 235                 240

Ala Ala Thr Gly Ala Leu Val Ala Val Ser Thr Asp Thr Gly Gly Ser
                245                 250                 255

Gly Ala Ser Ala Asp Asn Thr Ala Arg Lys Thr Val Asp Thr Phe Gly
            260                 265                 270
```

```
Gln Arg Thr Ser Ile Tyr Arg Gly Val Thr Arg His Arg Trp Thr Gly
            275                 280                 285
Arg Tyr Glu Ala His Leu Trp Asp Asn Ser Cys Arg Arg Glu Gly Gln
290                 295                 300
Thr Arg Lys Gly Arg Gln Val Tyr Leu Gly Gly Tyr Asp Lys Glu Glu
305                 310                 315                 320
Lys Ala Ala Arg Ala Tyr Asp Leu Ala Ala Leu Lys Tyr Trp Gly Pro
                325                 330                 335
Thr Thr Thr Thr Asn Phe Pro Val Asn Asn Tyr Glu Lys Glu Leu Glu
                340                 345                 350
Asp Met Lys His Met Thr Arg Gln Glu Phe Val Ala Ser Leu Arg Arg
                355                 360                 365
Lys Ser Ser Gly Phe Ser Arg Gly Ala Ser Ile Tyr Arg Gly Val Thr
            370                 375                 380
Arg His His Gln His Gly Arg Trp Gln Ala Arg Ile Gly Arg Val Ala
385                 390                 395                 400
Gly Asn Lys Asp Leu Tyr Leu Gly Thr Phe Ser Thr Gln Glu Glu Ala
                405                 410                 415
Ala Glu Ala Tyr Asp Ile Ala Ala Ile Lys Phe Arg Gly Leu Asn Ala
                420                 425                 430
Val Thr Asn Phe Asp Met Ser Arg Tyr Asp Val Lys Ser Ile Leu Asp
            435                 440                 445
Ser Ser Ala Leu Pro Ile Gly Ser Ala Lys Arg Leu Lys Glu Ala
450                 455                 460
Glu Ala Ala Ala Ser Ala Gln His His Ala Gly Val Val Ser Tyr Asp
465                 470                 475                 480
Val Gly Arg Ile Ala Ser Gln Leu Gly Asp Gly Gly Ala Leu Ala Ala
                485                 490                 495
Ala Tyr Gly Ala His Tyr His Gly Ala Trp Pro Thr Ile Ala Phe Gln
                500                 505                 510
Pro Ser Ala Ala Thr Gly Leu Tyr His Pro Tyr Ala Gln Pro Met Arg
            515                 520                 525
Gly Trp Cys Lys Gln Glu Gln Asp His Ala Val Ile Ala Ala Ala His
            530                 535                 540
Ser Leu Gln Glu Leu His His Leu Asn Leu Gly Ala Ala Gly Ala
545                 550                 555                 560
His Asp Phe Phe Ser Ala Gly Gln Gln Ala Ala Met His Gly Leu Gly
                565                 570                 575
Ser Met Asp Asn Ala Ser Leu Glu His Ser Thr Gly Ser Asn Ser Val
            580                 585                 590
Val Tyr Asn Gly Val Gly Asp Ser Asn Gly Ser Thr Val Val Gly Ser
            595                 600                 605
Gly Gly Tyr Met Met Pro Met Ser Ala Ala Thr Ala Thr Ala Thr Thr
            610                 615                 620
Ala Met Val Ser His Glu Gln Val His Ala Arg Ala Gln Gly Asp His
625                 630                 635                 640
His Asp Glu Ala Lys Gln Ala Ala Gln Met Gly Tyr Glu Ser Tyr Leu
                645                 650                 655
Val Asn Ala Glu Asn Tyr Gly Gly Arg Met Ser Ala Ala Trp Ala
                660                 665                 670
Thr Val Ser Ala Pro Pro Ala Ala Ser Ser Asn Asp Asn Met Ala Asp
            675                 680                 685
```

-continued

```
Val Gly His Gly Gly Ala Gln Leu Phe Ser Val Trp Asn Asp Thr
    690                 695                 700
```

<210> SEQ ID NO 20
<211> LENGTH: 703
<212> TYPE: PRT
<213> ORGANISM: Setaria italica

<400> SEQUENCE: 20

```
Met Ala Thr Val Asn Asn Trp Leu Ala Phe Ser Leu Ser Pro Gln Glu
1               5                   10                  15

Leu Pro Pro Thr Gln Thr Asp Ser Thr Leu Ile Ser Ala Ala Thr Thr
            20                  25                  30

Asp Asp Val Ser Gly Asp Val Cys Phe Asn Ile Pro Gln Asp Trp Ser
        35                  40                  45

Met Arg Gly Ser Glu Leu Ser Ala Leu Val Ala Glu Pro Lys Leu Glu
    50                  55                  60

Asp Phe Leu Gly Gly Ile Ser Phe Ser Glu Gln His His Lys Ala Asn
65                  70                  75                  80

Cys Asn Met Ile Pro Ser Thr Ser Ser Thr Ala Cys Tyr Ala Ser Ser
                85                  90                  95

Gly Ala Thr Ala Gly Tyr His His Gln Leu Tyr His Gln Pro Thr Ser
            100                 105                 110

Ser Ala Leu His Phe Ala Asp Ser Val Met Val Ala Ser Ser Ala Gly
        115                 120                 125

Gly Val His Asp Gly Gly Ala Met Leu Ser Ala Ala Ser Ala Asn Gly
    130                 135                 140

Ser Ala Gly Ala Gly Ala Ala Ser Ala Asn Gly Ser Gly Ser Ile Gly
145                 150                 155                 160

Leu Ser Met Ile Lys Asn Trp Leu Arg Ser Gln Pro Ala Pro Met Gln
                165                 170                 175

Pro Arg Val Ala Ala Ala Glu Ser Val Gln Gly Leu Ser Leu Ser Met
            180                 185                 190

Asn Met Ala Gly Ala Thr Gln Gly Ala Ala Gly Met Pro Leu Leu Ala
        195                 200                 205

Gly Glu Arg Gly Arg Ala Pro Glu Ser Val Ser Thr Ser Ala Gln Gly
    210                 215                 220

Gly Ala Val Val Thr Ala Pro Lys Glu Asp Ser Gly Gly Ser Gly Val
225                 230                 235                 240

Ala Ala Thr Gly Ala Leu Val Ala Val Ser Thr Asp Thr Gly Gly Ser
                245                 250                 255

Gly Ala Ser Ala Asp Asn Thr Ala Arg Lys Thr Val Asp Thr Phe Gly
            260                 265                 270

Gln Arg Thr Ser Ile Tyr Arg Gly Val Thr Arg His Arg Trp Thr Gly
        275                 280                 285

Arg Tyr Glu Ala His Leu Trp Asp Asn Ser Cys Arg Arg Glu Gly Gln
    290                 295                 300

Thr Arg Lys Gly Arg Gln Val Tyr Leu Gly Gly Tyr Asp Lys Glu Glu
305                 310                 315                 320

Lys Ala Ala Arg Ala Tyr Asp Leu Ala Ala Leu Lys Tyr Trp Gly Pro
                325                 330                 335

Thr Thr Thr Thr Asn Phe Pro Val Asn Asn Tyr Glu Lys Glu Leu Glu
            340                 345                 350

Asp Met Lys His Met Thr Arg Gln Glu Phe Val Ala Ser Leu Arg Arg
        355                 360                 365
```

Lys Ser Ser Gly Phe Ser Arg Gly Ala Ser Ile Tyr Arg Gly Val Thr
            370                 375                 380

Arg His His Gln His Gly Arg Trp Gln Ala Arg Ile Gly Arg Val Ala
385                 390                 395                 400

Gly Asn Lys Asp Leu Tyr Leu Gly Thr Phe Ser Thr Gln Glu Glu Ala
            405                 410                 415

Ala Glu Ala Tyr Asp Ile Ala Ala Ile Lys Phe Arg Gly Leu Asn Ala
            420                 425                 430

Val Thr Asn Phe Asp Met Ser Arg Tyr Asp Val Lys Ser Ile Leu Asp
            435                 440                 445

Ser Ser Ala Leu Pro Ile Gly Ser Ala Ala Lys Arg Leu Lys Glu Ala
450                 455                 460

Glu Ala Ala Ser Ala Gln His His Ala Gly Val Val Ser Tyr Asp
465                 470                 475                 480

Val Gly Arg Ile Ala Ser Gln Leu Gly Asp Gly Ala Leu Ala Ala
            485                 490                 495

Ala Tyr Gly Ala His Tyr His Gly Ala Trp Pro Thr Ile Ala Phe Gln
            500                 505                 510

Pro Ser Ala Ala Thr Gly Leu Tyr His Pro Tyr Ala Gln Pro Met Arg
            515                 520                 525

Gly Trp Cys Lys Gln Glu Gln Asp His Ala Val Ile Ala Ala Ala His
530                 535                 540

Ser Leu Gln Glu Leu His His Leu Asn Leu Gly Ala Ala Ala Gly Ala
545                 550                 555                 560

His Asp Phe Phe Ser Ala Gly Gln Gln Ala Met His Gly Leu Gly
            565                 570                 575

Ser Met Asp Asn Ala Ser Leu Glu His Ser Thr Gly Ser Asn Ser Val
            580                 585                 590

Val Tyr Asn Gly Val Gly Asp Ser Asn Gly Ser Thr Val Val Gly Ser
            595                 600                 605

Gly Gly Tyr Met Met Pro Met Ser Ala Ala Thr Ala Thr Ala Thr Thr
610                 615                 620

Ala Met Val Ser His Glu Gln Val His Ala Arg Ala Gln Gly Asp His
625                 630                 635                 640

His Asp Glu Ala Lys Gln Ala Ala Gln Met Gly Tyr Glu Ser Tyr Leu
            645                 650                 655

Val Asn Ala Glu Asn Tyr Gly Gly Arg Met Ser Ala Ala Trp Ala
            660                 665                 670

Thr Val Ser Ala Pro Pro Ala Ala Ser Ser Asn Asp Asn Met Ala Asp
            675                 680                 685

Val Gly His Gly Gly Ala Gln Leu Phe Ser Val Trp Asn Asp Thr
            690                 695                 700

<210> SEQ ID NO 21
<211> LENGTH: 687
<212> TYPE: PRT
<213> ORGANISM: Brachypodium distachyum

<400> SEQUENCE: 21

Met Ala Thr Val Asn Asn Trp Leu Gly Phe Ser Leu Ser Pro Gln Glu
1               5                   10                  15

Leu Pro Ser Ser Ala Ala Ala Ala Gly Asp Val Ser Gly Ala Asp
            20                  25                  30

Val Cys Phe Asn Ile Pro Gln Asp Trp Gly Met Arg Gly Ser Glu Leu

```
                35                  40                  45
Ser Ala Leu Val Ala Glu Pro Lys Leu Glu Asp Phe Leu Gly Gly Ile
 50                  55                  60

Ser Ser Tyr Ser Asp His His Lys Ala Ala Arg Ser Asn Asn Met Asn
 65                  70                  75                  80

Ile Asn Gly Ala Ala Cys Tyr Ala Ser Gly Ser Ser Gly Tyr
                 85                  90                  95

Gln Leu Tyr His Asp His Pro Asn Ser Leu Gln Phe Ala Asp Ser Val
                100                 105                 110

Met Val Ala Ser Ser Ala Gly Gly Val His Asn Glu His Gly Ile Met
                115                 120                 125

Ala Ser Thr Thr Ala Asn Gly Ala Gly Thr Asn Gly Gly Ile Gly Leu
130                 135                 140

Ser Met Ile Lys Ser Trp Leu Arg Ser Gln Pro Ala Pro Ala Gln Gln
145                 150                 155                 160

Glu Gln Gln Arg Ala Glu Gly Leu Ser Leu Ser Met Asn Met Pro Leu
                165                 170                 175

Leu Gln Ala Ala Ala Glu Thr Ser Leu Ser Thr Ser Ala Ala Gln
                180                 185                 190

Gln Gly Ser Arg Lys Glu Asn Asn Gly Ser Ser Ser Ala Gly Ser Gly
                195                 200                 205

Ala Val Val Ser Ala Gly Thr Thr Ser Ala Gly Ala Val Val Glu
210                 215                 220

Ser Pro Ala Ala Gly Arg Lys Thr Ala Asp Thr Phe Gly Gln Arg Thr
225                 230                 235                 240

Ser Ile Tyr Arg Gly Val Thr Arg His Arg Trp Thr Gly Arg Tyr Glu
                245                 250                 255

Ala His Leu Trp Asp Asn Ser Cys Arg Arg Glu Gly Gln Thr Arg Lys
                260                 265                 270

Gly Arg Gln Val Tyr Leu Gly Gly Tyr Asp Lys Glu Glu Lys Ala Ala
                275                 280                 285

Arg Ala Tyr Asp Leu Ala Ala Leu Lys Tyr Trp Gly Pro Thr Thr Thr
                290                 295                 300

Thr Asn Phe Pro Val Asp Asn Tyr Glu Lys Glu Leu Glu Glu Met Lys
305                 310                 315                 320

His Met Thr Arg Gln Glu Phe Val Ala Ser Leu Arg Arg Lys Ser Ser
                325                 330                 335

Gly Phe Ser Arg Gly Ala Ser Ile Tyr Arg Gly Val Thr Arg His His
                340                 345                 350

Gln His Gly Arg Trp Gln Ala Arg Ile Gly Arg Val Ala Gly Asn Lys
                355                 360                 365

Asp Leu Tyr Leu Gly Thr Phe Ser Thr Gln Glu Glu Ala Ala Glu Ala
                370                 375                 380

Tyr Asp Ile Ala Ala Ile Lys Phe Arg Gly Leu Asn Ala Val Thr Asn
385                 390                 395                 400

Phe Asp Met Ser Arg Tyr Asp Val Lys Ser Ile Leu Asp Ser Thr Ala
                405                 410                 415

Ala Leu Pro Val Gly Gly Thr Lys Arg Leu Arg Asp Ala Ala Ala
                420                 425                 430

Asp Gln His Tyr Gln Gln Arg Ala Gly Gly Val Val Ser Tyr Ala Ala
                435                 440                 445

Pro Gln Leu Gly Gly Val Asn Glu Thr Ala Leu Ala Tyr Gly Ala Pro
450                 455                 460
```

```
Tyr Tyr His His Gln Thr Ser Ala Ala Ala Trp Pro Thr Ile Ala Phe
465                 470                 475                 480

Gln Ala Ala Pro Gln Ala Ser Ser Gly His Gly His Met Leu Tyr His
                485                 490                 495

Pro Tyr Gly Gln Pro Leu Met Arg Gly Trp Cys Lys Gln Glu Gln Glu
            500                 505                 510

Gln Gly Gln Gly Gln Gln Glu Pro Asp His Ala Val Ile Ala Ala Ala
        515                 520                 525

His Ser Leu Gln Asp Leu His His Leu Asn Leu Gly Ala Gly Ala His
    530                 535                 540

Asp Phe Phe Ser Gln His Ala His Ala Met His Gln Gln Gln Gln Gln
545                 550                 555                 560

His Gly Gly Leu Gly Ser Val Asp Asn Asn Gly Ala Ala Ser Leu Glu
                565                 570                 575

His Ser Thr Gly Ser Asn Ser Val Val Tyr Asn Gly Ala Ala Ala Ala
            580                 585                 590

Gly Asp Thr Asn Asn Ser Tyr Met Leu Pro Pro Met Ser Ala Ala Ala
        595                 600                 605

Ala Ala Gly Phe Gly Leu Arg Asp Gln Gln Asp Glu Gly Gly Lys Met
610                 615                 620

Ala Tyr Glu Asn Phe Leu Leu Gly Ala Ala Thr Asp Gly Tyr Cys Gly
625                 630                 635                 640

Pro Gly Arg Met Ala Ala Thr Trp Thr Pro Val Ser Val Ser Ala Ala
                645                 650                 655

Gln Pro Val Ala Ala Thr Ser Ser Gly Ser Asp Met Ala Gly Ala Val
            660                 665                 670

Cys His Gly Gly Ala Gln Leu Phe Ser Val Trp Asn Asp Asp Ser
        675                 680                 685

<210> SEQ ID NO 22
<211> LENGTH: 2133
<212> TYPE: DNA
<213> ORGANISM: Zea mays

<400> SEQUENCE: 22
atggccactg tgaacaactg gctcgctttc tccctctccc cgcaggagct gccgccctcc      60
cagacgacgg actccacact catctcggcc gccaccgccg accatgtctc cggcgatgtc     120
tgcttcaaca tcccccaaga ttggagcatg aggggatcag agctttcggc gctcgtcgcg     180
gagccgaagc tggaggactt cctcggcggc atctccttct ccgagcagca tcacaaggcc     240
aactgcaaca tgatacccag cactagcagc acagtttgct acgcgagctc aggtgctagc     300
accggctacc atcaccagct gtaccaccag cccaccagct cagcgctcca cttcgcggac     360
tccgtaatgg tggcttcctc ggccggtgtc cacgacggcg gtgccatgct cagcgcggcc     420
gccgctaacg tgtcgctgg cgctgccagt gccaacggcg gcggcatcgg gctgtccatg     480
attaagaact ggctgcggag ccaaccggcg cccatgcagc cgagggtggc ggcggctgag     540
ggcgcgcagg gctctctctt gtccatgaac atggcgggga cgacccaagg cgctgctggc     600
atgccacttc tcgctggaga gcgcgcacgg gcgcccgaga gtgtatcgac gtcagcacag     660
ggtggagccg tcgtcgtcac ggcgccgaag gaggatagcg gtggcagcgg tgttgccggc     720
gctctagtag ccgtgagcac ggacacgggt ggcagcggcg gcgcgtcggc tgacaacacg     780
gcaaggaaga cggtggacac gttcgggcag cgcacgtcga tttaccgtgg cgtgacaagg     840
```

| | |
|---|---|
| catagatgga ctgggagata tgaggcacat ctttgggata acagttgcag aagggaaggg | 900 |
| caaactcgta agggtcgtca agtctattta ggtggctatg ataaagagga gaaagctgct | 960 |
| agggcttatg atcttgctgc tctgaagtac tggggtgcca caacaacaac aaattttcca | 1020 |
| gtgagtaact acgaaaagga gctcgaggac atgaagcaca tgacaaggca ggagtttgta | 1080 |
| gcgtctctga gaaggaagag cagtggtttc tccagaggtg catccattta caggggagtg | 1140 |
| actaggcatc accaacatgg aagatggcaa gcacggattg gacgagttgc agggaacaag | 1200 |
| gatctttact tgggcacctt cagcacccag gaggaggcag cggaggcgta cgacatcgcg | 1260 |
| gcgatcaagt tccgcggcct caacgccgtc accaacttcg acatgagccg ctacgacgtg | 1320 |
| aagagcatcc tggacagcag cgccctcccc atcggcagcg ccgccaagcg cctcaaggag | 1380 |
| gccgaggccg cagcgtccgc gcagcaccac cacgccggcg tggtgagcta cgacgtcggc | 1440 |
| cgcatcgcct cgcagctcgg cgacggcgga gccctggcgg cggcgtacgg cgcgcactac | 1500 |
| cacggcgccg cctggccgac catcgcgttc cagccgggcg ccgccagcac aggcctgtac | 1560 |
| cacccgtacg cgcagcagcc aatgcgcggc ggcgggtggt gcaagcagga gcaggaccac | 1620 |
| gcggtgatcg cggccgcgca cagcctgcag gacctccacc acctgaacct gggcgcggcc | 1680 |
| ggcgcgcacg acttttttctc ggcagggcag caggccgccg ccgctgcgat gcacggcctg | 1740 |
| ggtagcatcg acagtgcgtc gctcgagcac agcaccggct ccaactccgt cgtctacaac | 1800 |
| ggcggggtcg cgacagcaa cggcgccagc ccgtcggcg cagtggcgg tggctacatg | 1860 |
| atgccgatga gcgctgccgg agcaaccact acatcggcaa tggtgagcca cgagcaggtg | 1920 |
| catgcacggg cctacgacga agccaagcag gctgctcaga tggggtacga gagctacctg | 1980 |
| gtgaacgcgg agaacaatgg tggcggaagg atgtctgcat gggggactgt cgtgtctgca | 2040 |
| gccgcggcg cagcagcaag cagcaacgac aacatggccg ccgacgtcgg gaatggcggc | 2100 |
| gcgcagctct tcagtgtctg gaacgacact taa | 2133 |

<210> SEQ ID NO 23
<211> LENGTH: 909
<212> TYPE: DNA
<213> ORGANISM: Zea mays

<400> SEQUENCE: 23

| | |
|---|---|
| atggcggcca atgcgggcgg cggtggagcg ggaggaggca gcggcagcgg cagcgtggct | 60 |
| gcgccggcgg tgtgccgccc cagcggctcg cggtggacgc cgacgccgga gcagatcagg | 120 |
| atgctgaagg agctctacta cggctgcggc atccggtcgc ccagctcgga gcagatccag | 180 |
| cgcatcaccg ccatgctgcg gcagcacggc aagatcgagg gcaagaacgt cttctactgg | 240 |
| ttccagaacc acaaggcccg cgagcgccag aagcgccgcc tcaccagcct cgacgtcaac | 300 |
| gtgcccgccg ccggcgcggc cgacgccacc accagccaac tcggcgtcct ctcgctgtcg | 360 |
| tcgccgccgc cttcaggcgc ggcgcctccc tcgcccaccc tcggcttcta cgccgccggc | 420 |
| aatggcggcg gatcggctgt gctgctggac acagattccg actggggcag cagcggcgct | 480 |
| gctatggcca ccgagacatg cttcctgcag gactacatgg gcgtgacgga cacgggcagc | 540 |
| tcgtcgcagt ggccacgctt ctcgtcgtcg gacacgataa tggcggcggc cgcggcgcgg | 600 |
| gcggcgacga gcgggcgcc cgagacgctc cctctcttcc cgacctgcgg cgacgacggc | 660 |
| ggcagcggta gcagcagcta cttgccgttc tggggtgccg cgtccacaac tgccggcgcc | 720 |
| acttcttccg ttgcgatcca acagcaacac cagctgcagg agcagtacag cttttacagc | 780 |
| aacagcaaca gcacccagct ggccggcacc ggcaaccaag acgtatcggc aacagcagca | 840 |

```
gcagccgccg ccctggagct gagcctcagc tcatggtgct ccccttaccc tgctgcaggg    900
agtatgtga                                                             909

<210> SEQ ID NO 24
<211> LENGTH: 666
<212> TYPE: DNA
<213> ORGANISM: Zea mays

<400> SEQUENCE: 24
tcaggcgcgg cgcctccctc gcccaccctc ggcttctacg ccgccggcaa tggcggcgga     60
tcggctgtgc tgctggacac gagttccgac tggggcagca gcggcgctgc catggccacc    120
gagacatgct tcctgcaggt cggtgctgta gtacgttctt ttcttgggca ttgcgcgcag    180
tttcacgttc gtacgtacga gttgatcgcc gcgtcgttcc atccaccggt atatataact    240
gttaggtacg gcggtgcgcg cccgcaggac tacatgggcg tgacggacac gggcagctcg    300
tcgcagtggc cacgcttctc gtcgtcggac acgataatgg cggcggccgc ggcgcgggcg    360
gcgacgacgc gggcgcccga gacgctccct ctcttcccga cctgcggcga cgacggcggc    420
agcggtagca gcagctactt gccgttctgg ggtgccgcgt ccacaactgc cggcgccact    480
tcttccgttg cgatccagca gcaacaccag ctgcaggagc agtacagctt ttacagcaac    540
agcaacagca cccagctggc cggcaccggc aaccaagacg tatcggcaac agcagcagca    600
gccgccgccc tggagctgag cctcagctca tggtgctccc cttaccctgc tgcagggagt    660
atgtga                                                                666

<210> SEQ ID NO 25
<211> LENGTH: 3629
<212> TYPE: DNA
<213> ORGANISM: Zea mays

<400> SEQUENCE: 25
gcgggattgc cgcggggggag ggagattgtc gcggtgacgc cgagattgcc gctggggcga    60
gcgccgagat tgccggggga gggcgaggcg ggtgggatgc ggggtgcccc acggcagaac   120
cgtgcaccac tgtcgggctg tgaacgtcta caatacttac ttatgtagta gtagatatat   180
atatatatat atatataatg taaaacaata ttttaattat aatgtaaaca gtgttttaca   240
tgattatata caagatcgac tagatagagt ttaaggccat atctagcgga acaggtatat   300
aagcgtgcaa acaatgtttt tgttttgtac gctacactgt ttttagagtg gagttaacta   360
aaaccttaac ttttttttgc aaataaatct ctaaataatg tcgtactgta tacactcgag   420
atttccatcg cacaagacac gaaaaaatcc cgatcaattt aacgaacatt gttttgcatt   480
atagattata ttgtttacag aatgaagtta actaaaacct taaccttttg cagataaatc   540
tctaaatagt gccgtactgt atacactcga gatttccacc gcacaagaca tgagaaaatt   600
ccggtcgatt tgacaaagac tgggtgttat taattagagg aagcagatcc agccacatgt   660
tgtctcacat ctgatccccc acgtatagtc gtatacgttt ggcccaaacc tagctcgatc   720
catgtatgaa acacgtctcg tctcgccttc tacctccttt ttctatcaca ggagattaaa   780
gtgagagaga gagggcgctc aatgaactgc ggcattgaac aatggagctg caagagcaat   840
gatgcactag ctagtgtaat gcagtgcatg catggtagat tggtagcttg cctttgcagt   900
ttgcaccagg caccagcagc agctagaaga cgacagacga caggggtttg gctgctaggt   960
tgcggaaggg cagttaccag ttgccacaag gggagcctgg ccctctgcat cctcctcatg  1020
```

```
atagctctgt ctctctctct cacagacaca cacacagaga ctcttccaaa ttccgaagcg    1080
gccaatgcaa tgcaagagcc agccccggc cgtgtgtcaa cttcacttgt ctctctccaa    1140
aagatatcgt atcacccatg ccatgaccc ccctccccca gccccaacct atatcaccta    1200
gcgcagctac gctctcttct cccgctctcg ctctctgcat gctagctacc ttctagctat    1260
ctagcctcta ggtccaatgc actccctcct tataaacaag gaaccctcct tcgcctctct    1320
tgccatagac cggacaccgg agaggtcact gcacaggagc gctcaggaag gccgctgcgc    1380
tgagatagag gcatggcggc caatgcgggc ggcggtggag cgggaggagg cagcggcagc    1440
ggcagcgtgg ctgcgccggc ggtgtgccgc cccagcggct cgcggtggac gccgacgccg    1500
gagcagatca ggatgctgaa ggagctctac tacggctgcg gcatccggtc gcccagctcg    1560
gagcagatcc agcgcatcac cgccatgctg cggcagcacg gcaagatcga gggcaagaac    1620
gtcttctact ggttccagaa ccacaaggcc cgcgagcgcc agaagcgccg cctcaccagc    1680
ctcgacgtca acgtgcccgc cgccggcgcg gccgacgcca ccaccagcca actcggcgtc    1740
ctctcgctgt cgtcgccgcc ttcaggtatg tgcgtcagtg cgtgtggtgt gggtagtata    1800
tatatatata tatatatata tatatatata tatatatata tatatatata tatatatatg    1860
gcctctcttt gcattggcac gccaatcggc catcgagatc caatcatata tatcatccaa    1920
acgtatagta ttagtacatc tgtacatgtg actgcaaact gacgtgcacg cgtgtgcacc    1980
gtcgtcatca ctgatcaggc gcggcgcctc cctcgcccac cctcggcttc tacgccgccg    2040
gcaatggcgg cggatcggct gggctgctgg acacgagttc cgactggggc agcagcggcg    2100
ctgccatggc caccgagaca tgcttcctgc aggtgctgta gtacgttctt ttcttgggga    2160
ttgcgcgcag tttcacgtac gtacgtacgt tcgagtcgat cgccgcgtcg ttccatccac    2220
cggccggtat atataactgt tgggtacggc ggtgcgcgcc cgcaggacta catgggcgtg    2280
acggacacgg gcagctcgtc gcagtggcca tgcttctcgt cgtcggacac gataatggcg    2340 gcggcggcg ccgcggcgcg ggtggcgacg acgcgggcgc ccgagacact ccctctcttc    2400
ccgacctgcg gcgacgacga cgacgacgac agccagcccc cgccgcggcc gcggcacgca    2460
gtcccagtcc cggcaggcga gaccatccgc ggcggcggcg gcagcagcag cagctacttg    2520
ccgttctggg gtgccggtgc cgcgtccaca actgccggcg ccacttcttc cgttgcgatc    2580
cagcagcaac accagctgca ggagcagtac agcttttaca gcaacagcac ccagctggcc    2640
ggcaccggca gccaagacgt atcggcttca gcggccgccc tggagctgag cctcagctca    2700
tggtgctccc cttaccctgc tgcagggagc atgtgagagc aacgcgagct accactggga    2760
cgtgcgttgc tgtcattgtc ctaggttagt agctagtgcc agttactagt aagcatcagg    2820
cataggagta tgtagtagaa gcatgtctgg agaaaggcaa tagctagcgt ttgggagatc    2880
tctggcggta ctattattag atagcgaatt tgcatactat gcagcatgca tgttgccggc    2940
cgggcgggct ttagactcca gctactgcat gcgtgcatgc ggtggtcctc atgtatgtcg    3000
gcatgtgtgc gtgtgtgtgt ggcagcagca gcagcagtga attctagtgc agtggtggtg    3060
gttgtaacgt gtagtttggg ggcaggggca cagttgtgtc gaacttgtgc ggttgtccct    3120
tccttttgtg acttccagaa aagggaatga ggcctgcctg cgtgtctgct tttccatgct    3180
cacctcgcct gttgtctgtt gagacttcac tcagccctgt tggtgccttg tagttccagt    3240
tccagagcat atgcaggtgc aggaatggca tctctaccac tgctttcgac ttgttggctt    3300
gttttcttct atgatactag tgtacttgga ttgaatgatc acatttttg ctggcctcgt    3360 atctttgaaa tgatcatgtt aatttggtta cacataagac gataagggta ggtagttcaa    3420
```

| | | | |
|---|---|---|---|
| tgctattaga | aaactaggta | tttttagtta tattttaatc caggaaaaaa tatataaaaa | 3480 |
| ctaatcgtga | tatatagaaa | tacgcatatg caaacttagt ataataatta tgaatacaat | 3540 |
| agatagtaac | ctgattgtat | atacttttaa gggaaaatag atatggcaat gggcctcgat | 3600 |
| cttcgattct | ctgcggagaa | ttcttccat | 3629 |

<210> SEQ ID NO 26
<211> LENGTH: 3313
<212> TYPE: DNA
<213> ORGANISM: Zea mays

<400> SEQUENCE: 26

| | | | |
|---|---|---|---|
| aataatggtg | tacactcgag | atttccaccg cacaagacat gaaaaaatcc cggtaaattt | 60 |
| gacaaacact | tttttgcatt | gtaaactaca atatttatag agcggagtta actaaaacct | 120 |
| caacttttg | caaataaatc | tctaaatagt gcgggactgt atacactcga gatttccacc | 180 |
| gcacaagaca | tgagaaaatt | ccggtcaatt tgacaaagac tggatgttat taatcagagg | 240 |
| aagcagatca | agccacatgt | tgtctcacat ctgatccccc acgtattata cgtttggccc | 300 |
| aaacctagct | cgatccatgt | attaaacacg tctcgtttcg ccttctacct ccttttcta | 360 |
| tcacaggaga | ttaaagtgag | agagagaggg cgctcaatga actgcggcat tgaacaatgg | 420 |
| agctgcaaga | gcaatgatgc | actagctagt ataatgcaga agcaatgcat ggtagattgg | 480 |
| tagctagcct | ttgcagtttg | caccaggcac cagcagcagc tagaagacga cagacgacag | 540 |
| gggcttgact | aggttgcgga | agggcagttg ccagttgcca caaggggagc ctggacctct | 600 |
| gcatcctcct | catgatagct | ctgtctctct cacacacaca cagtcacaca gagacacgca | 660 |
| aatgacttct | gtctctaagg | ctatccgcag cggttccctc taaattttc cccctatatc | 720 |
| actttttgg | gtcacatcat | caatagttta tcccctactt tttcatctcc cgcagcggtt | 780 |
| cccctaaat | actcccccta | tactccacta caatataaaa tattattttc tatacctact | 840 |
| ttttacctac | tatcaatttt | tctactacta ttaattcaaa ccgggcccac acgaacagtg | 900 |
| caaggggag | agagagcgcg | cgctacagcc agcggagtgc tgttcatctc cgccgcgtgg | 960 |
| ggggcctcgc | agggggccgc | gctgcgggcg caggggcgcc cctgtagccg ccactcaagg | 1020 |
| ggagggggcg | gtcgcgcggc | gagcgctgcg gccagcctaa ctcttccaaa tttcgaagcg | 1080 |
| gccaatgcaa | gagccagccc | ccggccgtat gtcaacttca cttgtctctc tccaaaagat | 1140 |
| atcgtatcac | ccatgggcaa | tggccatgac ccccctccca gccccaacct atatcaccta | 1200 |
| gcgcagctac | gctctcttct | cccgctctcg ctctctgcat gctagctact ttctagctat | 1260 |
| ctagcctcta | ggtccaatgc | actccctcct tataaacaag gaaccctcct tcgcctctct | 1320 |
| tgccatagac | cggacaccgg | agagctaggt cacaggagcg ctcaggaagg ccgctgagat | 1380 |
| agaggcatgg | cggccaatgc | gggcggcggt ggagcgggag gaggcagcgg cagcgtggct | 1440 |
| gcgccggcgc | tgtgccgccc | cagcggctcg cggtggacgc cgacgccgga gcagatcagg | 1500 |
| atgctgaagg | agctctacta | cggctgcggc atccggtcgc ccagctcgga gcagatccag | 1560 |
| cgcatcaccg | ccatgctgcg | gcagcacggc aagatcgagg gcaagaacgt cttctactgg | 1620 |
| ttccagaacc | acaaggcccg | cgagcgccag aagcgccgcc tcaccagcct cgacgtcaac | 1680 |
| gtgcccgccg | ccggcgcggc | cgacgccacc accagccaac tcggcgtcct ctcgctgtcg | 1740 |
| tcgccgccgc | cttcaggtac | gtgcgtcagt gcgtgtggtg tgtgggtagt atatatggtc | 1800 |
| tctccttgca | ttggcacgcc | aatcggccat cgatccaatc atatcatcgt ccaaacgtat | 1860 |

| | |
|---|---:|
| atagtacatg tgactgcaaa ctgatgtgca ccgtcgtcat cactgatcag gcgcggcgcc | 1920 |
| tccctcgccc accctcggct tctacgccgc cggcaatggc ggcggatcgg ctgtgctgct | 1980 |
| ggacacgagt tccgactggg gcagcagcgg cgctgccatg gccaccgaga catgcttcct | 2040 |
| gcaggtcggt gctgtagtac gttcttttct tgggcattgc gcgcagtttc acgttcgtac | 2100 |
| gtacgagttg atcgccgcgt cgttccatcc accggtatat ataactgtta ggtacggcgg | 2160 |
| tgcgcgcccg caggactaca tgggcgtgac ggacacgggc agctcgtcgc agtggccacg | 2220 |
| cttctcgtcg tcggacacga taatggcggc ggccgcggcg cgggcggcga cgacgcgggc | 2280 |
| gcccgagacg ctccctctct tcccgacctg cggcgacgac ggcggcagcg gtagcagcag | 2340 |
| ctacttgccg ttctggggtg ccgcgtccac aactgccggc gccacttctt ccgttgcgat | 2400 |
| ccagcagcaa caccagctgc aggagcagta cagcttttac agcaacagca acagcaccca | 2460 |
| gctggccggc accggcaacc aagacgtatc ggcaacagca gcagcagccg ccgccctgga | 2520 |
| gctgagcctc agctcatggt gctcccctta ccctgctgca gggagtatgt gagagcaacg | 2580 |
| cgagctgcca ctgctcttca cttatgtctc tggaatggaa ggaggaggaa gtgagcatag | 2640 |
| cgttggtgcg ttgctgtcat tgtcctaggt tagtagctag tgccagttac tagtaagcat | 2700 |
| caggcatagg agtatgtagt agaagcatgc acgttgccgg ccagccaggc tttagacggg | 2760 |
| aaaagaattt ggtgcagccg gctgcaaaac aggatgttta cagccccac acaaaaaaaa | 2820 |
| aagattgacc ctacctgtaa caataataac acaactaaaa tgttatttga tggacctaca | 2880 |
| agtgggataa atccttcttt ttgtgaggtg ctgcaaacat tctggttcat caatttttt | 2940 |
| cctttagact ccagctactg catgcatgca tgcggtggtc ctcatgtatg tcggcgtgtg | 3000 |
| tgtgtggtag cagcagcagt gaattctcta gtgcagtggt ggtggttgta acgtgtagtt | 3060 |
| tggggggcagg ggcacagttg tgtcgaactt gtgcggttgt cccttccttt tgtgacttcc | 3120 |
| agaaaaagga atgagacctg catgtgtgtc tgcttttcca tgctcacctc gcctgttgtc | 3180 |
| tgttgagact tcactcagcc ctgctggtgc cttgtagttc cagttccaga gcatatgcag | 3240 |
| gtgcaggaat ggcatctcta ccactgcttt cgacttgttg gcttgttttc ttctatgata | 3300 |
| ctagtgtact tgg | 3313 |

<210> SEQ ID NO 27
<211> LENGTH: 909
<212> TYPE: DNA
<213> ORGANISM: Zea mays

<400> SEQUENCE: 27

| | |
|---|---:|
| atggcggcca atgcgggcgg cggtggagcg ggaggaggca gcggcagcgg cagcgtggct | 60 |
| gcgccggcgg tgtgccgccc cagcggctcg cggtggacgc cgacgccgga gcagatcagg | 120 |
| atgctgaagg agctctacta cggctgcggc atccggtcgc ccagctcgga gcagatccag | 180 |
| cgcatcaccg ccatgctgcg gcagcacggc aagatcgagg caagaacgt cttctactgg | 240 |
| ttccagaacc acaaggcccg cgagcgccag aagcgccgcc tcaccagcct cgacgtcaac | 300 |
| gtgcccgccg ccggcgcggc cgacgccacc accagccaac tcggcgtcct ctcgctgtcg | 360 |
| tcgccgccgc cttcaggcgc ggcgcctccc tcgcccaccc tcggcttcta cgccgccggc | 420 |
| aatggcggcg gatcggctgt gctgctggac acgagttccg actggggcag cagcggcgct | 480 |
| gctatgccca ccgagacatg cttcctgcag gactacatgg gcgtgacgga cacgggcagc | 540 |
| tcgtcgcagt ggccacgctt ctcgtcgtcg gacacgataa tggcggcggc cgcggcgcgg | 600 |
| gcggcgacga cgcgggcgcc cgagacgctc cctctcttcc cgacctgcgg cgacgacggc | 660 |

```
ggcagcggta gcagcagcta cttgccgttc tggggtgccg cgtccacaac tgccggcgcc    720
acttcttccg ttgcgatcca acagcaacac cagctgcagg agcagtacag cttttacagc    780
aacagcaaca gcacccagct ggccggcacc ggcaaccaag acgtatcggc aacagcagca    840
gcagccgccg ccctggagct gagcctcagc tcatggtgct cccccttaccc tgctgcaggg   900 agtatgtga                                                            909
```

<210> SEQ ID NO 28
<211> LENGTH: 879
<212> TYPE: DNA
<213> ORGANISM: Arabidopsis thaliana

<400> SEQUENCE: 28

```
atggagcctc ctcagcacca acatcaccac catcaggccg atcaagagtc cgggaacaac     60
aacaacaaca gtccggttc cggagggtac acttgcagac agacctccac cagatggaca    120
cctaccactg agcagatcaa gatcctgaag gagttgtact acaacaatgc catccgctcc    180
cctactgctg atcagattca gaagatcacc gctcgcctgc gtcaattcgg taagatcgag    240
ggtaagaacg tcttctactg gttccagaac cacaaggctc gtgagaggca gaagaagcgt    300
ttcaacggga ctaacatgac cactccttcc tcatcaccca attctgttat gatggccgcc    360
aacgaccact accatccttt gcttcatcac caccacggag ttcctatgca agacccgca    420 aactccgtca acgtgaagtt gaaccaggac catcacctct accaccacaa caagccctac    480
ccctctttca caacgggaa tctcaaccat gcctcctctg aaccgaatg tggagttgtc    540 aacgcctcca acggctacat gtcttcccac gtgtacggc ctatggagca agattgctcc    600
atgaactaca caacgttgg aggcggatgg caaacatgg atcaccacta ctcctccgct    660
ccctacaact tcttcgatag ggctaaacct ctcttcggct tggagggaca ccaagaagaa    720
gaggaatgcg gaggtgatgc ttacttggaa cacagaagga ctctcccctct cttcccaatg   780 cacggtgagg accacatcaa cggaggatct ggcgctatct ggaagtatgg acagtccgag    840
gtcagaccat gcgcttccct ggaattgaga ctgaactag                           879
```

<210> SEQ ID NO 29
<211> LENGTH: 876
<212> TYPE: DNA
<213> ORGANISM: Lotus japonicus

<400> SEQUENCE: 29

```
atggaacaac cacctcaaca acaacaacag aatgaggatg gtggtgggag tagtggtgga     60
aaaggggggt ttctgagcag gcaaagcagt acacggtgga ctcccaccac agaccagata   120
agaatattga aggagcttta ctacaacaat ggaataagat cccgagtgc agagcagatt    180 cagaggatct ctgctcggct gagacagtac ggcaagattg aaggcaagaa tgtcttttac    240
tggttccaga accacaaagc tagagagagg cagaagaaaa ggttcacttc tgaaactcat    300
cttcttccca atcccataca acaacaacaa agaaatggaa ctaatgctgc ttggaagcaa    360
cctgaagaac aacccattat taaccacacc aagtattcta gtaacaacat ttcagctcct    420
gcagggatca tcacttctgc tccatcttct tctgcagaga ttgtttctgt ggcagata    480 ggaaactttg ttatggatc tttgcctatg gaaaagagtt ttagggactg ctcaatatct    540
gctggaggca acacaggcta tgctggaagt gctataaacc acaacctggg atggatgggt    600
gtggatccat attcctcagc ctacaccaat ttctttgaca aaataaggcc aactgaagaa    660
```

| gaaaccatgg aagaagaagg acaagagaat ggttcaccag agattgaaac ccttcctta | 720 |
| ttcccgatgc atggtgagga cattcatagt ggctatttca acctcaagtc taattcttct | 780 |
| cactatgctg gtggctggta ccagactgaa gagggtact tcaacaatgg ttctcgtgct | 840 |
| tccttggagc tcagcctcaa atatcctgat tttgct | 876 |

```
<210> SEQ ID NO 30
<211> LENGTH: 888
<212> TYPE: DNA
<213> ORGANISM: Glycine max

<400> SEQUENCE: 30
```

| atggaacctc aacaacaaca acaacaagca caagggagcc aacaacaaca acaaaacgag | 60 |
| gatggtggca gtggaaaagg ggggtttctg agcaggcaaa gtagtacacg gtggactcca | 120 |
| acaaacgacc agataagaat attgaaggaa ctttactaca acaatggaat tagatccccg | 180 |
| agtgcagagc agattcagag gatctctgct aggctgaggc agtacggtaa gattgaaggc | 240 |
| aagaatgtct tttattggtt ccagaaccac aaagctcgag aaaggcagaa gaaaggttc | 300 |
| acttctgatc ataatcataa taatgtcccc atgcaaagac ccccaactaa tccttctgct | 360 |
| gcttggaaac ctgatctagc tgatcccatt cacaccacca gtattgtaa catctcttct | 420 |
| actgcaggga tctcttcggc atcatcttct gttgagatgg ttactgtggg acagatgggg | 480 |
| aattatgggt atggttctgt gcctatggag aaaagtttta gggactgctc gatatcagct | 540 |
| gggggtagca gtggccatgt tggattaata accacaact tggggtgggt tggtgtggac | 600 |
| ccatataatt cctcaaccta tgccaacttc tttgacaaaa taaggccaag tgatcaagaa | 660 |
| acccttgaag aagaagcaga gaacattggt gctactaaga ttgaaaccct cccttttattc | 720 |
| cctatgcacg gtgaggacat ccacggctat tgcaacctca gtctaattc gtataactat | 780 |
| gatggaaacg ctggtatcca tactgaagaa gggttcaaga atgcttctcg tgcttccttg | 840 |
| gagctcagtc tcaactccta cactcgcagg tctccagatt atgcttaa | 888 |

```
<210> SEQ ID NO 31
<211> LENGTH: 897
<212> TYPE: DNA
<213> ORGANISM: Camelina sativa

<400> SEQUENCE: 31
```

| atggagccac cgcagcatca gcatcatcac catcaagccg accagaaaag cggcaataac | 60 |
| aacaagtccg gttctggtgg ttacacttgt cgccaaacca gcacgaggtg gacaccaacg | 120 |
| acggagcaga tcaaaatgct caaagagctt tattacaata gtggaatccg gtcaccaaca | 180 |
| gcagatcaga tccagaagat cactgctagg ctgcgacagt tcggaaagat cgagggcaag | 240 |
| aacgtctttt actggttcca gaaccacaag gctcgtgagc gtcagaagaa gagattcaac | 300 |
| ggcacaacca tgaccacacc gtcttcatct cccaactcgg ttatgatggc taatgatcat | 360 |
| tatcatcaac atctccctct acttcaccat catcatggcg ttcccatgca gagacctgcg | 420 |
| aactccgtca acgttaaact taaccaagag catcatctct atcatcagaa caagtcatat | 480 |
| ccagcttca ataacgggaa tttaaatcat gcaagctcag gtactgaatg tggtgctgtt | 540 |
| aatgcttcta atggctactc aagtagccat atctatggat ctatggaaca agactgttct | 600 |
| atgaattaca caacgtaggg tgaggatgg acggcaaaca tggatcataa tcatcattac | 660 |
| tcatcagcac cttacaactt cttcgataga ccaaaacctc cgtttggtct agacggtcat | 720 |
| caggaagaag aagaatgtgg tggcgatgct tatctggaac atcgacgtac gcttcctctc | 780 |

```
ttccctatgc atggtgaaga tcacataaat ggtgccagct ggaagtatgg ccaactggac    840
ggtcatgatt gtcatggtag aggcccttgc gcttctcttg agcttcgttt gaactag      897
```

<210> SEQ ID NO 32
<211> LENGTH: 897
<212> TYPE: DNA
<213> ORGANISM: Capsella rubella

<400> SEQUENCE: 32

```
atggagccac cacagcatca gcatcatcat catcaagccg accaagaaag cggcaacaac    60
aacaacaagt ccggctctgg tggctacacg tgtcgccaaa ccagcactag gtggacacca   120
acgacggagc agatcagaat cctcaaggat ctttactaca acagtgcgat ccggtcacca   180
acagccgatc agatccagaa gatcaccgcg aggctgagac agtacgggaa gatcgaaggc   240
aagaacgtct tttactggtt ccagaaccat aaggctcgtg agcgtcagaa gaagagattc   300
aacggcacaa ccatgaccac tccatcttca tctcccaact cggttatggt ggctaatgat   360
cactatcatc ctctacttca ccatcatcat ggtgttccca tgcaaaggcc tgctaactcc   420
gtcaacgtca aacttaacca agaccatcat ctctatcatc agaacaagtc atatcccacc   480
ttcaacaatg gaatttaaa tcatggaagc tcaggtactg aatgtggtgt tgttaatgct    540
tctaatggct acatgagtag ccatgtctat ggatctatgg aacaagactg ttcaatgaac   600
tacaacaacg taggtactgg aggatacgga tcaaacatgg atcatagtca tcattactca   660
tctgcaccat acaacttctt tgatagatca aagcctctct tggtctaga aggtcatcaa    720 gaagatgaag aagaatatgg tataggcgat gcttatctgg aacatcgacg tacgcttcct   780
ctcttcccta tgcatggtga agatcacatg aacggtagtg gtgctagctg gaagtttgat   840
ggccgtgatt gccatggtag aggcccttgc gcttctcttg agcttcgtct gaactag      897
```

<210> SEQ ID NO 33
<211> LENGTH: 588
<212> TYPE: DNA
<213> ORGANISM: Arabis alpina

<400> SEQUENCE: 33

```
atggctactc atgtagccat tagaagcatt aacagcacca cattcagaac ctgaacttgc    60
atgatttaaa ttcccgttat tgaagctggg atatgatttg ttctgatgaa gcagatggtg   120
ttcttggtca tgaagcttaa cgttgagaga agcaggtctc tgcatggaaa caccatgatg   180
atgttgaaga agaggatgat gatgatggtt atgatgataa cgatcactgg ccatcataac   240
tgagttgggc gatgaagacg ttggtgtggt ggtcatggtt gtgccattga atctcttctt   300
ctgacgctca cgagccttat ggttctgaaa ccagtaaaag acgtttttgc cctcgatctt   360
accatattgt ctcagccttg cagagatctt ctggatctca tcagcagttg gtgaccggat   420
tccactattg tagtaaagat cttgaggat tctgatttgc tccgtggttg gagtccatct    480
cgtgctggtt tgacgacaag tgtaaccacc agaaccggac ttgttgttgt tgttgccgct   540
ttcttggtcg gcttgatgat gatgatgatg atgttgcggt ggctccat                588
```

<210> SEQ ID NO 34
<211> LENGTH: 873
<212> TYPE: DNA
<213> ORGANISM: Raphanus sativus

<400> SEQUENCE: 34

| atggagccac cgcaacatta ccatcaagcc gatcaagaaa gcggcaacaa caacaagtcc | 60 |
| gtctctggtg gttacacgtg tcgtcaaacg agcacaagat ggacaccaac aaccgatcaa | 120 |
| atcagaatac tcaaagatct ttactacaac aatggagtcc ggtcaccaac agccgaccag | 180 |
| atccagaaga tctctgcaac gctgagacag tacggaaaaa tcagggaaa aaatgtcttt | 240 |
| tactggtttc aaaaccataa ggctcgtgag cgacagaaga agagattcaa cagcacaacc | 300 |
| atggccacac caacgtcttc atcgcccaac tcggttatga tgatggctag tgatcaccat | 360 |
| catcatcatg gtgttaccat ccagagacct gctttggtca acgttaagct cgaccaagaa | 420 |
| aatcatatgt ttcaccagaa cagatcatat cccagctcca ataacgggag tataaatcat | 480 |
| gcaagttcag gcacggaata tggtgttttc ggcgcttcta atggctacat tagtaaccat | 540 |
| atctatggat ctatggaaca agactgttca atgagctaca acagcgtagg tggaggatgg | 600 |
| acaaacatgg atcataatca tcattactca actccagctt acaacttctt tgatagacca | 660 |
| tcgcctctgt ctggactaga aggtcatcaa gaagaaggac aatatggtgg cgattcttat | 720 |
| ctggaacatc gacgtacact tcctctcttc cctttgcacg gtgaggatca catcaacggt | 780 |
| ggtggtggtt ccatcttgaa gtacggacaa tcagacggtt gtgatcgtta tggtagaggc | 840 |
| ccttgtgctt ctcttaagct atgtctgaac tga | 873 |

<210> SEQ ID NO 35
<211> LENGTH: 885
<212> TYPE: DNA
<213> ORGANISM: Brassica napus

<400> SEQUENCE: 35

| atggagccag cgcaacatca ccatcaagcc gaccagaaa gcggcaacaa caacaagtcc | 60 |
| gtctctggtg gttacacgtg tcgtcaaacg agtacaagat ggacaccaac gaccgatcaa | 120 |
| atcagaatac tcaaagatct ttactacaac aacggagtcc ggtcaccaac agccgaccag | 180 |
| atccagaaga tctctgcaag gctgagacag tacggaaaga tcagggaaa aaatgtcttt | 240 |
| tactggtttc aaaaccataa ggctcgtgag cgacagaaga agagattcaa cagcacaacc | 300 |
| atgaccatac caacgtcttc atcgcccaac tcggttatga tggctagtga tcactatcac | 360 |
| cataaccatc atcatcatgg cgttaccatc cagagacctg ctttggtcaa cgttaagctc | 420 |
| gaccaagaaa atcatatgtt tcatcagaac agatcatatc ccagcttcaa taacgggaat | 480 |
| acaaatcatg caagttcagg cacggaatat ggtgttttca gtgcttctaa tggctacatt | 540 |
| agtagccata tctatgaacc tatggaacaa gactgttcaa tgagctacaa caacgtaggt | 600 |
| ggaggatgga caaacataga tcataatcac cattactcaa ctccagccta caacttctta | 660 |
| gatagaccaa tgcctctgtc tggactagaa ggtcatcatc aagaagaagg agaatatggt | 720 |
| ggcgatgctt atctggaaca tagacgcaca cttcctctct ccctttgca cggtgaggat | 780 |
| cacatcaacg gcggtggtgg ttccatctgg aagtacagac aatcggacgg ttgtgatcgt | 840 |
| tatggtagag gcccttgtgc ttctcttaag ctgtgtctga actga | 885 |

<210> SEQ ID NO 36
<211> LENGTH: 885
<212> TYPE: DNA
<213> ORGANISM: Brassica oleracea

<400> SEQUENCE: 36

| atggagccag cgcaacatca ccatcaagcc gaccagaaa gcggcaacaa caacaagtcc | 60 |
| gtctctggtg gttacacgtg tcgtcaaacg agtacaagat ggacaccaac gaccgatcaa | 120 |

```
atcagaatac tcaaagatct ttactacaac aacggagtcc ggtcaccaac agccgaccag      180
atccagaaga tctctgcaag gctgagacag tacggaaaga tcgagggaaa aaatgtcttt      240
tactggtttc aaaaccataa ggctcgtgag cgacagaaga agagattcaa cagcacaacc      300
atgaccatac caacgtcttc atcgcccaac tcggttatga tggctagtga tcactatcac      360
cataaccatc atcatcatgg cgttaccatc cagagacctg ctttggtcaa cgttaagctc      420
gaccaagaaa atcatatgtt tcatcagaac agatcatatc ccagcttcaa taacgggaat      480
ataaatcatg caagttcagg cacggaatat ggtgttttca gtgcttctaa tggctacatt      540
agtagccata tctatggacc tatggaacaa gactgttcaa tgagctacaa caacgtaggt      600
ggaggatgga caaatataga tcataatcac cattactcaa ctccagccta caacttctta      660
gatagaccaa tgcctctgtc tggactagaa ggtcatcatc aagaagaagg agaatatggt      720
ggcgatgctt atctggaaca tagacgcaca cttcctctct tccctttgca cggtgaggat      780
cacatcaacg gcggtggtgg ttccatctgg aagtacagac aatcggacgg ttgtgatcgt      840
tatggtagag gcccttgtgc ttctcttaag ctgtgtctga actga                     885
```

<210> SEQ ID NO 37
<211> LENGTH: 882
<212> TYPE: DNA
<213> ORGANISM: Helianthus annuus

<400> SEQUENCE: 37

```
atggaaactc aacaacaaca agcagatatt caagattttg ggaacaaaaa cagtaacacc       60
tatgcatgca ggcaaagcag tactaggtgg acacccacaa gtgatcagat cagaatactg      120
aaagagctct actacaacaa tggaatcaga tcaccaactg ctgatcagat tcagagaatc      180
gctgctcaac tcagacagta cggcaagatt gaaggcaaga acgtgtttta ttggttcag       240 aaccataaag ctcgtgaacg ccagaagaaa cggttcactc ctactgctcc tccaccaccg      300
tctcacttct ccgatcatat taaccaccat cttcccaacg ctgccccat gcagattccg       360 tctcaccacc accactacca ccatcaagaa ccaccacatg tctatgctca ccctcacaaa      420
ctctacacca ctcatcacat tggggttggt tcttcttcac aaggagtgat gggtgtaggg      480
tgtggctatg gatctgttgc tatggagaag agtttcagga agtgttcaat atcaccaccg      540
ggagagagta aggccacagg aggaattggc cggaatatcg gttcaagatc acggataagt      600
gtcgattcgt gttccttctt cgacacaatt aagccaaaga catatgagat gtttgagaat      660
catgatcaag atgaagaaca aggagagcct tcaactgaga tcgaaacact tccattattc      720
ccgattcacg acggcaacca tcatgatttc ttcggcatga ggacggcaaa tctgcaattg      780
gagcaaggca ctggaggtta ctacactgga ggaagctggt atcggtctga tgagagggcg      840
tctcttgagc tcagtctcaa ctcatatggt tattataact aa                        882
```

<210> SEQ ID NO 38
<211> LENGTH: 795
<212> TYPE: DNA
<213> ORGANISM: Populus trichocarpa

<400> SEQUENCE: 38

```
atggaacctc accaacaaca accaaatgag gataataacg gtggcgccaa agggaacttt       60
cttcgcaggc aaaccagtac aaggtggaat cccactactg accagataag aatattgaag      120
gaactgtact acatcaaagg tgttaggtcc ccaaatggag ctgagattca gcagatctct      180
```

```
gctaggctta gaaagtacgg caagattgaa ggcaagaatg tattttattg gtttcagaac      240
cataaagctc gtgagaggca aaagaaaaga ctcaccaatg aagtccccat gcaacaaaga      300
actgcctgga aacctgaaga ttattactct tacaagtact ccaacagtaa taataatcct      360
gggttttctt cggcttcttc atctgcaaat accggtgtgg ttactgttgg gcagacagat      420
agccatggat atggatcggt aaccatgcag gagaagaatt cttgggactg ttcagcacca      480
gctggtggta gcaatggtgc tggtagtgga tccatgagca atattaacta tggatcaggg      540
gttgacatta actctcacag ttcatcctat gctgtatttg gtcaagaaca agaagcagct      600
gcaaagattg agactcttcc tctatttcca atgcttggtg aggacatcag tagctctttc      660
aacatcaaca atatcaaccc agactttttat tacagtagcg gctgtggcta tggtgattat      720
ggcaatgaca cttcttcccg tacttccctg gaccttagtc tctactccta caatggccaa      780
ccacaagatt attaa                                                        795

<210> SEQ ID NO 39
<211> LENGTH: 843
<212> TYPE: DNA
<213> ORGANISM: Vitus vinifera

<400> SEQUENCE: 39
atggaacctc aacaacagct ccagcagcag cagcaacaaa accaacaaca gccaaacgag       60
gatagcggca gcagcaaagg cagttttctg tgcaggcaaa gcagtacacg ctggactcct      120
acaactgacc agataagaat attgaaggac ctttactaca acaatggagt taggtcccca      180
agtgctgaac agattcagag gatctcagct aggctgaggc agtacggcaa gatcgaaggc      240
aagaacgtct tttattggtt tcagaaccat aaagctcgtg aaaggcagaa gaagcgattc      300
actactgata tgcccatgca agatcccctt ggaaatgccg gttggagacc tgatgatccc      360
attcacaaca aatttcatac cattcccact cctgggatat cttccccatc ttcttcttct      420
tcacccagtg tgcttgctgt tgggcagatg ggaagctttg gatatggatc tgtggagagg      480
agttttacag actgttcaat atcagcaggt ggtggtcgtg gtggggttgg tggatctata      540
aaccagagct cgaatgggt tggcatggac ccatattctt catcttatgc actcttttgac      600 aagagaaaaa caatgggtga agcttcgaa gaagagcaag aagaagaagc aactccggag      660
attgaaacgc tcccactctt tcccatgcac gctgaggata tcactggctt ttgcaacatt      720
aagcccgaat ccgacgccta ctactccggc tggtacaggc ccgccgacgc caagaccagt      780
tcccgcactt tcttgagct tagcctcaac tcctacgccg gcaggtcccc ggattccccc      840
tga                                                                     843

<210> SEQ ID NO 40
<211> LENGTH: 879
<212> TYPE: DNA
<213> ORGANISM: Arabidopsis thaliana

<400> SEQUENCE: 40
atggagcctc ctcagcacca acatcaccac catcaggccg atcaagagtc cggaacaac       60 aacaacaaca gtccggttc cggagggtac acttgcagac agacctccac cagatggaca      120
cctaccactg agcagatcaa gatcctgaag gagttgtact acaacaatgc catccgctcc      180
cctactgctg atcagattca gaagatcacc gctcgcctgc gtcaattcgg taagatcgag      240
ggtaagaacg tcttctactg gttccagaac cacaaggctc gtgagaggca agaagagcgt      300
ttcaacggga ctaacatgac cactccttcc tcatcaccca ttctgttat gatggccgcc      360
```

| | | |
|---|---|---|
| aacgaccact | accatccttt gcttcatcac caccacggag ttcctatgca aagacccgca | 420 |
| aactccgtca | acgtgaagtt gaaccaggac catcacctct accaccacaa caagccctac | 480 |
| ccctctttca | acaacgggaa tctcaaccat gcctcctctg gaaccgaatg tggagttgtc | 540 |
| aacgcctcca | acggctacat gtcttcccac gtgtacggct ctatggagca agattgctcc | 600 |
| atgaactaca | acaacgttgg aggcggatgg gcaaacatgg atcaccacta ctcctccgct | 660 |
| ccctacaact | tcttcgatag ggctaaacct ctcttcggct tggagggaca ccaagaagaa | 720 |
| gaggaatgcg | gaggtgatgc ttacttggaa cacagaagga ctctccctct ctttccaatg | 780 |
| cacggtgagg | accacatcaa cggaggatct ggcgctatct ggaagtatgg acagtccgag | 840 |
| gtcagaccat | gcgcttccct ggaattgaga ctgaactag | 879 |

<210> SEQ ID NO 41
<211> LENGTH: 879
<212> TYPE: DNA
<213> ORGANISM: Lotus japonicus

<400> SEQUENCE: 41

| | | |
|---|---|---|
| atggaacaac | ctccccaaca gcagcaacaa aacgaagacg gaggcggatc aagtggggga | 60 |
| aaaggagggt | tcctcagtag gcagtccagt actaggtgga cacccaccac agaccagatt | 120 |
| cgcatcctca | aggagctcta ctacaacaac ggaatacgct caccctccgc agaacagatc | 180 |
| cagaggatct | ccgcaagact cagacagtac ggcaagatcg agggcaagaa cgtcttctac | 240 |
| tggttccaaa | accacaaagc ccgcgaaagg cagaagaagc gcttcaccag tgagacacac | 300 |
| ttgctgccca | acccaattca gcagcaacag cgcaacggaa caaacgcagc ttggaagcag | 360 |
| ccagaggagc | aacccatcat caaccacacc aagtactcct ccaacaacat atccgcaccc | 420 |
| gcagggatta | tcacaagtgc cccatcttct tccgcagaaa tagtctccgt ggggcagatc | 480 |
| ggaaacttcg | gatacggatc tctgccaatg gagaagtcct tcaggactg cagtatctca | 540 |
| gccggaggta | acacaggata cgccgggtct gctattaacc acaacctcgg atggatggga | 600 |
| gtcgacccat | actcctctgc ttacaccaac ttcttcgaca aaatacgccc aacagaggag | 660 |
| gagactatgg | aggaagaagg acaggagaac ggctcaccag aaatcgagac cctgcctttg | 720 |
| ttcccaatgc | acggagagga catccactcc ggctacttca acctcaagag taactcatcc | 780 |
| cactacgctg | gcggatggta ccaaactgag gaaggctact caacaacgg atcacgcgcc | 840 |
| agtctggagc | tgtccctgaa gtaccctgac ttcgcttag | 879 |

<210> SEQ ID NO 42
<211> LENGTH: 909
<212> TYPE: DNA
<213> ORGANISM: Medicago trunculata

<400> SEQUENCE: 42

| | | |
|---|---|---|
| atggaacaac | ctcagcagca gcagcaacca cagacccaac agcactctcc aaacaacgga | 60 |
| atcatggggt | ccagacagag ttccaccaga tggacccca caaccgacca gatccgcatt | 120 |
| ctcaaagacc | tctactacaa caacggaata aggtctccaa gtgccgagca aatccagagg | 180 |
| atctccgcaa | ggctcagaca gtacgggaag atcgagggca agaacgtctt ctactggttc | 240 |
| caaaaccaca | agccagaga gcgccagaaa aagcgcttca cctccgacgt caacgtcgtc | 300 |
| cctatcatcc | agcgcgcccc caacaacaat actatcataa gtgccgccaa ctggaagcct | 360 |
| gaccaccacg | aacaacagca gaacattaat gtccacacaa accactccac atacaacatc | 420 |

```
tcctccgctg gcctcagttc tgcttcctgc tcctcagcag aaatggtcac tgtggggcaa    480
ataggcaact acggctacgg gtctgtccca atggagaagt ctttccgcga atgcaccatc    540
tcagctggat gctcatcatc ccaggttggc tcaaccataa accccacat cggctggatc     600 ggacaccacg tcgacccata ttcaagtgcc tacgctaacc tcttcgagaa aatacgcccc    660
aacgaggaga tcatggaaga gtacgaccag ggacaggaaa acggttcccc agagatcgag    720
acactcccac tcttccctat gcacggaaa gacatccacg gagggtattg caacctcaaa     780
tcaaattcct ccaactacgg aggatggtac caggcagaag acgcagggtt catgtacgga    840
agtcgtacca cttctctcga gctcagtctg aactcctacg gatgcaggtc ccccgactac    900
gccaattaa                                                           909
```

<210> SEQ ID NO 43
<211> LENGTH: 924
<212> TYPE: DNA
<213> ORGANISM: Petunia hybrida

<400> SEQUENCE: 43

```
atggaaacag cacagcacca gcagaacaac caacagcact acctccacca cacctctcc     60 atcggacaag gaacaaacat cgaggacggc agtaacaaga caactcctc caacttcatg    120 tgcaggcaaa atagtacccg ctggacacca accactgacc agatcaggat attaaaggac    180
ctctactaca caacggagt cagatcacct accgctgaac agatccagag aatctccgcc    240
aagctcaggc agtacggcaa gatcgagggc aagaacgtct ctactggtt ccagaaccat    300 aaagcccgcg agagacaaaa gaagcgcctc atcgccgcag ccaccaccga taacactaac    360
ctcccaatgc agatgcagtt ccagagagga gtctggagat cctctgcaga cgaccccatc    420
caccacaagt atactaatcc aggagtgcac tgcccttcag cttcttccca cggagttctc    480
gcagtcggac agaacggcaa tcacggatac ggagccttgg caatggaaaa atccttccgc    540
gactgctcca tcagtccagg cagttccatg tcacaccacc accaccaaaa cttgcttgg     600 gcaggagtcg atccttattc ctcaaccaca acctacccct tcctcgagaa gaccaagcac    660
ttcgagaatg aaaccctcga agctgatgaa gagcagcaag aggaggacca ggagaactac    720
tactaccaaa ggaccaccct tgccatcgaa acctgcctc tcttccctat gcacgaggag     780
aacatctcct cctttctgcaa cctcaagcac caggagtcat ccggaggatt ctacaccgag    840
tggtacagag cagacgacaa cctcgcagca gccagagctt ccctcgagct ctccttgaac    900
tccttcatcg gcaactcctc ctag                                           924
```

<210> SEQ ID NO 44
<211> LENGTH: 864
<212> TYPE: DNA
<213> ORGANISM: Phaseolus vulgaris

<400> SEQUENCE: 44

```
atggaaccac agcagcccca gggcagtcaa ccaaacgagg acggtggaag tgggaaaggc     60
ggatttctct ccagacagtc ctccactagg tggactccaa ccactgacca gatcagaata    120
ctcaaagacc tctactacaa caacggaatc agatcccctt ccgcagaaca gatccaaagg    180
atctccgcta ggctcagaca gtacgggaag atcgagggca agaacgtctt ctactggttc    240
caaaaccaca aggccaggga gagacagaag aagaggttca cctccgacaa cgtccccatg    300
caaagacctg caccaacaaa tgctgcacct ccttggaaac ccgaccaaga ccccattcac    360
accaagtact ccaacatctc ctccacagga atctccagtg catcctcctc ctcagtcgag    420
```

```
atgatcaccg tcggacaaat ggggaactac gggtacggaa gtgtgccaat ggaaaagtcc      480
ttcagagact gctccatatc cgccggagga tcttccggtc atgttggaat aaaccacaac      540
ctcggctggg tgggagtcga tccttactct tctgcatacg ccaacttctt cgataaaata      600
agaccaaacg aagagaccct cgaggaagaa gaagaggagg aggaggagga agaagaagag      660
gacggaggag cagaaattga ccctccccc  ctgttcccaa tgcacggaga ggacattcac      720
ggctactgca acctcaagtc caacagttac aactacgacg caacggctg  gtatcacagt      780 gaggatggct tcaaaaacgg cagtagggcc tccctcgagc tctccctcaa ctcttacacc      840
agaagatccc ccgacttcgc atag                                             864
```

```
<210> SEQ ID NO 45
<211> LENGTH: 963
<212> TYPE: DNA
<213> ORGANISM: Zea mays

<400> SEQUENCE: 45
atggcggcca acgtgggcgc gggcaggagt gctggcggcg gcggagccgg cactggcact      60
ggcactgctg ctggcagcgg cggcgtgtcg acggccgtgt gccgccctag cggctcgcgg      120
tggacgccga cgccggagca gatcaggatc ctcaaggagc tctactacgg ctgcggcatc      180
cggtcgccca actcggagca gatccagcgc atcaccgcca tgctgcggca gcacggcaag      240
atcgagggca agaacgtctt ctactggttc cagaaccaca aggcccgcga gcgccagaag      300
cgccgcctca ccaacctcga cgtcaacgtg cccgtcgccg ccgacgacag cgcccaccgc      360
cttggcgtcc tctcgttgtc gccttcttca ggttgttcag gcgcggcgcc tccgtcgccc      420
accctcggct tctacgccgg cggcaatggc tccgctgtga tgctggacac gagttccgat      480
tggggcagcg ctgctgccat ggccactgag gcatgcttca tgcaggacta catgggcgtg      540
atgggcggcg cgtcaccgtg ggcatgctcc tcctcgtcgt cggaggaccc gatggcggcg      600
ctggcgctgg cgccgaaggt gacccgggcg cccgagacgc tccctctctt cccgaccggc      660
ggcggcggag acgataggca gccccgcgcg ccgcggcagt ctgtcccagc aggcgaggcc      720
atccgcggcg gcagcagcag cagcagctac cttccgttct ggggtgccgc gcccacccca      780
actggcagtg ccacttccgt tgcgatccag cagcaacacc agctgatgca gatgcaagag      840
cagtacagct tttacagcaa cgcccagctg ctgcccggca ccggcagcca ggatgcagca      900
gcaacatccc tggagctgag cctcagctcc tggtgctccc cttaccctgc agggaccatg      960
tga                                                                    963
```

```
<210> SEQ ID NO 46
<211> LENGTH: 978
<212> TYPE: DNA
<213> ORGANISM: Zea mays

<400> SEQUENCE: 46
atggcggcca atgcgggcgg cggtggagcg ggaggaggca gcggcagcgg cagcgtggct      60
gcgccggcgg tgtgccgccc cagcggctcg cggtggacgc cgacgccgga gcagatcagg      120
atgctgaagg agctctacta cggctgcggc atccggtcgc ccagctcgga gcagatccag      180
cgcatcaccg ccatgctgcg gcagcacggc aagatcgagg gcaagaacgt cttctactgg      240
ttccagaacc acaaggcccg cgagcgccag aagcgccgcc tcaccagcct cgacgtcaac      300
gtgcccgccg ccggcgcggc cgacgccacc accagccaac tcggcgtcct ctcgctgtcg      360
```

| | |
|---|---|
| tcgccgcctt caggcgcggc gcctccctcg cccacccctcg gcttctacgc cgccggcaat | 420 |
| ggcggcggat cggctgggct gctggacacg agttccgact ggggcagcag cggcgctgcc | 480 |
| atggccaccg agacatgctt cctgcaggac tacatgggcg tgacggacac gggcagctcg | 540 |
| tcgcagtggc catgcttctc gtcgtcggac acgataatgg cggcggcggc ggccgcggcg | 600 |
| cgggtggcga cgacgcgggc gcccgagaca ctccctctct tcccgacctg cggcgacgac | 660 |
| gacgacgacg acagccagcc cccgccgcgg ccgcggcacg cagtcccagt cccggcaggc | 720 |
| gagaccatcc gcggcggcgg cggcagcagc agcagctact tgccgttctg gggtgccggt | 780 |
| gccgcgtcca caactgccgg cgccacttct tccgttgcga tccagcagca acaccagctg | 840 |
| caggagcagt acagctttta cagcaacagc acccagctgg ccggcaccgg cagccaagac | 900 |
| gtatcggctt cagcggccgc cctggagctg agcctcagct catggtgctc cccttaccct | 960 |
| gctgcaggga gcatgtga | 978 |

<210> SEQ ID NO 47
<211> LENGTH: 666
<212> TYPE: DNA
<213> ORGANISM: Zea mays

<400> SEQUENCE: 47

| | |
|---|---|
| atggaggcgc tgagcgggcg ggtaggcgtc aagtgcgggc ggtggaaccc tacggcggag | 60 |
| caggtgaagg tcctgacgga gctcttccgc gcggggctgc ggacgcccag cacggagcag | 120 |
| atccagcgca tctccaccca cctcagcgcc ttcggcaagg tggagagcaa gaacgtcttc | 180 |
| tactggttcc agaaccacaa ggcccgcgag cgccaccacc acaagaagcg acgccgcggc | 240 |
| gcgtcgtcgt cctcccccga cagcggcagc ggcaggggaa gcaacaacga ggaagacggc | 300 |
| cgtggtgccg cctcgcagtc gcacgacgcc gacgccgacg ccgacctcgt gctgcaaccg | 360 |
| ccagagagca agcgggaggc cagaagctat ggccaccatc accggctcgt gacatgctac | 420 |
| gtcagggacg tggtggagca gcaggaggcg tcgccgtcgt gggagcggcc gacgagggag | 480 |
| gtggagacgc tagagctctt ccccctcaag tcgtacggcg acctcgaggc ggcggagaag | 540 |
| gtccggtcgt acgtcagagg aagcggcgcc accagcgagc agtgcaggga gttgtccttc | 600 |
| ttcgacgtcg tctccgccgg ccgggatccg ccgctcgagc tcaggctctg cagcttcggt | 660 |
| ccctag | 666 |

<210> SEQ ID NO 48
<211> LENGTH: 302
<212> TYPE: PRT
<213> ORGANISM: Zea mays

<400> SEQUENCE: 48

```
Met Ala Ala Asn Ala Gly Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95
```

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
        115                 120                 125

Pro Pro Ser Pro Thr Leu Gly Phe Tyr Ala Ala Gly Asn Gly Gly Gly
        130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Asp Thr
            180                 185                 190

Ile Met Ala Ala Ala Ala Arg Ala Ala Thr Thr Arg Ala Pro Glu
        195                 200                 205

Thr Leu Pro Leu Phe Pro Thr Cys Gly Asp Asp Gly Gly Ser Gly Ser
210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
            260                 265                 270

Gln Asp Val Ser Ala Thr Ala Ala Ala Ala Ala Leu Glu Leu Ser
        275                 280                 285

Leu Ser Ser Trp Cys Ser Pro Tyr Pro Ala Ala Gly Ser Met
290                 295                 300

<210> SEQ ID NO 49
<211> LENGTH: 343
<212> TYPE: PRT
<213> ORGANISM: Zea mays

<400> SEQUENCE: 49

Met Ala Ala Asn Ala Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Ser Gly Ala Ala Pro Pro
        115                 120                 125

Ser Pro Thr Leu Gly Phe Tyr Ala Ala Gly Asn Gly Gly Ser Ala
        130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Val Gly Ala Val Val Arg Ser Phe

```
            165                 170                 175
Leu Gly His Cys Ala Gln Phe His Val Arg Thr Tyr Glu Leu Ile Ala
            180                 185                 190

Ala Ser Phe His Pro Pro Val Tyr Ile Thr Val Arg Tyr Gly Gly Ala
        195                 200                 205

Arg Pro Gln Asp Tyr Met Gly Val Thr Asp Thr Gly Ser Ser Ser Gln
    210                 215                 220

Trp Pro Arg Phe Ser Ser Asp Thr Ile Met Ala Ala Ala Ala
225                 230                 235                 240

Arg Ala Ala Thr Thr Arg Ala Pro Glu Thr Leu Pro Leu Phe Pro Thr
                245                 250                 255

Cys Gly Asp Asp Gly Gly Ser Gly Ser Ser Tyr Leu Pro Phe Trp
                260                 265                 270

Gly Ala Ala Ser Thr Thr Ala Gly Ala Thr Ser Ser Val Ala Ile Gln
            275                 280                 285

Gln Gln His Gln Leu Gln Glu Gln Tyr Ser Phe Tyr Ser Asn Ser Asn
        290                 295                 300

Ser Thr Gln Leu Ala Gly Thr Gly Asn Gln Asp Val Ser Ala Thr Ala
305                 310                 315                 320

Ala Ala Ala Ala Leu Glu Leu Ser Leu Ser Ser Trp Cys Ser Pro
                325                 330                 335

Tyr Pro Ala Ala Gly Ser Met
            340

<210> SEQ ID NO 50
<211> LENGTH: 325
<212> TYPE: PRT
<213> ORGANISM: Zea mays

<400> SEQUENCE: 50

Met Ala Ala Asn Ala Gly Gly Gly Ala Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Pro Pro Ser Gly Ala Ala Pro
        115                 120                 125

Pro Ser Pro Thr Leu Gly Phe Tyr Ala Ala Gly Asn Gly Gly Gly Ser
    130                 135                 140

Ala Gly Leu Leu Asp Thr Ser Ser Asp Trp Gly Ser Ser Gly Ala Ala
145                 150                 155                 160

Met Ala Thr Glu Thr Cys Phe Leu Gln Asp Tyr Met Gly Val Thr Asp
                165                 170                 175

Thr Gly Ser Ser Ser Gln Trp Pro Cys Phe Ser Ser Ser Asp Thr Ile
            180                 185                 190
```

```
Met Ala Ala Ala Ala Ala Ala Arg Val Ala Thr Thr Arg Ala Pro
            195                 200                 205

Glu Thr Leu Pro Leu Phe Pro Thr Cys Gly Asp Asp Asp Asp Asp
    210                 215                 220

Ser Gln Pro Pro Arg Pro Arg His Ala Val Pro Val Pro Ala Gly
225                 230                 235                 240

Glu Thr Ile Arg Gly Gly Gly Ser Ser Ser Tyr Leu Pro Phe
                245                 250                 255

Trp Gly Ala Gly Ala Ala Ser Thr Thr Ala Gly Ala Thr Ser Ser Val
                260                 265                 270

Ala Ile Gln Gln Gln His Gln Leu Gln Glu Gln Tyr Ser Phe Tyr Ser
            275                 280                 285

Asn Ser Thr Gln Leu Ala Gly Thr Gly Ser Gln Asp Val Ser Ala Ser
    290                 295                 300

Ala Ala Ala Leu Glu Leu Ser Leu Ser Ser Trp Cys Ser Pro Tyr Pro
305                 310                 315                 320

Ala Ala Gly Ser Met
                325

<210> SEQ ID NO 51
<211> LENGTH: 300
<212> TYPE: PRT
<213> ORGANISM: Zea mays

<400> SEQUENCE: 51

Met Ala Ala Asn Ala Gly Gly Gly Ala Gly Gly Gly Ser Gly Ser
1               5                   10                  15

Val Ala Ala Pro Ala Val Cys Arg Pro Ser Gly Ser Arg Trp Thr Pro
                20                  25                  30

Thr Pro Glu Gln Ile Arg Met Leu Lys Glu Leu Tyr Tyr Gly Cys Gly
            35                  40                  45

Ile Arg Ser Pro Ser Ser Glu Gln Ile Gln Arg Ile Thr Ala Met Leu
    50                  55                  60

Arg Gln His Gly Lys Ile Glu Gly Lys Asn Val Phe Tyr Trp Phe Gln
65                  70                  75                  80

Asn His Lys Ala Arg Glu Arg Gln Lys Arg Arg Leu Thr Ser Leu Asp
                85                  90                  95

Val Asn Val Pro Ala Ala Gly Ala Ala Asp Ala Thr Thr Ser Gln Leu
                100                 105                 110

Gly Val Leu Ser Leu Ser Ser Pro Pro Ser Gly Ala Ala Pro Pro
            115                 120                 125

Ser Pro Thr Leu Gly Phe Tyr Ala Ala Gly Asn Gly Gly Gly Ser Ala
    130                 135                 140

Val Leu Leu Asp Thr Ser Ser Asp Trp Gly Ser Ser Gly Ala Ala Met
145                 150                 155                 160

Ala Thr Glu Thr Cys Phe Leu Gln Asp Tyr Met Gly Val Thr Asp Thr
                165                 170                 175

Gly Ser Ser Ser Gln Trp Pro Arg Phe Ser Ser Asp Thr Ile Met
            180                 185                 190

Ala Ala Ala Ala Ala Arg Ala Thr Thr Arg Ala Pro Glu Thr Leu
            195                 200                 205

Pro Leu Phe Pro Thr Cys Gly Asp Asp Gly Ser Gly Ser Ser Ser
    210                 215                 220

Tyr Leu Pro Phe Trp Gly Ala Ala Ser Thr Thr Ala Gly Ala Thr Ser
225                 230                 235                 240
```

Ser Val Ala Ile Gln Gln Gln His Gln Leu Gln Glu Gln Tyr Ser Phe
              245                 250                 255

Tyr Ser Asn Ser Asn Ser Thr Gln Leu Ala Gly Thr Gly Asn Gln Asp
        260                 265                 270

Val Ser Ala Thr Ala Ala Ala Ala Ala Leu Glu Leu Ser Leu Ser
    275                 280                 285

Ser Trp Cys Ser Pro Tyr Pro Ala Ala Gly Ser Met
    290                 295                 300

<210> SEQ ID NO 52
<211> LENGTH: 302
<212> TYPE: PRT
<213> ORGANISM: Zea mays

<400> SEQUENCE: 52

Met Ala Ala Asn Ala Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Ser Gly Ala Ala
        115                 120                 125

Pro Pro Ser Pro Thr Leu Gly Phe Tyr Ala Ala Gly Asn Gly Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Ser Asp Thr
            180                 185                 190

Ile Met Ala Ala Ala Ala Arg Ala Ala Thr Thr Arg Ala Pro Glu
        195                 200                 205

Thr Leu Pro Leu Phe Pro Thr Cys Gly Asp Asp Gly Gly Ser Gly Ser
    210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
            260                 265                 270

Gln Asp Val Ser Ala Thr Ala Ala Ala Ala Ala Leu Glu Leu Ser
        275                 280                 285

Leu Ser Ser Trp Cys Ser Pro Tyr Pro Ala Ala Gly Ser Met
    290                 295                 300

```
<210> SEQ ID NO 53
<211> LENGTH: 292
<212> TYPE: PRT
<213> ORGANISM: Arabidopsis thaliana

<400> SEQUENCE: 53

Met Glu Pro Pro Gln His Gln His His His Gln Ala Asp Gln Glu
1               5                   10                  15

Ser Gly Asn Asn Asn Asn Lys Ser Gly Ser Gly Gly Tyr Thr Cys
                20                  25                  30

Arg Gln Thr Ser Thr Arg Trp Thr Pro Thr Thr Glu Gln Ile Lys Ile
            35                  40                  45

Leu Lys Glu Leu Tyr Tyr Asn Asn Ala Ile Arg Ser Pro Thr Ala Asp
    50                  55                  60

Gln Ile Gln Lys Ile Thr Ala Arg Leu Arg Gln Phe Gly Lys Ile Glu
65                  70                  75                  80

Gly Lys Asn Val Phe Tyr Trp Phe Gln Asn His Lys Ala Arg Glu Arg
                85                  90                  95

Gln Lys Lys Arg Phe Asn Gly Thr Asn Met Thr Thr Pro Ser Ser Ser
                100                 105                 110

Pro Asn Ser Val Met Met Ala Ala Asn Asp His Tyr His Pro Leu Leu
            115                 120                 125

His His His His Gly Val Pro Met Gln Arg Pro Ala Asn Ser Val Asn
130                 135                 140

Val Lys Leu Asn Gln Asp His His Leu Tyr His His Asn Lys Pro Tyr
145                 150                 155                 160

Pro Ser Phe Asn Asn Gly Asn Leu Asn His Ala Ser Ser Gly Thr Glu
                165                 170                 175

Cys Gly Val Val Asn Ala Ser Asn Gly Tyr Met Ser Ser His Val Tyr
            180                 185                 190

Gly Ser Met Glu Gln Asp Cys Ser Met Asn Tyr Asn Asn Val Gly Gly
        195                 200                 205

Gly Trp Ala Asn Met Asp His His Tyr Ser Ser Ala Pro Tyr Asn Phe
210                 215                 220

Phe Asp Arg Ala Lys Pro Leu Phe Gly Leu Glu Gly His Gln Glu Glu
225                 230                 235                 240

Glu Glu Cys Gly Gly Asp Ala Tyr Leu Glu His Arg Arg Thr Leu Pro
                245                 250                 255

Leu Phe Pro Met His Gly Glu Asp His Ile Asn Gly Gly Ser Gly Ala
            260                 265                 270

Ile Trp Lys Tyr Gly Gln Ser Glu Val Arg Pro Cys Ala Ser Leu Glu
        275                 280                 285

Leu Arg Leu Asn
    290

<210> SEQ ID NO 54
<211> LENGTH: 292
<212> TYPE: PRT
<213> ORGANISM: Lotus japonicus

<400> SEQUENCE: 54

Met Glu Gln Pro Pro Gln Gln Gln Gln Asn Glu Asp Gly Gly Gly
1               5                   10                  15

Ser Ser Gly Gly Lys Gly Gly Phe Leu Ser Arg Gln Ser Ser Thr Arg
                20                  25                  30

Trp Thr Pro Thr Thr Asp Gln Ile Arg Ile Leu Lys Glu Leu Tyr Tyr
```

```
            35                  40                  45
Asn Asn Gly Ile Arg Ser Pro Ser Ala Glu Gln Ile Gln Arg Ile Ser
 50                  55                  60
Ala Arg Leu Arg Gln Tyr Gly Lys Ile Glu Gly Lys Asn Val Phe Tyr
 65                  70                  75                  80
Trp Phe Gln Asn His Lys Ala Arg Glu Arg Gln Lys Lys Arg Phe Thr
                     85                  90                  95
Ser Glu Thr His Leu Leu Pro Asn Pro Ile Gln Gln Gln Arg Asn
                100                 105                 110
Gly Thr Asn Ala Ala Trp Lys Gln Pro Glu Glu Gln Pro Ile Ile Asn
                115                 120                 125
His Thr Lys Tyr Ser Ser Asn Asn Ile Ser Ala Pro Ala Gly Ile Ile
        130                 135                 140
Thr Ser Ala Pro Ser Ser Ala Glu Ile Val Ser Val Gly Gln Ile
145                 150                 155                 160
Gly Asn Phe Gly Tyr Gly Ser Leu Pro Met Glu Lys Ser Phe Arg Asp
                165                 170                 175
Cys Ser Ile Ser Ala Gly Gly Asn Thr Gly Tyr Ala Gly Ser Ala Ile
                180                 185                 190
Asn His Asn Leu Gly Trp Met Gly Val Asp Pro Tyr Ser Ser Ala Tyr
            195                 200                 205
Thr Asn Phe Phe Asp Lys Ile Arg Pro Thr Glu Glu Thr Met Glu
        210                 215                 220
Glu Gly Gln Glu Asn Gly Ser Pro Glu Ile Glu Thr Leu Pro Leu
225                 230                 235                 240
Phe Pro Met His Gly Glu Asp Ile His Ser Gly Tyr Phe Asn Leu Lys
                245                 250                 255
Ser Asn Ser Ser His Tyr Ala Gly Gly Trp Tyr Gln Thr Glu Glu Gly
                260                 265                 270
Tyr Phe Asn Asn Gly Ser Arg Ala Ser Leu Glu Leu Ser Leu Lys Tyr
            275                 280                 285
Pro Asp Phe Ala
        290

<210> SEQ ID NO 55
<211> LENGTH: 295
<212> TYPE: PRT
<213> ORGANISM: Glycine max

<400> SEQUENCE: 55

Met Glu Pro Gln Gln Gln Gln Gln Ala Gln Gly Ser Gln Gln Gln
  1               5                  10                  15
Gln Gln Asn Glu Asp Gly Gly Ser Gly Lys Gly Gly Phe Leu Ser Arg
                 20                  25                  30
Gln Ser Ser Thr Arg Trp Thr Pro Thr Asn Asp Gln Ile Arg Ile Leu
            35                  40                  45
Lys Glu Leu Tyr Tyr Asn Asn Gly Ile Arg Ser Pro Ser Ala Glu Gln
         50                 55                  60
Ile Gln Arg Ile Ser Ala Arg Leu Arg Gln Tyr Gly Lys Ile Glu Gly
 65                  70                  75                  80
Lys Asn Val Phe Tyr Trp Phe Gln Asn His Lys Ala Arg Glu Arg Gln
                 85                  90                  95
Lys Lys Arg Phe Thr Ser Asp His Asn His Asn Asn Val Pro Met Gln
                100                 105                 110
```

```
Arg Pro Pro Thr Asn Pro Ser Ala Ala Trp Lys Pro Asp Leu Ala Asp
            115                 120                 125

Pro Ile His Thr Thr Lys Tyr Cys Asn Ile Ser Ser Thr Ala Gly Ile
130                 135                 140

Ser Ser Ala Ser Ser Ser Val Glu Met Val Thr Val Gly Gln Met Gly
145                 150                 155                 160

Asn Tyr Gly Tyr Gly Ser Val Pro Met Glu Lys Ser Phe Arg Asp Cys
                165                 170                 175

Ser Ile Ser Ala Gly Gly Ser Ser Gly His Val Gly Leu Ile Asn His
            180                 185                 190

Asn Leu Gly Trp Val Gly Val Asp Pro Tyr Asn Ser Ser Thr Tyr Ala
        195                 200                 205

Asn Phe Phe Asp Lys Ile Arg Pro Ser Asp Gln Glu Thr Leu Glu Glu
    210                 215                 220

Glu Ala Glu Asn Ile Gly Ala Thr Lys Ile Glu Thr Leu Pro Leu Phe
225                 230                 235                 240

Pro Met His Gly Glu Asp Ile His Gly Tyr Cys Asn Leu Lys Ser Asn
                245                 250                 255

Ser Tyr Asn Tyr Asp Gly Asn Gly Trp Tyr His Thr Glu Glu Gly Phe
            260                 265                 270

Lys Asn Ala Ser Arg Ala Ser Leu Glu Leu Ser Leu Asn Ser Tyr Thr
        275                 280                 285

Arg Arg Ser Pro Asp Tyr Ala
    290                 295

<210> SEQ ID NO 56
<211> LENGTH: 298
<212> TYPE: PRT
<213> ORGANISM: Camelina sativa

<400> SEQUENCE: 56

Met Glu Pro Pro Gln His Gln His His His Gln Ala Asp Gln Glu
1               5                   10                  15

Ser Gly Asn Asn Asn Lys Ser Gly Ser Gly Gly Tyr Thr Cys Arg Gln
                20                  25                  30

Thr Ser Thr Arg Trp Thr Pro Thr Thr Glu Gln Ile Lys Met Leu Lys
            35                  40                  45

Glu Leu Tyr Tyr Asn Ser Gly Ile Arg Ser Pro Thr Ala Asp Gln Ile
50                  55                  60

Gln Lys Ile Thr Ala Arg Leu Arg Gln Phe Gly Lys Ile Glu Gly Lys
65                  70                  75                  80

Asn Val Phe Tyr Trp Phe Gln Asn His Lys Ala Arg Glu Arg Gln Lys
                85                  90                  95

Lys Arg Phe Asn Gly Thr Thr Met Thr Thr Pro Ser Ser Ser Pro Asn
            100                 105                 110

Ser Val Met Met Ala Asn Asp His Tyr His Gln His Leu Pro Leu Leu
        115                 120                 125

His His His His Gly Val Pro Met Gln Arg Pro Ala Asn Ser Val Asn
    130                 135                 140

Val Lys Leu Asn Gln Glu His His Leu Tyr His Gln Asn Lys Ser Tyr
145                 150                 155                 160

Pro Ser Phe Asn Asn Gly Asn Leu Asn His Ala Ser Ser Gly Thr Glu
                165                 170                 175

Cys Gly Ala Val Asn Ala Ser Asn Gly Tyr Ser Ser Ser His Ile Tyr
            180                 185                 190
```

Gly Ser Met Glu Gln Asp Cys Ser Met Asn Tyr Asn Val Gly Gly
            195                 200                 205

Gly Trp Thr Ala Asn Met Asp His Asn His His Tyr Ser Ser Ala Pro
    210                 215                 220

Tyr Asn Phe Phe Asp Arg Pro Lys Pro Phe Gly Leu Asp Gly His
225                 230                 235                 240

Gln Glu Glu Glu Glu Cys Gly Gly Asp Ala Tyr Leu Glu His Arg Arg
                245                 250                 255

Thr Leu Pro Leu Phe Pro Met His Gly Glu Asp His Ile Asn Gly Ala
                260                 265                 270

Ser Trp Lys Tyr Gly Gln Leu Asp Gly His Asp Cys His Gly Arg Gly
                275                 280                 285

Pro Cys Ala Ser Leu Glu Leu Arg Leu Asn
                290                 295

<210> SEQ ID NO 57
<211> LENGTH: 298
<212> TYPE: PRT
<213> ORGANISM: Capsella rubella

<400> SEQUENCE: 57

Met Glu Pro Pro Gln His Gln His His His Gln Ala Asp Gln Glu
1               5                   10                  15

Ser Gly Asn Asn Asn Lys Ser Gly Ser Gly Tyr Thr Cys Arg
                20                  25                  30

Gln Thr Ser Thr Arg Trp Thr Pro Thr Thr Glu Gln Ile Arg Ile Leu
            35                  40                  45

Lys Asp Leu Tyr Tyr Asn Ser Ala Ile Arg Ser Pro Thr Ala Asp Gln
50                  55                  60

Ile Gln Lys Ile Thr Ala Arg Leu Arg Gln Tyr Gly Lys Ile Glu Gly
65              70                  75                  80

Lys Asn Val Phe Tyr Trp Phe Gln Asn His Lys Ala Arg Glu Arg Gln
                85                  90                  95

Lys Lys Arg Phe Asn Gly Thr Thr Met Thr Thr Pro Ser Ser Ser Pro
            100                 105                 110

Asn Ser Val Met Val Ala Asn Asp His Tyr His Pro Leu Leu His His
        115                 120                 125

His His Gly Val Pro Met Gln Arg Pro Ala Asn Ser Val Asn Val Lys
    130                 135                 140

Leu Asn Gln Asp His His Leu Tyr His Gln Asn Lys Ser Tyr Pro Thr
145                 150                 155                 160

Phe Asn Asn Gly Asn Leu Asn His Gly Ser Ser Gly Thr Glu Cys Gly
                165                 170                 175

Val Val Asn Ala Ser Asn Gly Tyr Met Ser Ser His Val Tyr Gly Ser
            180                 185                 190

Met Glu Gln Asp Cys Ser Met Asn Tyr Asn Asn Val Gly Thr Gly Gly
            195                 200                 205

Tyr Gly Ser Asn Met Asp His Ser His His Tyr Ser Ser Ala Pro Tyr
    210                 215                 220

Asn Phe Phe Asp Arg Ser Lys Pro Leu Phe Gly Leu Glu Gly His Gln
225                 230                 235                 240

Glu Asp Glu Glu Glu Tyr Gly Ile Gly Asp Ala Tyr Leu Glu His Arg
                245                 250                 255

Arg Thr Leu Pro Leu Phe Pro Met His Gly Glu Asp His Met Asn Gly

```
                260                 265                 270
Ser Gly Ala Ser Trp Lys Phe Asp Gly Arg Asp Cys His Gly Arg Gly
            275                 280                 285

Pro Cys Ala Ser Leu Glu Leu Arg Leu Asn
            290                 295

<210> SEQ ID NO 58
<211> LENGTH: 304
<212> TYPE: PRT
<213> ORGANISM: Arabis alpina

<400> SEQUENCE: 58

Met Glu Pro Pro Gln His His His His His Gln Ala Asp Gln Glu
1               5                   10                  15

Ser Gly Asn Asn Asn Lys Ser Gly Ser Gly Gly Tyr Thr Cys Arg
            20                  25                  30

Gln Thr Ser Thr Arg Trp Thr Pro Thr Thr Glu Gln Ile Arg Ile Leu
            35                  40                  45

Lys Asp Leu Tyr Tyr Asn Ser Gly Ile Arg Ser Pro Thr Ala Asp Glu
            50                  55                  60

Ile Gln Lys Ile Ser Ala Arg Leu Arg Gln Tyr Gly Lys Ile Glu Gly
65                  70                  75                  80

Lys Asn Val Phe Tyr Trp Phe Gln Asn His Lys Ala Arg Glu Arg Gln
                85                  90                  95

Lys Lys Arg Phe Asn Gly Thr Thr Met Thr Thr Thr Pro Thr Ser Ser
            100                 105                 110

Ser Pro Asn Ser Val Met Met Ala Ser Asp Arg Tyr His His Asn His
            115                 120                 125

His His His Pro Leu Leu Gln His His Gly Val Ser Met Gln Arg
            130                 135                 140

Pro Ala Ser Leu Asn Val Lys Leu His Asp Gln Glu His His Leu Leu
145                 150                 155                 160

His Gln Asn Lys Ser Tyr Pro Ser Phe Asn Asn Gly Asn Leu Asn His
                165                 170                 175

Ala Ser Ser Gly Ser Glu Cys Gly Ala Val Asn Ala Ser Asn Gly Tyr
            180                 185                 190

Met Ser Ser His Val Tyr Gly Ser Met Glu Gln Asp Tyr Ser Met Ser
            195                 200                 205

Asn Asn Asn Ile Gly Gly Gly Trp Ser Asn Met Asp His Asn His
210                 215                 220

His Tyr Ser Ser Pro Ala Tyr Asn Phe Phe Asp Arg Pro Lys Pro Leu
225                 230                 235                 240

Phe Gly Leu Glu Gly His Gln Glu Glu Asp Gln Tyr Gly Gly Asp Ala
                245                 250                 255

Tyr Leu Glu His Arg Arg Thr Leu Pro Leu Phe Pro Met His Gly Glu
            260                 265                 270

Asp His Ile Asn Gly Gly Gly Ala Ile Trp Lys Tyr Arg Gln Leu
            275                 280                 285

Asp Gly Leu Glu Leu Arg Leu Asn Ser Tyr Ala Gly Val Ala Pro Glu
            290                 295                 300

<210> SEQ ID NO 59
<211> LENGTH: 290
<212> TYPE: PRT
<213> ORGANISM: Raphanus sativus
```

<400> SEQUENCE: 59

Met Glu Pro Pro Gln His Tyr His Gln Ala Asp Gln Glu Ser Gly Asn
1               5                   10                  15

Asn Asn Lys Ser Val Ser Gly Gly Tyr Thr Cys Arg Gln Thr Ser Thr
            20                  25                  30

Arg Trp Thr Pro Thr Thr Asp Gln Ile Arg Ile Leu Lys Asp Leu Tyr
        35                  40                  45

Tyr Asn Asn Gly Val Arg Ser Pro Thr Ala Asp Gln Ile Gln Lys Ile
    50                  55                  60

Ser Ala Thr Leu Arg Gln Tyr Gly Lys Ile Glu Gly Lys Asn Val Phe
65                  70                  75                  80

Tyr Trp Phe Gln Asn His Lys Ala Arg Glu Arg Gln Lys Lys Arg Phe
                85                  90                  95

Asn Ser Thr Thr Met Ala Thr Pro Thr Ser Ser Ser Pro Asn Ser Val
            100                 105                 110

Met Met Met Ala Ser Asp His His His His Gly Val Thr Ile Gln
        115                 120                 125

Arg Pro Ala Leu Val Asn Val Lys Leu Asp Gln Glu Asn His Met Phe
130                 135                 140

His Gln Asn Arg Ser Tyr Pro Ser Ser Asn Asn Gly Ser Ile Asn His
145                 150                 155                 160

Ala Ser Ser Gly Thr Glu Tyr Gly Val Phe Gly Ala Ser Asn Gly Tyr
                165                 170                 175

Ile Ser Asn His Ile Tyr Gly Ser Met Glu Gln Asp Cys Ser Met Ser
            180                 185                 190

Tyr Asn Ser Val Gly Gly Gly Trp Thr Asn Met Asp His Asn His His
        195                 200                 205

Tyr Ser Thr Pro Ala Tyr Asn Phe Phe Asp Arg Pro Ser Pro Leu Ser
    210                 215                 220

Gly Leu Glu Gly His Gln Glu Glu Gly Gln Tyr Gly Gly Asp Ser Tyr
225                 230                 235                 240

Leu Glu His Arg Arg Thr Leu Pro Leu Phe Pro Leu His Gly Glu Asp
                245                 250                 255

His Ile Asn Gly Gly Gly Ser Ile Leu Lys Tyr Gly Gln Ser Asp
            260                 265                 270

Gly Cys Asp Arg Tyr Gly Arg Gly Pro Cys Ala Ser Leu Lys Leu Cys
        275                 280                 285

Leu Asn
    290

<210> SEQ ID NO 60
<211> LENGTH: 294
<212> TYPE: PRT
<213> ORGANISM: Brassica napus

<400> SEQUENCE: 60

Met Glu Pro Ala Gln His His Gln Ala Asp Gln Glu Ser Gly Asn
1               5                   10                  15

Asn Asn Lys Ser Val Ser Gly Gly Tyr Thr Cys Arg Gln Thr Ser Thr
            20                  25                  30

Arg Trp Thr Pro Thr Thr Asp Gln Ile Arg Ile Leu Lys Asp Leu Tyr
        35                  40                  45

Tyr Asn Asn Gly Val Arg Ser Pro Thr Ala Asp Gln Ile Gln Lys Ile
    50                  55                  60

```
Ser Ala Arg Leu Arg Gln Tyr Gly Lys Ile Glu Gly Lys Asn Val Phe
 65                  70                  75                  80

Tyr Trp Phe Gln Asn His Lys Ala Arg Glu Arg Gln Lys Lys Arg Phe
                 85                  90                  95

Asn Ser Thr Thr Met Thr Ile Pro Thr Ser Ser Ser Pro Asn Ser Val
                100                 105                 110

Met Met Ala Ser Asp His Tyr His His Asn His His His His Gly Val
                115                 120                 125

Thr Ile Gln Arg Pro Ala Leu Val Asn Val Lys Leu Asp Gln Glu Asn
            130                 135                 140

His Met Phe His Gln Asn Arg Ser Tyr Pro Ser Phe Asn Asn Gly Asn
145                 150                 155                 160

Thr Asn His Ala Ser Ser Gly Thr Glu Tyr Gly Val Phe Ser Ala Ser
                165                 170                 175

Asn Gly Tyr Ile Ser Ser His Ile Tyr Glu Pro Met Glu Gln Asp Cys
                180                 185                 190

Ser Met Ser Tyr Asn Asn Val Gly Gly Gly Trp Thr Asn Ile Asp His
                195                 200                 205

Asn His His Tyr Ser Thr Pro Ala Tyr Asn Phe Leu Asp Arg Pro Met
            210                 215                 220

Pro Leu Ser Gly Leu Glu Gly His His Gln Glu Glu Gly Glu Tyr Gly
225                 230                 235                 240

Gly Asp Ala Tyr Leu Glu His Arg Arg Thr Leu Pro Leu Phe Pro Leu
                245                 250                 255

His Gly Glu Asp His Ile Asn Gly Gly Gly Ser Ile Trp Lys Tyr
                260                 265                 270

Arg Gln Ser Asp Gly Cys Asp Arg Tyr Gly Arg Gly Pro Cys Ala Ser
            275                 280                 285

Leu Lys Leu Cys Leu Asn
            290

<210> SEQ ID NO 61
<211> LENGTH: 294
<212> TYPE: PRT
<213> ORGANISM: Brassica oleracea

<400> SEQUENCE: 61

Met Glu Pro Ala Gln His His His Gln Ala Asp Gln Glu Ser Gly Asn
  1               5                  10                  15

Asn Asn Lys Ser Val Ser Gly Gly Tyr Thr Cys Arg Gln Thr Ser Thr
                 20                  25                  30

Arg Trp Thr Pro Thr Thr Asp Gln Ile Arg Ile Leu Lys Asp Leu Tyr
             35                  40                  45

Tyr Asn Asn Gly Val Arg Ser Pro Thr Ala Asp Gln Ile Gln Lys Ile
     50                  55                  60

Ser Ala Arg Leu Arg Gln Tyr Gly Lys Ile Glu Gly Lys Asn Val Phe
 65                  70                  75                  80

Tyr Trp Phe Gln Asn His Lys Ala Arg Glu Arg Gln Lys Lys Arg Phe
                 85                  90                  95

Asn Ser Thr Thr Met Thr Ile Pro Thr Ser Ser Ser Pro Asn Ser Val
                100                 105                 110

Met Met Ala Ser Asp His Tyr His His Asn His His His His Gly Val
                115                 120                 125

Thr Ile Gln Arg Pro Ala Leu Val Asn Val Lys Leu Asp Gln Glu Asn
            130                 135                 140
```

```
His Met Phe His Gln Asn Arg Ser Tyr Pro Ser Phe Asn Asn Gly Asn
145                 150                 155                 160

Ile Asn His Ala Ser Ser Gly Thr Glu Tyr Gly Val Phe Ser Ala Ser
                165                 170                 175

Asn Gly Tyr Ile Ser Ser His Ile Tyr Gly Pro Met Glu Gln Asp Cys
            180                 185                 190

Ser Met Ser Tyr Asn Asn Val Gly Gly Gly Trp Thr Asn Ile Asp His
            195                 200                 205

Asn His His Tyr Ser Thr Pro Ala Tyr Asn Phe Leu Asp Arg Pro Met
    210                 215                 220

Pro Leu Ser Gly Leu Glu Gly His His Gln Glu Gly Glu Tyr Gly
225                 230                 235                 240

Gly Asp Ala Tyr Leu Glu His Arg Arg Thr Leu Pro Leu Phe Pro Leu
                245                 250                 255

His Gly Glu Asp His Ile Asn Gly Gly Gly Ser Ile Trp Lys Tyr
            260                 265                 270

Arg Gln Ser Asp Gly Cys Asp Arg Tyr Gly Arg Gly Pro Cys Ala Ser
            275                 280                 285

Leu Lys Leu Cys Leu Asn
    290

<210> SEQ ID NO 62
<211> LENGTH: 298
<212> TYPE: PRT
<213> ORGANISM: Helianthus annuus

<400> SEQUENCE: 62

Met Glu Thr Gln Gln Gln Ala Asp Ile Gln Asp Phe Gly Asn Lys
1               5                   10                  15

Asn Ser Asn Thr Tyr Ala Cys Arg Gln Ser Ser Thr Arg Trp Thr Pro
                20                  25                  30

Thr Ser Asp Gln Ile Arg Ile Leu Lys Glu Leu Tyr Tyr Asn Asn Gly
            35                  40                  45

Ile Arg Ser Pro Thr Ala Asp Gln Ile Gln Arg Ile Ala Ala Gln Leu
50                  55                  60

Arg Gln Tyr Gly Lys Ile Glu Gly Lys Asn Val Phe Tyr Trp Phe Gln
65                  70                  75                  80

Asn His Lys Ala Arg Glu Arg Gln Lys Lys Arg Phe Thr Pro Thr Ala
                85                  90                  95

Pro Pro Pro Pro Ser His Phe Ser Asp His Ile Asn His His Leu Pro
                100                 105                 110

Asn Ala Ala Pro Met Gln Ile Pro Ser His His His Tyr His His
            115                 120                 125

Gln Glu Pro Pro His Val Tyr Ala His Pro His Lys Leu Tyr Thr Thr
    130                 135                 140

His His Ile Gly Thr His Asn Ile Arg Val Gly Ser Ser Ser Gln Gly
145                 150                 155                 160

Val Met Gly Val Gly Cys Gly Tyr Gly Ser Val Ala Met Glu Lys Ser
                165                 170                 175

Phe Arg Lys Cys Ser Ile Ser Pro Pro Gly Glu Ser Lys Ala Thr Gly
            180                 185                 190

Gly Ile Gly Arg Asn Ile Gly Ser Arg Ser Arg Ile Ser Val Asp Ser
            195                 200                 205

Cys Ser Phe Phe Asp Thr Ile Lys Pro Lys Thr Tyr Glu Met Phe Glu
```

```
                         210                 215                 220
Asn Arg Asp Gln Asp Glu Glu Gln Gly Glu Pro Ser Thr Glu Ile Glu
225                 230                 235                 240

Thr Leu Pro Leu Phe Pro Ile His Asp Gly Asn His His Asp Phe Phe
                245                 250                 255

Gly Met Arg Thr Ala Asn Leu Pro Leu Glu Gln Gly Thr Gly Gly Tyr
                260                 265                 270

Tyr Thr Gly Gly Ser Trp Tyr Arg Ser Asp Glu Arg Ala Ser Leu Glu
                275                 280                 285

Leu Ser Leu Asn Ser Tyr Gly Tyr Tyr Asn
            290                 295

<210> SEQ ID NO 63
<211> LENGTH: 264
<212> TYPE: PRT
<213> ORGANISM: Populus trichocarpa

<400> SEQUENCE: 63

Met Glu Pro His Gln Gln Pro Asn Glu Asp Asn Gly Gly Ala
1               5                   10                  15

Lys Gly Asn Phe Leu Cys Arg Gln Thr Ser Thr Arg Trp Asn Pro Thr
                20                  25                  30

Thr Asp Gln Ile Arg Ile Leu Lys Glu Leu Tyr Tyr Ile Lys Gly Val
            35                  40                  45

Arg Ser Pro Asn Gly Ala Glu Ile Gln Gln Ile Ser Ala Arg Leu Arg
        50                  55                  60

Lys Tyr Gly Lys Ile Glu Gly Lys Asn Val Phe Tyr Trp Phe Gln Asn
65                  70                  75                  80

His Lys Ala Arg Glu Arg Gln Lys Lys Arg Leu Thr Asn Glu Val Pro
                85                  90                  95

Met Gln Gln Arg Thr Ala Trp Lys Pro Glu Asp Tyr Tyr Ser Tyr Lys
            100                 105                 110

Tyr Ser Asn Ser Asn Asn Asn Pro Gly Phe Ser Ser Ala Ser Ser Ser
        115                 120                 125

Ala Asn Thr Gly Val Val Thr Val Gly Gln Thr Asp Ser His Gly Tyr
    130                 135                 140

Gly Ser Val Thr Met Gln Glu Lys Asn Ser Trp Asp Cys Ser Ala Pro
145                 150                 155                 160

Ala Gly Gly Ser Asn Gly Ala Gly Ser Gly Ser Met Ser Asn Ile Asn
                165                 170                 175

Tyr Gly Ser Gly Val Asp Ile Asn Ser His Ser Ser Ser Tyr Ala Val
            180                 185                 190

Phe Gly Gln Glu Gln Glu Ala Ala Ala Lys Ile Glu Thr Leu Pro Leu
        195                 200                 205

Phe Pro Met Leu Gly Glu Asp Ile Ser Ser Ser Phe Asn Ile Asn Asn
    210                 215                 220

Ile Asn Pro Asp Phe Tyr Ser Ser Gly Cys Gly Tyr Gly Asp Tyr
225                 230                 235                 240

Gly Asn Asp Thr Ser Ser Arg Thr Ser Leu Asp Leu Ser Leu Tyr Ser
                245                 250                 255

Tyr Asn Gly Gln Pro Gln Asp Tyr
            260

<210> SEQ ID NO 64
<211> LENGTH: 280
```

```
<212> TYPE: PRT
<213> ORGANISM: Vitus vinifera

<400> SEQUENCE: 64

Met Glu Pro Gln Gln Leu Gln Gln Gln Gln Gln Asn Gln Gln
1               5                   10                  15

Gln Pro Asn Glu Asp Ser Gly Ser Lys Gly Ser Phe Leu Cys Arg
            20                  25                  30

Gln Ser Ser Thr Arg Trp Thr Pro Thr Thr Asp Gln Ile Arg Ile Leu
            35                  40                      45

Lys Asp Leu Tyr Tyr Asn Asn Gly Val Arg Ser Pro Ser Ala Glu Gln
            50                  55                  60

Ile Gln Arg Ile Ser Ala Arg Leu Arg Gln Tyr Gly Lys Ile Glu Gly
65                  70                  75                  80

Lys Asn Val Phe Tyr Trp Phe Gln Asn His Lys Ala Arg Glu Arg Gln
                85                  90                  95

Lys Lys Arg Phe Thr Thr Asp Met Pro Met Gln Arg Ser Leu Gly Asn
                100                 105                 110

Ala Gly Trp Arg Pro Asp Asp Pro Ile His Asn Lys Phe His Thr Ile
            115                 120                 125

Pro Thr Pro Gly Ile Ser Ser Pro Ser Ser Ser Ser Pro Ser Val
130                 135                 140

Leu Ala Val Gly Gln Met Gly Ser Phe Gly Tyr Gly Ser Val Glu Arg
145                 150                 155                 160

Ser Phe Thr Asp Cys Ser Ile Ser Ala Gly Gly Arg Gly Val
                165                 170                 175

Gly Gly Ser Ile Asn Gln Ser Phe Glu Trp Val Gly Met Asp Pro Tyr
            180                 185                 190

Ser Ser Ser Tyr Ala Leu Phe Asp Lys Arg Lys Thr Met Gly Glu Ser
            195                 200                 205

Phe Glu Glu Glu Gln Glu Glu Glu Ala Thr Pro Glu Ile Glu Thr Leu
            210                 215                 220

Pro Leu Phe Pro Met His Ala Glu Asp Ile Thr Gly Phe Cys Asn Ile
225                 230                 235                 240

Lys Pro Glu Ser Asp Ala Tyr Tyr Ser Gly Trp Tyr Arg Pro Ala Asp
                245                 250                 255

Ala Lys Thr Ser Ser Arg Thr Ser Leu Glu Leu Ser Leu Asn Ser Tyr
                260                 265                 270

Ala Gly Arg Ser Pro Asp Ser Pro
            275                 280

<210> SEQ ID NO 65
<211> LENGTH: 292
<212> TYPE: PRT
<213> ORGANISM: Arabidopsis thaliana

<400> SEQUENCE: 65

Met Glu Pro Pro Gln His Gln His His His Gln Ala Asp Gln Glu
1               5                   10                  15

Ser Gly Asn Asn Asn Asn Lys Ser Gly Ser Gly Gly Tyr Thr Cys
            20                  25                  30

Arg Gln Thr Ser Thr Arg Trp Thr Pro Thr Thr Glu Gln Ile Lys Ile
            35                  40                  45

Leu Lys Glu Leu Tyr Tyr Asn Asn Ala Ile Arg Ser Pro Thr Ala Asp
50                  55                  60
```

```
Gln Ile Gln Lys Ile Thr Ala Arg Leu Arg Gln Phe Gly Lys Ile Glu
 65                  70                  75                  80

Gly Lys Asn Val Phe Tyr Trp Phe Gln Asn His Lys Ala Arg Glu Arg
                 85                  90                  95

Gln Lys Lys Arg Phe Asn Gly Thr Asn Met Thr Thr Pro Ser Ser Ser
            100                 105                 110

Pro Asn Ser Val Met Met Ala Ala Asn Asp His Tyr His Pro Leu Leu
            115                 120                 125

His His His His Gly Val Pro Met Gln Arg Pro Ala Asn Ser Val Asn
130                 135                 140

Val Lys Leu Asn Gln Asp His His Leu Tyr His His Asn Lys Pro Tyr
145                 150                 155                 160

Pro Ser Phe Asn Asn Gly Asn Leu Asn His Ala Ser Ser Gly Thr Glu
                165                 170                 175

Cys Gly Val Val Asn Ala Ser Asn Gly Tyr Met Ser Ser His Val Tyr
                180                 185                 190

Gly Ser Met Glu Gln Asp Cys Ser Met Asn Tyr Asn Asn Val Gly Gly
            195                 200                 205

Gly Trp Ala Asn Met Asp His His Tyr Ser Ser Ala Pro Tyr Asn Phe
210                 215                 220

Phe Asp Arg Ala Lys Pro Leu Phe Gly Leu Glu Gly His Gln Glu Glu
225                 230                 235                 240

Glu Glu Cys Gly Gly Asp Ala Tyr Leu Glu His Arg Arg Thr Leu Pro
                245                 250                 255

Leu Phe Pro Met His Gly Glu Asp His Ile Asn Gly Ser Gly Ala
            260                 265                 270

Ile Trp Lys Tyr Gly Gln Ser Glu Val Arg Pro Cys Ala Ser Leu Glu
            275                 280                 285

Leu Arg Leu Asn
290

<210> SEQ ID NO 66
<211> LENGTH: 292
<212> TYPE: PRT
<213> ORGANISM: Lotus japonicus

<400> SEQUENCE: 66

Met Glu Gln Pro Pro Gln Gln Gln Gln Asn Glu Asp Gly Gly
  1               5                  10                  15

Ser Ser Gly Gly Lys Gly Gly Phe Leu Ser Arg Gln Ser Ser Thr Arg
                 20                  25                  30

Trp Thr Pro Thr Thr Asp Gln Ile Arg Ile Leu Lys Glu Leu Tyr Tyr
             35                  40                  45

Asn Asn Gly Ile Arg Ser Pro Ser Ala Glu Gln Ile Gln Arg Ile Ser
 50                  55                  60

Ala Arg Leu Arg Gln Tyr Gly Lys Ile Glu Gly Lys Asn Val Phe Tyr
 65                  70                  75                  80

Trp Phe Gln Asn His Lys Ala Arg Glu Arg Gln Lys Lys Arg Phe Thr
                 85                  90                  95

Ser Glu Thr His Leu Leu Pro Asn Pro Ile Gln Gln Gln Arg Asn
            100                 105                 110

Gly Thr Asn Ala Ala Trp Lys Gln Pro Glu Glu Gln Pro Ile Ile Asn
            115                 120                 125

His Thr Lys Tyr Ser Ser Asn Asn Ile Ser Ala Pro Ala Gly Ile Ile
130                 135                 140
```

```
Thr Ser Ala Pro Ser Ser Ala Glu Ile Val Ser Val Gly Gln Ile
145                 150                 155                 160

Gly Asn Phe Gly Tyr Gly Ser Leu Pro Met Glu Lys Ser Phe Arg Asp
                165                 170                 175

Cys Ser Ile Ser Ala Gly Gly Asn Thr Gly Tyr Ala Gly Ser Ala Ile
            180                 185                 190

Asn His Asn Leu Gly Trp Met Gly Val Asp Pro Tyr Ser Ser Ala Tyr
            195                 200                 205

Thr Asn Phe Phe Asp Lys Ile Arg Pro Thr Glu Glu Thr Met Glu
        210                 215                 220

Glu Glu Gly Gln Glu Asn Gly Ser Pro Glu Ile Glu Thr Leu Pro Leu
225                 230                 235                 240

Phe Pro Met His Gly Glu Asp Ile His Ser Gly Tyr Phe Asn Leu Lys
                245                 250                 255

Ser Asn Ser Ser His Tyr Ala Gly Gly Trp Tyr Gln Thr Glu Glu Gly
            260                 265                 270

Tyr Phe Asn Asn Gly Ser Arg Ala Ser Leu Glu Leu Ser Leu Lys Tyr
            275                 280                 285

Pro Asp Phe Ala
    290

<210> SEQ ID NO 67
<211> LENGTH: 302
<212> TYPE: PRT
<213> ORGANISM: Medicago trunculata

<400> SEQUENCE: 67

Met Glu Gln Pro Gln Gln Gln Gln Pro Gln Thr Gln His Ser
1               5                   10                  15

Pro Asn Asn Gly Ile Met Gly Ser Arg Gln Ser Ser Thr Arg Trp Thr
                20                  25                  30

Pro Thr Thr Asp Gln Ile Arg Ile Leu Lys Asp Leu Tyr Tyr Asn Asn
            35                  40                  45

Gly Ile Arg Ser Pro Ser Ala Glu Gln Ile Gln Arg Ile Ser Ala Arg
50                  55                  60

Leu Arg Gln Tyr Gly Lys Ile Glu Gly Lys Asn Val Phe Tyr Trp Phe
65                  70                  75                  80

Gln Asn His Lys Ala Arg Glu Arg Gln Lys Arg Phe Thr Ser Asp
                85                  90                  95

Val Asn Val Val Pro Ile Ile Gln Arg Ala Pro Asn Asn Thr Ile
            100                 105                 110

Ile Ser Ala Ala Asn Trp Lys Pro Asp His His Glu Gln Gln Gln Asn
            115                 120                 125

Ile Asn Val His Thr Asn His Ser Thr Tyr Asn Ile Ser Ser Ala Gly
            130                 135                 140

Leu Ser Ser Ala Ser Cys Ser Ser Ala Glu Met Val Thr Val Gly Gln
145                 150                 155                 160

Ile Gly Asn Tyr Gly Tyr Gly Ser Val Pro Met Glu Lys Ser Phe Arg
                165                 170                 175

Glu Cys Thr Ile Ser Ala Gly Cys Ser Ser Gln Val Gly Ser Thr
            180                 185                 190

Ile Asn Pro His Ile Gly Trp Ile Gly His His Val Asp Pro Tyr Ser
            195                 200                 205

Ser Ala Tyr Ala Asn Leu Phe Glu Lys Ile Arg Pro Asn Glu Glu Ile
```

```
            210                 215                 220
Met Glu Glu Tyr Asp Gln Gly Gln Asn Gly Ser Pro Glu Ile Glu
225                 230                 235                 240

Thr Leu Pro Leu Phe Pro Met His Gly Glu Asp Ile His Gly Gly Tyr
                245                 250                 255

Cys Asn Leu Lys Ser Asn Ser Ser Asn Tyr Gly Gly Trp Tyr Gln Ala
                260                 265                 270

Glu Asp Ala Gly Phe Met Tyr Gly Ser Arg Thr Thr Ser Leu Glu Leu
                275                 280                 285

Ser Leu Asn Ser Tyr Gly Cys Arg Ser Pro Asp Tyr Ala Asn
                290                 295                 300

<210> SEQ ID NO 68
<211> LENGTH: 307
<212> TYPE: PRT
<213> ORGANISM: Petunia hybrida

<400> SEQUENCE: 68

Met Glu Thr Ala Gln His Gln Gln Asn Asn Gln Gln His Tyr Leu His
1               5                   10                  15

Gln His Leu Ser Ile Gly Gln Gly Thr Asn Ile Glu Asp Gly Ser Asn
                20                  25                  30

Lys Asn Asn Ser Ser Asn Phe Met Cys Arg Gln Asn Ser Thr Arg Trp
                35                  40                  45

Thr Pro Thr Thr Asp Gln Ile Arg Ile Leu Lys Asp Leu Tyr Tyr Asn
                50                  55                  60

Asn Gly Val Arg Ser Pro Thr Ala Glu Gln Ile Gln Arg Ile Ser Ala
65              70                  75                  80

Lys Leu Arg Gln Tyr Gly Lys Ile Glu Gly Lys Asn Val Phe Tyr Trp
                85                  90                  95

Phe Gln Asn His Lys Ala Arg Glu Arg Gln Lys Lys Arg Leu Ile Ala
                100                 105                 110

Ala Ala Thr Thr Asp Asn Thr Asn Leu Pro Met Gln Met Gln Phe Gln
                115                 120                 125

Arg Gly Val Trp Arg Ser Ala Asp Asp Pro Ile His His Lys Tyr
                130                 135                 140

Thr Asn Pro Gly Val His Cys Pro Ser Ala Ser Ser His Gly Val Leu
145                 150                 155                 160

Ala Val Gly Gln Asn Gly Asn His Gly Tyr Gly Ala Leu Ala Met Glu
                165                 170                 175

Lys Ser Phe Arg Asp Cys Ser Ile Ser Pro Gly Ser Ser Met Ser His
                180                 185                 190

His His His Gln Asn Phe Ala Trp Ala Gly Val Asp Pro Tyr Ser Ser
                195                 200                 205

Thr Thr Thr Tyr Pro Phe Leu Glu Lys Thr Lys His Phe Glu Asn Glu
                210                 215                 220

Thr Leu Glu Ala Asp Glu Gln Gln Glu Glu Asp Gln Glu Asn Tyr
225                 230                 235                 240

Tyr Tyr Gln Arg Thr Thr Ser Ala Ile Glu Thr Leu Pro Leu Phe Pro
                245                 250                 255

Met His Glu Glu Asn Ile Ser Ser Phe Cys Asn Leu Lys His Gln Glu
                260                 265                 270

Ser Ser Gly Gly Phe Tyr Thr Glu Trp Tyr Arg Ala Asp Asp Asn Leu
                275                 280                 285
```

```
Ala Ala Ala Arg Ala Ser Leu Glu Leu Ser Leu Asn Ser Phe Ile Gly
    290                 295                 300

Asn Ser Ser
305
```

<210> SEQ ID NO 69
<211> LENGTH: 287
<212> TYPE: PRT
<213> ORGANISM: Phaseolus vulgaris

<400> SEQUENCE: 69

```
Met Glu Pro Gln Gln Pro Gln Gly Ser Gln Pro Asn Glu Asp Gly Gly
1               5                   10                  15

Ser Gly Lys Gly Gly Phe Leu Ser Arg Gln Ser Ser Thr Arg Trp Thr
                20                  25                  30

Pro Thr Thr Asp Gln Ile Arg Ile Leu Lys Asp Leu Tyr Tyr Asn Asn
            35                  40                  45

Gly Ile Arg Ser Pro Ser Ala Glu Gln Ile Gln Arg Ile Ser Ala Arg
        50                  55                  60

Leu Arg Gln Tyr Gly Lys Ile Glu Gly Lys Asn Val Phe Tyr Trp Phe
65                  70                  75                  80

Gln Asn His Lys Ala Arg Glu Arg Gln Lys Arg Phe Thr Ser Asp
                85                  90                  95

Asn Val Pro Met Gln Arg Pro Ala Pro Thr Asn Ala Ala Pro Pro Trp
                100                 105                 110

Lys Pro Asp Gln Asp Pro Ile His Thr Lys Tyr Ser Asn Ile Ser Ser
            115                 120                 125

Thr Gly Ile Ser Ser Ala Ser Ser Ser Val Glu Met Ile Thr Val
        130                 135                 140

Gly Gln Met Gly Asn Tyr Gly Tyr Gly Ser Val Pro Met Glu Lys Ser
145                 150                 155                 160

Phe Arg Asp Cys Ser Ile Ser Ala Gly Gly Ser Ser His Val Gly
                165                 170                 175

Ile Asn His Asn Leu Gly Trp Val Gly Val Asp Pro Tyr Ser Ser Ala
            180                 185                 190

Tyr Ala Asn Phe Phe Asp Lys Ile Arg Pro Asn Glu Glu Thr Leu Glu
        195                 200                 205

Glu Glu Glu Glu Glu Glu Glu Glu Glu Glu Asp Gly Gly Ala
    210                 215                 220

Glu Ile Glu Thr Leu Pro Leu Phe Pro Met His Gly Glu Asp Ile His
225                 230                 235                 240

Gly Tyr Cys Asn Leu Lys Ser Asn Ser Tyr Asn Tyr Asp Gly Asn Gly
                245                 250                 255

Trp Tyr His Ser Glu Asp Gly Phe Lys Asn Gly Ser Arg Ala Ser Leu
            260                 265                 270

Glu Leu Ser Leu Asn Ser Tyr Thr Arg Arg Ser Pro Asp Phe Ala
        275                 280                 285
```

<210> SEQ ID NO 70
<211> LENGTH: 320
<212> TYPE: PRT
<213> ORGANISM: Zea mays

<400> SEQUENCE: 70

```
Met Ala Ala Asn Val Gly Ala Gly Arg Ser Ala Gly Gly Gly Gly Ala
1               5                   10                  15
```

Gly Thr Gly Thr Gly Thr Ala Ala Gly Ser Gly Val Ser Thr Ala
            20                  25                  30

Val Cys Arg Pro Ser Gly Ser Arg Trp Thr Pro Thr Pro Glu Gln Ile
        35                  40                  45

Arg Ile Leu Lys Glu Leu Tyr Tyr Gly Cys Gly Ile Arg Ser Pro Asn
    50                  55                  60

Ser Glu Gln Ile Gln Arg Ile Thr Ala Met Leu Arg Gln His Gly Lys
65                  70                  75                  80

Ile Glu Gly Lys Asn Val Phe Tyr Trp Phe Gln Asn His Lys Ala Arg
                85                  90                  95

Glu Arg Gln Lys Arg Arg Leu Thr Asn Leu Asp Val Asn Val Pro Val
            100                 105                 110

Ala Ala Asp Asp Ser Ala His Arg Leu Gly Val Leu Ser Leu Ser Pro
        115                 120                 125

Ser Ser Gly Cys Ser Gly Ala Ala Pro Pro Ser Pro Thr Leu Gly Phe
    130                 135                 140

Tyr Ala Gly Gly Asn Gly Ser Ala Val Met Leu Asp Thr Ser Ser Asp
145                 150                 155                 160

Trp Gly Ser Ala Ala Ala Met Ala Thr Glu Ala Cys Phe Met Gln Asp
                165                 170                 175

Tyr Met Gly Val Met Gly Gly Ala Ser Pro Trp Ala Cys Ser Ser Ser
            180                 185                 190

Ser Ser Glu Asp Pro Met Ala Ala Leu Ala Leu Ala Pro Lys Val Thr
        195                 200                 205

Arg Ala Pro Glu Thr Leu Pro Leu Phe Pro Thr Gly Gly Gly Gly Asp
    210                 215                 220

Asp Arg Gln Pro Pro Arg Pro Arg Gln Ser Val Pro Ala Gly Glu Ala
225                 230                 235                 240

Ile Arg Gly Gly Ser Ser Ser Ser Tyr Leu Pro Phe Trp Gly Ala
                245                 250                 255

Ala Pro Thr Pro Thr Gly Ser Ala Thr Ser Val Ala Ile Gln Gln Gln
            260                 265                 270

His Gln Leu Met Gln Met Gln Glu Gln Tyr Ser Phe Tyr Ser Asn Ala
        275                 280                 285

Gln Leu Leu Pro Gly Thr Gly Ser Gln Asp Ala Ala Ala Thr Ser Leu
    290                 295                 300

Glu Leu Ser Leu Ser Ser Trp Cys Ser Pro Tyr Pro Ala Gly Thr Met
305                 310                 315                 320

<210> SEQ ID NO 71
<211> LENGTH: 325
<212> TYPE: PRT
<213> ORGANISM: Zea mays

<400> SEQUENCE: 71

Met Ala Ala Asn Ala Gly Gly Gly Gly Ala Gly Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45

Cys Gly Ile Arg Ser Pro Ser Ser Glu Gln Ile Gln Arg Ile Thr Ala
    50                  55                  60

Met Leu Arg Gln His Gly Lys Ile Glu Gly Lys Asn Val Phe Tyr Trp
65                  70                  75                  80

```
Phe Gln Asn His Lys Ala Arg Glu Arg Gln Lys Arg Leu Thr Ser
                85                  90                  95

Leu Asp Val Asn Val Pro Ala Ala Gly Ala Asp Ala Thr Thr Ser
            100                 105                 110

Gln Leu Gly Val Leu Ser Leu Ser Ser Pro Ser Gly Ala Ala Pro
        115                 120                 125

Pro Ser Pro Thr Leu Gly Phe Tyr Ala Ala Gly Asn Gly Gly Ser
    130                 135                 140

Ala Gly Leu Leu Asp Thr Ser Ser Asp Trp Gly Ser Ser Gly Ala Ala
145                 150                 155                 160

Met Ala Thr Glu Thr Cys Phe Leu Gln Asp Tyr Met Gly Val Thr Asp
                165                 170                 175

Thr Gly Ser Ser Ser Gln Trp Pro Cys Phe Ser Ser Ser Asp Thr Ile
                180                 185                 190

Met Ala Ala Ala Ala Ala Ala Arg Val Ala Thr Thr Arg Ala Pro
                195                 200                 205

Glu Thr Leu Pro Leu Phe Pro Thr Cys Gly Asp Asp Asp Asp Asp
                210                 215                 220

Ser Gln Pro Pro Arg Pro Arg His Ala Val Pro Val Pro Ala Gly
225                 230                 235                 240

Glu Thr Ile Arg Gly Gly Gly Ser Ser Ser Tyr Leu Pro Phe
                245                 250                 255

Trp Gly Ala Gly Ala Ala Ser Thr Thr Ala Gly Ala Thr Ser Ser Val
                260                 265                 270

Ala Ile Gln Gln Gln His Gln Leu Gln Glu Gln Tyr Ser Phe Tyr Ser
                275                 280                 285

Asn Ser Thr Gln Leu Ala Gly Thr Gly Ser Gln Asp Val Ser Ala Ser
                290                 295                 300

Ala Ala Ala Leu Glu Leu Ser Leu Ser Ser Trp Cys Ser Pro Tyr Pro
305                 310                 315                 320

Ala Ala Gly Ser Met
                325

<210> SEQ ID NO 72
<211> LENGTH: 221
<212> TYPE: PRT
<213> ORGANISM: Zea mays

<400> SEQUENCE: 72

Met Glu Ala Leu Ser Gly Arg Val Gly Val Lys Cys Gly Arg Trp Asn
1               5                   10                  15

Pro Thr Ala Glu Gln Val Lys Val Leu Thr Glu Leu Phe Arg Ala Gly
                20                  25                  30

Leu Arg Thr Pro Ser Thr Glu Gln Ile Gln Arg Ile Ser Thr His Leu
            35                  40                  45

Ser Ala Phe Gly Lys Val Glu Ser Lys Asn Val Phe Tyr Trp Phe Gln
        50                  55                  60

Asn His Lys Ala Arg Glu Arg His His His Lys Lys Arg Arg Arg Gly
65                  70                  75                  80

Ala Ser Ser Ser Ser Pro Asp Ser Gly Ser Gly Arg Gly Ser Asn Asn
                85                  90                  95

Glu Glu Asp Gly Arg Gly Ala Ala Ser Gln Ser His Asp Ala Asp Ala
                100                 105                 110

Asp Ala Asp Leu Val Leu Gln Pro Pro Glu Ser Lys Arg Glu Ala Arg
```

```
              115                 120                 125
Ser Tyr Gly His His Arg Leu Val Thr Cys Tyr Val Arg Asp Val
            130                 135                 140

Val Glu Gln Gln Glu Ala Ser Pro Ser Trp Glu Arg Pro Thr Arg Glu
145                 150                 155                 160

Val Glu Thr Leu Glu Leu Phe Pro Leu Lys Ser Tyr Gly Asp Leu Glu
                165                 170                 175

Ala Ala Glu Lys Val Arg Ser Tyr Val Arg Gly Ser Gly Ala Thr Ser
            180                 185                 190

Glu Gln Cys Arg Glu Leu Ser Phe Phe Asp Val Val Ser Ala Gly Arg
            195                 200                 205

Asp Pro Pro Leu Glu Leu Arg Leu Cys Ser Phe Gly Pro
210                 215                 220
```

<210> SEQ ID NO 73
<211> LENGTH: 368
<212> TYPE: DNA
<213> ORGANISM: Zea mays

<400> SEQUENCE: 73

| | | | | | |
|---|---|---|---|---|---|
| atggcggcca | atgcgggcgg | cggtggagcg | ggaggaggca | gcggcagcgg | cagcgtggct | 60 |
| gcgccggcgg | tgtgccgccc | cagcggctcg | cggtggacgc | cgacgccgga | gcagatcagg | 120 |
| atgctgaagg | agctctacta | cggctgcggc | atccggtcgc | ccagctcgga | gcagatccag | 180 |
| cgcatcaccg | ccatgctgcg | gcagcacggc | aagatcgagg | gcaagaacgt | cttctactgg | 240 |
| ttccagaacc | acaaggcccg | cgagcgccag | aagcgccgcc | tcaccagcct | cgacgtcaac | 300 |
| gtgcccgccg | ccggcgcggc | cgacgccacc | accagccaac | tcggcgtcct | ctcgctgtcg | 360 |
| tcgccgcc | | | | | | 368 |

<210> SEQ ID NO 74
<211> LENGTH: 971
<212> TYPE: DNA
<213> ORGANISM: Zea mays

<400> SEQUENCE: 74

| | | | | | |
|---|---|---|---|---|---|
| ccctagctcc | ctgcggctgt | tacgcggtcc | cccatcaatc | ttctgttctt | gcggttgtag | 60 |
| cctgtgtaac | agtgctagag | tatgtatgat | aaataggttt | taagtctgct | acatgacat | 120 |
| tttttattgt | ggaagagaca | tataaaaatt | agagagagtg | gttctcatgc | aacggcggac | 180 |
| ggcccggtgc | taaaagagct | tcaagacaaa | ataatgaaac | aggaagagag | tagatttatc | 240 |
| taagagccaa | ctttattata | tgaatgtgtt | tattgttggc | tttagatgat | atggtaagga | 300 |
| gttagagcta | ataatagata | ggctctatta | ttattattat | taattaaact | cgctctaagg | 360 |
| aggaaagtgg | gaggaaggga | cgaggacgaa | gactactgga | agcatcgtgc | atggatgatg | 420 |
| gatgtggtgt | ctcttaatgt | aggtggccgg | aggatgtacg | tgttaattgc | gcgataagca | 480 |
| ctcagatcca | accgcaaact | acctccacac | tgacacactg | atagagagaa | agagagacct | 540 |
| ccgacgactg | ccgccgcaga | tgagccacgt | acgtatacga | cgtctgccgg | ccggctcagg | 600 |
| ctgccgccat | caccctgctc | gaaagtcgcg | ttaggcggcg | ccagctacat | aggagtatct | 660 |
| agtctagcca | gttagtatac | tactactgcg | ctgatgatga | attaactctg | catagatact | 720 |
| gtacttgcct | ccctccaaca | cccaaccacc | tcctgctcgg | ctcttaataa | cttggacacg | 780 |
| gatcgatgcc | atccaaggaa | gaacacgacg | acgacgacga | acatccacc | atgcaagctt | 840 |
| gcatccatac | gccgatacgc | gtgcatccat | ccatccacca | ttatttccat | tttccaccga | 900 |

| | | |
|---|---|---|
| tcacacgtac acaggcctat ttaaggagcg acatcccact gcaactctcc tcaccactca | | 960 |
| tcaccagcta g | | 971 |

<210> SEQ ID NO 75
<211> LENGTH: 896
<212> TYPE: DNA
<213> ORGANISM: Zea mays

<400> SEQUENCE: 75

| | |
|---|---|
| gtgcagcgtg acccggtcgt gccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag ttttatcttt ttagtgtgca tgtgttctcc ttttttttg | 300 |
| caaatagctt cacctatata atacttcatc cattttatta gtacatccat ttagggttta | 360 |
| gggttaatgg ttttataga ctaattttt tagtacatct attttattct attttagcct | 420 |
| ctaaattaag aaaactaaaa ctctattta gttttttat ttaataattt agatataaaa | 480 |
| tagaataaaa taaagtgact aaaaattaaa caaatacct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggacccct ctcgagagtt ccgctccacc gttggacttg | 720 |
| ctccgctgtc ggcatccaga aattgcgtgg cggagcggca gacgtgagcc ggcacggcag | 780 |
| gcggcctcct cctcctctca cggcaccggc agctacgggg gattccttc ccaccgctcc | 840 |
| ttcgctttcc cttcctcgcc cgccgtaata aatagacacc cctccacac cctctt | 896 |

<210> SEQ ID NO 76
<211> LENGTH: 189
<212> TYPE: DNA
<213> ORGANISM: Solanum tuberosum

<400> SEQUENCE: 76

| | |
|---|---|
| gtaagtttct gcttctacct ttgatatata tataataatt atcattaatt agtagtaata | 60 |
| taatatttca aatatttttt tcaaaataaa agaatgtagt atatagcaat tgcttttctg | 120 |
| tagtttataa gtgtgtatat tttaatttat aactttttcta atatatgacc aaaacatggt | 180 |
| gatgtgcag | 189 |

<210> SEQ ID NO 77
<211> LENGTH: 795
<212> TYPE: DNA
<213> ORGANISM: Escherichia coli

<400> SEQUENCE: 77

| | |
|---|---|
| atggttgaac aagatggatt gcacgcaggt tctccggccg cttgggtgga gaggctattc | 60 |
| ggctatgact gggcacaaca gacaatcggc tgctctgatg ccgccgtgtt ccggctgtca | 120 |
| gcgcagggc gcccggttct ttttgtcaag accgacctgt ccggtgccct gaatgaactg | 180 |
| caggacgagg cagcgcggct atcgtggctg gccacgacgg gcgttccttg cgcagctgtg | 240 |
| ctcgacgttg tcactgaagc gggaagggac tggctgctat tgggcgaagt gccggggcag | 300 |
| gatctcctgt catctcacct tgctcctgcc gagaaagtat ccatcatggc tgatgcaatg | 360 |

```
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgatgatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795

<210> SEQ ID NO 78
<211> LENGTH: 48
<212> TYPE: DNA
<213> ORGANISM: Artificial
<220> FEATURE:
<223> OTHER INFORMATION: donor DNA homology arm 1

<400> SEQUENCE: 78
gaagttccta ttccgaagtt cctattctct agaaagtata ggaacttc                 48

<210> SEQ ID NO 79
<211> LENGTH: 48
<212> TYPE: DNA
<213> ORGANISM: Artificial
<220> FEATURE:
<223> OTHER INFORMATION: donor DNA homology arm 2

<400> SEQUENCE: 79
gaagttccta ttccgaagtt cctattcttc aaaaagtata ggaacttc                 48

<210> SEQ ID NO 80
<211> LENGTH: 20
<212> TYPE: DNA
<213> ORGANISM: Artificial
<220> FEATURE:
<223> OTHER INFORMATION: gRNA

<400> SEQUENCE: 80
ggattccgcg gaaatgggtg                                               20

<210> SEQ ID NO 81
<211> LENGTH: 19
<212> TYPE: DNA
<213> ORGANISM: Artificial
<220> FEATURE:
<223> OTHER INFORMATION: gRNA

<400> SEQUENCE: 81
gtcaaggaca tacgagacc                                                19

<210> SEQ ID NO 82
<211> LENGTH: 77
<212> TYPE: DNA
<213> ORGANISM: Artificial
<220> FEATURE:
<223> OTHER INFORMATION: gRNA

<400> SEQUENCE: 82
gttttagagc tagaaatagc aagttaaaat aaggctagtc cgttatcaac ttgaaaaagt    60
ggcaccgagt cggtgct                                                  77
```

```
<210> SEQ ID NO 83
<211> LENGTH: 297
<212> TYPE: DNA
<213> ORGANISM: Arabidopsis thaliana

<400> SEQUENCE: 83
acgtgcgcca aggacatcca aaaagcagcc gcggaggcgg cactcgcctt tcaggacgag      60
acctgcgaca ccaccaccac caaccacggc ctcgacatgg aggagaccat ggtcgaagcc     120
atctacaccc ccgagcagag cgagggcgcc ttctacatgg acgaagagac aatgttcggc     180
atgccaaccc tcctcgacaa catggccgaa ggcatgctgc tgccgccccc gagcgtccag     240
tggaaccaca actacgacgg cgaaggcgac ggggatgtgt ccctgtggag ctactag        297

<210> SEQ ID NO 84
<211> LENGTH: 1000
<212> TYPE: DNA
<213> ORGANISM: Zea mays

<400> SEQUENCE: 84
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga gggggcatca     480
aagatctggc tgtgtttcca gctgtttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaaatgct     660
attcgaattt ctactagcag taagtcgtgt ttagaaatta ttttttttata tacctttttt     720 ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga     960
gtggagcgta ccttataaac cgagccgcaa gcaccgaatt                          1000

<210> SEQ ID NO 85
<211> LENGTH: 18
<212> TYPE: DNA
<213> ORGANISM: Artificial
<220> FEATURE:
<223> OTHER INFORMATION: gRNA

<400> SEQUENCE: 85
gcctttgcag tttgcacc                                                    18

<210> SEQ ID NO 86
<211> LENGTH: 18
<212> TYPE: DNA
<213> ORGANISM: Artificial
<220> FEATURE:
<223> OTHER INFORMATION: gRNA
```

```
<400> SEQUENCE: 86
gcctttgcag tttgcacc                                                    18

<210> SEQ ID NO 87
<211> LENGTH: 18
<212> TYPE: DNA
<213> ORGANISM: Artificial
<220> FEATURE:
<223> OTHER INFORMATION: gRNA

<400> SEQUENCE: 87
gttgccacaa ggggagcc                                                    18

<210> SEQ ID NO 88
<211> LENGTH: 20
<212> TYPE: DNA
<213> ORGANISM: Artificial
<220> FEATURE:
<223> OTHER INFORMATION: gRNA

<400> SEQUENCE: 88
gcaaatgact tctgtctcta                                                  20

<210> SEQ ID NO 89
<211> LENGTH: 20
<212> TYPE: DNA
<213> ORGANISM: Artificial
<220> FEATURE:
<223> OTHER INFORMATION: gRNA

<400> SEQUENCE: 89
gactcttcca aatttcgaag                                                  20

<210> SEQ ID NO 90
<211> LENGTH: 20
<212> TYPE: DNA
<213> ORGANISM: Artificial
<220> FEATURE:
<223> OTHER INFORMATION: gRNA

<400> SEQUENCE: 90
gtcgtatcac ccatgggcaa                                                  20

<210> SEQ ID NO 91
<211> LENGTH: 971
<212> TYPE: DNA
<213> ORGANISM: Zea mays

<400> SEQUENCE: 91
ccctagctcc ctgcggctgt tacgcggtcc cccatcaatc ttctgttctt gcggttgtag      60
cctgtgtaac agtgctagag tatgtatgat aaataggttt taagtctgct tacatgacat     120 ttttttattgt ggaagagaca tataaaaatt agagagagtg gttctcatgc aacggcggac    180
ggcccggtgc taaaagagct tcaagacaaa ataatgaaac aggaagagag tagatttatc    240
taagagccaa ctttattata tgaatgtgtt tattgttggc tttagatgat atggtaagga    300
gttagagcta ataatagata ggctctatta ttattattat taattaaact cgctctaagg    360
aggaaagtgg gaggaaggga cgaggacgaa gactactgga agcatcgtgc atggatgatg    420
gatgtggtgt ctcttaatgt aggtggccgg aggatgtacg tgttaattgc gcgataagca    480
ctcagatcca accgcaaact acctccacac tgacacactg atagagagaa agagagacct    540
ccgacgactg ccgccgcaga tgagccacgt acgtatacga cgtctgccgg ccggctcagg    600
```

```
ctgccgccat caccctgctc gaaagtcgcg ttaggcggcg ccagctacat aggagtatct      660
agtctagcca gttagtatac tactactgcg ctgatgatga attaactctg catagatact      720
gtacttgcct ccctccaaca cccaaccacc tcctgctcgg ctcttaataa cttggacacg      780
gatcgatgcc atccaaggaa gaacacgacg acgacgacgg aacatccacc atgcaagctt      840
gcatccatac gccgatacgc gtgcatccat ccatccacca ttatttccat tttccaccga      900
tcacacgtac acaggcctat ttaaggagcg acatcccact gcaactctcc tcaccactca      960
tcaccagcta g                                                           971
```

```
<210> SEQ ID NO 92
<211> LENGTH: 91
<212> TYPE: DNA
<213> ORGANISM: Zea mays

<400> SEQUENCE: 92
ctctagcaaa gcacttgcca tctaccgacc gccgcattcc aaacagcccg acgagctagc      60
agagcggcag gcacctccct cctcaaggaa c                                     91
```

```
<210> SEQ ID NO 93
<211> LENGTH: 1200
<212> TYPE: DNA
<213> ORGANISM: Setarica italica

<400> SEQUENCE: 93
tagcgtggca tttggcaccg ccgcacacta tgcgagctag gagtgctagt ttacagatga      60
aactatgaaa ccaagaaaac acaattgtcc gtagctagcg cgtggcgtcg tgtcaagctt     120
cacacagtat cttcgttctt cactataaat cgcgcctgtt gttcgtgaga cccaccaccg     180
tggataacag tccctaata ataagcgatc aacagcactg ctgatggctg aacaccgagg      240
cgccgccgcg cgtaaccatc cgccggagca gcccgtcgtg ccggcgaacg acgccttccc     300
cgaccgcgcc cagcagctct gcctcgacgc cgggcgcgcg ctcgcgatgt gcggcgtgct     360
cgtcgccgtc cctcccgcat tttacgcgtc gacgtcgcgg acgacaccgc acttgccttc     420
gtcggcttcg tcctctggat catcggtgcg tggctgtgcc tcctggcgct cacgcccttg     480
gctccacggg cggtgagggc gggcggggcc gccgccagca ccttgctgat caggtgcctg     540 tcccttttcat gaactactag cgcccgcgcc cgcggccgcc gggcacaaga gaacacatcg     600
atgttcgctg cgtacgtcag caataaggca ctctttgtca gtagtcgagt gcatatgttg     660
ggtgtttgcc ctgggagatt tcaagtgttg tggccattat cccgcaggat aaaaaatcgg     720
cggcttttgg attgatacgg aaaataacga tgtttcatgc tcgtgttgtg tgtgtgacat     780
cttgtcagcc aagtttttaa ccgttgctac tccccctctg tgggctcagt gtgtggaccg     840
gaatacgtcg tacataggcc gtagcctaag cccaatatgc cgttttttcag gttggcctgt    900 gtgacgacaa gcgggtctca aaagcccatc acgcaactgg cctgcaatta ttggaggaga     960
gcgcgtcgag ttggttccag aggctgcgtg gtggggccgg actctgcgac gacctctcgt    1020
tcgcgtccga tttggttgcc gtgagccgtg acgtaacgcc tccttccgtt cctccctata    1080
taagttccac ccccgggtcc ggtttcccca agccccagtg accccgatc ccgatcgcga     1140 aatctccgca cccgccggca agggaccgaa gcaagcctct ctcccgaccg tcgcatcaag    1200
```

```
<210> SEQ ID NO 94
<211> LENGTH: 1021
<212> TYPE: DNA
```

<213> ORGANISM: Setarica italica

<400> SEQUENCE: 94

| gtacgcgtcc gctcgatctg tcctcttcct tctcgatttg acttgctgtg gtgcccgatc | 60 |
| acgggatcag aatcgcacca gtgtagattt cgcatgttct aagatgtgtt agtttccagg | 120 |
| ctaatccagt tctcttgacg cccgatccga tcgagctccg tgtttatttc agcctaatcg | 180 |
| tagtattccc ctaaaatttc ctcattaggg ggttcgcaag attgttggtc gacaggttca | 240 |
| cttatgctcg atcgcttact tttagtcgat tcatgctgcg tactattgtt gccccccgtg | 300 |
| gttttatctt ttctcgtgtg aaatccagta gatatagtag atatcgtagc attaggtttt | 360 |
| aattcaatcg attgattatt gtatcatcaa aattgagaag ttcgaatcat gcctatcatg | 420 |
| ctgcctcaac cgaaatcctg tatattgaag tttcaattca attgattgat cattcattag | 480 |
| attcaaccaa aatctagaag gttagatgac gcatgtcatg ctgcctgcgt agtttacctt | 540 |
| tgatctgttt atgattacct tatcagtagg atatttgtga ttttgggaag tagcactaac | 600 |
| tgattcatgc tgacatgatg ttccctttca gattatactg ttgagtccta tctaattgat | 660 |
| gctttgtatg ctatatgaat acgtcatggt aaattagcag ttaattagca tattagcaat | 720 |
| tgggcgtacc tcatcaggat tgctcttgta gatgtgtgtg gtgatgtttc ttgttcaatt | 780 |
| catgttctgc tttaaaagta tgtgttctct gtttgttaat taagattcat ggttataatg | 840 |
| atttggacct aattaatcag ggttgccctt ttagatgcgt ggttacttgt tgagttcatt | 900 |
| tttttcctgc tatagttgta tgcgtttgtt cattcatggt tagatttgat ttgtttcttc | 960 |
| tctattccat gccttccata tacttcaatt gtagcttaac atgagatttc tgtatatgca | 1020 |
| g | 1021 |

<210> SEQ ID NO 95
<211> LENGTH: 310
<212> TYPE: DNA
<213> ORGANISM: Solanum tuberosum

<400> SEQUENCE: 95

| ctagacttgt ccatcttctg gattggccaa cttaattaat gtatgaaata aaaggatgca | 60 |
| cacatagtga catgctaatc actataatgt gggcatcaaa gttgtgtgtt atgtgtaatt | 120 |
| actagttatc tgaataaaag agaaagagat catccatatt tcttatccta aatgaatgtc | 180 |
| acgtgtcttt ataattcttt gatgaaccag atgcatttca ttaaccaaat ccatatacat | 240 |
| ataaatatta atcatatata attaatatca attgggttag caaaacaaat ctagtctagg | 300 |
| tgtgttttgc | 310 |

<210> SEQ ID NO 96
<211> LENGTH: 870
<212> TYPE: DNA
<213> ORGANISM: Sorghum bicolor

<400> SEQUENCE: 96

| gcccttactt taacgcctct aaccaacacc cctttatctt tataaggaac aataaacaga | 60 |
| atttgcccca ctgttctaaa tcacctaata atatccccag ctaaaaacaa taaggtttc | 120 |
| ctagaattaa gacaagcatg actgttcctc caggagggtt tggaacattg ttgcagtctt | 180 |
| gcagatacgg gcgaagggtg agaaacagag cggagggctg gaggtgacct cggtagtcga | 240 |
| cgccggagtt gagcttgaca acgacggggc ggcccctgat ggacttgagg aagtccgatg | 300 |
| gcgtcttcac cgtcccgccg gcgcccgagg cgggcctgtc gctgccgccg ccgccgctgc | 360 |

| | | |
|---|---|---|
| tcatcttgcg cgctgtgccc ccggcggtgt ccctgtgttg cggatcgcgg gtgggccagg | 420 | |
| tggatgcgag ggcgacccgt ttggactccg gccggagccg ccggatccct ggtcggtgtc | 480 | |
| agtgccgttt actctgggcc ccacgtgtca gtaccgtctg tagatgacaa caacccgtcg | 540 | |
| tccacagtca tgtccaaaat atcctttctt cttttttttc gattcggata tctatcttcc | 600 | |
| tttttttttt ccaaaaatct tcttgacgca ccagcgcgca cgtttgtggt aaacgccgac | 660 | |
| acgtcggtcc cacgtcgata daccccaccc accagtgagt agcgtgtacg tattcggggg | 720 | |
| tgacggacgt gtcgccgtcg tcttgctagt cccattccca tctgagccac acatctctga | 780 | |
| acaaaaaaaa ggagggaggc ctccacgcac atcccctcc gtgccacccg ccccaaaccc | 840 | |
| tcgcgccgcc tccgagacag ccgccgcaac | 870 | |

<210> SEQ ID NO 97
<211> LENGTH: 1917
<212> TYPE: DNA
<213> ORGANISM: Zea mays

<400> SEQUENCE: 97

| | | |
|---|---|---|
| atggccaccg ccgccgccgc gtctaccgcg ctcactggcg ccactaccgc tgcgcccaag | 60 | |
| gcgaggcgcc gggcgcacct cctggccacc cgccgcgccc tcgccgcgcc catcaggtgc | 120 | |
| tcagcggcgt caccgccat gccgatggct ccccggcca cccgctccg gccgtggggc | 180 | |
| cccaccgagc cccgcaaggg tgctgacatc ctcgtcgagt ccctcgagcg ctgcggcgtc | 240 | |
| cgcgacgtct tcgcctaccc cggcggcgcg tccatggaga tccaccaggc actcacccgc | 300 | |
| tcccccgtca tcgccaacca cctcttccgc cacgagcaag gggaggcctt tgccgcctcc | 360 | |
| ggctacgcgc gctcctcggg ccgcgtcggc gtctgcatcg ccacctccgg ccccggcgcc | 420 | |
| accaacctag tctccgcgct cgccgacgcg ctgctcgatt ccgtcccat ggtcgccatc | 480 | |
| acgggacagg tggcgcgacg catgattggc accgacgcct tccaggagac gcccatcgtc | 540 | |
| gaggtcaccc gctccatcac caagcacaac tacctggtcc tcgacgtcga cgacatcccc | 600 | |
| cgcgtcgtgc aggaggcttt cttcctcgcc tcctctggtc gaccagggcc ggtgcttgtc | 660 | |
| gacatcccca aggacatcca gcagcagatg gcggtgcctg tctgggacaa gcccatgagt | 720 | |
| ctgcctgggt acattgcgcg ccttcccaag ccccctgcga ctgagttgct tgagcaggtg | 780 | |
| ctgcgtcttg ttggtgaatc gcggcgccct gttcttatg tgggcggtgg ctgcgcagca | 840 | |
| tctggtgagg agttgcgacg ctttgtggag ctgactggaa tcccggtcac aactactctt | 900 | |
| atgggcctcg gcaacttccc cagcgacgac ccactgtctc tgcgcatgct aggtatgcat | 960 | |
| gggacggtgt atgcaaatta tgcagtggat aaggccgatc tgttgcttgc acttggtgtg | 1020 | |
| cggtttgatg atcgcgtgac aggaagatt gaggcttttg caagcagggc taagattgtg | 1080 | |
| cacgttgata ttgatccggc tgagattggc aagaacaagc agccacatgt gtccatctgt | 1140 | |
| gcagatgtta agcttgcttt gcagggcatg aatgctcttc ttgaaggaag cacatcaaag | 1200 | |
| aagagctttg actttggctc atggaacgat gagttggatc agcagaagag ggaattcccc | 1260 | |
| cttgggtata aacatctaa tgaggagatc cagccacaat atgctattca ggttcttgat | 1320 | |
| gagctgacga aaggcgaggc catcatcggc acaggtgttg gcagcacca gatgtgggcg | 1380 | |
| gcacagtact acacttacaa gcggccaagg cagtggttgt cttcagctgg tcttggggct | 1440 | |
| atgggatttg gtttgccggc tgctgctggt gcttctgtgg caaacccagg tgtcactgtt | 1500 | |
| gttgacatcg atggagatgg tagctttctc atgaacgttc aggagctagc tatgatccga | 1560 | |

| | |
|---|---|
| attgagaacc tcccagtgaa ggtctttgtg ctaaacaacc agcacctggg gatggtggtg | 1620 |
| cagttggagg acaggttcta taaggccaac agagcgcaca catactgggg aaacccagag | 1680 |
| aatgaaagtg agatatatcc agatttcgtg acgatcgcca aagggttcaa cattccagcg | 1740 |
| gtccgtgtga caaagaagaa cgaagtccgc gcagcgataa agaagatgct cgagactcca | 1800 |
| gggccgtacc tcttggatat aatcgtccca caccaggagc atgtgttgcc tatgatccct | 1860 |
| agtggtgggg ctttcaagga tatgatcctg gatggtgatg gcaggactgt gtactga | 1917 |

<210> SEQ ID NO 98
<211> LENGTH: 997
<212> TYPE: DNA
<213> ORGANISM: Sorghum bicolor

<400> SEQUENCE: 98

| | |
|---|---|
| gccagatcct cggtgtacaa ataacccgtc ttatcctatg agacgggccg gcgtcagtgt | 60 |
| gttctggagg aatttttatg tcagagcctt tttctttgtg tgcttgatgt agatgccaag | 120 |
| ggaagcttat tggctgttga agcttgatgc aaaataaatt atggaactct gttttttgtt | 180 |
| tatctaataa taactagcaa atatgcttcc attgcattga actaacagc cttttgtgtt | 240 |
| tccaagtttt atttttgtgac aatgtcatct atttcaatta gttgtggaat cggaaacttg | 300 |
| caggactaac ttggaaactc caatccctca gcatcctgga ctttttcctg gtgtaatcca | 360 |
| tgtagatatt attttaatca tcatttagt tctggaggtt tttccatctc cggttttgct | 420 |
| cccctttctt caaaaaaaaa aaaaaatgc cgtaggcgcc gcaacgccca cctgttgttc | 480 |
| aaactcatgg gcacgagtgg ctcgaagatt ttatacaaca attgctgtag tttcaccgtt | 540 |
| gctggtgaag aagcatttt ttaaaaaaat atagtggtat tcatttaat tagtttagtt | 600 |
| gtgcagcgag caaaatttgg acatgctctg ctcggaatct gatcgaccta gacacagatt | 660 |
| agcagcagta gctttgtcat ctgttccaag agttgcgatc tgatagaaga aaaaaaaacc | 720 |
| ttcccttcaa tgtaaaaccg aaactaacaa gaaagaagca cagtgccgtt taggcaagta | 780 |
| tggagtacgt attaagcatg tagaaggcca tgcatgaacc actaacaaga aagaagcgca | 840 |
| gtgccattca gcaagcata agcatgtaga ttggcatgca tgaacaacta acagtagatc | 900 |
| gtctctggtc tgattagaag ttttttggga agccaagaaa tcatgtacaa ctggttccat | 960 |
| ctcaaattcc gtggcaaaaa gaggcctaag caacata | 997 |

<210> SEQ ID NO 99
<211> LENGTH: 881
<212> TYPE: DNA
<213> ORGANISM: Oryza sativa

<400> SEQUENCE: 99

| | |
|---|---|
| tgacatctta tagtctgcaa cctctcgtgt ctgaattcct atctttatca agtgttattg | 60 |
| cttccacgac tataggacag ctttcgtcga aagcttttgc tcatgtgatc tcgaaggatt | 120 |
| catctagtct gattttcgt gacttgtatc ggttttattg gattcatcca acatatatca | 180 |
| ataaaaaatg agttgtgttt cctttcttcc tagttcagtt aaaattattt ccctcctgcg | 240 |
| cttgtgctgt aattgtctgt gtacctgttg tttgtgactg tgttagttcc cttggatatg | 300 |
| atttcgtatt tgatatgtac atggagatag cttagcttca ttattggagt atgaagttag | 360 |
| tatgacatag tcactctcct ggaaaattga cactgcaaac catatttta ttctgaacca | 420 |
| caaatcctag tcagtccgct ggcatatgcc gtccgtttgc tgaatccaga acgtgggttt | 480 |
| ggagatgtac ggctgagatg cctctatgcg aaggggattt cgtggtgaaa cgagatggga | 540 |

```
gtagagcaac gcccgtggaa gatgcttcaa acttccacac ttttgagcaa cgatcggcag    600
tagtaaggta gacgatttca agatcaaagc atatgaagat aaacaacatc aacaacaaaa    660
tttgttgggg ttctatagag agaaacagag ctacatacat acactgtttt gtatctacca    720
tctgagatga tgaaaagatg aaaaactaaa gaatgccccg gcgccaacgc caggacacgc    780
cgcgcgcgcg tcacccgagc catctcttga cccagccggc gctgtatatt tacacacgtt    840
gcagcatcga tcaccacctg ttcgatcgcg tcgccgtcac c                        881
```

<210> SEQ ID NO 100
<211> LENGTH: 264
<212> TYPE: PRT
<213> ORGANISM: Escherichia coli

<400> SEQUENCE: 100

```
Met Val Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Asp Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 101
<211> LENGTH: 98
<212> TYPE: PRT
<213> ORGANISM: Arabidopsis thaliana

<400> SEQUENCE: 101

```
Thr Cys Ala Lys Asp Ile Gln Lys Ala Ala Glu Ala Ala Leu Ala
1               5                  10                 15

Phe Gln Asp Glu Thr Cys Asp Thr Thr Thr Asn His Gly Leu Asp
                20                  25                 30

Met Glu Glu Thr Met Val Glu Ala Ile Tyr Thr Pro Glu Gln Ser Glu
                35                  40                 45

Gly Ala Phe Tyr Met Asp Glu Thr Met Phe Gly Met Pro Thr Leu
        50                  55                  60

Leu Asp Asn Met Ala Glu Gly Met Leu Leu Pro Pro Pro Ser Val Gln
65                  70                  75                 80

Trp Asn His Asn Tyr Asp Gly Glu Gly Asp Gly Asp Val Ser Leu Trp
                        85                  90                  95

Ser Tyr

<210> SEQ ID NO 102
<211> LENGTH: 4293
<212> TYPE: DNA
<213> ORGANISM: Streptococcus pyogenes

<400> SEQUENCE: 102
```

| | | | | | |
|---|---|---|---|---|---|
| atggacaaga | agtacagcat | cggcctcgac | atcggcacca | actcggtggg | ctgggccgtc | 60 |
| atcacggacg | aatataaggt | cccgtcgaag | aagttcaagg | tcctcggcaa | tacagaccgc | 120 |
| cacagcatca | agaaaaactt | gatcggcgcc | ctcctgttcg | atagcggcga | gaccgcggag | 180 |
| gcgaccaggc | tcaagaggac | cgccaggaga | cggtacacta | ggcgcaagaa | caggatctgc | 240 |
| tacctgcagg | agatcttcag | caacgagatg | gcgaaggtgg | acgactcctt | cttccaccgc | 300 |
| ctggaggaat | cattcctggt | ggaggaggac | aagaagcatg | agcggcaccc | aatcttcggc | 360 |
| aacatcgtcg | acgaggtaag | tttctgcttc | tacctttgat | atatatataa | taattatcat | 420 |
| taattagtag | taatataata | tttcaaatat | ttttttcaaa | ataaaagaat | gtagtatata | 480 |
| gcaattgctt | ttctgtagtt | tataagtgtg | tatatttaa | tttataactt | ttctaatata | 540 |
| tgaccaaaac | atggtgatgt | gcaggtggcc | taccacgaga | agtacccgac | aatctaccac | 600 |
| ctccggaaga | actggtgga | cagcacagac | aaggcggacc | tccggctcat | ctaccttgcc | 660 |
| ctcgcgcata | tgatcaagtt | ccgcggccac | ttcctcatcg | agggcgacct | gaacccggac | 720 |
| aactccgacg | tggacaagct | gttcatccag | ctcgtgcaga | cgtacaatca | actgttcgag | 780 |
| gagaacccca | taaacgctag | cggcgtggac | gccaaggcca | tcctctcggc | caggctctcg | 840 |
| aaatcaagaa | ggctggagaa | ccttatcgcg | cagttgccag | cgaaaagaa | gaacggcctc | 900 |
| ttcggcaacc | ttattgcgct | cagcctcggc | ctgacgccga | acttcaaatc | aaacttcgac | 960 |
| ctcgcggagg | acgccaagct | ccagctctca | aaggacacct | acgacgacga | cctcgacaac | 1020 |
| ctcctggccc | agataggaga | ccagtacgcg | gacctcttcc | tcgccgccaa | gaacctctcc | 1080 |
| gacgctatcc | tgctcagcga | catccttcgg | gtcaacaccg | aaattaccaa | ggcaccgctg | 1140 |
| tccgccagca | tgattaaacg | ctacgacgag | caccatcagg | acctcacgct | gctcaaggca | 1200 |
| ctcgtccgcc | agcagctccc | cgagaagtac | aaggagatct | tcttcgacca | atcaaaaaac | 1260 |
| ggctacgcgg | gatatatcga | cggcggtgcc | agccaggaag | agttctacaa | gttcatcaaa | 1320 |
| ccaatcctgg | agaagatgga | cggcaccgag | gagttgctgg | tcaagctcaa | cagggaggac | 1380 |
| ctcctcagga | agcagaggac | cttcgacaac | ggctccatcc | cgcatcagat | ccacctgggc | 1440 |
| gaactgcatg | ccatcctgcg | cgcgccagga | gacttctacc | cgttcctgaa | ggataaccgg | 1500 |

```
gagaagatcg agaagatctt gacgttccgc atcccatact acgtgggccc gctggctcgc   1560
ggcaactccc ggttcgcctg gatgacccgg aagtcggagg agaccatcac accctggaac   1620
tttgaggagg tggtcgataa gggcgctagc gctcagagct tcatcgagcg catgaccaac   1680
ttcgataaaa acctgcccaa tgaaaaagtc ctccccaagc actcgctgct ctacgagtac   1740
ttcaccgtgt acaacgagct caccaaggtc aaatacgtca ccgagggcat gcggaagccg   1800
gcgttcctga gcggcgagca gaagaaggcg atagtggacc tcctcttcaa gaccaacagg   1860
aaggtgaccg tgaagcaatt aaaagaggac tacttcaaga aaatagagtg cttcgactcc   1920
gtggagatct cgggcgtgga ggatcggttc aacgcctcac tcggcacgta tcacgacctc   1980
ctcaagatca ttaaagacaa ggacttcctc gacaacgagg agaacgagga catcctcgag   2040
gacatcgtcc tcaccctgac cctgttcgag gaccgcgaaa tgatcgagga gaggctgaag   2100
acctacgcgc acctgttcga cgacaaggtc atgaaacagc tcaagaggcg ccgctacact   2160
ggttggggaa ggctgtcccg caagctcatt aatggcatca gggacaagca gagcggcaag   2220
accatcctgg acttcctcaa gtccgacggg ttcgccaacc gcaacttcat gcagctcatt   2280
cacgacgact cgctcacgtt caaggaagac atccagaagg cacaggtgag cgggcagggt   2340
gactccctcc acgaacacat cgccaacctg gccggctcgc cggccattaa aaagggcatc   2400
ctgcagacgg tcaaggtcgt cgacgagctc gtgaaggtga tgggccggca caagcccgaa   2460
aatatcgtca tagagatggc cagggagaac cagaccaccc aaaaagggca gaagaactcg   2520
cgcgagcgga tgaaacggat cgaggagggc attaaagagc tcgggtccca gatcctgaag   2580
gagcaccccg tggaaaatac ccagctccag aatgaaaagc tctacctcta ctacctgcag   2640
aacggccgcg acatgtacgt ggaccaggag ctggacatta atcggctatc ggactacgac   2700
gtcgaccaca tcgtgccgca gtcgttcctc aaggacgata gcatcgacaa caaggtgctc   2760
acccggtcgg ataaaaatcg gggcaagagc gacaacgtgc ccagcgagga ggtcgtgaag   2820
aagatgaaaa actactggcg ccagctcctc aacgcgaaac tgatcaccca gcgcaagttc   2880
gacaacctga cgaaggcgga acgcggtggc ttgagcgaac tcgataaggc gggcttcata   2940
aaaaggcagc tggtcgagac gcgccagatc acgaagcatg tcgcccagat cctggacagc   3000
cgcatgaata ctaagtacga tgaaaacgac aagctgatcc gggaggtgaa ggtgatcacg   3060
ctgaagtcca agctcgtgtc ggacttccgc aaggacttcc agttctacaa ggtccgcgag   3120
atcaacaact accaccacgc ccacgacgcc tacctgaatg cggtggtcgg gaccgccctg   3180
atcaagaagt acccgaagct ggagtcggag ttcgtgtacg gcgactacaa ggtctacgac   3240
gtgcgcaaaa tgatcgccaa gtccgagcag gagatcggca aggccacggc aaaatacttc   3300
ttctactcga acatcatgaa cttcttcaag accgagatca ccctcgcgaa cggcgagatc   3360
cgcaagcgcc cgctcatcga aaccaacggc gagacgggcg agatcgtctg ggataagggc   3420
cgggatttcg cgacggtccg caaggtgctc tccatgccgc aagtcaatat cgtgaaaaag   3480
acggaggtcc agacgggcgg gttcagcaag gagtccatcc tcccgaagcg caactccgac   3540
aagctcatcg cgaggaagaa ggattgggac ccgaaaaaat atggcggctt cgacagcccg   3600
accgtcgcat acagcgtcct cgtcgtggcg aaggtggaga agggcaagtc aaagaagctc   3660
aagtccgtga aggagctgct cgggatcacg attatggagc ggtcctcctt cgagaagaac   3720
ccgatcgact tcctagaggc caagggatat aaggaggtca agaaggacct gattattaaa   3780
ctgccgaagt actcgctctt cgagctggaa acggccgcca agaggatgct cgcctccgca   3840
ggcgagttgc agaagggcaa cgagctcgcc ctcccgagca aatacgtcaa tttcctgtac   3900
```

```
ctcgctagcc actatgaaaa gctcaagggc agcccggagg acaacgagca gaagcagctc    3960
ttcgtggagc agcacaagca ttacctggac gagatcatcg agcagatcag cgagttctcg    4020
aagcgggtga tcctcgccga cgcgaacctg acaaggtgc  tgtcggcata taacaagcac    4080
cgcgacaaac caatacgcga gcaggccgaa aatatcatcc acctcttcac cctcaccaac    4140
ctcggcgctc cggcagcctt caagtacttc gacaccacga ttgaccggaa gcggtacacg    4200
agcacgaagg aggtgctcga tgcgacgctg atccaccaga gcatcacagg gctctatgaa    4260
acacgcatcg acctgagcca gctgggcgga gac                                 4293
```

<210> SEQ ID NO 103
<211> LENGTH: 375
<212> TYPE: DNA
<213> ORGANISM: Streptococcus pyogenes

<400> SEQUENCE: 103

```
atggacaaga agtacagcat cggcctcgac atcggcacca actcggtggg ctgggccgtc      60
atcacggacg aatataaggt cccgtcgaag aagttcaagg tcctcggcaa tacagaccgc     120
cacagcatca agaaaaactt gatcggcgcc ctcctgttcg atagcggcga gaccgcggag     180
gcgaccaggc tcaagaggac cgccaggaga cggtacacta ggcgcaagaa caggatctgc     240
tacctgcagg agatcttcag caacgagatg gcgaaggtgg acgactcctt cttccaccgc     300
ctggaggaat cattcctggt ggaggaggac aagaagcatg agcggcaccc aatcttcggc     360
aacatcgtcg acgag                                                     375
```

<210> SEQ ID NO 104
<211> LENGTH: 3729
<212> TYPE: DNA
<213> ORGANISM: Streptococcus pyogenes

<400> SEQUENCE: 104

```
gtggcctacc acgagaagta cccgacaatc taccacctcc ggaagaaact ggtggacagc      60
acagacaagg cggacctccg gctcatctac cttgccctcg cgcatatgat caagttccgc     120
ggccacttcc tcatcgaggg cgacctgaac ccggacaact ccgacgtgga caagctgttc     180
atccagctcg tgcagacgta caatcaactg ttcgaggaga accccataaa cgctagcggc     240
gtggacgcca aggccatcct ctcggccagg ctctcgaaat caagaaggct ggagaacctt     300
atcgcgcagt tgccaggcga aaagaagaac ggcctcttcg gcaaccttat tgcgctcagc     360
ctcggcctga cgccgaactt caaatcaaac ttcgacctcg cggaggacgc caagctccag     420
ctctcaaagg acacctacga cgacgacctc gacaacctcc tggcccagat aggagaccag     480
tacgcggacc tcttcctcgc cgccaagaac ctctccgacg ctatcctgct cagcgacatc     540
cttcgggtca caccgaaaat taccaaggca ccgctgtccg ccagcatgat taaacgctac     600
gacgagcacc atcaggacct cacgctgctc aaggcactcg tccgccagca gctcccggag     660
aagtacaagg agatcttctt cgaccaatca aaaaacggct acgcgggata tatcgacggc     720
ggtgccagcc aggaagagtt ctacaagttc atcaaaccaa tcctggagaa gatggacggc     780
accgaggagt tgctggtcaa gctcaacagg gaggacctcc tcaggaagca ggaggacttc     840
gacaacggct ccatcccgca tcagatccac ctgggcgaac tgcatgccat cctgcggcgc     900
caggaggact tctaccgtt  cctgaaggat aaccggaga  agatcgagaa gatcttgacg     960
ttccgcatcc catactacgt gggcccgctg gctcgcggca actcccggtt cgcctggatg    1020
```

-continued

| | |
|---|---|
| acccggaagt cggaggagac catcacaccc tggaactttg aggaggtggt cgataagggc | 1080 |
| gctagcgctc agagcttcat cgagcgcatg accaacttcg ataaaaacct gcccaatgaa | 1140 |
| aaagtcctcc ccaagcactc gctgctctac gagtacttca ccgtgtacaa cgagctcacc | 1200 |
| aaggtcaaat acgtcaccga gggcatgcgg aagccggcgt tcctgagcgg cgagcagaag | 1260 |
| aaggcgatag tggacctcct cttcaagacc aacaggaagg tgaccgtgaa gcaattaaaa | 1320 |
| gaggactact tcaagaaaat agagtgcttc gactccgtgg agatctcggg cgtggaggat | 1380 |
| cggttcaacg cctcactcgg cacgtatcac gacctcctca agatcattaa agacaaggac | 1440 |
| ttcctcgaca acgaggagaa cgaggacatc ctcgaggaca tcgtcctcac cctgacccctg | 1500 |
| ttcgaggacc gcgaaatgat cgaggagagg ctgaagacct acgcgcacct gttcgacgac | 1560 |
| aaggtcatga acagctcaa gaggcgccgc tacactggtt ggggaaggct gtcccgcaag | 1620 |
| ctcattaatg gcatcaggga caagcagagc ggcaagacca tcctggactt cctcaagtcc | 1680 |
| gacgggttcg ccaaccgcaa cttcatgcag ctcattcacg acgactcgct cacgttcaag | 1740 |
| gaagacatcc agaaggcaca ggtgagcggg cagggtgact ccctccacga acacatcgcc | 1800 |
| aacctggccg gctcgccggc cattaaaaag gcatcctgc agacggtcaa ggtcgtcgac | 1860 |
| gagctcgtga aggtgatggg ccggcacaag cccgaaaata tcgtcataga gatggccagg | 1920 |
| gagaaccaga ccacccaaaa agggcagaag aactcgcgcg agcggatgaa acggatcgag | 1980 |
| gagggcatta aagagctcgg gtcccagatc ctgaaggagc ccccgtggaa aaatacccag | 2040 |
| ctccagaatg aaaagctcta cctctactac ctgcagaacg ccgcgacat gtacgtggac | 2100 |
| caggagctgg acattaatcg gctatcggac tacgacgtcg accacatcgt gccgcagtcg | 2160 |
| ttcctcaagg acgatagcat cgacaacaag gtgctcaccc ggtcggataa aaatcggggc | 2220 |
| aagagcgaca acgtgcccag cgaggaggtc gtgaagaaga tgaaaaacta ctggcgccag | 2280 |
| ctcctcaacg cgaaactgat cacccagcgc aagttcgaca acctgacgaa ggcggaacgc | 2340 |
| ggtggcttga cgaactcga taaggcgggc ttcataaaaa ggcagctggt cgagacgcgc | 2400 |
| cagatcacga agcatgtcgc ccagatcctg gacagccgca tgaatactaa gtacgatgaa | 2460 |
| aacgacaagc tgatccggga ggtgaaggtg atcacgctga agtccaagct cgtgtcggac | 2520 |
| ttccgcaagg acttccagtt ctacaaggtc cgcgagatca acaactacca ccacgcccac | 2580 |
| gacgcctacc tgaatgcggt ggtcgggacc gccctgatca agaagtaccc gaagctggag | 2640 |
| tcggagttcg tgtacggcga ctacaaggtc tacgacgtgc gcaaaatgat cgccaagtcc | 2700 |
| gagcaggaga tcggcaaggc cacggcaaaa tacttcttct actcgaacat catgaacttc | 2760 |
| ttcaagaccg agatcaccct cgcgaacggc gagatccgca agcgcccgct catcgaaacc | 2820 |
| aacggcgaga cgggcgagat cgtctgggat aagggccggg atttcgcgac ggtccgcaag | 2880 |
| gtgctctcca tgccgcaagt caatatcgtg aaaaagacgg aggtccagac gggcgggttc | 2940 |
| agcaaggagt ccatcctccc gaagcgcaac tccgacaagc tcatcgcgag gaagaaggat | 3000 |
| tgggacccga aaaatatgg cggcttcgac agcccgaccg tcgcatacag cgtcctcgtc | 3060 |
| gtggcgaagg tggagaaggg caagtcaaag aagctcaagt ccgtgaagga gctgctcggg | 3120 |
| atcacgatta tggagcggtc ctccttcgag aagaacccga tcgacttcct agaggccaag | 3180 |
| ggatataagg aggtcaagaa ggacctgatt attaaactgc cgaagtactc gctcttcgag | 3240 |
| ctggaaaacg gccgcaagag gatgctcgcc tccgcaggcg agttgcagaa gggcaacgag | 3300 |
| ctcgccctcc cgagcaaata cgtcaatttc ctgtacctcg ctagccacta tgaaaagctc | 3360 |
| aagggcagcc cggaggacaa cgagcagaag cagctcttcg tggagcagca caagcattac | 3420 |

| | |
|---|---|
| ctggacgaga tcatcgagca gatcagcgag ttctcgaagc gggtgatcct cgccgacgcg | 3480 |
| aacctggaca aggtgctgtc ggcatataac aagcaccgcg acaaaccaat acgcgagcag | 3540 |
| gccgaaaata tcatccacct cttcacccctc accaacctcg gcgctccggc agccttcaag | 3600 |
| tacttcgaca ccacgattga ccggaagcgg tacacgagca cgaaggaggt gctcgatgcg | 3660 |
| acgctgatcc accagagcat cacagggctc tatgaaacac gcatcgacct gagccagctg | 3720 |
| ggcggagac | 3729 |

<210> SEQ ID NO 105
<211> LENGTH: 4293
<212> TYPE: DNA
<213> ORGANISM: Streptococcus pyogenes

<400> SEQUENCE: 105

| | |
|---|---|
| atggacaaga agtacagcat cggcctcgcc atcggcacca actcggtggg ctgggccgtc | 60 |
| atcacggacg aatataaggt cccgtcgaag aagttcaagg tcctcggcaa tacagaccgc | 120 |
| cacagcatca agaaaaactt gatcggcgcc ctcctgttcg atagcggcga accgcggag | 180 |
| gcgaccaggc tcaagaggac cgccaggaga cggtacacta ggcgcaagaa caggatctgc | 240 |
| tacctgcagg agatcttcag caacgagatg gcgaaggtgg acgactcctt cttccaccgc | 300 |
| ctggaggaat cattcctggt ggaggaggac aagaagcatg agcggcaccc aatcttcggc | 360 |
| aacatcgtcg acgaggtaag tttctgcttc tacctttgat atatatataa taattatcat | 420 |
| taattagtag taatataata tttcaaatat ttttttcaaa ataaaagaat gtagtatata | 480 |
| gcaattgctt ttctgtagtt tataagtgtg tatattttaa tttataactt ttctaatata | 540 |
| tgaccaaaac atggtgatgt gcaggtggcc taccacgaga agtacccgac aatctaccac | 600 |
| ctccggaaga aactggtgga cagcacagac aaggcggacc tccggctcat ctaccttgcc | 660 |
| ctcgcgcata tgatcaagtt ccgcggccac ttcctcatcg agggcgacct gaacccggac | 720 |
| aactccgacg tggacaagct gttcatccag ctcgtgcaga cgtacaatca actgttcgag | 780 |
| gagaacccca taaacgctag cggcgtggac gccaaggcca tcctctcggc caggctctcg | 840 |
| aaaatcaagaa ggctggagaa ccttatcgcg cagttgccag gcgaaaagaa gaacggcctc | 900 |
| ttcggcaacc ttattgcgct cagcctcggc ctgacgccga acttcaaatc aaacttcgac | 960 |
| ctcgcggagg acgccaagct ccagctctca aggacacct acgacgacga cctcgacaac | 1020 |
| ctcctggccc agataggaga ccagtacgcg gacctcttcc tcgccgccaa gaacctctcc | 1080 |
| gacgctatcc tgctcagcga catccttcgg gtcaacaccg aaattaccaa ggcaccgctg | 1140 |
| tccgccagca tgattaaacg ctacgacgag caccatcagg acctcacgct gctcaaggca | 1200 |
| ctcgtccgca gcagctcccc gagaagtac aaggagatct tcttcgacca atcaaaaaac | 1260 |
| ggctacgcgg gatatatcga cggcggtgcc agccaggaag agttctacaa gttcatcaaa | 1320 |
| ccaatcctgg agaagatgga cggcaccgag gagttgctgg tcaagctcaa cagggaggac | 1380 |
| ctcctcagga agcagaggac cttcgacaac ggctccatcc cgcatcagat ccacctgggc | 1440 |
| gaactgcatg ccatcctgcg cgcgcaggag gacttctacc cgttcctgaa ggataaccgg | 1500 |
| gagaagatcg agaagatctt gacgttccgc atcccatact acgtgggccc gctggctcgc | 1560 |
| ggcaactccc ggttcgcctg gatgacccgg aagtcggagg agaccatcac ccctggaac | 1620 |
| tttgaggagg tggtcgataa gggcgctagc gctcagagct catcgagcg catgaccaac | 1680 |
| ttcgataaaa acctgcccaa tgaaaaagtc ctccccaagc actcgctgct ctacgagtac | 1740 |

-continued

```
ttcaccgtgt acaacgagct caccaaggtc aaatacgtca ccgagggcat gcggaagccg   1800
gcgttcctga gcggcgagca gaagaaggcg atagtggacc tcctcttcaa gaccaacagg   1860
aaggtgaccg tgaagcaatt aaaagaggac tacttcaaga aaatagagtg cttcgactcc   1920
gtggagatct cgggcgtgga ggatcggttc aacgcctcac tcggcacgta tcacgacctc   1980
ctcaagatca ttaaagacaa ggacttcctc gacaacgagg agaacgagga catcctcgag   2040
gacatcgtcc tcaccctgac cctgttcgag gaccgcgaaa tgatcgagga gaggctgaag   2100
acctacgcgc acctgttcga cgacaaggtc atgaaacagc tcaagaggcg ccgctacact   2160
ggttggggaa ggctgtcccg caagctcatt aatggcatca gggacaagca gagcggcaag   2220
accatcctgg acttcctcaa gtccgacggg ttcgccaacc gcaacttcat gcagctcatt   2280
cacgacgact cgctcacgtt caaggaagac atccagaagg cacaggtgag cgggcagggt   2340
gactccctcc acgaacacat cgccaacctg gccggctcgc cggccattaa aaagggcatc   2400
ctgcagacgg tcaaggtcgt cgacgagctc gtgaaggtga tgggccggca caagcccgaa   2460
aatatcgtca tagagatggc cagggagaac cagaccaccc aaaaagggca gaagaactcg   2520
cgcgagcgga tgaaacggat cgaggagggc attaaagagc tcgggtccca gatcctgaag   2580
gagcaccccg tggaaaatac ccagctccag aatgaaaagc tctacctcta ctacctgcag   2640
aacggccgcg acatgtacgt ggaccaggag ctggacatta atcggctatc ggactacgac   2700
gtcgacgcca tcgtgccgca gtcgttcctc aaggacgata gcatcgacaa caaggtgctc   2760
acccggtcgg ataaaaatcg gggcaagagc gacaacgtgc cgagcgagga ggtcgtgaag   2820
aagatgaaaa actactggcg ccagctcctc aacgcgaaac tgatcaccca gcgcaagttc   2880
gacaacctga cgaaggcgga acgcggtggc ttgagcgaac tcgataaggc gggcttcata   2940
aaaaggcagc tggtcgagac gcgccagatc acgaagcatg tcgcccagat cctggacagc   3000
cgcatgaata ctaagtacga tgaaaacgac aagctgatcc gggaggtgaa ggtgatcacg   3060
ctgaagtcca agctcgtgtc ggacttccgc aaggacttcc agttctacaa ggtccgcgag   3120
atcaacaact accaccacgc ccacgacgcc tacctgaatg cggtggtcgg gaccgccctg   3180
atcaagaagt acccgaagct ggagtcgagt tcgtgtacg gcgactacaa ggtctacgac   3240
gtgcgcaaaa tgatcgccaa gtccgagcag gagatcggca aggccacggc aaaatacttc   3300
ttctactcga acatcatgaa cttcttcaag accgagatca ccctcgcgaa cggcgagatc   3360
cgcaagcgcc cgctcatcga aaccaacggc gagacgggcg agatcgtctg ggataagggc   3420
cgggatttcg cgacggtccg caaggtgctc tccatgccgc aagtcaatat cgtgaaaaag   3480
acggaggtcc agacgggcgg gttcagcaag gagtccatcc tcccgaagcg caactccgac   3540
aagctcatcg cgaggaagaa ggattgggac ccgaaaaaat atggcggctt cgacagcccg   3600
accgtcgcat acagcgtcct cgtcgtggcg aaggtggaga agggcaagtc aaagaagctc   3660
aagtccgtga aggagctgct cgggatcacg attatggagc ggtcctcctt cgagaagaac   3720
ccgatcgact tcctagaggc aagggatat aaggaggtca gaaggaccgt gattattaaa   3780
ctgccgaagt actcgctctt cgagctggaa acggccgca agaggatgct cgcctccgca   3840
ggcgagttgc agaagggcaa cgagctcgcc ctcccgagca aatacgtcaa tttcctgtac   3900
ctcgctagcc actatgaaaa gctcaagggc agcccggagg acaacgagca gaagcagctc   3960
ttcgtggagc agcacaagca ttacctggac gagatcatcg agcagatcag cgagttctcg   4020
aagcgggtga tcctgccga cgcgaacctg gacaaggtgc tgtcggcata taacaagcac   4080
cgcgacaaac caatacgcga gcaggccgaa aatatcatcc acctcttcac cctcaccaac   4140
```

-continued

```
ctcggcgctc cggcagcctt caagtacttc gacaccacga ttgaccggaa gcggtacacg    4200
agcacgaagg aggtgctcga tgcgacgctg atccaccaga gcatcacagg gctctatgaa    4260
acacgcatcg acctgagcca gctgggcgga gac                                 4293
```

<210> SEQ ID NO 106
<211> LENGTH: 360
<212> TYPE: PRT
<213> ORGANISM: Artificial
<220> FEATURE:
<223> OTHER INFORMATION: WUS consensus sequence

<400> SEQUENCE: 106

```
Met Ala Ala Asn Ala Gly Gly Gly Ala Gly Gly Ser Gly Ser
1               5                   10                  15

Gly Ser Val Ala Ala Pro Ala Val Cys Arg Pro Ser Gly Ser Arg Trp
                20                  25                  30

Thr Pro Thr Pro Glu Gln Ile Arg Met Leu Lys Glu Leu Tyr Tyr Gly
            35                  40                  45

Cys Gly Ile Arg Ser Pro Ser Ser Glu Gln Ile Gln Arg Ile Thr Ala
        50                  55                  60

Met Leu Arg Gln His Gly Lys Ile Glu Gly Lys Asn Val Phe Tyr Trp
65                  70                  75                  80

Phe Gln Asn His Lys Ala Arg Glu Arg Gln Lys Arg Arg Leu Thr Ser
                85                  90                  95

Leu Asp Val Asn Val Pro Ala Ala Gly Ala Ala Asp Ala Thr Thr Ser
            100                 105                 110

Gln Leu Gly Val Leu Ser Leu Ser Ser Pro Pro Asn Ser Gly Ala Ala
        115                 120                 125

Pro Pro Ser Pro Thr Leu Gly Phe Tyr Ala Ala Gly Asn Gly Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Asn Asn Asn Asn
                165                 170                 175

Asn Asn Asn Asn Asn Asn Asn Asn Asn Asn Asn Asn Asn Asn
            180                 185                 190

Asn Asn Asn Asn Asn Asn Asn Tyr Met Gly Val Thr Asp Thr Gly
        195                 200                 205

Ser Ser Ser Gln Trp Pro Arg Phe Ser Ser Asp Thr Ile Met Ala
    210                 215                 220

Ala Ala Ala Ala Arg Ala Asn Asn Ala Thr Thr Arg Ala Pro Glu Thr
225                 230                 235                 240

Leu Pro Leu Phe Pro Thr Cys Gly Asp Asp Gly Gly Ser Gly Ser Asn
                245                 250                 255

Asn Asn Asn Asn Asn Asn Asn Asn Asn Asn Asn Asn Asn Asn
            260                 265                 270

Asn Asn Asn Asn Asn Asn Asn Ser Ser Tyr Leu Pro Phe Trp Gly
        275                 280                 285

Asn Asn Ala Ala Ser Thr Thr Ala Gly Ala Thr Ser Ser Val Ala Ile
    290                 295                 300

Gln Gln Gln His Gln Leu Gln Glu Gln Tyr Ser Phe Tyr Ser Asn Ser
305                 310                 315                 320

Asn Ser Thr Gln Leu Ala Gly Thr Gly Asn Gln Asp Val Ser Ala Thr
                325                 330                 335
```

```
Ala Ala Ala Ala Ala Ala Leu Glu Leu Ser Leu Ser Ser Trp Cys Ser
            340                 345                 350

Pro Tyr Pro Ala Ala Gly Ser Met
        355                 360

<210> SEQ ID NO 107
<211> LENGTH: 1368
<212> TYPE: PRT
<213> ORGANISM: Streptococcus pyogenes

<400> SEQUENCE: 107

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145             150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225             230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305             310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
```

```
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375             380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
```

-continued

Thr Thr Gln Lys Gly Gln Lys Asn Ser Arg Glu Arg Met Lys Arg Ile
        770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
Gly Lys Ser Asp Asn Val Pro Ser Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
                915                 920                 925
Lys His Val Ala Gln Ile Leu Asp Ser Arg Met Asn Thr Lys Tyr Asp
                930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
            1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170

```
Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 108
<211> LENGTH: 125
<212> TYPE: PRT
<213> ORGANISM: Streptococcus pyogenes

<400> SEQUENCE: 108

Met Asp Lys Lys Tyr Ser Ile Gly Leu Asp Ile Gly Thr Asn Ser
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu
        115                 120                 125

<210> SEQ ID NO 109
<211> LENGTH: 1243
<212> TYPE: PRT
<213> ORGANISM: Streptococcus pyogenes

<400> SEQUENCE: 109
```

```
Val Ala Tyr His Glu Lys Tyr Pro Thr Ile Tyr His Leu Arg Lys Lys
1               5                   10                  15

Leu Val Asp Ser Thr Asp Lys Ala Asp Leu Arg Leu Ile Tyr Leu Ala
            20                  25                  30

Leu Ala His Met Ile Lys Phe Arg Gly His Phe Leu Ile Glu Gly Asp
        35                  40                  45

Leu Asn Pro Asp Asn Ser Asp Val Asp Lys Leu Phe Ile Gln Leu Val
    50                  55                  60

Gln Thr Tyr Asn Gln Leu Phe Glu Glu Asn Pro Ile Asn Ala Ser Gly
65                  70                  75                  80

Val Asp Ala Lys Ala Ile Leu Ser Ala Arg Leu Ser Lys Ser Arg Arg
                85                  90                  95

Leu Glu Asn Leu Ile Ala Gln Leu Pro Gly Glu Lys Lys Asn Gly Leu
            100                 105                 110

Phe Gly Asn Leu Ile Ala Leu Ser Leu Gly Leu Thr Pro Asn Phe Lys
        115                 120                 125

Ser Asn Phe Asp Leu Ala Glu Asp Ala Lys Leu Gln Leu Ser Lys Asp
    130                 135                 140

Thr Tyr Asp Asp Leu Asp Asn Leu Leu Ala Gln Ile Gly Asp Gln
145                 150                 155                 160

Tyr Ala Asp Leu Phe Leu Ala Ala Lys Asn Leu Ser Asp Ala Ile Leu
                165                 170                 175

Leu Ser Asp Ile Leu Arg Val Asn Thr Glu Ile Thr Lys Ala Pro Leu
            180                 185                 190

Ser Ala Ser Met Ile Lys Arg Tyr Asp Glu His His Gln Asp Leu Thr
        195                 200                 205

Leu Leu Lys Ala Leu Val Arg Gln Gln Leu Pro Glu Lys Tyr Lys Glu
    210                 215                 220

Ile Phe Phe Asp Gln Ser Lys Asn Gly Tyr Ala Gly Tyr Ile Asp Gly
225                 230                 235                 240

Gly Ala Ser Gln Glu Glu Phe Tyr Lys Phe Ile Lys Pro Ile Leu Glu
                245                 250                 255

Lys Met Asp Gly Thr Glu Glu Leu Leu Val Lys Leu Asn Arg Glu Asp
            260                 265                 270

Leu Leu Arg Lys Gln Arg Thr Phe Asp Asn Gly Ser Ile Pro His Gln
    275                 280                 285

Ile His Leu Gly Glu Leu His Ala Ile Leu Arg Arg Gln Glu Asp Phe
290                 295                 300

Tyr Pro Phe Leu Lys Asp Asn Arg Glu Lys Ile Glu Lys Ile Leu Thr
305                 310                 315                 320

Phe Arg Ile Pro Tyr Tyr Val Gly Pro Leu Ala Arg Gly Asn Ser Arg
                325                 330                 335

Phe Ala Trp Met Thr Arg Lys Ser Glu Glu Thr Ile Thr Pro Trp Asn
            340                 345                 350

Phe Glu Glu Val Val Asp Lys Gly Ala Ser Ala Gln Ser Phe Ile Glu
    355                 360                 365

Arg Met Thr Asn Phe Asp Lys Asn Leu Pro Asn Glu Lys Val Leu Pro
370                 375                 380

Lys His Ser Leu Leu Tyr Glu Tyr Phe Thr Val Tyr Asn Glu Leu Thr
385                 390                 395                 400

Lys Val Lys Tyr Val Thr Glu Gly Met Arg Lys Pro Ala Phe Leu Ser
                405                 410                 415

Gly Glu Gln Lys Lys Ala Ile Val Asp Leu Leu Phe Lys Thr Asn Arg
```

```
              420                 425                 430
Lys Val Thr Val Lys Gln Leu Lys Glu Asp Tyr Phe Lys Ile Glu
            435                 440                 445
Cys Phe Asp Ser Val Glu Ile Ser Gly Val Glu Asp Arg Phe Asn Ala
450                 455                 460
Ser Leu Gly Thr Tyr His Asp Leu Leu Lys Ile Ile Lys Asp Lys Asp
465                 470                 475                 480
Phe Leu Asp Asn Glu Glu Asn Glu Asp Ile Leu Glu Asp Ile Val Leu
                485                 490                 495
Thr Leu Thr Leu Phe Glu Asp Arg Glu Met Ile Glu Glu Arg Leu Lys
            500                 505                 510
Thr Tyr Ala His Leu Phe Asp Asp Lys Val Met Lys Gln Leu Lys Arg
            515                 520                 525
Arg Arg Tyr Thr Gly Trp Gly Arg Leu Ser Arg Lys Leu Ile Asn Gly
            530                 535                 540
Ile Arg Asp Lys Gln Ser Gly Lys Thr Ile Leu Asp Phe Leu Lys Ser
545                 550                 555                 560
Asp Gly Phe Ala Asn Arg Asn Phe Met Gln Leu Ile His Asp Asp Ser
                565                 570                 575
Leu Thr Phe Lys Glu Asp Ile Gln Lys Ala Gln Val Ser Gly Gln Gly
            580                 585                 590
Asp Ser Leu His Glu His Ile Ala Asn Leu Ala Gly Ser Pro Ala Ile
            595                 600                 605
Lys Lys Gly Ile Leu Gln Thr Val Lys Val Val Asp Glu Leu Val Lys
            610                 615                 620
Val Met Gly Arg His Lys Pro Glu Asn Ile Val Ile Glu Met Ala Arg
625                 630                 635                 640
Glu Asn Gln Thr Thr Gln Lys Gly Gln Lys Asn Ser Arg Glu Arg Met
                645                 650                 655
Lys Arg Ile Glu Glu Gly Ile Lys Glu Leu Gly Ser Gln Ile Leu Lys
                660                 665                 670
Glu His Pro Val Glu Asn Thr Gln Leu Gln Asn Glu Lys Leu Tyr Leu
                675                 680                 685
Tyr Tyr Leu Gln Asn Gly Arg Asp Met Tyr Val Asp Gln Glu Leu Asp
            690                 695                 700
Ile Asn Arg Leu Ser Asp Tyr Asp Val Asp His Ile Val Pro Gln Ser
705                 710                 715                 720
Phe Leu Lys Asp Asp Ser Ile Asp Asn Lys Val Leu Thr Arg Ser Asp
                725                 730                 735
Lys Asn Arg Gly Lys Ser Asp Asn Val Pro Ser Glu Glu Val Val Lys
            740                 745                 750
Lys Met Lys Asn Tyr Trp Arg Gln Leu Leu Asn Ala Lys Leu Ile Thr
            755                 760                 765
Gln Arg Lys Phe Asp Asn Leu Thr Lys Ala Glu Arg Gly Gly Leu Ser
            770                 775                 780
Glu Leu Asp Lys Ala Gly Phe Ile Lys Arg Gln Leu Val Glu Thr Arg
785                 790                 795                 800
Gln Ile Thr Lys His Val Ala Gln Ile Leu Asp Ser Arg Met Asn Thr
                805                 810                 815
Lys Tyr Asp Glu Asn Asp Lys Leu Ile Arg Glu Val Lys Val Ile Thr
            820                 825                 830
Leu Lys Ser Lys Leu Val Ser Asp Phe Arg Lys Asp Phe Gln Phe Tyr
            835                 840                 845
```

```
Lys Val Arg Glu Ile Asn Asn Tyr His His Ala His Asp Ala Tyr Leu
850                 855                 860

Asn Ala Val Val Gly Thr Ala Leu Ile Lys Lys Tyr Pro Lys Leu Glu
865                 870                 875                 880

Ser Glu Phe Val Tyr Gly Asp Tyr Lys Val Tyr Asp Val Arg Lys Met
                885                 890                 895

Ile Ala Lys Ser Glu Gln Glu Ile Gly Lys Ala Thr Ala Lys Tyr Phe
            900                 905                 910

Phe Tyr Ser Asn Ile Met Asn Phe Phe Lys Thr Glu Ile Thr Leu Ala
            915                 920                 925

Asn Gly Glu Ile Arg Lys Arg Pro Leu Ile Glu Thr Asn Gly Glu Thr
930                 935                 940

Gly Glu Ile Val Trp Asp Lys Gly Arg Asp Phe Ala Thr Val Arg Lys
945                 950                 955                 960

Val Leu Ser Met Pro Gln Val Asn Ile Val Lys Lys Thr Glu Val Gln
                965                 970                 975

Thr Gly Gly Phe Ser Lys Glu Ser Ile Leu Pro Lys Arg Asn Ser Asp
                980                 985                 990

Lys Leu Ile Ala Arg Lys Lys Asp Trp Asp Pro Lys Lys Tyr Gly Gly
            995                 1000                1005

Phe Asp Ser Pro Thr Val Ala Tyr Ser Val Leu Val Val Ala Lys
    1010                1015                1020

Val Glu Lys Gly Lys Ser Lys Lys Leu Lys Ser Val Lys Glu Leu
    1025                1030                1035

Leu Gly Ile Thr Ile Met Glu Arg Ser Ser Phe Glu Lys Asn Pro
    1040                1045                1050

Ile Asp Phe Leu Glu Ala Lys Gly Tyr Lys Glu Val Lys Lys Asp
    1055                1060                1065

Leu Ile Ile Lys Leu Pro Lys Tyr Ser Leu Phe Glu Leu Glu Asn
    1070                1075                1080

Gly Arg Lys Arg Met Leu Ala Ser Ala Gly Glu Leu Gln Lys Gly
    1085                1090                1095

Asn Glu Leu Ala Leu Pro Ser Lys Tyr Val Asn Phe Leu Tyr Leu
    1100                1105                1110

Ala Ser His Tyr Glu Lys Leu Lys Gly Ser Pro Glu Asp Asn Glu
    1115                1120                1125

Gln Lys Gln Leu Phe Val Glu Gln His Lys His Tyr Leu Asp Glu
    1130                1135                1140

Ile Ile Glu Gln Ile Ser Glu Phe Ser Lys Arg Val Ile Leu Ala
    1145                1150                1155

Asp Ala Asn Leu Asp Lys Val Leu Ser Ala Tyr Asn Lys His Arg
    1160                1165                1170

Asp Lys Pro Ile Arg Glu Gln Ala Glu Asn Ile Ile His Leu Phe
    1175                1180                1185

Thr Leu Thr Asn Leu Gly Ala Pro Ala Ala Phe Lys Tyr Phe Asp
    1190                1195                1200

Thr Thr Ile Asp Arg Lys Arg Tyr Thr Ser Thr Lys Glu Val Leu
    1205                1210                1215

Asp Ala Thr Leu Ile His Gln Ser Ile Thr Gly Leu Tyr Glu Thr
    1220                1225                1230

Arg Ile Asp Leu Ser Gln Leu Gly Gly Asp
    1235                1240
```

<210> SEQ ID NO 110
<211> LENGTH: 1425
<212> TYPE: PRT
<213> ORGANISM: Streptococcus pyogenes

<400> SEQUENCE: 110

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ser Phe
        115                 120                 125

Cys Phe Tyr Leu Tyr Ile Tyr Asn Asn Tyr His Leu Val Val Ile Tyr
    130                 135                 140

Phe Lys Tyr Phe Phe Gln Asn Lys Arg Met Tyr Ile Ala Ile Ala Phe
145                 150                 155                 160

Leu Phe Ile Ser Val Tyr Ile Leu Ile Tyr Asn Phe Ser Asn Ile Pro
                165                 170                 175

Lys His Gly Asp Val Gln Val Ala Tyr His Glu Lys Tyr Pro Thr Ile
            180                 185                 190

Tyr His Leu Arg Lys Lys Leu Val Asp Ser Thr Asp Lys Ala Asp Leu
        195                 200                 205

Arg Leu Ile Tyr Leu Ala Leu Ala His Met Ile Lys Phe Arg Gly His
    210                 215                 220

Phe Leu Ile Glu Gly Asp Leu Asn Pro Asp Asn Ser Asp Val Asp Lys
225                 230                 235                 240

Leu Phe Ile Gln Leu Val Gln Thr Tyr Asn Gln Leu Phe Glu Glu Asn
                245                 250                 255

Pro Ile Asn Ala Ser Gly Val Asp Ala Lys Ala Ile Leu Ser Ala Arg
            260                 265                 270

Leu Ser Lys Ser Arg Arg Leu Glu Asn Leu Ile Ala Gln Leu Pro Gly
        275                 280                 285

Glu Lys Lys Asn Gly Leu Phe Gly Asn Leu Ile Ala Leu Ser Leu Gly
    290                 295                 300

Leu Thr Pro Asn Phe Lys Ser Asn Phe Asp Leu Ala Glu Asp Ala Lys
305                 310                 315                 320

Leu Gln Leu Ser Lys Asp Thr Tyr Asp Asp Asp Leu Asp Asn Leu Leu
                325                 330                 335

Ala Gln Ile Gly Asp Gln Tyr Ala Asp Leu Phe Leu Ala Ala Lys Asn
            340                 345                 350

Leu Ser Asp Ala Ile Leu Leu Ser Asp Ile Leu Arg Val Asn Thr Glu
        355                 360                 365

Ile Thr Lys Ala Pro Leu Ser Ala Ser Met Ile Lys Arg Tyr Asp Glu
    370                 375                 380
```

```
His His Gln Asp Leu Thr Leu Leu Lys Ala Leu Val Arg Gln Gln Leu
385                 390                 395                 400

Pro Glu Lys Tyr Lys Glu Ile Phe Phe Asp Gln Ser Lys Asn Gly Tyr
                405                 410                 415

Ala Gly Tyr Ile Asp Gly Gly Ala Ser Gln Glu Glu Phe Tyr Lys Phe
            420                 425                 430

Ile Lys Pro Ile Leu Glu Lys Met Asp Gly Thr Glu Glu Leu Leu Val
        435                 440                 445

Lys Leu Asn Arg Glu Asp Leu Leu Arg Lys Gln Arg Thr Phe Asp Asn
450                 455                 460

Gly Ser Ile Pro His Gln Ile His Leu Gly Glu Leu His Ala Ile Leu
465                 470                 475                 480

Arg Arg Gln Glu Asp Phe Tyr Pro Phe Leu Lys Asp Asn Arg Glu Lys
                485                 490                 495

Ile Glu Lys Ile Leu Thr Phe Arg Ile Pro Tyr Tyr Val Gly Pro Leu
            500                 505                 510

Ala Arg Gly Asn Ser Arg Phe Ala Trp Met Thr Arg Lys Ser Glu Glu
        515                 520                 525

Thr Ile Thr Pro Trp Asn Phe Glu Glu Val Val Asp Lys Gly Ala Ser
530                 535                 540

Ala Gln Ser Phe Ile Glu Arg Met Thr Asn Phe Asp Lys Asn Leu Pro
545                 550                 555                 560

Asn Glu Lys Val Leu Pro Lys His Ser Leu Leu Tyr Glu Tyr Phe Thr
                565                 570                 575

Val Tyr Asn Glu Leu Thr Lys Val Lys Tyr Val Thr Glu Gly Met Arg
            580                 585                 590

Lys Pro Ala Phe Leu Ser Gly Glu Gln Lys Lys Ala Ile Val Asp Leu
        595                 600                 605

Leu Phe Lys Thr Asn Arg Lys Val Thr Val Lys Gln Leu Lys Glu Asp
610                 615                 620

Tyr Phe Lys Lys Ile Glu Cys Phe Asp Ser Val Glu Ile Ser Gly Val
625                 630                 635                 640

Glu Asp Arg Phe Asn Ala Ser Leu Gly Thr Tyr His Asp Leu Leu Lys
                645                 650                 655

Ile Ile Lys Asp Lys Asp Phe Leu Asp Asn Glu Glu Asn Glu Asp Ile
            660                 665                 670

Leu Glu Asp Ile Val Leu Thr Leu Thr Leu Phe Glu Asp Arg Glu Met
        675                 680                 685

Ile Glu Glu Arg Leu Lys Thr Tyr Ala His Leu Phe Asp Asp Lys Val
690                 695                 700

Met Lys Gln Leu Lys Arg Arg Arg Tyr Thr Gly Trp Gly Arg Leu Ser
705                 710                 715                 720

Arg Lys Leu Ile Asn Gly Ile Arg Asp Lys Gln Ser Gly Lys Thr Ile
                725                 730                 735

Leu Asp Phe Leu Lys Ser Asp Gly Phe Ala Asn Arg Asn Phe Met Gln
            740                 745                 750

Leu Ile His Asp Asp Ser Leu Thr Phe Lys Glu Asp Ile Gln Lys Ala
        755                 760                 765

Gln Val Ser Gly Gln Gly Asp Ser Leu His Glu His Ile Ala Asn Leu
770                 775                 780

Ala Gly Ser Pro Ala Ile Lys Lys Gly Ile Leu Gln Thr Val Lys Val
785                 790                 795                 800
```

```
Val Asp Glu Leu Val Lys Val Met Gly Arg His Lys Pro Glu Asn Ile
            805                 810                 815

Val Ile Glu Met Ala Arg Glu Asn Gln Thr Thr Gln Lys Gly Gln Lys
    820                 825                 830

Asn Ser Arg Glu Arg Met Lys Arg Ile Glu Glu Gly Ile Lys Glu Leu
        835                 840                 845

Gly Ser Gln Ile Leu Lys Glu His Pro Val Glu Asn Thr Gln Leu Gln
850                 855                 860

Asn Glu Lys Leu Tyr Leu Tyr Tyr Leu Gln Asn Gly Arg Asp Met Tyr
865                 870                 875                 880

Val Asp Gln Glu Leu Asp Ile Asn Arg Leu Ser Asp Tyr Asp Val Asp
            885                 890                 895

Ala Ile Val Pro Gln Ser Phe Leu Lys Asp Asp Ser Ile Asp Asn Lys
            900                 905                 910

Val Leu Thr Arg Ser Asp Lys Asn Arg Gly Lys Ser Asp Asn Val Pro
        915                 920                 925

Ser Glu Glu Val Val Lys Lys Met Lys Asn Tyr Trp Arg Gln Leu Leu
930                 935                 940

Asn Ala Lys Leu Ile Thr Gln Arg Lys Phe Asp Asn Leu Thr Lys Ala
945                 950                 955                 960

Glu Arg Gly Gly Leu Ser Glu Leu Asp Lys Ala Gly Phe Ile Lys Arg
            965                 970                 975

Gln Leu Val Glu Thr Arg Gln Ile Thr Lys His Val Ala Gln Ile Leu
        980                 985                 990

Asp Ser Arg Met Asn Thr Lys Tyr Asp Glu Asn Asp Lys Leu Ile Arg
        995                 1000                1005

Glu Val Lys Val Ile Thr Leu Lys Ser Lys Leu Val Ser Asp Phe
    1010                1015                1020

Arg Lys Asp Phe Gln Phe Tyr Lys Val Arg Glu Ile Asn Asn Tyr
    1025                1030                1035

His His Ala His Asp Ala Tyr Leu Asn Ala Val Val Gly Thr Ala
    1040                1045                1050

Leu Ile Lys Lys Tyr Pro Lys Leu Glu Ser Glu Phe Val Tyr Gly
    1055                1060                1065

Asp Tyr Lys Val Tyr Asp Val Arg Lys Met Ile Ala Lys Ser Glu
    1070                1075                1080

Gln Glu Ile Gly Lys Ala Thr Ala Lys Tyr Phe Phe Tyr Ser Asn
    1085                1090                1095

Ile Met Asn Phe Phe Lys Thr Glu Ile Thr Leu Ala Asn Gly Glu
    1100                1105                1110

Ile Arg Lys Arg Pro Leu Ile Glu Thr Asn Gly Glu Thr Gly Glu
    1115                1120                1125

Ile Val Trp Asp Lys Gly Arg Asp Phe Ala Thr Val Arg Lys Val
    1130                1135                1140

Leu Ser Met Pro Gln Val Asn Ile Val Lys Lys Thr Glu Val Gln
    1145                1150                1155

Thr Gly Gly Phe Ser Lys Glu Ser Ile Leu Pro Lys Arg Asn Ser
    1160                1165                1170

Asp Lys Leu Ile Ala Arg Lys Lys Asp Trp Asp Pro Lys Lys Tyr
    1175                1180                1185

Gly Gly Phe Asp Ser Pro Thr Val Ala Tyr Ser Val Leu Val Val
    1190                1195                1200

Ala Lys Val Glu Lys Gly Lys Ser Lys Lys Leu Lys Ser Val Lys
```

-continued

| | | 1205 | | | | 1210 | | | | 1215 | | |
|---|---|---|---|---|---|---|---|---|---|---|---|---|
| Glu | Leu | Leu | Gly | Ile | Thr | Ile | Met | Glu | Arg | Ser | Ser | Phe Glu Lys |
| | | 1220 | | | | 1225 | | | | 1230 | | |
| Asn | Pro | Ile | Asp | Phe | Leu | Glu | Ala | Lys | Gly | Tyr | Lys | Glu Val Lys |
| | | 1235 | | | | 1240 | | | | 1245 | | |
| Lys | Asp | Leu | Ile | Ile | Lys | Leu | Pro | Lys | Tyr | Ser | Leu | Phe Glu Leu |
| | | 1250 | | | | 1255 | | | | 1260 | | |
| Glu | Asn | Gly | Arg | Lys | Arg | Met | Leu | Ala | Ser | Ala | Gly | Glu Leu Gln |
| | | 1265 | | | | 1270 | | | | 1275 | | |
| Lys | Gly | Asn | Glu | Leu | Ala | Leu | Pro | Ser | Lys | Tyr | Val | Asn Phe Leu |
| | | 1280 | | | | 1285 | | | | 1290 | | |
| Tyr | Leu | Ala | Ser | His | Tyr | Glu | Lys | Leu | Lys | Gly | Ser | Pro Glu Asp |
| | | 1295 | | | | 1300 | | | | 1305 | | |
| Asn | Glu | Gln | Lys | Gln | Leu | Phe | Val | Glu | Gln | His | Lys | His Tyr Leu |
| | | 1310 | | | | 1315 | | | | 1320 | | |
| Asp | Glu | Ile | Ile | Glu | Gln | Ile | Ser | Glu | Phe | Ser | Lys | Arg Val Ile |
| | | 1325 | | | | 1330 | | | | 1335 | | |
| Leu | Ala | Asp | Ala | Asn | Leu | Asp | Lys | Val | Leu | Ser | Ala | Tyr Asn Lys |
| | | 1340 | | | | 1345 | | | | 1350 | | |
| His | Arg | Asp | Lys | Pro | Ile | Arg | Glu | Gln | Ala | Glu | Asn | Ile Ile His |
| | | 1355 | | | | 1360 | | | | 1365 | | |
| Leu | Phe | Thr | Leu | Thr | Asn | Leu | Gly | Ala | Pro | Ala | Ala | Phe Lys Tyr |
| | | 1370 | | | | 1375 | | | | 1380 | | |
| Phe | Asp | Thr | Thr | Ile | Asp | Arg | Lys | Arg | Tyr | Thr | Ser | Thr Lys Glu |
| | | 1385 | | | | 1390 | | | | 1395 | | |
| Val | Leu | Asp | Ala | Thr | Leu | Ile | His | Gln | Ser | Ile | Thr | Gly Leu Tyr |
| | | 1400 | | | | 1405 | | | | 1410 | | |
| Glu | Thr | Arg | Ile | Asp | Leu | Ser | Gln | Leu | Gly | Gly | Asp | |
| | | 1415 | | | | 1420 | | | | 1425 | | |

USE OF MORPHOGENIC FACTORS FOR THE IMPROVEMENT OF GENE EDITING

CROSS-REFERENCE TO RELATED APPLICATIONS

This application is a 371 National Phase Entry of PCT/US19/21631 filed on 11 Mar. 2019, which claims the benefit of U.S. Provisional Patent Application Ser. No. 62/641,733 filed 12 Mar. 2018 and of U.S. Provisional Patent Application Ser. No. 62/641,725 filed 12 Mar. 2018, each of which are herein incorporated by reference in their entireties.

REFERENCE TO SEQUENCE LISTING SUBMITTED ELECTRONICALLY

The official copy of the sequence listing is submitted electronically via EFS-Web as an ASCII formatted sequence listing with a file named 7495-US-PCT_SequenceListing_ST25.txt created on 19 Aug. 2020 and having a size of 276,850 bytes and is filed concurrently with the specification. The sequence listing comprised in this ASCII formatted document is part of the specification and is herein incorporated by reference in its entirety.

FIELD OF THE INVENTION

The present disclosure relates generally to the field of plant molecular biology, specifically the targeted modification of polynucleotides in plants.

BACKGROUND

Standard methods for genome modification of an organism have multiple steps that may limit speed and efficiency, and can negatively impact product development timelines. In plants, there are growing season limitations that can further delay the creation and testing of plants comprising modified polynucleotides. For example, many standard methods of transformation and regeneration require the use of high auxin or cytokinin levels and require steps involving either embryogenic callus formation or organogenesis, leading to procedures that take many weeks before producing plants for growth in a greenhouse setting following transformation.

Currently, plant genetic transformation and genome modification protocols require delivery of various DNA vectors coding for different components, including for example double-strand break reagents (Cas9 nuclease and guide RNA (gRNA)), a selectable marker, morphogenic factors (for example, ODP2, BBM, and WUS) and donor DNA (in case of a polynucleotide insertion or a swap).

Multiple, co-delivered DNA molecules tend to co-integrate into a DSB site through a non-homologous end joining (NHEJ) repair pathway, significantly reducing the efficiency of homology directed repair (HDR)-based genome editing. Modifying protocols for the delivery of some components, such as a morphogenic factor, and minimizing delivery of DNA may be beneficial and lead to higher frequencies of quality HDR events.

There remains a need for a faster, more efficient system to produce organisms comprising desired polynucleotide modifications quickly and efficiently.

SUMMARY OF INVENTION

In some aspects, methods and compositions are provided for editing a polynucleotide in the genome of a cell, by introduction of a double-strand-break-inducing agent and a morphogenic factor.

In some aspects, the morphogenic factor is provided to the same cell as the cell receiving, or comprising, the double-strand-break-inducing agent. In some aspects, the morphogenic factor is provided to a different cell than the cell receiving, or comprising, the double-strand-break inducing agent. In some aspects, the morphogenic factor is provided on the same construct as that comprising a double-strand-break-inducing agent. In some aspects, the morphogenic factor is provided on a different construct as that comprising a double-strand break-inducing agent. In some aspects, a construct is provided that comprises a heterologous polynucleotide for introduction into a target cell, wherein said construct may optionally further comprise either a morphogenic factor, a double-strand-break-inducing agent, or both.

In some aspects, the morphogenic factor is provided on the same recombinant DNA vector as a heterologous polynucleotide, wherein the morphogenic factor is located outside of the TDNA borders of the vector.

In some aspects, the morphogenic factor is endogenous to the cell receiving, or comprising, the double-strand-break-inducing agent, and expression or activity of the endogenous morphogenic factor is altered. In some aspects, the alteration is up-regulation. In some aspects, the alteration is down-regulation.

In some aspects, a cell penetrating peptide is linked to the morphogenic factor, enabling its movement between cells.

In some aspects, the morphogenic factor is co-introduced with RepA.

In some aspects, combinations of other aspects are utilized to improve polynucleotide modification. For example, in one non-limiting embodiment, a cell penetrating peptide is linked to a morphogenic factor that is provided to an adjacent cell to the one receiving, or comprising, the double-strand-break-inducing agent. For example, in one non-limiting embodiment, an endogenous morphogenic factor is upregulated in a cell adjacent to the cell receiving, or comprising, the double-strand-break-inducing agent. Any combination of any aspect described herein may be utilized to improve polynucleotide modification by a double-strand-break-inducing agent provided to a cell.

In some aspects, the morphogenic factor is provided as a polynucleotide sequence encoding a polypeptide. In some aspects, the morphogenic factor shares at least 80%, at least 85%, at least 90%, at least 95%, at least 96%, at least 97%, at least 98%, at least 99%, at least 99.5%, or greater than 99.5% identity with a sequence selected from the group consisting of: SEQID NOs: 6-10, 17-21, and 48-73. In some aspects, the morphogenic factor shares at least 80%, at least 85%, at least 90%, at least 95%, at least 96%, at least 97%, at least 98%, at least 99%, at least 99.5%, or greater than 99.5% identity with a sequence selected from the group consisting of: SEQID NOs: 1-5, 11-16, 22, and 23-47. In some aspects, the morphogenic factor is selected from the group consisting of: Wuschel, Ovule Development Protein, and Babyboom. In some aspects the morphogenic factor is selected from the group consisting of: WUS1, WUS2, WUS3, WOX2A, WOX4, WOX5, WOX9, BBM2, BMN2, BMN3, and ODP2.

In some aspects, the morphogenic factor is operably linked to a heterologous promoter.

In any aspect, the editing of a polynucleotide may be selected from the group consisting of: insertion of at least one polynucleotide, deletion of at least one polynucleotide, modification of at least one polynucleotide, substitution of at least one polynucleotide, and a combination of at least two of the preceding.

In some aspects, the double-strand-break-inducing agent comprises a Cas endonuclease, a TALEN, a zinc finger endonuclease, a meganuclease, or a restriction endonuclease.

In some aspects, the Cas endonuclease has one or more mutations, that eliminate double-strand break activity and/or single-strand nicking activity.

In some aspects, the double-strand-break-inducing agent is provided as a ribonucleoprotein complex comprising a Cas endonuclease protein and a guide RNA.

In some aspects, the method or composition may further comprise a heterologous polynucleotide donor DNA molecule introduced into said target cell.

In some aspects, the modification of a polynucleotide confers a benefit to an organism comprising, or derived from, said target cell. In some aspects, said benefit is selected from the group consisting of: improved health, improved growth, improved fertility, improved fecundity, improved environmental tolerance, improved vigor, improved disease resistance, improved disease tolerance, improved tolerance to a heterologous molecule, improved fitness, improved physical characteristic, greater mass, increased production of a biochemical molecule, decreased production of a biochemical molecule, upregulation of a gene, downregulation of a gene, upregulation of a biochemical pathway, downregulation of a biochemical pathway, stimulation of cell reproduction, and suppression of cell reproduction.

In some aspects, the cell is a eukaryotic cell. In some aspects, the cell is a plant cell. In some aspects, the plant cell. In some aspects, the plant cell is obtained from or derived from a monocot or dicot plant. In some aspects, the plant cell is obtained from or derived from a monocot selected from the group consisting of: *Zea mays, Sorghum bicolor, Sorghum vulgare, Triticum aestivum, Medicago sativa, Oryza sativa, Setaria italica*, and *Saccharum* spp. In some aspects, the plant cell is obtained from or derived from a dicot selected from the group consisting of: *Helianthus annuus, Glycine max, Nicotiana tabacum, Gossypium barbadense, Gossypium hirsutum, Manihot esculenta, Beta vulgaris, Brassica* spp., and *Arabidposis thaliana*.

In some aspects, editing of a polynucleotide in the genome of a plant cell via any of the compositions or methods described herein results in the modulation of a trait of agronomic importance in a plant, selected from the group consisting of: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein composition, altered oil composition, increased biomass, increased shoot length, increased root length, improved root architecture, modulation of a metabolite, modulation of the proteome, increased seed weight, altered seed carbohydrate composition, altered seed oil composition, altered seed protein composition, and altered seed nutrient composition; as compared to an isoline plant not comprising or derived from a cell whose genome was edited with said double-strand-break-inducing agent.

In some aspects, methods and compositions are provided for editing a polynucleotide in the genome of a cell, by introduction of a double-strand-break-inducing agent and a morphogenic factor, wherein said cell does not have the morphogenic factor stably integrated into its genome.

In some aspects, methods and compositions are provided for editing a polynucleotide in the genome of a cell, by introduction of a double-strand-break-inducing agent and a morphogenic factor, wherein the morphogenic factor is co-introduced with REPA.

In some aspects, methods and compositions are provided for editing a polynucleotide in the genome of a cell, by introduction of a double-strand-break-inducing agent and a morphogenic factor, wherein the morphogenic factor is co-introduced with a polynucleotide encoding deactivated Cas9 molecule fused to a repressor, wherein said polynucleotide is located outside of the T-DNA borders.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

FIG. 2E shows the protein sequence differences between the WUS2 from a recombinant vector (polynucleotide SEQID NOs: 73 (exon 1) and 24 (exon 2) encoding polypeptide SEQID NO:49), from a native B73 maize plant (polynucleotide SEQID NO:25 encoding polypeptide SEQID NO:50), and from a native Variety 1 maize plant (polynucleotide SEQID NO:26 encoding polypeptide SEQID NO:51). The consensus sequence is given as SEQID NO:106.

Figure 3:
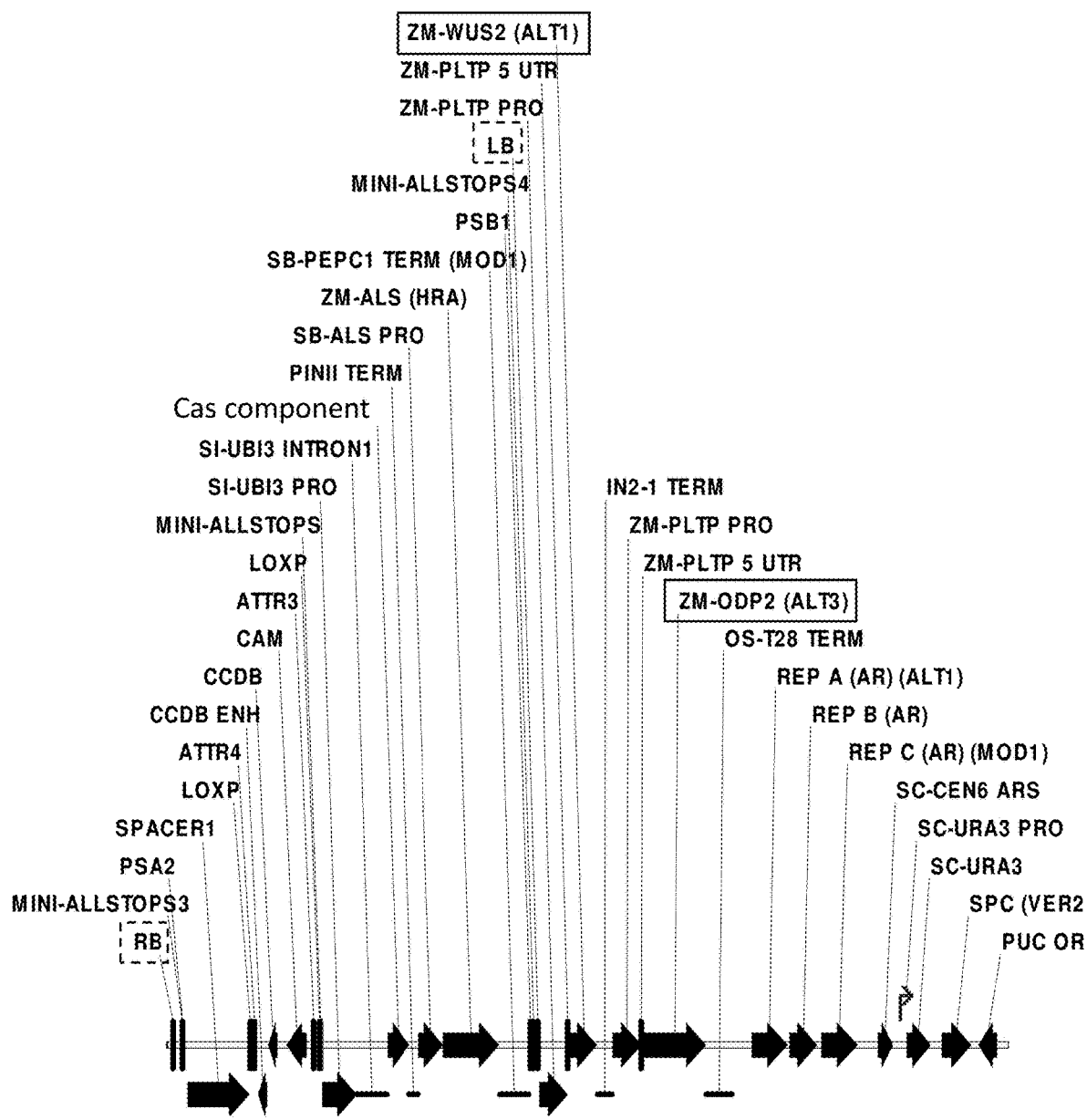

FIG. 3 depicts an example of a recombinant vector comprising morphogenic factor polynucleotides outside of the left border.

Table 1 depicts some of the compositions useful for the methods described herein, given as SEQID NOs: 1-110.

TABLE 1

Sequence Descriptions

| SEQ ID NO | Description | Type | Genus | Species |
|---|---|---|---|---|
| 1 | Z. mays BBM2 coding sequence | DNA | Zea | mays |
| 2 | Oryza sativa BBM1 coding sequence | DNA | Oryza | sativa |
| 3 | Oryza sativa BBM2 coding sequence | DNA | Oryza | sativa |
| 4 | Oryza sativa BBM3 coding sequence | DNA | Oryza | sativa |
| 5 | Sorghum bicolor BBM2 coding sequence | DNA | Sorghum | bicolor |
| 6 | Z. mays BBM2 protein sequence | PRT | Zea | mays |
| 7 | Oryza sativa BBM1 protein sequence | PRT | Oryza | sativa |
| 8 | Oryza sativa BBM2 protein sequence | PRT | Oryza | sativa |
| 9 | Oryza sativa BBM3 protein sequence | PRT | Oryza | sativa |
| 10 | Sorghum bicolor BBM2 protein sequence | PRT | Sorghum | bicolor |
| 11 | Z. mays ODP2 coding sequence | DNA | Zea | mays |
| 12 | Z. mays ODP2 coding sequence (synthetic) | DNA | Zea | mays |
| 13 | Sorghum bicolor ODP2 coding sequence | DNA | Sorghum | bicolor |
| 14 | Setaria italica ODP2 coding sequence | DNA | Setaria | italica |
| 15 | Brachypodium distachyum ODP2 coding sequence | DNA | Brachypodium | distachyum |
| 16 | Sorghum bicolor ODP2 genomic sequence | DNA | Sorghum | bicolor |
| 17 | ODP2 (ALT3) | PRT | Zea | mays |
| 18 | Z. mays ODP2 protein sequence | PRT | Zea | mays |
| 19 | Sorghum bicolor ODP2 protein sequence | PRT | Sorghum | bicolor |
| 20 | Setaria italica ODP2 protein sequence | PRT | Setaria | italica |
| 21 | Brachypodium distachyum ODP2 coding sequence | PRT | Brachypodium | distachyum |
| 22 | odp2 (ALT3) | DNA | Zea | mays |
| 23 | wus | DNA | Zea | mays |
| 24 | wus2 artificial vector exon 2 | DNA | Zea | mays |
| 25 | wus2 B73 | DNA | Zea | mays |
| 26 | wus2 Variety 1 | DNA | Zea | mays |
| 27 | wus2 (ALT1) | DNA | Zea | mays |
| 28 | Arabidopsis thaliana WUS coding sequence | DNA | Arabidopsis | thaliana |
| 29 | Lotus japonicus WUS coding sequence | DNA | Lotus | japonicus |
| 30 | Glycine max WUS coding sequence | DNA | Glycine | max |
| 31 | Camelina sativa WUS coding sequence | DNA | Camelina | sativa |
| 32 | Capsella rubella WUS coding sequence | DNA | Capsella | rubella |
| 33 | Arabis alpina WUS coding sequence | DNA | Arabis | alpina |
| 34 | Raphanus sativus WUS coding sequence | DNA | Raphanus | sativus |
| 35 | Brassica napus WUS coding sequence | DNA | Brassica | napus |
| 36 | Brassica oleracea var. oleracea WUS coding sequence | DNA | Brassica | oleracea |
| 37 | Helianthus annuus WUS coding sequence | DNA | Helianthus | annuus |
| 38 | Populus trichocarpa WUS coding sequence | DNA | Populus | trichocarpa |
| 39 | Vitus vinifera WUS coding sequence | DNA | Vitus | vinifera |
| 40 | Arabidopsis thaliana WUS coding sequence (soy optimized) | DNA | Arabidopsis | thaliana |
| 41 | Lotus japonicus WUS coding sequence (soy optimized) | DNA | Lotus | japonicus |
| 42 | Medicago trunculata WUS coding sequence (soy optimized) | DNA | Medicago | trunculata |
| 43 | Petunia hybrida WUS coding sequence (soy optimized) | DNA | Petunia | hybrida |
| 44 | Phaseolus vulgaris WUS coding sequence (soy optimized) | DNA | Phaseolus | vulgaris |
| 45 | 3-ZM-WUS1-Z. mays WUS1 coding sequence | DNA | Zea | mays |
| 46 | 5-ZM-WUS2-Z. mays WUS2 coding sequence | DNA | Zea | mays |
| 47 | 7-ZM-WUS3-Z. mays WUS3 coding sequence | DNA | Zea | mays |
| 48 | WUS | PRT | Zea | mays |
| 49 | WUS artificial vector | PRT | Zea | mays |
| 50 | WUS2 B73 | PRT | Zea | mays |
| 51 | WUS2 Variety 1 | PRT | Zea | mays |
| 52 | WUS2 (ALT1) | PRT | Zea | mays |
| 53 | Arabidopsis thaliana WUS protein sequence | PRT | Arabidopsis | thaliana |
| 54 | Lotus japonicus WUS protein sequence | PRT | Lotus | japonicus |
| 55 | Glycine max WUS protein sequence | PRT | Glycine | max |
| 56 | Camelina sativa WUS protein sequence | PRT | Camelina | sativa |
| 57 | Capsella rubella WUS protein sequence | PRT | Capsella | rubella |
| 58 | Arabis alpina WUS protein sequence | PRT | Arabis | alpina |
| 59 | Raphanus sativus WUS protein sequence | PRT | Raphanus | sativus |
| 60 | Brassica napus WUS protein sequence | PRT | Brassica | napus |
| 61 | Brassica oleracea var. oleracea WUS protein sequence | PRT | Brassica | oleracea |
| 62 | Helianthus annuus WUS protein sequence | PRT | Helianthus | annuus |
| 63 | Populus trichocarpa WUS protein sequence | PRT | Populus | trichocarpa |
| 64 | Vitus vinifera WUS protein sequence | PRT | Vitus | vinifera |
| 65 | Arabidopsis thaliana WUS protein sequence | PRT | Arabidopsis | thaliana |
| 66 | Lotus japonicus WUS protein sequence | PRT | Lotus | japonicus |
| 67 | Medicago trunculata WUS protein sequence | PRT | Medicago | trunculata |
| 68 | Petunia hybrida WUS protein sequence | PRT | Petunia | hybrida |
| 69 | Phaseolus vulgaris WUS protein sequence | PRT | Phaseolus | vulgaris |
| 70 | 4-ZM-WUS1-Z. mays WUS1 protein sequence | PRT | Zea | mays |
| 71 | 6-ZM-WUS2-Z. mays WUS2 protein sequence | PRT | Zea | mays |
| 72 | 8-ZM-WUS3-Z. mays WUS3 protein sequence | PRT | Zea | mays |
| 73 | wus2 artificial vector exon 1 | DNA | Zea | mays |
| 74 | PLTP promoter | DNA | Zea | mays |
| 75 | UBI promoter | DNA | Zea | mays |
| 76 | potato LS1 intron 2 | DNA | Solanum | tuberosum |
| 77 | donor DNA GOI (NPTII selectable marker) | DNA | Escherichia | coli |

TABLE 1-continued

Sequence Descriptions

| SEQID NO | Description | Type | Genus | Species |
|---|---|---|---|---|
| 78 | donor DNA homology arm 1 | DNA | Artificial | |
| 79 | donor DNA homology arm 2 | DNA | Artificial | |
| 80 | gRNA (gene deletion site 1) | DNA | Artificial | |
| 81 | gRNA (gene deletion site 2) | DNA | Artificial | |
| 82 | gRNA (Example 3 site specific gene insertion) | DNA | Artificial | |
| 83 | At-cbf1a | DNA | Arabidopsis | thaliana |
| 84 | polIII promoter | DNA | Zea | mays |
| 85 | gRNA | DNA | Artificial | |
| 86 | gRNA C5 (Example 4) | DNA | Artificial | |
| 87 | gRNA C3 (Example 4) | DNA | Artificial | |
| 88 | gRNA C9 (Example 4) | DNA | Artificial | |
| 89 | gRNA A9 (Example 4) | DNA | Artificial | |
| 90 | gRNA A4 (Example 4) | DNA | Artificial | |
| 91 | PLTP promoter | DNA | Zea | mays |
| 92 | PLTP 5'UTR | DNA | Zea | mays |
| 93 | UBI1 promoter | DNA | Setarica | italica |
| 94 | UBI3 intron 1 | DNA | Setarica | italica |
| 95 | PINII terminator | DNA | Solarium | tuberosum |
| 96 | ALS promoter | DNA | Sorghum | bicolor |
| 97 | ALS (HRA) | DNA | Zea | mays |
| 98 | PEPC1terminator | DNA | Sorghum | bicolor |
| 99 | T28 terminator | DNA | Oryza | sativa |
| 100 | NPTII selectable marker | PRT | Escherichia | coli |
| 101 | At-CBFIA | PRT | Arabidopsis | thaliana |
| 102 | cas9 (with ST-L1S intron, SV40 NLS, VIRD2 NLS) | DNA | Streptococcus | pyogenes |
| 103 | cas9 exon 1 | DNA | Streptococcus | pyogenes |
| 104 | cas9 exon 2 | DNA | Streptococcus | pyogenes |
| 105 | cas9 (D10A + H840A) | DNA | Streptococcus | pyogenes |
| 106 | consensus sequence for WUS (n = any or no amino acid) - FIG. 2E | PRT | Artificial | |
| 107 | Cas9 | PRT | Streptococcus | pyogenes |
| 108 | Cas9 exon 1 | PRT | Streptococcus | pyogenes |
| 109 | Cas9 exon 2 | PRT | Streptococcus | pyogenes |
| 110 | dCas9 (D10A + H840A) | PRT | Streptococcus | pyogenes |

DETAILED DESCRIPTION

Various compositions and methods for modifying a polynucleotide target site in a cell, for example a plant cell, are provided. The modification can include an insertion, deletion, mutation, replacement, or molecular alteration of a nucleotide sequence. The target site is modified through the activity of a double-strand break-inducing agent that recognizes a recognition sequence within the target site.

Double-strand breaks induced by double-strand inducing agents can result in the induction of DNA repair mechanisms, including the non-homologous end-joining pathway, and homologous recombination. Error-prone DNA repair mechanisms can produce mutations at double-strand break sites. The nonhomologous end-joining (NHEJ) pathways are the most common repair mechanism that serve to bring the broken polynucleotide ends together (Bleuyard et al. (2006) *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik et al. (2000) *EMBO J* 19:5562-6). If two different double-strand breaks occur, however, the free ends from different breaks can be ligated to one another, resulting in chromosomal deletions (Siebert and Puchta (2002) *Plant Cell* 14:1121-31), or chromosomal translocations between different chromosomes (Pacher et al. (2007) *Genetics* 175:21-9).

Episomal DNA molecules, for example T-DNAs, can also be ligated into the double-strand break, resulting in integration of the episomal DNA molecule into the host genome (Chilton and Que (2003) *Plant Physiol* 133:956-65; Salomon and Puchta (1998) *EMBO J* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (S, G2, M phases of a cell cycle) (Molinier et al. (2004) *Plant Cell* 16:342-52). Heterologous, ectopic and/or epigenic DNA sequences may also serve as a DNA repair template for homologous recombination (Puchta (1999) *Genetics* 152:1173-81).

DNA double-strand breaks (DSBs) appear to be an effective factor to stimulate homologous recombination pathways in every organism tested to date (Puchta et al. (1995) *Plant Mol Biol* 28:281-92; Tzfira and White (2005) *Trends Biotechnol* 23:567-9; Puchta (2005) *J Exp Bot* 56:1-14). For example, using DNA break-inducing a, a two- to nine-fold increase of homologous recombination was observed between artificially constructed homologous DNA repeats in plants (Puchta et al. (1995) *Plant Mol Biol* 28:281-92). Thus, double-strand break-inducing agents can be used for targeted modification of polynucleotides in organisms and the provision of one or more morphogenic proteins enhances the frequency of targeted modification.

Morphogenic proteins can enhance the rate of targeted modification of a target site in a cell of an organism, such as a plant, that has been induced by a double-strand break-inducing agent. In some methods, at least one morphogenic protein and a double-strand break-inducing agent are introduced into a cell having a target site with at least one recognition sequence. The double-strand break-inducing agent recognizes the recognition sequence and introduces a double-strand break at or near the recognition sequence to produce a modified target site. Modifications to the target site can include a deletion, replacement, mutation, chemical or molecular modification, homologous recombination, or insertion of a nucleotide sequence. In certain embodiments, the target site is stably integrated into the genome of the plant. In some of these embodiments, the genomic target site is a native genomic target site. These methods can be used to stimulate recombination at a target site, integrate polynucleotides into a target site, invert or excise a polynucleotide, directly select transformed organisms, minimize or eliminate expression resulting from random integration into the genome of an organism, combine multiple transfer cassettes, silence genes, and characterize transcriptional regulatory regions.

The methods disclosed herein involve the use of a morphogenic factor, such as babyboom (BBM)/ovule development protein (ODP) and/or Wuschel (WUS), that serves to enhance and promote the polynucleotide modification effected by the double-strand-break-inducing agent. The morphogenic factor may be provided to a cell as a protein or as a polynucleotide encoding a protein. In one aspect, a heterologous morphogenic factor is provided to the target cell. In one aspect, an endogenous morphogenic factor in the target cell or adjacent cell is activated or upregulated. In one aspect, a morphogenic factor is provided to an adjacent cell instead of to the target cell, whereby the target cell benefits from the presence of the morphogenic factor in the adjacent cell. In one aspect, the morphogenic factor is provided to the target cell as part of a transformation cassette, with the polynucleotide encoding the morphogenic factor located outside of the transformation borders such that its integration into the target cell genome is transient.

Here we describe different approaches for cellular genome editing to leverage the benefits of morphogenic factors, without stably integrating the morphogenic factor into the target cell that receives the double-strand-break agent components for targeted polynucleotide modification. Such approaches include: leveraging the expression of an endogenous morphogenic factor in the target cell or adjacent cell, delivery of a morphogenic factor to a different cell than the target cell, and/or providing the morphogenic factor to the target cell as part of a recombinant vector wherein said morphogenic factor lies outside of the T-DNA borders.

These novel methods provide improved efficiency of genome editing, improved percentage of regenerated transformed plants, lower attrition rate of the target cells/organisms, and reduced integration of unwanted DNA.

Definitions

Terms used in the claims and specification are defined as set forth below unless otherwise specified. It must be noted that, as used in the specification and the appended claims, the singular forms "a," "an" and "the" include plural referents unless the context clearly dictates otherwise.

The term "genome" refers to the entire complement of genetic material (genes and non-coding sequences) that is present in each cell of an organism, or virus or organelle; and/or a complete set of chromosomes inherited as a (haploid) unit from one parent. The term "genome" as it applies to a prokaryotic and eukaryotic cell or organism cells encompasses not only chromosomal DNA found within the nucleus, but organelle DNA found within subcellular components (e.g., mitochondria, or plastid) of the cell.

The terms "provided (to)" and "introduced (into)" are used interchangeably herein. In another aspect, it is meant that a particular composition becomes functionally associated with a cell or other molecule. In one aspect, it is meant that a particular composition is taken up by the cell into its interior.

By the term "endogenous" it is meant a sequence or other molecule that naturally occurs in a cell or organism. In one aspect, an endogenous polynucleotide is normally found in the genome of a cell; that is, not heterologous.

The term "heterologous" refers to the difference between the original environment, location, or composition of a particular polynucleotide or polypeptide sequence and its current environment, location, or composition. Non-limiting examples include differences in taxonomic derivation (e.g., a polynucleotide sequence obtained from *Zea mays* would be heterologous if inserted into the genome of an *Oryza sativa* plant, or of a different variety or cultivar of *Zea mays*; or a polynucleotide obtained from a bacterium was introduced into a cell of a plant), or sequence (e.g., a polynucleotide sequence obtained from *Zea mays*, isolated, modified, and re-introduced into a maize plant). As used herein, "heterologous" in reference to a sequence can refer to a sequence that originates from a different species, variety, foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, one or more compositions, such as those provided herein, may be entirely synthetic.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA and/or RNA-DNA that is single- or double-stranded, optionally comprising synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The relationship between two or more polynucleotides or polypeptides may be determined. Polynucleotide and polypeptide sequences, fragments thereof, variants thereof, and the structural relationships of these sequences can be described by the terms "homology", "homologous", "substantially identical", "substantially similar" and "corresponding substantially" which are used interchangeably herein. These refer to polypeptide or nucleic acid sequences wherein changes in one or more amino acids or nucleotide bases do not affect the function of the molecule, such as the ability to mediate gene expression or to produce a certain phenotype. These terms also refer to modification(s) of nucleic acid sequences that do not substantially alter the functional properties of the resulting nucleic acid relative to the initial, unmodified nucleic acid. These modifications include deletion, substitution, and/or insertion of one or more nucleotides in the nucleic acid fragment.

Sequence relationships may be defined by their composition comparisons, or by their ability to hybridize, or by their ability to engage in homologous recombination.

Methods of alignment of sequences for comparison are well known in the art. Thus, the determination of percent sequence identity between any two sequences can be accomplished using a mathematical algorithm. Sequence alignments and percent identity or similarity calculations may be determined using a variety of comparison methods designed to detect homologous sequences including, but not limited to, the MegAlign program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Sequence identity" or "identity" in the context of nucleic acid or polypeptide sequences refers to the nucleic acid bases or amino acid residues in two sequences that are the same when aligned for maximum correspondence over a specified comparison window. The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

The "Clustal V method of alignment" corresponds to the alignment method labeled Clustal V (described by Higgins and Sharp, (1989) CABIOS 5:151-153; Higgins et al., (1992) Comput Appl Biosci 8:189-191) and found in the MegAlign program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. The "Clustal W method of alignment" corresponds to the alignment method labeled Clustal W (described by Higgins and Sharp, (1989) CABIOS 5:151-153; Higgins et al., (1992) Comput Appl Biosci 8:189-191) and found in the MegAlign v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program. Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) Proc. Natl. Acad. Sci. USA 89:10915). GAP uses the algorithm of Needleman and Wunsch, (1970) J Mol Biol 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases. "BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence. As used herein, "percent sequence identity" means the value determined by comparing two aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

As used herein, an "isolated" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture media components when produced by recombinant techniques, or substantially free of chemical precursors or other molecules when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest molecules.

As used herein, polynucleotide or polypeptide is "recombinant" when it is artificial or engineered, or derived from an artificial or engineered protein or nucleic acid. For example, a polynucleotide that is inserted into a vector or any other heterologous location, e.g., in a genome of another organism, such that it is not associated with nucleotide sequences that normally flank the polynucleotide as it is found in nature is a recombinant polynucleotide. A polypeptide expressed in vitro or in vivo from a recombinant polynucleotide is an example of a recombinant polypeptide. Likewise, a polynucleotide sequence that does not appear in nature, for example, a variant of a naturally occurring gene, is recombinant.

The terms "recombinant polynucleotide", "recombinant nucleotide", "recombinant DNA" and "recombinant DNA construct" are used interchangeably herein. A recombinant construct comprises an artificial or heterologous combination of nucleic acid sequences, e.g., regulatory and coding sequences that are not found together in nature. For example, a transfer cassette can comprise restriction sites and a heterologous polynucleotide of interest. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments provided herein. The skilled artisan will also recognize that different independent transformation events will result in different levels and patterns of expression (Jones et al., EMBO J. 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

A "centimorgan" (cM) or "map unit" is the distance between two polynucleotide sequences, linked genes, markers, target sites, loci, or any pair thereof, wherein 1% of the products of meiosis are recombinant. Thus, a centimorgan is equivalent to a distance equal to a 1% average recombination frequency between the two linked genes, markers, target sites, loci, or any pair thereof.

"Open reading frame" is abbreviated ORF.

"Gene" includes a nucleic acid fragment that expresses a functional molecule such as, but not limited to, a specific protein, including regulatory sequences preceding (5' non-coding sequences) and following (3' non-coding sequences)

the coding sequence. "Native gene" refers to a gene as found in its natural endogenous location with its own regulatory sequences.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include, but are not limited to, promoters, translation leader sequences, 5' untranslated sequences, 3' untranslated sequences, introns, polyadenylation target sequences, RNA processing sites, effector binding sites, and stem-loop structures.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, the term "morphogenic gene" means a gene that when ectopically expressed stimulates formation of a somatically-derived structure that can produce a plant. More precisely, ectopic expression of the morphogenic gene stimulates the de novo formation of a somatic embryo or an organogenic structure, such as a shoot meristem, that can produce a plant. This stimulated de novo formation occurs either in the cell in which the morphogenic gene is expressed, or in a neighboring cell. A morphogenic gene can be a transcription factor that regulates expression of other genes, or a gene that influences hormone levels in a plant tissue, both of which can stimulate morphogenic changes. As used herein, the term "morphogenic factor" means a morphogenic gene and/or the protein expressed by a morphogenic gene.

A "promoter" is a region of DNA involved in recognition and binding of RNA polymerase and other proteins to initiate transcription. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

Promoters that cause a gene to be expressed in most cell types at most times are commonly referred to as "constitutive promoters". The term "inducible promoter" refers to a promoter that selectively express a coding sequence or functional RNA in response to the presence of an endogenous or exogenous stimulus, for example by chemical compounds (chemical inducers) or in response to environmental, hormonal, chemical, and/or developmental signals. Inducible or regulated promoters include, for example, promoters induced or regulated by light, heat, stress, flooding or drought, salt stress, osmotic stress, phytohormones, wounding, or chemicals such as ethanol, abscisic acid (ABA), jasmonate, salicylic acid, or safeners.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) Mol Biotechnol 3:225 236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) Plant Cell 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre-mRNA. "Messenger RNA" or "mRNA" refers to the RNA that is without introns and that can be translated into protein by the cell. "cDNA" refers to a DNA that is complementary to, and synthesized from, an mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated yet has an effect on cellular processes. The terms "complement" and "reverse complement" are used interchangeably herein with respect to mRNA transcripts, and are meant to define the antisense RNA of the message.

The terms "5'-cap" and "7-methylguanylate (m7G) cap" are used interchangeably herein. A 7-methylguanylate residue is located on the 5' terminus of messenger RNA (mRNA) in eukaryotes. RNA polymerase II (Pol II) transcribes mRNA in eukaryotes. Messenger RNA capping occurs generally as follows: The most terminal 5' phosphate group of the mRNA transcript is removed by RNA terminal phosphatase, leaving two terminal phosphates. A guanosine monophosphate (GMP) is added to the terminal phosphate of the transcript by a guanylyl transferase, leaving a 5'-5' triphosphate-linked guanine at the transcript terminus. Finally, the 7-nitrogen of this terminal guanine is methylated by a methyl transferase.

The terminology "not having a 5'-cap" herein is used to refer to RNA having, for example, a 5'-hydroxyl group instead of a 5'-cap. Such RNA can be referred to as "uncapped RNA", for example. Uncapped RNA can better accumulate in the nucleus following transcription, since 5'-capped RNA is subject to nuclear export. One or more RNA components herein are uncapped.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product (e.g., an mRNA, guide RNA, or a protein) in either precursor or mature form.

By "domain" it is meant a contiguous stretch of nucleotides (that can be RNA, DNA, and/or RNA-DNA-combination sequence) or amino acids.

The term "conserved domain" or "motif" means a set of polynucleotides or amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "fragment" refers to a contiguous set of polynucleotides or polypeptides. In one embodiment, a fragment is 2, 3, 4, 5, 6, 7 8, 9, 10, 11, 12, 13, 14, 15, 16, 17, 18, 19, 20, or greater than 20 contiguous polynucleotides. In one embodiment, a fragment is 2, 3, 4, 5, 6, 7 8, 9, 10, 11, 12, 13, 14, 15, 16, 17, 18, 19, 20, or greater than 20 contiguous polypeptides. A fragment may or may not exhibit the function of a sequence sharing some percent identity over the length of said fragment.

The terms "fragment that is functionally equivalent", "functional fragment", and "functionally equivalent fragment" are used interchangeably herein. These terms refer to a portion or subsequence of a nucleic acid fragment or polypeptide that displays the same activity or function as the longer sequence from which it derives. In one example, the fragment retains the ability to alter gene expression, create a double strand nick or break, or produce a certain phenotype whether or not the fragment encodes the whole protein as found in nature. In some aspects, part of the activity is retained. In some aspects, all of the activity is retained.

The terms "variant that is functionally equivalent", "functional variant", and "functionally equivalent variant" are used interchangeably herein. These terms refer to a nucleic acid fragment or polypeptide that displays the same activity or function as the source sequence from which it derives, but differs from the source sequence by at least one nucleotide or amino acid. In one example, the variant retains the ability to alter gene expression, create a double strand nick or break, or produce a certain phenotype. In some aspects, part of the activity is retained. In some aspects, all of the activity is retained.

A functional fragment or functional variant shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 150, at least 150, between 150 and 200, at least 200, between 200 and 250, at least 250, between 250 and 300, at least 300, between 300 and 350, at least 350, between 350 and 400, at least 400, between 400 and 450, at least 500, or greater than 500 contiguous amino acids of a native source polynucleotide or polypeptide, and retains at least partial activity.

"Modified", "edited", or "altered", with respect to a polynucleotide or target sequence, refers to a nucleotide sequence that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, (iv) association of another molecule or atom via covalent, ionic, or hydrogen bonding, or (v) any combination of (i)-(iv).

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates comprising target sites.

A "mature" protein refers to a post-translationally processed polypeptide (i.e., one from which any pre- or propeptides present in the primary translation product have been removed).

"Precursor" protein refers to the primary product of translation of mRNA (i.e., with pre- and propeptides still present). Pre- and propeptides may be but are not limited to intracellular localization signals.

An "optimized" polynucleotide is a sequence that has been optimized for improved expression in a particular heterologous host cell.

A "codon-modified gene" or "codon-preferred gene" or "codon-optimized gene" is a gene having its frequency of codon usage designed to mimic the frequency of preferred codon usage of the host cell.

A "plant-optimized nucleotide sequence" is a nucleotide sequence that has been optimized for expression in plants, particularly for increased expression in plants. A plant-optimized nucleotide sequence includes a codon-optimized gene. A plant-optimized nucleotide sequence can be synthesized by modifying a nucleotide sequence encoding a protein such as, for example, a Cas endonuclease as disclosed herein, using one or more plant-preferred codons for improved expression. See, for example, Campbell and Gowri (1990) Plant Physiol. 92:1-11 for a discussion of host-preferred codon usage.

The terms "plasmid", "vector" and "cassette" refer to a linear or circular extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector comprising a gene and having elements in addition to the gene that facilitates transformation of a particular host cell. "Expression cassette" refers to a specific vector comprising a gene and having elements in addition to the gene that allow for expression of that gene in a host.

A "polynucleotide of interest" includes any nucleotide sequence encoding a protein or polypeptide that improves desirability of an organism, for example, animals or plants. Polynucleotides of interest: include, but are not limited to, polynucleotides encoding important traits for agronomics, herbicide-resistance, insecticidal resistance, disease resistance, nematode resistance, herbicide resistance, microbial resistance, fungal resistance, viral resistance, fertility or sterility, grain characteristics, commercial products, phenotypic marker, or any other trait of agronomic or commercial importance. A polynucleotide of interest may additionally be utilized in either the sense or anti-sense orientation. Further, more than one polynucleotide of interest may be utilized together, or "stacked", to provide additional benefit.

As used herein, a "genomic region of interest" is a segment of a chromosome in the genome of a plant that is desirable for introducing a double-strand break, a polynucleotide of interest, or a trait of interest. The genomic region of interest can include, for example, one or more polynucleotides of interest. Generally, a genomic region of interest of the present invention comprises a segment of chromosome that is 0-15 centimorgan (cM).

The terms "knock-out", "gene knock-out" and "genetic knock-out" are used interchangeably herein. A knock-out represents a DNA sequence of a cell that has been rendered partially or completely inoperative by targeting with a DSB agent; for example, a DNA sequence prior to knock-out could have encoded an amino acid sequence, or could have had a regulatory function (e.g., promoter).

The terms "knock-in", "gene knock-in, "gene insertion" and "genetic knock-in" are used interchangeably herein. A knock-in represents the replacement or insertion of a DNA sequence at a specific DNA sequence in cell by targeting with a DSB agemt (for example by homologous recombination (HR), wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

"Introducing" is intended to mean presenting to a target, such as a cell or organism, a polynucleotide or polypeptide or polynucleotide-protein complex, in such a manner that the component(s) gains access to the interior of a cell of the organism or to the cell itself.

Generally, "host" refers to an organism or cell into which a heterologous component (polynucleotide, polypeptide, other molecule, cell) has been introduced. As used herein, a "host cell" refers to an in vivo or in vitro eukaryotic cell, prokaryotic cell (e.g., bacterial or archaeal cell), or cell from a multicellular organism (e.g., a cell line) cultured as a unicellular entity, into which a heterologous polynucleotide or polypeptide has been introduced. In some embodiments, the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, an insect cell, a mammalian cell, a pig cell, a cow cell, a goat cell, a sheep cell, a rodent cell, a rat cell, a mouse cell, a non-human primate cell, and a human cell. In some cases, the cell is in vitro. In some cases, the cell is in vivo.

As used herein, the terms "target site", "target sequence", and "target polynucleotide" are used interchangeably herein and refer to a polynucleotide sequence in the genome of a plant cell or yeast cell that comprises a recognition site for a double-strand-break-inducing agent.

A "target cell" is a cell that comprises a target sequence and is the object for receipt of a particular double-strand-break-inducing agent.

A "break-inducing agent" is a composition that creates a cleavage in at least one strand of a polynucleotide. In some aspect, a break-inducing agent may be capable of, or have its activity altered such that it is capable of, creating a break in only one strand of a polynucleotide. Producing a single-strand-break in a double-stranded target sequence may be referred to herein as "nicking" the target sequence.

The term "double-strand-break-inducing agent", or equivalently "double-strand-break agent" or "DSB agent", as used herein refers to any composition which produces a double-strand break in a target polynucleotide sequence; that is, creates a break in both strands of a double stranded polynucleotide. Examples of a DSB agent include, but are not limited to: meganucleases, TAL effector nucleases, Argonautes, Zinc Finger nucleases, and Cas endonucleases (either individually or as part of a ribonucleoprotein complex). Producing the double-strand break in a target sequence may be referred to herein as "cutting" or "cleaving" the target sequence. In some aspects, the DSB agent is a nuclease. In some aspects, the DSB agent is an endonuclease. An "endonuclease" refers to an enzyme that cleaves the phosphodiester bond within a polynucleotide chain. In some embodiments, the double-strand break results in a "blunt" end of a double-stranded polynucleotide, wherein both strands are cut directly across from each other with no nucleotide overhang generated. A "blunt" end cut of a double-stranded polynucleotide is created when a first cleavage of the first stand polynucleotide backbone occurs between a first set of two nucleotides on one strand, and a second cleavage of the second strand polynucleotide backbone occurs between a second set of two nucleotides on the opposite strand, wherein each of the two nucleotides of the first set are hydrogen bonded to one of the two nucleotides of the second set, resulting in cut strands with no nucleotide on the cleaved end that is not hydrogen bonded to another nucleotide on the opposite strand. In some embodiments, the double-strand break results in a "sticky" end of a double-stranded polynucleotide, wherein cuts are made between nucleotides of dissimilar relative positions on each of the two strands, resulting in a polynucleotide overhang of one strand compared to the other. A "sticky" end cut of a double-stranded polynucleotide is created when a first cleavage of the first strand polynucleotide backbone occurs between a first set of two nucleotides on one strand, and a second cleavage of the second strand polynucleotide backbone occurs between a second set of two nucleotides on the opposite strand, wherein no more than one nucleotide of the first set is hydrogen bonded to one of the nucleotides of the second set on the opposite strand, resulting in an "overhang" of at least one polynucleotide on one of the two strands wherein the lengths of the two resulting cut strands are not identical. In some embodiments, the DSB agent comprises more than one type of molecule. In one non-limiting example, the DSB agent comprises an endonuclease protein and a polynucleotide, for example a Cas endonuclease and a guide RNA. In some aspects, the DSB agent is a fusion protein comprising a plurality of polypeptides. In one non-limiting example, the DSB agent is a Cas endonuclease with a deactivated nuclease domain, and another polypeptide with nuclease activity.

As used herein, the term "recognition site" refers to a polynucleotide sequence to which a double-strand-break-inducing agent is capable of alignment, and may optionally contact, bind, and/or effect a double-strand break. The terms "recognition site" and "recognition sequence" are used interchangeably herein. The recognition site can be an endogenous site in a host (such as a yeast, animal, or plant) genome, or alternatively, the recognition site can be heterologous to the host (yeast, animal, or plant) and thereby not be naturally occurring in the genome, or the recognition site can be found in a heterologous genomic location compared to where it occurs in nature. The length and the composition of a recognition site can be characteristic of, and may be specific to, a particular double-strand-break-inducing agent. The cleavage site of a DSB agent may be the same or different than the recognition site, and may be the same or different than the binding site.

As used herein, the term "endogenous recognition (or binding or cleavage) site" refers to a double-strand-break-inducing agent recognition (or binding or cleavage) site that is endogenous or native to the genome of a host (such as a plant, animal, or yeast) and is located at the endogenous or native position of that recognition (or binding or cleavage) site in the genome of the host (such as a plant, animal, or yeast). The length of the recognition (or binding or cleavage) site can vary, and includes, for example, recognition (or binding or cleavage) sites that are at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or more than 70 nucleotides in length. The composition of the recognition (or binding or cleavage) site can vary, and includes, for example, a plurality of specific nucleotides whose compositions are recognized by the DSB agent. In some aspects, the plurality of specific nucleotides is contiguous in the primary sequence. In some aspects, the plurality of specific nucleotides is non-contiguous in the primary sequence. It is further possible that the recognition site could be palindromic, that is, the sequence on one strand reads the same in the opposite direction on the complementary strand. The binding and/or nick/cleavage site could be within the recognition sequence or the binding and/or nick/cleavage site could be outside of the recognition sequence. In another variation, the DSB cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs.

As used herein, the term "target recognition site" refers to the polynucleotide sequence to which a double-strand-break-inducing agent is capable of aligning perfectly (i.e., zero nucleotide mismatches, gaps, or insertions), and in some aspects, induces a double-strand break.

As used herein, the term "target binding site" refers to the polynucleotide sequence at which the double-strand-break-inducing agent is capable of forming a functional association, and to which it forms bonds with complementary nucleotides of the target polynucleotide strand, with perfect alignment (i.e., zero nucleotide mismatches, gaps, or insertions).

As used herein, the term "target cleavage site" refers to the polynucleotide sequence at which a double-strand-break-inducing agent is capable of producing a double-strand break, with perfect alignment (i.e., zero nucleotide mismatches, gaps, or insertions).

"CRISPR" (Clustered Regularly Interspaced Short Palindromic Repeats) loci refers to certain genetic loci encoding components of DNA cleavage systems, for example, used by bacterial and archaeal cells to destroy foreign DNA (Horvath and Barrangou, 2010, Science 327:167-170; WO2007025097, published 1 Mar. 2007). A CRISPR locus can consist of a CRISPR array, comprising short direct repeats (CRISPR repeats) separated by short variable DNA sequences (called spacers), which can be flanked by diverse Cas (CRISPR-associated) genes.

As used herein, an "effector" or "effector protein" is a protein that encompasses an activity including recognizing, binding to, and/or cleaving or nicking a polynucleotide target. The "effector complex" of a CRISPR system includes Cas proteins involved in crRNA and target recognition and binding. Some of the component Cas proteins may additionally comprise domains involved in target polynucleotide cleavage.

The term "Cas protein" refers to a polypeptide encoded by a Cas (CRISPR-associated) gene. A Cas protein includes but is not limited to: the novel Cas-delta protein disclosed herein, a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease" or "Cas effector protein", that when in complex with a suitable polynucleotide component, is capable of recognizing, binding to, and optionally nicking or cleaving all or part of a specific polynucleotide target sequence. A Cas endonuclease described herein comprises one or more nuclease domains. The Cas-delta endonucleases of the disclosure may include those having RuvC or RuvC-like nuclease domains. A Cas protein is further defined as a functional fragment or functional variant of a native Cas protein, or a protein that shares at least 50%, between 50% and 55%, at least 55%, between 55% and 60%, at least 60%, between 60% and 65%, at least 65%, between 65% and 70%, at least 70%, between 70% and 75%, at least 75%, between 75% and 80%, at least 80%, between 80% and 85%, at least 85%, between 85% and 90%, at least 90%, between 90% and 95%, at least 95%, between 95% and 96%, at least 96%, between 96% and 97%, at least 97%, between 97% and 98%, at least 98%, between 98% and 99%, at least 99%, between 99% and 100%, or 100% sequence identity with at least 50, between 50 and 100, at least 100, between 100 and 150, at least 150, between 150 and 200, at least 200, between 200 and 250, at least 250, between 250 and 300, at least 300, between 300 and 350, at least 350, between 350 and 400, at least 400, between 400 and 450, at least 500, or greater than 500 contiguous amino acids of a native Cas protein, and retains at least partial activity.

The terms "cascade" and "cascade complex" are used interchangeably herein and include reference to a multi-subunit protein complex that can assemble with a polynucleotide forming a polynucleotide-protein complex (PNP). Cascade is a PNP that relies on the polynucleotide for complex assembly and stability, and for the identification of target nucleic acid sequences. Cascade functions as a surveillance complex that finds and optionally binds target nucleic acids that are complementary to a variable targeting domain of the guide polynucleotide.

The terms "cleavage-ready Cascade", "crCascade", "cleavage-ready Cascade complex", "crCascade complex", "cleavage-ready Cascade system", "CRC" and "crCascade system", are used interchangeably herein and include reference to a multi-subunit protein complex that can assemble with a polynucleotide forming a polynucleotide-protein complex (PNP), wherein one of the cascade proteins is a Cas endonuclease capable of recognizing, binding to, and optionally unwinding, nicking, or cleaving all or part of a target sequence.

As used herein, the term "guide polynucleotide", relates to a polynucleotide sequence that can form a complex with a Cas endonuclease, including the Cas endonuclease described herein, and enables the Cas endonuclease to recognize, optionally bind to, and optionally cleave a DNA target site. The guide polynucleotide sequence can be a RNA sequence, a DNA sequence, or a combination thereof (a RNA-DNA combination sequence).

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, optionally bind to, and optionally nick or cleave (introduce a single or double-strand break) the DNA target site.

The term "variable targeting domain" or "VT domain" is used interchangeably herein and includes a nucleotide sequence that can hybridize (is complementary) to one strand (nucleotide sequence) of a double strand DNA target site. The percent complementation between the first nucleotide sequence domain (VT domain) and the target sequence can be at least 50%, 51%, 52%, 53%, 54%, 55%, 56%, 57%, 58%, 59%, 60%, 61%, 62%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" (of a guide polynucleotide) is used interchangeably herein and includes a nucleotide sequence that interacts with a Cas endonuclease polypeptide. A CER domain comprises a (trans-acting) tracrNucleotide mate sequence followed by a tracrNucleotide sequence. The CER domain can be composed of a DNA sequence, a RNA sequence, a modified DNA sequence, a modified RNA sequence (see for example US20150059010A1, published 26 Feb. 2015), or any combination thereof.

As used herein, the terms "guide polynucleotide/Cas endonuclease complex", "guide polynucleotide/Cas endonuclease system", "guide polynucleotide/Cas complex", "guide polynucleotide/Cas system" and "guided Cas system" "Polynucleotide-guided endonuclease", "PGEN" are used interchangeably herein and refer to at least one guide polynucleotide and at least one Cas endonuclease, that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double-strand break) the DNA target site. A guide polynucleotide/Cas endonuclease complex herein can comprise Cas protein(s) and suitable polynucleotide component(s) of any of the known CRISPR systems (Horvath and Barrangou, 2010, Science 327:167-170; Makarova et al. 2015, Nature Reviews Microbiology Vol. 13:1-15; Zetsche et al., 2015, Cell 163, 1-13; Shmakov et al., 2015, Molecular Cell 60, 1-13).

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double-strand break) the DNA target site.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

As used herein, "donor DNA" is a DNA construct that comprises a polynucleotide of interest to be inserted into the target site of a Cas endonuclease.

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

As used herein, "homologous recombination" (HR) includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

The term "plant" generically includes whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. A "plant element" is intended to reference either a whole plant or a plant component, which may comprise differentiated and/or undifferentiated tissues, for example but not limited to plant tissues, parts, and cell types. In one embodiment, a plant element is one of the following: whole plant, seedling, meristematic tissue, ground tissue, vascular tissue, dermal tissue, seed, leaf, root, shoot, stem, flower, fruit, stolon, bulb, tuber, corm, keiki, shoot, bud, tumor tissue, and various forms of cells and culture (e.g., single cells, protoplasts, embryos, callus tissue). The term "plant organ" refers to plant tissue or a group of tissues that constitute a morphologically and functionally distinct part of a plant. As used herein, a "plant element" is synonymous to a "portion" of a plant, and refers to any part of the plant, and can include distinct tissues and/or organs, and may be used interchangeably with the term "tissue" throughout. Similarly, a "plant reproductive element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keiki, or bud. The plant element may be in plant or in a plant organ, tissue culture, or cell culture.

"Progeny" comprises any subsequent generation of an organism, produced via sexual or asexual reproduction.

As used herein, the term "plant part" refers to plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, as well as the parts themselves. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The term "monocotyledonous" or "monocot" refers to the subclass of angiosperm plants also known as "monocotyledoneae", whose seeds typically comprise only one embryonic leaf, or cotyledon. The term includes references to whole plants, plant elements, plant organs (e.g., leaves, stems, roots, etc.), seeds, plant cells, and progeny of the same.

The term "dicotyledonous" or "dicot" refers to the subclass of angiosperm plants also knows as "dicotyledoneae", whose seeds typically comprise two embryonic leaves, or cotyledons. The term includes references to whole plants, plant elements, plant organs (e.g., leaves, stems, roots, etc.), seeds, plant cells, and progeny of the same.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

The term "isoline" is a comparative term, and references organisms that are genetically identical, but differ in treatment. In one example, two genetically identical maize plant embryos may be separated into two different groups, one receiving a treatment (such as the introduction of a CRISPR-Cas effector endonuclease) and one control that does not receive such treatment. Any phenotypic differences between the two groups may thus be attributed solely to the treatment and not to any inherency of the plant's endogenous genetic makeup.

The compositions and methods herein may provide for an improved "agronomic trait" or "trait of agronomic importance" or "trait of agronomic interest" to a plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

"Agronomic trait potential" is intended to mean a capability of a plant element for exhibiting a phenotype, preferably an improved agronomic trait, at some point during its life cycle, or conveying said phenotype to another plant element with which it is associated in the same plant.

The terms "decreased," "fewer," "slower" and "increased" "faster" "enhanced" "greater" as used herein refers to a decrease or increase in a characteristic of the modified plant element or resulting plant compared to an unmodified plant element or resulting plant. For example, a decrease in a characteristic may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400%) or more lower than the untreated control and an increase may be at least 1%, at least 2%, at least 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%), at least about 400% or more higher than the control.

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "mole" or "umole" mean micromole(s), "g" means gram(s), "µg" or "ug" means microgram(s), "ng" means nanogram(s), "U" means unit(s), "bp" means base pair(s) and "kb" means kilobase(s).

Compositions for Modifying the Genome of a Target Cell
Morphogenic Factors

The present disclosure comprises methods and compositions for producing genomic modifications in an organism using a double-strand-break agent and a morphogenic factor. Morphogenic factors can enhance the rate, efficiency, and efficacy of targeted polynucleotide modification by a number of mechanisms, some of which are related to the capability of stimulating growth of a cell or tissue, including but not limited to promoting progression through the cell cycle, inhibiting cell death, such as apoptosis, stimulating cell division, and/or stimulating embryogenesis. The polynucleotides can fall into several categories, including but not limited to, cell cycle stimulatory polynucleotides, developmental polynucleotides, anti-apoptosis polynucleotides, hormone polynucleotides, transcription factors, or silencing constructs targeted against cell cycle repressors or pro-apoptotic factors. Methods and compositions for rapid and efficient transformation of plants by transforming cells of plant explants with an expression construct comprising a heterologous nucleotide encoding a morphogenic factor are described in US Patent Application Publication No. US2017/0121722 (published 4 May 2017).

A morphogenic factor (gene or protein) may involved in plant metabolism, organ development, stem cell development, cell growth stimulation, organogenesis, somatic embryogenesis initiation, accelerated somatic embryo maturation, initiation and/or development of the apical meristem, initiation and/or development of shoot meristem, or a combination thereof.

In some aspects, the morphogenic factor is a molecule selected from one or more of the following categories: 1) cell cycle stimulatory polynucleotides including plant viral replicase genes such as RepA, cyclins, E2F, prolifera, cdc2 and cdc25; 2) developmental polynucleotides such as Lecl, Knl family, WUSCHEL, Zwille, BBM, Ainteguments (ANT), FUS3, and members of the Knotted family, such as Knl, STM, OSH1, and SbH1; 3) anti-apoptosis polynucleotides such as CED9, Bc12, Bcl-X(L), Bcl-W, A1, McL-1, Macl, Boo, and Bax-inhibitors; 4) hormone polynucleotides such as IPT, TZS, and CKI-1; and 5) silencing constructs targeted against cell cycle repressors, such as Rb, CK1, prohibitin, and weel, or stimulators of apoptosis such as APAF-1, bad, bax, CED-4, and caspase-3, and repressors of plant developmental transitions, such as Pickle and WD polycomb genes including FIE and Medea. The polynucleotides can be silenced by any known method such as antisense, RNA interference, cosuppression, chimerplasty, or transposon insertion.

In some aspects, the morphogenic gene is a member of the WUS/WOX gene family (WUS1, WUS2, WUS3, WOX2A, WOX4, WOX5, or WOX9) see U.S. Pat. Nos. 7,348,468 and 7,256,322 and United States Patent Application publications 20170121722 and 20070271628; Laux et al. (1996) Development 122:87-96; and Mayer et al. (1998) Cell 95:805-815; van der Graaff et al., 2009, Genome Biology 10:248; Dolzblasz et al., 2016, Mol. Plant 19:1028-39. The Wuschel protein, designated hereafter as WUS, plays a key role in the initiation and maintenance of the apical meristem, which contains a pool of pluripotent stem cells (Endrizzi, et al., (1996) Plant Journal 10:967-979; Laux, et al., (1996) Development 122:87-96; and Mayer, et al., (1998) Cell 95:805-815). Modulation of WUS/WOX is expected to modulate plant and/or plant tissue phenotype including plant metabolism, organ development, stem cell development, cell growth stimulation, organogenesis, somatic embryogenesis initiation, accelerated somatic embryo maturation, initiation and/or development of the apical meristem, initiation and/or development of shoot meristem, or a combination thereof. WUS encodes a novel homeodomain protein which presumably functions as a transcriptional regulator (Mayer, et al., (1998) Cell 95:805-815). The stem cell population of *Arabidopsis* shoot meristems is believed to be maintained by a regulatory loop between the CLAVATA (CLV) genes which promote organ initiation and the WUS gene which is required for stem cell identity, with the CLV genes repressing WUS at the transcript level, and WUS expression being sufficient to induce meristem cell identity and the expression of the stem cell marker CLV3 (Brand, et al., (2000) Science 289:617-619; Schoof, et al., (2000) Cell 100:635-644). Expression of *Arabidopsis* WUS can induce stem cells in vegetative tissues, which can differentiate into somatic embryos (Zuo, et al. (2002) Plant J 30:349-359). Also of interest in this regard would be a MYB118 gene (see U.S. Pat. No. 7,148,402), MYB115 gene (see Wang et al. (2008) Cell Research 224-235), a BABYBOOM gene (BBM; see Boutilier et al. (2002) Plant Cell 14:1737-1749), or a CLAVATA gene (see, for example, U.S. Pat. No. 7,179,963).

In some embodiments, the morphogenic gene or protein is a member of the AP2/ERF family of proteins. The AP2/ERF family of proteins is a plant-specific class of putative transcription factors that regulate a wide variety of developmental processes and are characterized by the presence of an AP2 DNA binding domain that is predicted to form an amphipathic alpha helix that binds DNA (PFAM Accession PF00847). The AP2 domain was first identified in APETALA2, an *Arabidopsis* protein that regulates meristem identity, floral organ specification, seed coat development, and floral homeotic gene expression. The AP2/ERF proteins have been subdivided into distinct subfamilies based on the presence of conserved domains. Initially, the family was divided into two subfamilies based on the number of DNA binding domains, with the ERF subfamily having one DNA binding domain, and the AP2 subfamily having 2 DNA binding domains. As more sequences were identified, the family was subsequently subdivided into five subfamilies: AP2, DREB, ERF, RAV, and others. (Sakuma et al. (2002) *Biochem Biophys Res Comm* 290:998-1009).

Members of the APETALA2 (AP2) family of proteins function in a variety of biological events, including but not limited to, development, plant regeneration, cell division, embryogenesis, and morphogenic (see, e.g., Riechmann and Meyerowitz (1998) *Biol Chem* 379:633-646; Saleh and Pages (2003) *Genetika* 35:37-50 and Database of *Arabidopsis* Transcription Factors at daft.cbi.pku.edu.cn). The AP2 family includes, but is not limited to, AP2, ANT, Glossy15, AtBBM, BnBBM, and maize ODP2/BBM.

Other morphogenic genes useful in the present disclosure include, but are not limited to, Ovule Development Protein 2 (ODP2) polypeptides, and related polypeptides, e.g., Babyboom (BBM) protein family proteins. In an aspect, the polypeptide comprising the two AP2-DNA binding domains is an ODP2, BBM2, BMN2, or BMN3 polypeptide. The ODP2 polypeptides of the disclosure contain two predicted APETALA2 (AP2) domains and are members of the AP2 protein family (PFAM Accession PF00847). The AP2 family of putative transcription factors has been shown to regulate a wide range of developmental processes, and the family members are characterized by the presence of an AP2 DNA binding domain. This conserved core is predicted to form an amphipathic alpha helix that binds DNA. The AP2 domain was first identified in APETALA2, an *Arabidopsis* protein that regulates meristem identity, floral organ specification, seed coat development, and floral homeotic gene expression. The AP2 domain has now been found in a variety of proteins. The ODP2 polypeptides share homology with several polypeptides within the AP2 family, e.g., see FIG. 1 of U.S. Pat. No. 8,420,893, which is incorporated herein by reference in its entirety, provides an alignment of the maize and rice ODP2 polypeptides with eight other proteins having two AP2 domains. A consensus sequence of all proteins appearing in the alignment of U.S. Pat. No. 8,420,893 is also provided in FIG. 1 therein.

In some embodiments, the morphogenic factor is a babyboom (BBM) polypeptide, which is a member of the AP2 family of transcription factors. The BBM protein from *Arabidopsis* (AtBBM) is preferentially expressed in the developing embryo and seeds and has been shown to play a central role in regulating embryo-specific pathways. Overexpression of AtBBM has been shown to induce spontaneous formation of somatic embryos and cotyledon-like structures on seedlings. See, Boutiler et al. (2002) *The Plant Cell* 14:1737-1749. The maize BBM protein also induces embryogenesis and promotes transformation (See, U.S. Pat. No. 7,579,529, which is herein incorporated by reference in its entirety). Thus, BBM polypeptides stimulate proliferation, induce embryogenesis, enhance the regenerative capacity of a plant, enhance transformation, and as demonstrated herein, enhance rates of targeted polynucleotide modification. As used herein "regeneration" refers to a morphogenic response that results in the production of new tissues, organs, embryos, whole plants or parts of whole plants that are derived from a single cell or a group of cells. Regeneration may proceed indirectly via a callus phase or directly, without an intervening callus phase. "Regenerative capacity" refers to the ability of a plant cell to undergo regeneration.

Other morphogenic genes useful in the present disclosure include, but are not limited to, LEC1 (Lotan et al., 1998, Cell 93:1195-1205), LEC2 (Stone et al., 2008, PNAS 105:3151-3156; Belide et al., 2013, Plant Cell Tiss. Organ Cult 113:543-553), KN1/STM (Sinha et al., 1993. Genes Dev 7:787-795), the IPT gene from *Agrobacterium* (Ebinuma and Komamine, 2001, In vitro Cell. Dev Biol—Plant 37:103-113), MONOPTEROS-DELTA (Ckurshumova et al., 2014, New Phytol. 204:556-566), the *Agrobacterium* AV-6b gene (Wabiko and Minemura 1996, Plant Physiol. 112:939-951), the combination of the *Agrobacterium* IAA-h and IAA-m genes (Endo et al., 2002, Plant Cell Rep., 20:923-928), the *Arabidopsis* SERK gene (Hecht et al., 2001, Plant Physiol. 127:803-816), the Arabiopsis AGL15 gene (Harding et al., 2003, Plant Physiol. 133:653-663), and the FUSCA gene (Castle and Meinke, Plant Cell 6:25-41), and the PICKLE gene (Ogas et al., 1999, PNAS 96:13839-13844).

The morphogenic factor can be derived from a monocot. In various aspects, the morphogenic factor is derived from barley, maize, millet, oats, rice, rye, *Setaria* sp., Sorghum, sugarcane, switchgrass, triticale, turfgrass, or wheat.

The morphogenic factor can be derived from a dicot. The morphogenic factor can be derived from kale, cauliflower, broccoli, mustard plant, cabbage, pea, clover, alfalfa, broad bean, tomato, cassava, soybean, canola, alfalfa, sunflower, safflower, tobacco, *Arabidopsis*, or cotton.

The present disclosure encompasses isolated or substantially purified polynucleotide or polypeptide morphogenic factor compositions.

The morphogenic factor may be altered in various ways including amino acid substitutions, deletions, truncations, and insertions. Methods for such manipulations are generally known in the art. For example, amino acid sequence variants of the morphogenic proteins can be prepared by mutations in the DNA. Methods for mutagenesis and nucleotide sequence alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, polynucleotides or polypeptides having homology to a known morphogenic factor and/or sharing conserved functional domains can be identified by screening sequence databases using programs such as BLAST, or using standard nucleic acid hybridization techniques known in the art, for example as described in Tijssen (1993) Laboratory Techniques in Biochemistry and Molecular Biology—Hybridization with Nucleic Acid Probes, Part I, Chapter 2 (Elsevier, N.Y.); Ausubel et al., eds. (1995) Current Protocols in Molecular Biology, Chapter 2 (Greene Publishing and Wiley-Interscience, NY); and, Sambrook et al. (1989) Molecular Cloning: A Laboratory Manual (2d ed., Cold Spring Harbor Laboratory Press, Plainview, N.Y.).

In some aspects, the morphogenic gene is selected from the group consisting of: SEQID NOs:1-5, 11-16, 22, and 23-47. In some aspects, the morphogenic protein is selected from the group consisting of: SEQID NOs: 6-10, 17-21, and 48-73.

In some aspects, a plurality of morphogenic factors is selected. When multiple morphogenic factors are used, the polynucleotides encoding each of the factors can be present on the same expression cassette or on separate expression cassettes. Likewise, the polynucleotide(s) encoding the morphogenic factor(s) and the polynucleotide encoding the double-strand break-inducing agent can be located on the same or different expression cassettes. When two or more factors are coded for by separate expression cassettes, the expression cassettes can be provided to the organism simultaneously or sequentially.

In some aspects, the expression of the morphogenic factor is transient. In some aspects, the expression of the morphogenic factor is constitutive. In some aspects, the expression of the morphogenic factor is specific to a particular tissue or cell type. In some aspects, the expression of the morphogenic factor is temporally regulated. In some aspects, the expression of the morphogenic factor is regulated by an environmental condition, such as temperature, time of day, or other factor. In some aspects, the expression of the morphogenic factor is stable. In some aspects, expression of the morphogenic factor is controlled. The controlled expression may be a pulsed expression of the morphogenic factor for a particular period of time. Alternatively, the morphogenic factor may be expressed in only some transformed cells and not expressed in others. The control of expression of the morphogenic factor can be achieved by a variety of methods as disclosed herein.

Double Strand Break Agents

A double-strand-break-inducing agent (equivalently, "double-strand-break agent" or "DSB agent") described herein may be introduced to a target polynucleotide to create a "functional association". A "functional association" means that the DSB agent is introduced to a target polynucleotide molecule, may optionally bind to it, and is capable of producing a double-strand-break on the backbone of the target polynucleotide to which it is introduced. The position (location with respect to the polynucleotide sequence) and nature (blunt-end, sticky-end, or mixed) of the double-strand break is dependent upon the exact DSB agent used.

The term "double-strand-break-inducing agent" as used herein refers to any composition which produces a double-strand break in a target sequence in the genome of an organism. Double-strand-break-inducing agents may be proteins that include but are not limited to: restriction endonucleases (see e.g. Roberts et al., (2003) Nucleic Acids Res 1:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.)), meganucleases (see e.g., WO 2009/114321; Gao et al. (2010) Plant Journal 1:176-187), TAL effector nucleases or TALENs (see e.g., US20110145940, Christian, M., T. Cermak, et al. 2010. Targeting DNA double-strand breaks with TAL effector nucleases. Genetics 186(2): 757-61 and Boch et al., (2009), Science 326(5959): 1509-12), zinc finger nucleases (see e.g. Kim, Y. G., J. Cha, et al. (1996). "Hybrid restriction enzymes: zinc finger fusions to FokI cleavage"), and CRISPR-Cas endonucleases (see e.g. WO2007/025097 application published Mar. 1, 2007).

An "engineered double-strand-break-inducing agent" refers to any double-strand-break-inducing agent that is engineered (modified or derived) from its native form to specifically recognize and induce a double-strand break in the desired recognition site. Thus, an engineered double-strand-break-inducing agent can be derived from a native, naturally-occurring nuclease or it could be artificially created or synthesized. The modification of the nuclease can be as little as one nucleotide. In some embodiments, the engineered double-strand-break-inducing agent induces a double-strand break in a recognition site, wherein the recognition site was not a sequence that would have been recognized by a native (non-engineered or non-modified) double-strand-break-inducing agent. Producing a double-strand break in a recognition site or other DNA can be referred to herein as "cutting" or "cleaving" the recognition site or other DNA.

In some aspects, the DSB agent can be provided as a polypeptide, that can be purified and substantially free of other molecules, or can be in association with one or more heterologous components. In one embodiment, the DSB agent is a polypeptide and a polynucleotide. In one embodiment, the DSB agent is a fusion protein, comprising two or more domains, wherein one domain can effect the cleavage of a target polynucleotide. In one embodiment, the DSB agent is a plurality of polypeptides.

In some aspects, the DSB agent can be provided via a polynucleotide encoding the DSB agent polypeptide. Such a polynucleotide encoding may optionally be modified to substitute codons having a higher frequency of usage in a particular host cell or organism, as compared to the naturally-occurring polynucleotide sequence. For example, the polynucleotide encoding the DSB agent can be modified to substitute codons having a higher frequency of usage in a maize or soybean plant, as compared to the naturally occurring polynucleotide sequence.

Restriction Endonucleases

Endonucleases include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and cleavage typically occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (Roberts et al., (2003) Nucleic Acids Res 1:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.)).

Meganucleases

A "meganuclease" refers to a homing endonuclease, which like restriction endonucleases, bind and cut at a specific recognition site, however the recognition sites for meganucleases are typically longer, about 18 bp or more. In some embodiments of the invention, the meganuclease has been engineered (or modified) to cut a specific endogenous recognition sequence, wherein the endogenous target sequence prior to being cut by the engineered double-strand-break-inducing agent was not a sequence that would have been recognized by a native (non-engineered or non-modified) endonuclease.

A "meganuclease polypeptide" refers to a polypeptide having meganuclease activity and thus capable of producing a double-strand break in the recognition sequence.

Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing open reading frames, introns, and inteins, respectively. For example, intron-, intein-, and free-standing gene encoded meganuclease from *Saccharomyces cerevisiae* are denoted I-SceI, PI-SceI, and F-SceII, respectively. Meganuclease domains, structure and function are known, see for example, Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Examples of meganucleases include, but are not limited to: I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PculP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP, PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any functional variants or fragments thereof.

Argonautes

Small non-coding RNAs are one type of contributor to gene regulation, and require a unique class of proteins called Argonautes. Argonaute proteins are highly specialized binding modules that can bind small non-coding RNAs and control protein synthesis, affect messenger RNA stability and even participate in the production of a new class of small RNAs, Piwi-interacting RNAs. Argonautes coordinate downstream gene-silencing events by interacting with other protein factors.

First identified in plants and subsequently discovered to be ubiquitous in many organisms, Argonaute proteins are defined by the presence of PAZ (Piwi-Argonaute-Zwille) and PIWI domains. They are evolutionarily conserved and can be phylogenetically subdivided into the Ago subfamily and the Piwi subfamily. Ago proteins are ubiquitously expressed and bind to siRNAs or miRNAs to guide post-transcriptional gene silencing either by destabilization of the mRNA or by translational repression. The expression of Piwi proteins is mostly restricted to the germ line and Piwi proteins associate with piRNAs to facilitate silencing of mobile genetic elements.

Many Argonaute proteins bind RNA guides to cleave foreign RNA, while others are capable of cleaving plasmid and genomic DNA. *Natronobacterium gregoryi* Argonaute uses 5' phosphorylated DNA guides (rather than the RNA guides employed by Cas9 or Cpf1), without requiring a PAM sequence, to randomly remove 1-20 nucleotides from the cleavage site specified by the gDNA.

TAL Effector Nucleases (TALENs)

TAL effector nucleases are a class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, for example, Fok1. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkq704; and Miller et al. (2011) Nature Biotechnology 29:143-148; all of which are herein incorporated by reference.

Zinc-Finger Endonucleases

Zinc fingers are structural domains found in eukaryotic proteins which control gene transcription. The zinc finger domain of the Cys$_2$His$_2$class of ZFPs is a polypeptide structural motif folded around a bound zinc ion, and has a sequence of the form —X$_3$-Cys-X$_{2-4}$-Cys-X$_{12}$-His-X$_{3-5}$-His-X$_4$— (wherein X is any amino acid). The zinc finger is an independent folding domain which uses a zinc ion to stabilize the packing of an antiparallel β-sheet against an α-helix. There is a great deal of sequence variation in the amino acids designated as X, however, the two consensus histidine and cysteine residues are invariant. Although most ZFPs have a similar three-dimensional structure, they bind polynucleotides having a wide range of nucleotide sequences. the binding of the zinc finger domain is dependent on the sequence of the polynucleotides other than those which directly contact amino acids within the zinc finger domain.

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically Fok1). The cleavage domain dimerizes in order to cleave DNA; therefore, a pair of ZFNs are required to target non-palindromic target polynucleotides.

Cas Endonucleases

As used herein, the term "Cas gene" refers to a gene that is generally coupled, associated or close to or in the vicinity of flanking CRISPR loci.

"CRISPR" (Clustered Regularly Interspaced Short Palindromic Repeats) loci refers to certain genetic loci encoding components of DNA cleavage systems, for example, used by bacterial and archaeal cells to destroy foreign DNA (Horvath and Barrangou, 2010, *Science* 327:167-170; WO2007025097, published 1 Mar. 2007). A CRISPR locus can consist of a CRISPR array, comprising short direct repeats (CRISPR repeats) separated by short variable DNA sequences (called spacers), which can be flanked by diverse Cas (CRISPR-associated) genes.

Cas endonucleases, either as single effector proteins or in an effector complex with other components, unwind the DNA duplex at the target sequence and optionally cleave at least one DNA strand, as mediated by recognition of the target sequence by a polynucleotide (such as, but not limited to, a crRNA or guide RNA) that is in complex with the Cas effector protein. Such recognition and cutting of a target sequence by a Cas endonuclease typically occurs if the correct protospacer-adjacent motif (PAM) is located at or adjacent to the 3' end of the DNA target sequence.

Many Cas endonucleases have been described to date that can recognize specific PAM sequences (WO2016186953 published 24 Nov. 2016, WO2016186946 published 24 Nov. 2016, and Zetsche B et al. 2015. Cell 163, 1013) and cleave the target DNA at a specific position.

Cas endonucleases may be capable of forming a complex with a guide polynucleotide (e.g., guide RNA or gRNA) that is capable of recognizing, binding to, and optionally nicking, unwinding, or cleaving all or part of a target sequence. In some aspects, the guide polynucleotide/Cas endonuclease complex is capable of introducing a double-strand-break into a target polynucleotide. In some aspects, the guide polynucleotide comprises solely RNA, solely DNA, a chimeric molecule comprising both DNA and RNA, and/or comprises a chemically modified nucleotide. The guide polynucleotide (e.g., guide RNA) may be a single guide RNA (sgRNA) that is capable of binding to a sequence on the target polynucleotide.

Alternatively, a Cas endonuclease herein may lack DNA cleavage or nicking activity, but can still specifically bind to a DNA target sequence when complexed with a suitable RNA component. (See also U.S. Patent Application US20150082478 published 19 Mar. 2015 and US20150059010 published 26 Feb. 2015).

Cas endonucleases may occur as individual effectors (Class 2 CRISPR systems) or as part of larger effector complexes (Class I CRISPR systems).

Cas endonucleases include, but are not limited to, Cas endonucleases identified from the following systems: Class 1, Class 2, Type I, Type II, Type III, Type IV, Type V, and Type VI. In some aspects, the Cas endonuclease is Cas3 (a feature of Class 1 type I systems), Cas9 (a feature of Class 2 type II systems) or Cas12 (Cpf1) (a feature of Class 2 type V systems).

Cas endonucleases and effector proteins can be used for targeted genome editing (via simplex and multiplex double-strand breaks and nicks) and targeted genome regulation (via tethering of epigenetic effector domains to either the Cas protein or sgRNA. A Cas endonuclease can also be engineered to function as an RNA-guided recombinase, and via RNA tethers could serve as a scaffold for the assembly of multiprotein and nucleic acid complexes (Mali et al., 2013, *Nature Methods* Vol. 10: 957-963).

A Cas endonuclease, effector protein, functional variant, or a functional fragment thereof, for use in the disclosed methods, can be isolated from a native source, or from a recombinant source where the genetically modified host cell is modified to express the nucleic acid sequence encoding the protein. Alternatively, the Cas protein can be produced using cell free protein expression systems, or be synthetically produced. Effector Cas nucleases may be isolated and introduced into a heterologous cell, or may be modified from its native form to exhibit a different type or magnitude of activity than what it would exhibit in its native source. Such modifications include but are not limited to: fragments, variants, substitutions, deletions, and insertions.

Fragments and variants of Cas endonucleases and Cas effector proteins can be obtained via methods such as site-directed mutagenesis and synthetic construction. Methods for measuring endonuclease activity are well known in the art such as, but not limiting to, WO2013166113 published 7 Nov. 2013, WO2016186953 published 24 Nov. 2016, and WO2016186946 published 24 Nov. 2016.

Some uses for guide RNA/Cas endonuclease systems have been described (see for example: US20150082478 A1 published 19 Mar. 2015, WO2015026886 published 26 Feb. 2015, and US20150059010 published 26 Feb. 2015) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Polynucleotides of Interest

Polynucleotides of interest are further described herein and include polynucleotides reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for genetic engineering will change accordingly.

General categories of polynucleotides of interest include, for example, genes of interest involved in information, such as zinc fingers, those involved in communication, such as kinases, and those involved in housekeeping, such as heat shock proteins. More specific polynucleotides of interest include, but are not limited to, genes involved in crop yield, grain quality, crop nutrient content, starch and carbohydrate quality and quantity as well as those affecting kernel size, sucrose loading, protein quality and quantity, nitrogen fixation and/or utilization, fatty acid and oil composition, genes encoding proteins conferring resistance to abiotic stress (such as drought, nitrogen, temperature, salinity, toxic metals or trace elements, or those conferring resistance to toxins such as pesticides and herbicides), genes encoding proteins conferring resistance to biotic stress (such as attacks by fungi, viruses, bacteria, insects, and nematodes, and development of diseases associated with these organisms).

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389.

Polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS, also referred to as acetohydroxyacid synthase, AHAS), in particular the sulfonylurea (UK: sulphonylurea) type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and 9,187,762. The bar gene encodes resistance to the herbicide basta, the nptII gene encodes resistance to the antibiotics kanamycin and geneticin, and the ALS-gene mutants encode resistance to the herbicide chlorsulfuron.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See U.S. Pat. Nos. 5,283,184 and 5,034,323.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that comprises it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins (such as green fluorescent protein (GFP), cyan (CFP), yellow (YFP), red (RFP), and blue (BFP), (Shaner et al., 2005, Nature Methods 2:905-909)), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying agent, chemical, etc.; and, the inclusion of a DNA sequences required for a specific modification (e.g., methylation) that allows its identification.

Additional selectable markers include genes that confer resistance to herbicidal compounds, such as sulphonylureas, glufosinate ammonium, bromoxynil, imidazolinones, and 2,4-dichlorophenoxyacetate (2,4-D). See for example, Acetolactase synthase (ALS) for resistance to sulfonylureas, imidazolinones, triazolopyrimidine sulfonamides, pyrimidinylsalicylates and sulphonylaminocarbonyl-triazolinones (Shaner and Singh, 1997, Herbicide Activity: Toxicol Biochem Mol Biol 69-110); glyphosate resistant 5-enolpyruvylshikimate-3-phosphate (EPSPS) (Saroha et al. 1998, J. Plant Biochemistry & Biotechnology Vol 7:65-72);

Polynucleotides of interest includes genes that can be stacked or used in combination with other traits, such as but not limited to herbicide resistance or any other trait described herein. Polynucleotides of interest and/or traits can be stacked together in a complex trait locus as described in US20130263324 published 3 Oct. 2013 and in WO/2013/112686, published 1 Aug. 2013.

A polypeptide of interest includes any protein or polypeptide that is encoded by a polynucleotide of interest described herein.

Further provided are methods for identifying at least one plant cell, comprising in its genome, a polynucleotide of interest integrated at the target site. A variety of methods are available for identifying those plant cells with insertion into the genome at or near to the target site. Such methods can be viewed as directly analyzing a target sequence to detect any change in the target sequence, including but not limited to PCR methods, sequencing methods, nuclease digestion, Southern blots, and any combination thereof. See, for example, US20090133152 published 21 May 2009. The method also comprises recovering a plant from the plant cell comprising a polynucleotide of interest integrated into its genome. The plant may be sterile or fertile. It is recognized that any polynucleotide of interest can be provided, integrated into the plant genome at the target site, and expressed in a plant.

Target Sites

The target site may be part of the organism's native genome or integrated therein or may be present on an episomal polynucleotide. The genomic target sequence may be on any region of any chromosome, and may or may not be in a region encoding a protein or RNA. The target site may be native to the cell or heterologous. In some embodiments, the heterologous target sequence may have been transgenically inserted into the organism's genome, and may be on any region of any chromosome, including an artificial or satellite chromosome, and may or may not be in a region encoding a protein or RNA. In some aspects, the target site polynucleotide is of nuclear origin (genomic), and may be either endogenous to the cell or may be heterologous (e.g. an introduced transgene). In some aspects, the target site polynucleotide is a plasmid or vector that exists within the cell or has been introduced. In some aspects, the target site polynucleotide exists in the cytoplasm of the cell (extra-nuclear). In some aspects, the target site polynucleotide exists in another organelle of the cell (e.g. plastid or mitochondrion). It is recognized that the cell or the organism may comprise multiple target sites, which may be located at one or multiple loci within or across chromosomes. Multiple independent manipulations of each target site in the organism can be performed using the presently disclosed methods.

The target site comprises at least one recognition sequence. The length of the recognition site sequence can vary, and includes, for example, sequences that are at least about 3, 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 80, 90, 100, or more nucleotides in length. In some embodiments, the recognition site is of a sufficient length to only be present in a genome of an organism one time. In some embodiments, the recognition site is palindromic, that is, the sequence on one strand reads the same in the opposite direction on the complementary strand. The double-strand break-inducing agent recognizes the recognition sequence and introduces a double-strand break at or near the recognition sequence. The nick/cleavage site could be within the sequence that is specifically recognized by the agent or the nick/cleavage site could be outside of the sequence that is specifically recognized by the agent. In some embodiments, the double-strand break is introduced about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, or more nucleotides away from the recognition sequence.

In some embodiments, the cleavage occurs at nucleotide positions immediately opposite each other to produce a blunt end cut or, in alternative embodiments, the cuts are staggered to produce single-stranded overhangs, also called "sticky ends", which can be either 5' overhangs, or 3' overhangs. The recognition sequence can be endogenous (native) or heterologous to the plant cell. When the recognition site is an endogenous sequence, it may be recognized by a naturally-occurring, or native double-strand break-inducing agent. Alternatively, an endogenous recognition sequence may be recognized and/or bound by a modified or engineered double-strand break-inducing agent designed or selected to specifically recognize the endogenous recognition sequence to produce a double-strand break.

Expression Elements

Any polynucleotide encoding a Cas protein or other CRISPR system component disclosed herein may be functionally linked to a heterologous expression element, to facilitate transcription or regulation in a host cell. Such expression elements include but are not limited to: promoter, leader, intron, and terminator. Expression elements may be "minimal"—meaning a shorter sequence derived from a native source, that still functions as an expression regulator or modifier. Alternatively, an expression element may be "optimized"—meaning that its polynucleotide sequence has been altered from its native state in order to function with a more desirable characteristic in a particular host cell (for example, but not limited to, a bacterial promoter may be "maize-optimized" to improve its expression in corn plants). Alternatively, an expression element may be "synthetic"— meaning that it is designed in silico and synthesized for use in a host cell. Synthetic expression elements may be entirely synthetic, or partially synthetic (comprising a fragment of a naturally-occurring polynucleotide sequence).

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels.

A plant promoter includes a promoter capable of initiating transcription in a plant cell. For a review of plant promoters, see, Potenza et al., 2004, In vitro Cell Dev Biol 40:1-22; Porto et al., 2014, Molecular Biotechnology (2014), 56(1), 38-49.

Constitutive promoters include, for example, the core CaMV 35S promoter (Odell et al., (1985) Nature 313:810-2); rice actin (McElroy et al., (1990) Plant Cell 2:163-71); ubiquitin (Christensen et al., (1989) Plant Mol Biol 12:619-32; ALS promoter (U.S. Pat. No. 5,659,026) and the like.

Tissue-preferred promoters can be utilized to target enhanced expression within a particular plant tissue. Tissue-preferred promoters include, for example, WO2013103367 published 11 Jul. 2013, Kawamata et al., (1997) Plant Cell Physiol 38:792-803; Hansen et al., (1997) Mol Gen Genet 254:337-43; Russell et al., (1997) Transgenic Res 6:157-68; Rinehart et al., (1996) Plant Physiol 112:1331-41; Van Camp et al., (1996) Plant Physiol 112:525-35; Canevascini et al., (1996) Plant Physiol 112:513-524; Lam, (1994) Results Probl Cell Differ 20:181-96; and Guevara-Garcia et al., (1993) Plant J 4:495-505. Leaf-preferred promoters include, for example, Yamamoto et al., (1997) Plant J 12:255-65; Kwon et al., (1994) Plant Physiol 105:357-67; Yamamoto et al., (1994) Plant Cell Physiol 35:773-8; Gotor et al., (1993) Plant J 3:509-18; Orozco et al., (1993) Plant Mol Biol 23:1129-38; Matsuoka et al., (1993) Proc. Natl. Acad. Sci. USA 90:9586-90; Simpson et al., (1958) EMBO J 4:2723-9; Timko et al., (1988) Nature 318:57-8. Root-preferred promoters include, for example, Hire et al., (1992) Plant Mol Biol 20:207-18 (soybean root-specific glutamine synthase gene); Miao et al., (1991) Plant Cell 3:11-22 (cytosolic glutamine synthase (GS)); Keller and Baumgartner, (1991) Plant Cell 3:1051-61 (root-specific control element in the GRP 1.8 gene of French bean); Sanger et al., (1990) Plant Mol Biol 14:433-43 (root-specific promoter of *A. tumefaciens* mannopine synthase (MAS)); Bogusz et al., (1990) Plant Cell 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) Plant Mol Biol 29:759-72); and rolB promoter (Capana et al., (1994) Plant Mol Biol 25:681-91; phaseolin gene (Mural et al., (1983) Science 23:476-82; Sengopta-Gopalen et al., (1988) Proc. Natl. Acad. Sci. USA 82:3320-4). See also, U.S. Pat. Nos. 5,837,876; 5,750,386; 5,633,363; 5,459, 252; 5,401,836; 5,110,732 and 5,023,179.

Seed-preferred promoters include both seed-specific promoters active during seed development, as well as seed-germinating promoters active during seed germination. See, Thompson et al., (1989) BioEssays 10:108. Seed-preferred promoters include, but are not limited to, Cim1 (cytokinin-induced message); cZ19B1 (maize 19 kDa zein); and milps (myo-inositol-1-phosphate synthase); and for example, those disclosed in WO2000011177 published 2 Mar. 2000 and U.S. Pat. No. 6,225,529. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO2000012733 published 9 Mar. 2000, where seed-preferred promoters from END1 and END2 genes are disclosed.

Chemical inducible (regulated) promoters can be used to modulate the expression of a gene in a prokaryotic and eukaryotic cell or organism through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) Plant Cell Physiol 38:568-77), the maize GST promoter (GST-II-27, WO1993001294 published 21 Jan. 1993), activated by hydrophobic electrophilic compounds used as pre-emergent herbicides, and the tobacco PR-1a promoter (Ono et al., (2004) Biosci Biotechnol Biochem 68:803-7) activated by salicylic acid. Other chemical-regulated promoters include steroid-responsive promoters (see, for example, the glucocorticoid-inducible promoter (Schena et al., (1991) Proc. Natl. Acad. Sci. USA 88:10421-5; McNellis et al., (1998) Plant J 14:247-257); tetracycline-inducible and tetracycline-repressible promoters (Gatz et al., (1991) Mol Gen Genet 227:229-37; U.S. Pat. Nos. 5,814,618 and 5,789, 156).

Pathogen inducible promoters induced following infection by a pathogen include, but are not limited to those regulating expression of PR proteins, SAR proteins, beta-1, 3-glucanase, chitinase, etc.

A stress-inducible promoter includes the RD29A promoter (Kasuga et al. (1999) Nature Biotechnol. 17:287-91). One of ordinary skill in the art is familiar with protocols for simulating stress conditions such as drought, osmotic stress, salt stress and temperature stress and for evaluating stress tolerance of plants that have been subjected to simulated or naturally-occurring stress conditions.

Another example of an inducible promoter useful in plant cells, is the ZmCAS1 promoter, described in US20130312137 published 21 Nov. 2013.

New promoters of various types useful in plant cells are constantly being discovered; numerous examples may be found in the compilation by Okamuro and Goldberg, (1989) In The Biochemistry of Plants, Vol. 115, Stumpf and Conn, eds (New York, N.Y.: Academic Press), pp. 1-82.

Examples of promoters useful for the expression of morphogenic factors in cells include, but are not limited to: Figwort Mosaic Virus (FMV) promoter, FMV enhanced promoter, MMV enhanced promoter, Cauliflower Mosaic Virus (CaMV) promoter, CaMV enhanced promoter, 35S promoter, enhanced 35S promoter, minimal promoters, plant PLTP promoter, plant Ubiquitin promoter, plant Heat Shock Protein promoter, Nopaline Synthase (nos) promoter, plant Elongation Factor (EF) promoter, those described in U.S. Patent Application Publication No. 2017/0121722 (published 4 May 2017), those described in U.S. Pat. No. 8,710,206.

Polynucleotide Constructs

One or more of the polynucleotide compositions herein may be provided to a cell as part of a expression construct, plasmid, or vector. Said construct may comprise one or more expression cassettes for transcription in the cell.

The transcriptional cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the potato proteinase inhibitor (PinII) gene or sequences from Ti-plasmid of *A. tumefaciens*, such as the nopaline synthase, octopine synthase and opaline synthase termination regions. See also, Guerineau et al., (1991) Mol. Gen. Genet. 262: 141-144; Proudfoot (1991) Cell 64: 671-674; Sanfacon et al. (1991) Genes Dev. 5: 141-149; Mogen et al. (1990) Plant Cell 2: 1261-1272; Munroe et al. (1990) Gene 91: 151-158; Ballas et al. 1989) Nucleic Acids Res. 17: 7891-7903; Joshi et al. (1987) Nucleic Acid Res. 15: 9627-9639.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5'noncoding region) (Elroy-Stein, O., Fuerst, T. R., and Moss, B. (1989) PNAS USA, 86: 6126-6130); potyvirus leaders, for example, TEV leader (Tobacco Etch Virus) (Allison et al. (1986); MDMV leader (Maize Dwarf Mosaic Virus); Virology, 154: 9-20), and human immunoglobulin heavy-chain binding protein (BiP), (Macejak, D. G., and P. Sarnow (1991) Nature, 353: 90-94; untranslated leader from the coat protein MARNA of alfalfa mosaic virus (AMV RNA 4), (Jobling, S. A., and Gehrke, L., (1987) Nature, 325: 622-625; tobacco mosaic virus leader (TMV), (Gallie et al. (1989) Molecular Biology of RNA, pages 237-256, Gallie et al. (1987) Nucl. Acids Res. 15: 3257-3273; maize chlorotic mottle virus leader (MCMV) (Lornmel, S. A. et al. (1991) Virology, 81: 382-385). See also, Della-Cioppa et al. (1987) Plant Physiology, 84: 965-968; and endogenous maize 5' untranslated sequences. Other methods known to enhance translation can also be utilized, for example, introns, and the like.

The expression cassettes may contain one or more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Modification of a Target Polynucleotide in a Cell

According to the presently disclosed methods, morphogenic factors are used to enhance the modification of a target site polynucleotide within a cell that is effected by DSB agent activity. In some aspects, the morphogenic factor and the DSB agent may be introduced into the same cell. In some aspects, the morphogenic factor and the DSB agent may each be introduced into a different cell. In some aspects, the morphogenic factor may be endogenous to the cell receiving the DSB agent. In some aspects, the morphogenic factor may be endogenous to a cell other than that receiving the DSB agent. In some aspects, the morphogenic factor is a heterologous molecule to the cell into which it is introduced. In some aspects, the morphogenic factor is provided on a particle. In some aspects, the morphogenic factor is provided as part of a transformation vector. In some aspects, the morphogenic factor is provided as a sequence outside of the T-DNA borders on a transformation vector. In some aspects, the introduction of the morphogenic factor to the cell results in transient association of the morphogenic factor with the cell. In some aspects, the introduction of the morphogenic factor to the cell results in the morphogenic factor becoming stably integrated into the genome of the recipient cell.

The guide polynucleotides, Cas endonucleases, polynucleotide modification templates, donor DNAs, guide polynucleotide/Cas endonuclease systems disclosed herein, and any one combination thereof, optionally further comprising one or more morphogenic factors, further comprising one more polynucleotide(s) of interest, can be introduced into a cell. Cells include, but are not limited to, human, non-human, animal, bacterial, fungal, insect, yeast, non-conventional yeast, and plant cells as well as plants and seeds produced by the methods described herein.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, N.Y. (1989). Transformation methods are well known to those skilled in the art and are described infra.

Vectors and constructs include circular plasmids, and linear polynucleotides, comprising a polynucleotide of interest and optionally other components including linkers, adapters, regulatory or analysis. In some examples a recognition site and/or target site can be comprised within an intron, coding sequence, 5' UTRs, 3' UTRs, and/or regulatory regions.

The introduction of a morphogenic factor into a cell can enhance the rate of targeted integration of a polynucleotide of interest. In these methods, at least one morphogenic factor is introduced into a cell and a double-strand break-inducing agent is introduced, along with a transfer cassette comprising the polynucleotide of interest. As used herein, a "transfer cassette" refers to a polynucleotide that can be introduced into a cell, wherein the polynucleotide comprises a polynucleotide of interest that is to be inserted into a target site of a cell. The introduction of a double-strand break can result in the integration of the polynucleotide of interest through non-homologous end joining or if the transfer cassette comprises at least one region of homology to the target site, the polynucleotide of interest can be integrated through homologous recombination.

A double-strand-break-inducing agent polynucleotide may be provided in expression cassettes for expression in a cell of interest. The cassette can include 5' and 3' regulatory sequences operably linked to an endonuclease polynucleotide or functional variant or functional fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally comprise at least one additional gene to be co-transformed into the organism. Alternatively, the additional gene(s) can be provided on multiple expression cassettes. Such an expression cassette is provided with a plurality of restriction sites and/or recombination sites for insertion of the endonuclease polynucleotide or functional variant or functional fragment thereof to be under the transcriptional regulation of the regulatory regions. The expression cassette may additionally comprise one or more selectable marker gene(s).

In some aspects, the DSB agent comprises a Cas endonuclease that is in a functional combination with a guide polynucleotide, that is capable of recognizing, binding to, and cleaving or nicking a target polynucleotide. In some aspects, the functional combination is a ribonucleoprotein complex.

In one embodiment, the expression constructs of the disclosure comprise a promoter operably linked to a nucleotide sequence encoding a Cas gene (or plant optimized, including a Cas endonuclease gene described herein) and a promoter operably linked to a guide RNA of the present disclosure. The promoter is capable of driving expression of an operably linked nucleotide sequence in a prokaryotic or eukaryotic cell/organism. In some aspects, the polynucleotides encoding the Cas gene and the guide RNA are on the same transformation vector. In some aspects, the polynucleotides encoding the Cas gene and the guide RNA are provided on different vectors. In some aspects, the polynucleotides encoding the Cas gene and the guide RNA are provided to the target cell concurrently. In some aspects, the polynucleotides encoding the Cas gene and the guide RNA are provided to the target cell sequentially.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

A method of expressing RNA components such as gRNA in eukaryotic cells for performing Cas9-mediated DNA targeting has been to use RNA polymerase III (Pol III) promoters, which allow for transcription of RNA with precisely defined, unmodified, 5'- and 3'-ends (DiCarlo et al., *Nucleic Acids Res.* 41: 4336-4343; Ma et al., *Mol. Ther. Nucleic Acids* 3:e161). This strategy has been successfully applied in cells of several different species including maize and soybean (US20150082478 published 19 Mar. 2015). Methods for expressing RNA components that do not have a 5' cap have been described (WO2016/025131 published 18 Feb. 2016).

In some aspects, the Cas endonuclease and guide polynucleotide complex effects a double-strand break in a target polynucleotide, that results in a single base insertion, deletion, or modification (SDN1). In some aspects, the complex effects a double-strand break in a target polynucleotide, and a donor polynucleotide may change the sequence of the target (SDN2). In some aspects, the complex effects a double-strand break in a target polynucleotide, and new genetic material may be added into the break site (SDN3).

DNA double-strand breaks appear to be an effective factor to stimulate homologous recombination pathways (Puchta et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, a two- to nine-fold increase of homologous recombination was observed between artificially constructed homologous DNA repeats in plants (Puchta et al., (1995) *Plant Mol Biol* 28:281-92). In maize protoplasts, experiments with linear DNA molecules demonstrated enhanced homologous recombination between plasmids (Lyznik et al., (1991) *Mol Gen Genet* 230:209-18).

Homology-directed repair (HDR) is a mechanism in cells to repair double-stranded and single stranded DNA breaks. Homology-directed repair includes homologous recombination (HR) and single-strand annealing (SSA) (Lieber. 2010 *Annu. Rev. Biochem.* 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. *PNAS* (0027-8424), 111 (10), p. E924-E932).

Alteration of the genome of a prokaryotic and eukaryotic cell or organism cell, for example, through homologous recombination (HR), is a powerful tool for genetic engineering. Homologous recombination has been demonstrated in plants (Halfter et al., (1992) *Mol Gen Genet* 231:186-93) and insects (Dray and Gloor, 1997, *Genetics* 147:689-99). Homologous recombination has also been accomplished in other organisms. For example, at least 150-200 bp of homology was required for homologous recombination in the parasitic protozoan *Leishmania* (Papadopoulou and Dumas, (1997) *Nucleic Acids Res* 25:4278-86). In the filamentous fungus *Aspergillus nidulans*, gene replacement has been accomplished with as little as 50 bp flanking homology (Chaveroche et al., (2000) *Nucleic Acids Res* 28:e97). Targeted gene replacement has also been demonstrated in the ciliate *Tetrahymena thermophila* (Gaertig et al., (1994) *Nucleic Acids Res* 22:5391-8). In mammals, homologous recombination has been most successful in the mouse using pluripotent embryonic stem cell lines (ES) that can be grown in culture, transformed, selected and introduced into a mouse embryo (Watson et al., 1992, Recombinant DNA, 2nd Ed., Scientific American Books distributed by WH Freeman & Co.).

Various methods and compositions can be employed to obtain a cell or organism having a polynucleotide of interest inserted in a target site for a Cas endonuclease. Such methods can employ homologous recombination (HR) to provide integration of the polynucleotide of interest at the target site. In one method described herein, a polynucleotide of interest is introduced into the organism cell via a donor DNA construct.

The donor DNA construct further comprises a first and a second region of homology that flank the polynucleotide of interest. The first and second regions of homology of the donor DNA share homology to a first and a second genomic region, respectively, present in or flanking the target site of the cell or organism genome.

In some aspects, the donor DNA is provided to the target cell on the same transformation construct as the polynucleotide encoding either the Cas9 and the guide RNA, or on the same construct as the polynucleotides encoding both the Cas9 and the guide RNA. In some aspects, the donor DNA is provided to the target cell on a different transformation construct as the polynucleotide encoding either the Cas9 and the guide RNA.

The donor DNA can be tethered to the guide polynucleotide. Tethered donor DNAs can allow for co-localizing target and donor DNA, useful in genome editing, gene insertion, and targeted genome regulation, and can also be useful in targeting post-mitotic cells where function of endogenous HR machinery is expected to be highly diminished (Mali et al., 2013, *Nature Methods* Vol. 10: 957-963).

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, between 98% and 99%, 99%, between 99% and 100%, or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) *Current Protocols*, (Greene Publishing Associates, Inc. and John Wiley & Sons, Inc.); and, Tijssen (1993) *Laboratory Techniques in Biochemistry and Molecular Biology—Hybridization with Nucleic Acid Probes,* (Elsevier, New York).

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some instances the regions of homology share significant sequence homology to the genomic sequence immediately flanking the target site, it is recognized that the regions of homology can be designed to have sufficient homology to regions that may be further 5' or 3' to the target site. The regions of homology can also have homology with a fragment of the target site along with downstream genomic regions In one embodiment, the first region of homology further comprises a first fragment of the target site and the second region of homology comprises a second fragment of the target site, wherein the first and second fragments are dissimilar.

The process for editing a genomic sequence combining DSB and modification templates generally comprises: introducing into a host cell a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB. Genome editing using DSB-inducing agents, such as Cas-gRNA complexes, has been described, for example in US20150082478 published on 19 Mar. 2015, WO2015026886 published on 26 Feb. 2015, WO2016007347 published 14 Jan. 2016, and WO/2016/025131 published on 18 Feb. 2016.

In some aspects, the Cas endonuclease is part of a Cleavage Ready Cascade (crCascade) Complexes. Following characterization of the guide RNA and PAM sequence, components of the cleavage ready Cascade (crCascade) complex and associated CRISPR RNA (crRNA) may be utilized to modify chromosomal DNA in other organisms including plants. To facilitate optimal expression and nuclear localization (for eukaryotic cells), the genes comprising the crCascade may be optimized as described in WO2016186953 published 24 Nov. 2016, and then delivered into cells as DNA expression cassettes by methods known in the art. The components necessary to comprise an active crCascade complex may also be delivered as RNA with or without modifications that protect the RNA from degradation or as mRNA capped or uncapped (Zhang, Y. et al., 2016, *Nat. Commun.* 7:12617) or Cas protein guide polynucleotide complexes (WO2017070032 published 27 Apr. 2017), or any combination thereof. Additionally, a part or part(s) of the crCascade complex and crRNA may be expressed from a DNA construct while other components are delivered as RNA with or without modifications that protect the RNA from degradation or as mRNA capped or uncapped (Zhang et al. 2016 *Nat. Commun.* 7:12617) or Cas protein guide polynucleotide complexes (WO2017070032 published 27 Apr. 2017) or any combination thereof. To produce crRNAs in-vivo, tRNA derived elements may also be used to recruit endogenous RNAses to cleave crRNA transcripts into mature forms capable of guiding the crCascade complex to its DNA target site, as described, for example, in WO2017105991 published 22 Jun. 2017. crCascade nickase complexes may be utilized separately or concertedly to generate a single or multiple DNA nicks on one or both DNA strands. Furthermore, the cleavage activity of the Cas endonuclease may be deactivated by altering key catalytic residues in its cleavage domain (Sinkunas, T. et al., 2013, *EMBO J.* 32:385-394) resulting in a RNA guided helicase that may be used to enhance homology directed repair, induce transcriptional activation, or remodel local DNA structures. Moreover, the activity of the Cas cleavage and helicase domains may both be knocked-out and used in combination with other DNA cutting, DNA nicking, DNA binding, transcriptional activation, transcriptional repression, DNA remodeling, DNA deamination, DNA unwinding, DNA recombination enhancing, DNA integration, DNA inversion, and DNA repair agents.

The transcriptional direction of the tracrRNA for the CRISPR-Cas system (if present) and other components of the CRISPR-Cas system (such as variable targeting domain, crRNA repeat, loop, anti-repeat) can be deduced as described in WO2016186946 published 24 Nov. 2016, and WO2016186953 published 24 Nov. 2016.

As described herein, once the appropriate guide RNA requirement is established, the PAM preferences for each new system disclosed herein may be examined. If the cleavage ready Cascade (crCascade) complex results in degradation of the randomized PAM library, the crCascade complex can be converted into a nickase by disabling the ATPase dependent helicase activity either through mutagenesis of critical residues or by assembling the reaction in the absence of ATP as described previously (Sinkunas, T. et al., 2013, *EMBO J.* 32:385-394). Two regions of PAM randomization separated by two protospacer targets may be utilized to generate a double-stranded DNA break which may be captured and sequenced to examine the PAM sequences that support cleavage by the respective crCascade complex.

In one embodiment, the invention describes a method for modifying a target site in the genome of a cell, the method comprising introducing into a cell at least one PGEN described herein, and identifying at least one cell that has a modification at said target, wherein the modification at said target site is selected from the group consisting of (i) a replacement of at least one nucleotide, (ii) a deletion of at least one nucleotide, (iii) an insertion of at least one nucleotide, and (iv) any combination of (i)-(iii).

The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

A knock-out may be produced by an indel (insertion or deletion of nucleotide bases in a target DNA sequence through NHEJ), or by specific removal of sequence that reduces or completely destroys the function of sequence at or near the targeting site.

A guide polynucleotide/Cas endonuclease induced targeted mutation can occur in a nucleotide sequence that is located within or outside a genomic target site that is recognized and cleaved by the Cas endonuclease.

The method for editing a nucleotide sequence in the genome of a cell can be a method without the use of an exogenous selectable marker by restoring function to a non-functional gene product.

In one embodiment, the invention describes a method for modifying a target site in the genome of a cell, the method comprising introducing into a cell at least one PGEN described herein and at least one donor DNA, wherein said donor DNA comprises a polynucleotide of interest, and optionally, further comprising identifying at least one cell that said polynucleotide of interest integrated in or near said target site.

In one aspect, the methods disclosed herein may employ homologous recombination (HR) to provide integration of the polynucleotide of interest at the target site.

Various methods and compositions can be employed to produce a cell or organism having a polynucleotide of interest inserted in a target site via activity of a CRISPR-Cas system component described herein. In one method described herein, a polynucleotide of interest is introduced into the organism cell via a donor DNA construct. As used herein, "donor DNA" is a DNA construct that comprises a polynucleotide of interest to be inserted into the target site of a Cas endonuclease. The donor DNA construct further comprises a first and a second region of homology that flank the polynucleotide of interest. The first and second regions of homology of the donor DNA share homology to a first and a second genomic region, respectively, present in or flanking the target site of the cell or organism genome.

The donor DNA can be tethered to the guide polynucleotide. Tethered donor DNAs can allow for co-localizing target and donor DNA, useful in genome editing, gene insertion, and targeted genome regulation, and can also be useful in targeting post-mitotic cells where function of endogenous HR machinery is expected to be highly diminished (Mali et al., 2013, *Nature Methods* Vol. 10: 957-963).

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also be described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) *Current Protocols*, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

Episomal DNA molecules can also be ligated into the double-strand break, for example, integration of T-DNAs into chromosomal double-strand breaks (Chilton and Que, (2003) *Plant Physiol* 133:956-65; Salomon and Puchta, (1998) *EMBO J.* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) *Plant Cell* 16:342-52). Ectopic and/or epigenic DNA sequences may also serve as a DNA repair template for homologous recombination (Puchta, (1999) *Genetics* 152: 1173-81).

In one embodiment, the disclosure comprises a method for editing a nucleotide sequence in the genome of a cell, the method comprising introducing into at least one PGEN described herein, and a polynucleotide modification template, wherein said polynucleotide modification template comprises at least one nucleotide modification of said nucleotide sequence, and optionally further comprising selecting at least one cell that comprises the edited nucleotide sequence.

The guide polynucleotide/Cas endonuclease system can be used in combination with at least one polynucleotide modification template to allow for editing (modification) of a genomic nucleotide sequence of interest. (See also US20150082478, published 19 Mar. 2015 and WO2015026886 published 26 Feb. 2015).

Polynucleotides of interest and/or traits can be stacked together in a complex trait locus as described in WO2012129373 published 27 Sep. 2012, and in WO2013112686, published 1 Aug. 2013. The guide polynucleotide/Cas endonuclease system described herein provides for an efficient system to generate double-strand breaks and allows for traits to be stacked in a complex trait locus.

A guide polynucleotide/Cas system as described herein, mediating gene targeting, can be used in methods for directing heterologous gene insertion and/or for producing complex trait loci comprising multiple heterologous genes in a fashion similar as disclosed in WO2012129373 published 27 Sep. 2012, where instead of using a double-strand break inducing agent to introduce a gene of interest, a guide polynucleotide/Cas system as disclosed herein is used. By inserting independent transgenes within 0.1, 0.2, 0.3, 0.4, 0.5, 1.0, 2, or even 5 centimorgans (cM) from each other, the transgenes can be bred as a single genetic locus (see, for example, US20130263324 published 3 Oct. 2013 or WO2012129373 published 14 Mar. 2013). After selecting a plant comprising a transgene, plants comprising (at least) one transgenes can be crossed to form an F1 that comprises both transgenes. In progeny from these F1 (F2 or BC1) 1/500 progeny would have the two different transgenes recombined onto the same chromosome. The complex locus can then be bred as single genetic locus with both transgene traits. This process can be repeated to stack as many traits as desired.

Further uses for guide RNA/Cas endonuclease systems have been described (See for example: US20150082478 published 19 Mar. 2015, WO2015026886 published 26 Feb. 2015, US20150059010 published 26 Feb. 2015, WO2016007347 published 14 Jan. 2016, and PCT application WO2016025131 published 18 Feb. 2016) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Resulting characteristics from the gene editing compositions and methods described herein may be evaluated. Chromosomal intervals that correlate with a phenotype or trait of interest can be identified. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for a particular trait. In one embodiment, the chromosomal interval comprises at least one QTL, and furthermore, may indeed comprise more than one QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL. The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

Thus, the disclosed methods and compositions can further comprise compositions and methods for the directional, targeted integration of exogenous nucleotides into a transformed plant are provided. In an aspect, the disclosed methods use novel recombination sites in a gene targeting system which facilitates directional targeting of desired genes and nucleotide sequences into corresponding recombination sites previously introduced into the target plant genome.

In an aspect, a nucleotide sequence flanked by two non-identical recombination sites is introduced into one or more cells of an explant derived from the target organism's genome establishing a target site for insertion of nucleotide sequences of interest. Once a stable plant or cultured tissue is established a second construct, or nucleotide sequence of interest, flanked by corresponding recombination sites as those flanking the target site, is introduced into the stably transformed plant or tissues in the presence of a recombinase protein. This process results in exchange of the nucleotide sequences between the non-identical recombination sites of the target site and the transfer cassette.

It is recognized that the transformed plant prepared in this manner may comprise multiple target sites; i.e., sets of non-identical recombination sites. In this manner, multiple manipulations of the target site in the transformed plant are available. By target site in the transformed plant is intended a DNA sequence that has been inserted into the transformed plant's genome and comprises non-identical recombination sites.

Cells and Organisms

The methods and composition of the present disclosure may be used to improve genomic polynucleotide modification of a cell or organism.

In some aspects, the cell or organism is a prokaryote, for example but not limited to *E. coli*.

In some aspects, the cell or organism is from the Animal kingdom, for example a mammalian cell, for example a human cell. In some aspects, the cell is selected from the group consisting of: mouse connective tissue cell, mouse fibroblast, mouse embryonic stem cell, mouse monocyte, mouse macrophage, mouse spleen cell, mouse 3T3 NIH cell, mouse L cell, rat fibroblast, rat hepatoma, human lymphoma cell, human keratinocyte, human small cell lung cancer cell, human lymphocyte EBV transformed, human embryonic kidney cell, HEK293 cell, Chinese hamster ovary (CHO) cell, feline kidney cell, African green monkey kidney cell, SV 40 transformed cell, African monkey kidney cell, canine primary hepatocyte, chick embryonic fibroblast cell, HeLa cell, myeloma cell, bovine fetal heart cell, human egg, mouse egg, *Xenopus* egg, bovine egg, porcine egg, sheep egg, sheep or bovine udder epithelial cell, sheep embryonic epidermal cell, mouse blastocyst, stem cells, Syrian hamster kidney cell fibroblasts BHK-1 cell, monkey kidney epithelial cell BSC, mouse myeloma lymphoid cell MPC, frog egg cells RHP, and human nasopharyngeal tumor KB cell.

In some aspects, the cell or organism is from the Plant kingdom. In some aspects, the plant is a monocot. In some aspects, the plant is a dicot. Examples of plant species of interest include, but are not limited to, *Arabidposis*, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale), Sorghum (Sorghum bicolor, Sorghum vulgare), millet (e.g., pearl millet (Pennisetum glaucum), proso millet (Panicum miliaceum), foxtail millet (Setaria italica), finger millet (Eleusine coracana)), teff (Eragrostis tef), sunflower (Helianthus annuus), safflower (Carthamus tinctorius), wheat (Triticum aestivum), soybean (Glycine max), tobacco (Nicotiana tabacum), potato (Solanum tuberosum), peanuts (Arachis hypogaea), cotton (Gossypium barbadense, Gossypium hirsutum), sweet potato (Ipomoea batatus), cassava (Manihot esculenta), coffee (Coffea spp.), coconut (Cocos nucifera), pineapple (Ananas comosus), Citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidentale), Macadamia (Macadamia integrifolia), almond (Prunus amygdalus), sugar beets (Beta vulgaris), sugarcane (Saccharum spp.), oats, barley, vegetables, ornamentals, and conifers. Vegetables include tomatoes (Lycopersicon esculentum), lettuce (e.g., Lactuca sativa), green beans (Phaseolus vulgaris), lima beans (Phaseolus limensis), peas (Lathyrus spp.), and members of the genus Cucumis such as cucumber (C. sativus), cantaloupe (C. cantalupensis), and musk melon (C. melo).

The methods and compositions described herein do not depend on a particular method for introducing a sequence into an organism or cell, only that the polynucleotide or polypeptide gains access to the interior of at least one cell of the organism. Introducing includes reference to the incorporation of a nucleic acid into a eukaryotic or prokaryotic cell where the nucleic acid may be incorporated into the genome of the cell, and includes reference to the transient (direct) provision of a nucleic acid, protein or polynucleotide-protein complex (PGEN, RGEN) to the cell.

Methods for introducing polynucleotides or polypeptides or a polynucleotide-protein complex into cells or organisms are known in the art including, but not limited to, microinjection, electroporation, stable transformation methods, transient transformation methods, ballistic particle acceleration (particle bombardment), whiskers mediated transformation, Agrobacterium-mediated transformation, direct gene transfer, viral-mediated introduction, transfection, transduction, cell-penetrating peptides, mesoporous silica nanoparticle (MSN)-mediated direct protein delivery, topical applications, sexual crossing, sexual breeding, and any combination thereof.

For example, the guide polynucleotide (guide RNA, crNucleotide+tracrNucleotide, guide DNA and/or guide RNA-DNA molecule) can be introduced into a cell directly (transiently) as a single stranded or double stranded polynucleotide molecule. The guide RNA (or crRNA+tracrRNA) can also be introduced into a cell indirectly by introducing a recombinant DNA molecule comprising a heterologous nucleic acid fragment encoding the guide RNA (or crRNA+tracrRNA), operably linked to a specific promoter that is capable of transcribing the guide RNA (crRNA+tracrRNA molecules) in said cell. The specific promoter can be, but is not limited to, a RNA polymerase III promoter, which allow for transcription of RNA with precisely defined, unmodified, 5'- and 3'-ends (Ma et al., 2014, Mol. Ther. Nucleic Acids 3:e161; DiCarlo et al., 2013, Nucleic Acids Res. 41: 4336-4343; WO2015026887, published 26 Feb. 2015). Any promoter capable of transcribing the guide RNA in a cell can be used and includes a heat shock/heat inducible promoter operably linked to a nucleotide sequence encoding the guide RNA.

The Cas endonuclease, such as the Cas endonuclease described herein, can be introduced into a cell by directly introducing the Cas polypeptide itself (referred to as direct delivery of Cas endonuclease), the mRNA encoding the Cas protein, and/or the guide polynucleotide/Cas endonuclease complex itself, using any method known in the art. The Cas endonuclease can also be introduced into a cell indirectly by introducing a recombinant DNA molecule that encodes the Cas endonuclease. The endonuclease can be introduced into a cell transiently or can be incorporated into the genome of the host cell using any method known in the art. Uptake of the endonuclease and/or the guided polynucleotide into the cell can be facilitated with a Cell Penetrating Peptide (CPP) as described in WO2016073433 published 12 May 2016. Any promoter capable of expressing the Cas endonuclease in a cell can be used and includes a heat shock/heat inducible promoter operably linked to a nucleotide sequence encoding the Cas endonuclease.

Direct delivery of a polynucleotide modification template into plant cells can be achieved through particle mediated delivery, and any other direct method of delivery, such as but not limiting to, polyethylene glycol (PEG)-mediated transfection to protoplasts, whiskers mediated transformation, electroporation, particle bombardment, cell-penetrating peptides, or mesoporous silica nanoparticle (MSN)-mediated direct protein delivery can be successfully used for delivering a polynucleotide modification template in eukaryotic cells, such as plant cells.

The donor DNA can be introduced by any means known in the art. The donor DNA may be provided by any transformation method known in the art including, for example, Agrobacterium-mediated transformation or biolistic particle bombardment. The donor DNA may be present transiently in the cell or it could be introduced via a viral replicon. In the presence of the Cas endonuclease and the target site, the donor DNA is inserted into the transformed plant's genome.

Direct delivery of any one of the guided Cas system components can be accompanied by direct delivery (co-delivery) of other mRNAs that can promote the enrichment and/or visualization of cells receiving the guide polynucleotide/Cas endonuclease complex components. For example, direct co-delivery of the guide polynucleotide/Cas endonuclease components (and/or guide polynucleotide/Cas endonuclease complex itself) together with mRNA encoding phenotypic markers (such as but not limiting to transcriptional activators such as CRC (Bruce et al. 2000 The Plant Cell 12:65-79) can enable the selection and enrichment of cells without the use of an exogenous selectable marker by restoring function to a non-functional gene product as described in WO2017070032 published 27 Apr. 2017.

Introducing a guide RNA/Cas endonuclease complex described herein, into a cell includes introducing the individual components of said complex either separately or combined into the cell, and either directly (direct delivery of a ribonucleoprotein complex, or RNP, as RNA for the guide and protein for the Cas endonuclease and Cas protein subunits, or functional fragments thereof) or via recombination constructs expressing the components (guide RNA, Cas endonuclease, Cas protein subunits, or functional fragments thereof). Introducing a guide RNA/Cas endonuclease complex (RNP) into a cell includes the guide RNA/Cas endonuclease complex as a ribonucleotide-protein into the cell. The ribonucleotide-protein can be assembled prior to being introduced into the cell as described herein. The components comprising the guide RNA/Cas endonuclease ribonucleotide protein (at least one Cas endonuclease, at least one guide RNA, at least one Cas protein subunits) can be assembled in vitro or assembled by any means known in the art prior to being introduced into a cell (targeted for genome modification as described herein).

Plant cells differ from human and animal cells in that plant cells comprise a plant cell wall which may act as a barrier to the direct delivery of the RNP and/or of the direct delivery of the RNP components.

In some aspects, direct delivery of the RNP into plant cells can be achieved through particle mediated delivery (particle bombardment). Based on the experiments described herein, a skilled artesian can envision that any other direct method of delivery, such as but not limiting to, polyethylene glycol (PEG)-mediated transfection to protoplasts, electroporation, cell-penetrating peptides, or mesoporous silica nanoparticle (MSN)-mediated direct protein delivery, can be successfully used for delivering RNP into plant cells.

Direct delivery of the RNP, allows for genome editing at a target site in the genome of a cell which can be followed by rapid degradation of the complex, and only a transient presence of the complex in the cell. This transient presence of the RNP complex may lead to reduced off-target effects. In contrast, delivery of RNP components (guide RNA, Cas endonuclease) via plasmid DNA sequences can result in constant expression of RNPs from these plasmids which can intensify off target effects (Cradick, T. J. et al. (2013) *Nucleic Acids Res* 41:9584-9592; Fu, Y et al. (2014) *Nat. Biotechnol.* 31:822-826).

Direct delivery can be achieved by combining any one component of the guide RNA/Cas endonuclease complex (RNP) (such as at least one guide RNA, at least one Cas protein, and at least one Cas protein), with a particle delivery matrix comprising a microparticle (such as but not limited to of a gold particle, tungsten particle, and silicon carbide whisker particle) (see also WO2017070032 published 27 Apr. 2017).

In one aspect, the guide polynucleotide/Cas endonuclease complex is a complex wherein the guide RNA and Cas endonuclease protein forming the guide RNA/Cas endonuclease complex are introduced into the cell as RNA and protein, respectively.

In one aspect, the guide polynucleotide/Cas endonuclease complex is a complex wherein the guide RNA and Cas endonuclease protein and the at least one protein subunit of a Cas protein forming the guide RNA/Cas endonuclease complex are introduced into the cell as RNA and proteins, respectively.

In one aspect, the guide polynucleotide/Cas endonuclease complex is a complex wherein the guide RNA and Cas endonuclease protein and the at least one protein subunit of a Cascade forming the guide RNA/Cas endonuclease complex (cleavage ready cascade) are preassembled in vitro and introduced into the cell as a ribonucleotide-protein complex.

Protocols for introducing polynucleotides, polypeptides or polynucleotide-protein complexes into eukaryotic cells, such as plants or plant cells are known and include microinjection (Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6, *Agrobacterium*-mediated transformation (U.S. Pat. Nos. 5,563,055 and 5,981,840), whiskers mediated transformation (Ainley et al. 2013, *Plant Biotechnology Journal* 11:1126-1134; Shaheen A. and M. Arshad 2011 Properties and Applications of Silicon Carbide (2011), 345-358 Editor(s): Gerhardt, Rosario. Publisher: InTech, Rijeka, Croatia. CODEN: 69PQBP; ISBN: 978-953-307-201-2), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in Plant Cell, Tissue, and Organ Culture: Fundamental Methods, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) In vitro Cell *Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in The Experimental Manipulation of Ovule Tissues, ed. Chapman et al., (*Longman*, New York), pp. 197-209 (pollen); Kaeppler et al., (1990) *Plant Cell Rep* 9:415-8) and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into plant or plant cells by contacting cells or organisms with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931.

The polynucleotide or recombinant DNA construct can be provided to or introduced into a prokaryotic and eukaryotic cell or organism using a variety of transient transformation methods. Such transient transformation methods include, but are not limited to, the introduction of the polynucleotide construct directly into the plant.

Nucleic acids and proteins can be provided to a cell by any method including methods using molecules to facilitate the uptake of anyone or all components of a guided Cas system (protein and/or nucleic acids), such as cell-penetrating peptides and nanocarriers. See also US20110035836 published 10 Feb. 2011, and EP2821486A1 published 7 Jan. 2015.

Other methods of introducing polynucleotides into a prokaryotic and eukaryotic cell or organism or plant part can be used, including plastid transformation methods, and the methods for introducing polynucleotides into tissues from seedlings or mature seeds.

Stable transformation is intended to mean that the nucleotide construct introduced into an organism integrates into a genome of the organism and is capable of being inherited by the progeny thereof. Transient transformation is intended to mean that a polynucleotide is introduced into the organism and does not integrate into a genome of the organism or a polypeptide is introduced into an organism. Transient transformation indicates that the introduced composition is only temporarily expressed or present in the organism.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

The methods and composition of the disclosure can utilize a variety of transformation methods as appropriate. That is, transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320-334), electroporation (Riggs et al. (1986) Proc. Natl. Acad. Sci. USA 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) EMBO J. 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Bio-technology 6:923-926). Also see Weissinger et al. (1988) Ann. Rev. Genet. 22:421-477; Sanford et al. (1987) Particulate Science and Technology 5:27-37 (onion); Christou et al. (1988) Plant Physiol. 87:671-674 (soybean); McCabe et al. (1988) Bio/Technology 6:923-926 (soybean); Finer and McMullen (1991) In Vitro Cell Dev. Biol. 27P:175-182 (soybean); Singh et al. (1998) Theor. Appl. Genet. 96:319-324 (soybean); Datta et al. (1990) Biotechnology 8:736-740 (rice); Klein et al. (1988) Proc. Natl. Acad. Sci. USA 85:4305-4309 (maize); Klein et al. (1988) Biotechnology 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440-444 (maize); Fromm et al. (1990) Biotechnology 8:833-839 (maize); Hooykaas-Van Slogteren et al. (1984) Nature (London) 311:763-764; Bowen et al., U.S. Pat. No. 5,736,369 (cereals); Bytebier et al. (1987) Proc. Natl. Acad. Sci. USA 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9:415-418 and Kaeppler et al. (1992) Theor. Appl. Genet. 84:560-566 (whisker-mediated transformation); D'Halluin et al. (1992) Plant Cell 4:1495-1505 (electroporation); Li et al. (1993) Plant Cell Reports 12:250-255 and Christou and Ford (1995) Annals of Botany 75:407-413 (rice); Osjoda et al. (1996) Nature Biotechnology 14:745-750 (maize via *Agrobacterium tumefaciens*); all of which are herein incorporated by reference.

The polynucleotides introduced into an explant by the disclosed methods and compositions can be operably linked to a suitable promoter. "Promoter" means a region of DNA that is upstream from the start of transcription and is involved in recognition and binding of RNA polymerase and other proteins to initiate transcription, either including or not including the 5' UTR. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as from *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissues are referred to as "tissue specific". A "cell type" specific promoter primarily drives expression in certain cell types in one or more organs, for example, vascular cells in roots or leaves. An "inducible" or "repressible" promoter can be a promoter which is under either environmental or exogenous control. Examples of environmental conditions that may affect transcription by inducible promoters include anaerobic conditions, or certain chemicals, or the presence of light. Alternatively, exogenous control of an inducible or repressible promoter can be affected by providing a suitable chemical or other agent that via interaction with target polypeptides result in induction or repression of the promoter. Tissue specific, tissue preferred, cell type specific, and inducible promoters constitute the class of "non-constitutive" promoters. A "constitutive" promoter is a promoter which is active under most conditions. Promoters useful in the present disclosure include those disclosed in WO2017/112006 and those disclosed in U.S. Provisional Application 62/562,663.

Methods are available in the art for synthesizing plant-preferred genes. See, for example, U.S. Pat. Nos. 5,380,831, and 5,436,391, and Murray et al. (1989) *Nucleic Acids Res.* 17:477-498. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

As used herein, "antisense orientation" includes reference to a polynucleotide sequence that is operably linked to a promoter in an orientation where the antisense strand is transcribed. The antisense strand is sufficiently complementary to an endogenous transcription product such that translation of the endogenous transcription product is often inhibited. "Operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The expression cassette can include in the 5'-3' direction of transcription, a transcriptional and translational initiation region (i.e., a promoter), an endonuclease polynucleotide or functional variant or functional fragment thereof, and a transcriptional and translational termination region (i.e., termination region) functional in the recipient organism. The regulatory regions (i.e., promoters, transcriptional regulatory regions, and translational termination regions) and/or the endonuclease polynucleotide or functional variant or functional fragment thereof may be native/analogous to the host cell or to each other. Alternatively, the regulatory regions and/or the endonuclease polynucleotide of or functional variant or functional fragment thereof may be heterologous to the host cell or to each other.

While it may be desired in some embodiments to express the sequences using heterologous promoters, the native promoter sequences to the polynucleotide encoding the double-strand-break-inducing agent may alternatively be used. Such constructs can change expression levels of the polynucleotide in the cell. Thus, the phenotype of recipient cell can be altered.

Where appropriate, the polynucleotides may be optimized for increased expression in the recipient cell or organism. That is, the polynucleotides can be synthesized using organism-preferred codons for improved expression. See, for example, Campbell and Gowri (1990) *Plant Physiol.* 92:1-11 for a discussion of host-preferred codon usage in plants.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. The above list of selectable marker genes is not meant to be limiting. Any selectable marker gene may be used with any of the methods or compositions disclosed herein.

In some aspects, the DSB agent may be introduced into a target cell and the morphogenic factor may be introduced into the same target cell.

In some aspects, the DSB agent may be introduced into a target cell and the morphogenic factor may be introduced into a different cell. In some aspects, the target cell and the different cell may each comprise the same target polynucleotide. In some aspects, the different cell is an "adjacent" cell. As used herein, the term "adjacent cell" (or the plural "adjacent cells") is used to describe a cell that is part of the same organism, the same tissue, in the same cell culture, or in the same cell layer as the target cell, but is not the same cell as the target cell. In some aspects, the adjacent cell is in physical contact with the target cell. In some aspects, the adjacent cell is separated from the target cell, for example by at another cell.

Traits of Agronomic Importance

The methods and compositions provided herein, which provide for improved efficacy of DSB agent activity on a target polynucleotide in a cell by use of a morphogenic factor, are useful for the production of organisms, including plants, with desirable characteristics including traits of importance.

As used herein, "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring uptake of carbon dioxide, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance. An "enhanced trait" as used in describing the aspects of the present disclosure includes improved or enhanced water use efficiency or drought tolerance, osmotic stress tolerance, high salinity stress tolerance, heat stress tolerance, enhanced cold tolerance, including cold germination tolerance, increased yield, enhanced nitrogen use efficiency, early plant growth and development, late plant growth and development, enhanced seed protein, and enhanced seed oil production.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

The compositions and methods herein may provide for an improved "agronomic trait" or "trait of agronomic importance" or "trait of agronomic interest" to a plant, which may include, but not be limited to, the following: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein content, altered oil content, increased biomass, increased shoot length, increased root length, improved root architecture, modulation of a metabolite, modulation of the proteome, increased seed weight, altered seed carbohydrate composition, altered seed oil composition, altered seed protein composition, altered seed nutrient composition, as compared to an isoline plant not comprising a modification derived from the methods or compositions herein.

Many agronomic traits can affect "yield", including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per ear, seed size, composition of seed (starch, oil, protein) and characteristics of seed fill. Also of interest is the generation of transgenic plants that demonstrate desirable phenotypic properties that may or may not confer an increase in overall plant yield. Such properties include enhanced plant morphology, plant physiology or improved components of the mature seed harvested from the transgenic plant.

"Increased yield" of a transgenic plant of the present disclosure may be evidenced and measured in a number of ways, including test weight, seed number per plant, seed weight, seed number per unit area (i.e. seeds, or weight of seeds, per acre), bushels per acre, tons per acre, kilo per hectare. For example, maize yield may be measured as production of shelled corn kernels per unit of production area, e.g. in bushels per acre or metric tons per hectare, often reported on a moisture adjusted basis, e.g., at 15.5% moisture. Increased yield may result from improved utilization of key biochemical compounds, such as nitrogen, phosphorous and carbohydrate, or from improved tolerance to environmental stresses, such as cold, heat, drought, salt, and attack by pests or pathogens. Trait-enhancing recombinant DNA may also be used to provide transgenic plants having improved growth and development, and ultimately increased yield, as the result of modified expression of plant growth regulators or modification of cell cycle or photosynthesis pathways.

Aspects

Aspect 1: A method of editing a polynucleotide in the genome of a target cell, comprising: (a) providing a double-strand-break-inducing agent to the target cell, and (b) providing a morphogenic factor to an adjacent cell.

Aspect 2: A method of editing a polynucleotide in the genome of a target cell, comprising: (a) providing a double-strand-break-inducing agent to the target cell, and (b) upregulating the transcription of an endogenous morphogenic factor gene in the genome of said target cell or in the genome of an adjacent cell.

Aspect 3: A method of editing a polynucleotide in the genome of a target cell, comprising: (a) providing a double-strand-break-inducing agent into the target cell, (b) providing to the target cell or to an adjacent cell a T-DNA vector comprising a gene for a morphogenic factor outside of said left border and said right border.

Aspect 4: A method of editing a polynucleotide in the genome of a target cell, comprising: (a) providing to the target cell a double-strand-break-inducing agent, and (b) providing a morphogenic factor to the target cell or to an adjacent cell; wherein either the double-strand-break-inducing agent of (a) or the morphogenic factor of (b) or both further comprise(s) a cell penetrating peptide motif at its 3' end, its 5' end, or both ends.

Aspect 5: A method of editing a polynucleotide in the genome of a target cell, comprising: (a) providing to a cell a first vector comprising a polynucleotide encoding a double-strand-break-inducing agent, and (b) providing a morphogenic factor to the target cell or to an adjacent cell; wherein the first vector further comprises outside of the T-DNA borders a repressor fused to a gene encoding a Cas endonuclease that lacks nuclease activity, wherein said repressor is capable of binding to a regulatory element operably linked to the polynucleotide encoding the double-strand-break-inducing agent of (a).

Aspect 6: A method of editing a polynucleotide in the genome of a target cell, comprising: (a) providing to the target cell a double-strand-break-inducing agent, (b) providing to a cell a composition selected from the group consisting of: i. a molecule that stimulates the expression of an endogenous morphogenic factor in the cell, and ii. a T-DNA vector comprising a gene for a morphogenic factor outside of said left border and said right border, wherein the cell of (a) is the same cell as the cell of (b), and wherein either the double-strand-break-inducing agent of (a) or the composition of (b) or both further comprise(s) a cell penetrating peptide motif at its 3' end, its 5' end, or both ends.

Aspect 7: A method of editing a polynucleotide in the genome of a target cell, comprising: (a) providing to the target cell a double-strand-break-inducing agent, (b) providing to a cell a composition selected from the group consisting of: i. a morphogenic factor, ii. a molecule that stimulates the expression of an endogenous morphogenic factor, and iii. a T-DNA vector comprising a polynucleotide of interest between the left border and the right border, further comprising a gene for a morphogenic factor outside of said left border and said right border; wherein the cell of (a) is different than the cell of (b), and wherein either the double-strand-break-inducing agent of (a) or the composition of (b) or both further comprise(s) a cell penetrating peptide motif at its 3' end, its 5' end, or both ends.

Aspect 8: The method of any of Aspects 1-6, wherein the morphogenic factor is selected from the group consisting of: Wuschel, Ovule Development Protein, and Babyboom.

Aspect 9: The method of any of Aspects 1-6, wherein the composition of (a) is provided on a different construct than the composition of (b).

Aspect 10: The method of any of Aspects 1-6, wherein the composition of (a) is provided on the same construct as the composition of (b).

Aspect 11: The method of any of Aspects 1-6, wherein the morphogenic factor is provided as a polynucleotide sequence encoding a polypeptide.

Aspect 12: The method of any of Aspects 1-6, wherein the morphogenic factor shares at least 80% identity with a sequence selected from the group consisting of: SEQID NOs: 6-10, 17-21, and 48-73.

Aspect 13: The method of any of Aspects 1-6, wherein the morphogenic factor is provided as a polypeptide.

Aspect 14: The method of any of Aspects 1-6, wherein the morphogenic factor is encoded by a polynucleotide that shares at least 80% identity with a sequence selected from the group consisting of: SEQID NOs:1-5, 11-16, 22, and 23-47.

Aspect 15: The method of any of Aspects 1-6, wherein the morphogenic factor is selected from the group consisting of: WUS1, WUS2, WUS3, WOX2A, WOX4, WOX5, WOX9, BBM2, BMN2, BMN3, and ODP2.

Aspect 16: The method of any of Aspects 1-6, wherein said editing is selected from the group consisting of: insertion of at least one polynucleotide, deletion of at least one polynucleotide, modification of at least one polynucleotide, substitution of at least one polynucleotide, and a combination of at least two of the preceding.

Aspect 17: The method of any of Aspects 1-6, wherein said double-strand-break-inducing agent comprises a Cas endonuclease, a TALEN, a meganuclease, a zinc-finger endonuclease, or a restriction endonuclease.

Aspect 18: The method of any of Aspects 1-6, wherein said double-strand-break-inducing agent is provided as a ribonucleoprotein complex comprising a Cas endonuclease protein and a guide RNA.

Aspect 19: The method of any of Aspects 1-6, further comprising introducing a heterologous polynucleotide donor DNA molecule into said target cell.

Aspect 20: The method of any of Aspects 1-6, wherein the morphogenic factor is operably linked to a heterologous promoter.

Aspect 21: The method of Aspect 19, wherein said promoter is selected from the group consisting of: a ZM-PLTP promoter, a ZM-PLTP1 promoter, a ZM-PLTP2 promoter, a SB-PLTP1 promoter, a SB-PLTP2 promoter, a SB-PLTP3 promoter, an OS-PLTP1 promoter, an OS-PLTP2 promoter, a SI-PLTP1 promoter, a ZM-FBP1 promoter, a ZM-RFP promoter, a ZM-APMP promoter, a ZM-RfeSP promoter, a ZM-CRR6 promoter, a ZM-G3K promoter, a ZM-CAB7 promoter, a ZM-UBR promoter, a ZM-HBP promoter, a ZM-PS1-N promoter, a ZM-SDR promoter, an OS-SDR promoter, a SB-SDR promoter, a ZM-SDR(long) promoter, a ZM-LGL promoter, a ZM-LEA14-A promoter, a ZM-LEA34-D promoter, a GM-LTP3 promoter, a GM-EF1A promoter, a GM-HBSTART3 promoter, a GM-HBSTART3 (TRUNCATED) promoter, an AT-ML1 promoter, a GM-ML1-Like promoter, a GM-ML1-Like (TRUNCATED) promoter, a ZM-HBSTART3 promoter, an OS-HBSTART3 promoter, an AT-PDF1 P2 promoter, a GM-PDF1 promoter, a GM-PDF1 (TRUNCATED) promoter, a SB-PDF1 promoter, an OS-PDF1 promoter, an OS-PDF1 (TRUNCATED) promoter, a PT-PDF1 promoter, a PT-PDF1 (TRUNCATED) promoter, a SI-PDF1 promoter, a SI-PDF1 (TRUNCATED) promoter, an AT-PDF2 promoter, a GM-PDF2 promoter, a GM-PDF2 (TRUNCATED) promoter, a ZM-GL1 promoter, an AT-PDF2a promoter, an AT-PDF2a (TRUNCATED) promoter, a GM-PDF2a promoter, a GM-PDF2a (TRUNCATED) promoter, an OS-PDF2 promoter, an OS-PDF2 (TRUNCATED) promoter, a PT-PDF2 promoter, a PT-PDF2 (TRUNCATED) promoter, a VV-PDF2 promoter, a VV-PDF2 (TRUNCATED) promoter, a7M-PDF2 promoter, a SI-PDF2 promoter, a SI-PDF2 (TRUNCATED) promoter, aVV-PDF2a promoter, a PT-PDF2a promoter, a PT-PDF2a (TRUNCATED) promoter, a MT-PDF2 promoter, a MT-PDF2 (TRUNCATED) promoter, an AT-HDG2 promoter, a GM-HDG2 promoter, a GM-HDG2 (TRUNCATED) promoter, a SB-HDG2 promoter, a SB-HDG2 (TRUNCATED) promoter, an AT-CER6 promoter, an AT-CER60 promoter, an AT-CER60 (TRUNCATED) promoter, a GM-CER6 promoter, a GM-CER6 (TRUNCATED) promoter, a PT-CER6 promoter, a PT-CER6 (TRUNCATED) promoter, a VV-CER6 promoter, a VV-CER6 (TRUNCATED) promoter, a SB-CER6 promoter, a ZM-CER6 promoter, a SI-CER6 promoter, a SI-CER6 (TRUNCATED) promoter, an OS-CER6 promoter, an OS-CER6 (TRUNCATED) promoter, a GM-HBSTART2 promoter, a GM-MATE1 promoter, a GM-NED1 promoter; a SB-GL1 promoter, an OS-GL1 promoter, an AT-GL1 promoter, a GM-GL1 promoter, an AT-ANL1 promoter, a ZM-OCL1 promoter, and an OS-OCL1 promoter.

Aspect 22: The method of Aspect 18, wherein said donor DNA molecule comprises a polynucleotide that confers a benefit to an organism comprising, or derived from, said target cell.

Aspect 23: The method of Aspect 21, wherein said benefit is selected from the group consisting of: improved health, improved growth, improved fertility, improved fecundity, improved environmental tolerance, improved vigor, improved disease resistance, improved disease tolerance, improved tolerance to a heterologous molecule, improved fitness, improved physical characteristic, greater mass, increased production of a biochemical molecule, decreased production of a biochemical molecule, upregulation of a gene, downregulation of a gene, upregulation of a biochemical pathway, downregulation of a biochemical pathway, stimulation of cell reproduction, and suppression of cell reproduction.

Aspect 24: The method of any of Aspects 1-6, wherein said cell is a plant cell.

Aspect 25: The method of Aspect 23, wherein said plant cell is obtained from or derived from a monocot or dicot plant.

Aspect 26: The method of Aspect 24, wherein the monocot selected from the group consisting of: *Zea mays, Sorghum bicolor, Sorghum vulgare, Triticum aestivum, Medicago sativa, Oryza sativa, Setaria italica*, and *Saccharum* spp.

Aspect 27: The method of Aspect 24, wherein the dicot selected from the group consisting of: *Helianthus annuus, Glycine max, Nicotiana tabacum, Gossypium barbadense, Gossypium hirsutum, Manihot esculenta, Beta vulgaris, Brassica* spp., and *Arabidposis thaliana*.

Aspect 28: The method of any of Aspects 1-6, wherein said editing of a polynucleotide in the genome of the cell modulates a trait of agronomic importance in a plant, selected from the group consisting of: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein composition, altered oil composition, increased biomass, increased shoot length, increased root length, improved root architecture, modulation of a metabolite, modulation of the proteome, increased seed weight, altered seed carbohydrate composition, altered seed oil composition, altered seed protein composition, and altered seed nutrient composition; as compared to an isoline plant not comprising or derived from a cell whose genome was edited with said double-strand-break-inducing agent.

Aspect 29: A plant derived from a plant cell produced by the method of any of Aspects 1-6, wherein said plant does not have a heterologous morphogenic factor stably integrated into its genome.

Aspect 30: Any of the preceding aspects, wherein the morphogenic factor is engineered or synthetic, wherein the engineered or synthetic morphogenic factor has an altered type or level of activity as compared to a non-engineered or non-synthetic morphogenic factor.

Aspect 31: Any of the preceding aspects, wherein the Cas endonuclease is provided as a polypeptide, or wherein the Cas endonuclease is provided as a polynucleotide encoding a Cas endonuclease polypeptide, or wherein the Cas endonuclease is provided as a ribonucleoprotein complex with a guide polynucleotide.

While the invention has been particularly shown and described with reference to a preferred embodiment and various alternate embodiments, it will be understood by persons skilled in the relevant art that various changes in form and details can be made therein without departing from the spirit and scope of the invention. For instance, while the particular examples below may illustrate the methods and embodiments described herein using a specific plant, the principles in these examples may be applied to any plant. Therefore, it will be appreciated that the scope of this invention is encompassed by the embodiments of the inventions recited herein and in the specification rather than the specific examples that are exemplified below. All cited patents and publications referred to in this application are herein incorporated by reference in their entirety, for all purposes, to the same extent as if each were individually and specifically incorporated by reference.

EXAMPLES

The following are examples of specific embodiments of some aspects of the invention. The examples are offered for illustrative purposes only, and are not intended to limit the scope of the invention in any way. Efforts have been made to ensure accuracy with respect to numbers used (e.g., amounts, temperatures, etc.), but some experimental error and deviation should, of course, be allowed for.

Example 1: Particle Bombardment Transformation of Corn Plants

In this example, transformation of immature maize embryos via particle bombardment is described. It is understood that a similar protocol may be used for the transformation of other plants, such as (but not limited to): soybean, cotton, canola, wheat, rice, Sorghum, or sunflower.

Prior to bombardment, 10-12 DAP immature embryos are isolated from ears of a corn plant and placed on culture medium plus 16% sucrose for three hours to plasmolyze the scutellar cells.

Single plasmids or multiple plasmids may be used for each particle bombardment. In one example, a plurality of plasmids include: 1) a plasmid comprising a donor cassette, 2) a plasmid comprising an expression cassette for the double-strand-break-inducing agent, and 3) a plasmid comprising an expression cassette for the morphogenic factor.

To attach the DNA to 0.6 μm gold particles, the plasmids are mixed by adding 10 μl of each plasmid together in a low-binding microfuge tube (Sorenson Bioscience 39640T). To this suspension, 50 μl of 0.6 μm gold particles (30 μg/μl) and 1.0 μl of Transit 20/20 (Cat No MIR5404, Mirus Bio LLC) are added, and the suspension is placed on a rotary shaker for 10 minutes. The suspension is centrifuged at 10,000 RPM (9400×g) and the supernatant is discarded. The gold particles are re-suspended in 120 μl of 100% ethanol, briefly sonicated at low power and 10 μl is pipetted onto each carrier disc. The carrier discs are then air-dried to remove all the remaining ethanol. Particle bombardment is performed using a Biolistics PDF-1000, at 28 inches of Mercury using a 200 PSI rupture disc.

After particle bombardment, the immature embryos are selected on 506J medium modified to contain 12.5 g/l mannose and 5 g/l maltose and no sucrose. After 10-12 weeks on selection, plantlets are regenerated and analyzed using qPCR.

Example 2: *Agrobacterium*-Mediated Transformation of Corn Plants

In this example, transformation of immature maize embryos via *Agrobacterium* mediation is described. It is understood that a similar protocol may be used for the transformation of other plants, such as (but not limited to): soybean, cotton, canola, wheat, rice, Sorghum, or sunflower.

Preparation of *Agrobacterium* Master Plate.

*Agrobacterium tumefaciens* harboring a binary donor vector is streaked out from a −80° C. frozen aliquot onto solid 12V medium and cultured at 28° C. in the dark for 2-3 days to make a master plate.

Growing *Agrobacterium* on Solid Medium.

A single colony or multiple colonies of *Agrobacterium* are picked from the master plate and streaked onto a second plate containing 8101 medium and incubated at 28° C. in the dark overnight.

*Agrobacterium* infection medium (700 medium A; 5 ml) and 100 mM 3′-5′-Dimethoxy-4′-hydroxyacetophenone (acetosyringone; 5 μL) are added to a 14 mL conical tube in a hood. About 3 full loops of *Agrobacterium* from the second plate are suspended in the tube and the tube was then vortexed to make an even suspension. One mL is transferred to a spectrophotometer tube and the optical density (550 nm) of the suspension is adjusted to a reading of about 0.35-1.0. The *Agrobacterium* concentration is approximately 0.5 to $2.0×10^9$ cfu/mL. The final *Agrobacterium* suspension is aliquoted into 2 mL microcentrifuge tubes, each containing about 1 mL of the suspension. The suspensions are then used as soon as possible.

Growing *Agrobacterium* on Liquid Medium.

Alternatively, *Agrobacterium* can be prepared for transformation by growing in liquid medium. One day before infection, a 125 ml flask is prepared with 30 ml of 557A medium (10.5 g/l potassium phosphate dibasic, 4.5 g/l potassium phosphate monobasic anhydrous, 1 g/l ammonium sulfate, 0.5 g/l sodium citrate dehydrate, 10 g/l sucrose, 1 mM magnesium sulfate) and 30 µL spectinomycin (50 mg/mL) and 30 µL acetosyringone (20 mg/mL). A half loopful of *Agrobacterium* from a second plate is suspended into the flasks and placed on an orbital shaker set at 200 rpm and incubated at the 28° C. overnight. The *Agrobacterium* culture is centrifuged at 5000 rpm for 10 min. The supernatant is removed and the *Agrobacterium* infection medium with acetosyringone solution was added. The bacteria are resuspended by vortex and the optical density (550 nm) of *Agrobacterium* suspension is adjusted to a reading of about 0.35 to 2.0.

Maize Transformation.

Ears of a maize (*Zea mays* L.) cultivar are surface-sterilized for 15-20 min in 20% (v/v) bleach (5.25% sodium hypochlorite) plus 1 drop of Tween 20 followed by 3 washes in sterile water. Immature embryos (IEs) are isolated from ears and are placed in 2 ml of the *Agrobacterium* infection medium with acetosyringone solution. The optimal size of the embryos varies based on the inbred, but for transformation with WUS2 and ODP2 a wide size range of immature embryo sizes could be used. The solution is drawn off and 1 ml of *Agrobacterium* suspension was added to the embryos and the tube vortexed for 5-10 sec. The microfuge tube is allowed to stand for 5 min in the hood. The suspension of *Agrobacterium* and embryos are poured onto 7101 (or 562V) co-cultivation medium (see Table 2). Any embryos left in the tube are transferred to the plate using a sterile spatula. The *Agrobacterium* suspension is drawn off and the embryos placed axis side down on the media. The plate is sealed with Parafilm M® film (moisture resistant flexible plastic, available at Bemis Company, Inc., 1 Neenah Center 4$^{th}$ floor, PO Box 669, Neenah, Wis. 54957) and incubated in the dark at 21° C. for 1-3 days of co-cultivation.

Embryos are transferred to resting medium (605T medium) without selection. Three to 7 days later, they are transferred to maturation medium (289Q medium) supplemented with a selective agent

Example 3: Delivery of a Morphogenic Factor to an Adjacent Cell Improves CRISPR-Cas Mediated Polynucleotide Modification of Target Cells This example demonstrates that delivery of DNA vector encoding for WUS protein on a separate set of gold particles into maize immature embryo cells is sufficient to support embryogenesis and plant regeneration with targeted mutations/deletions or site-specific insertions and no WUS gene integration with practical frequencies.

Previously, plant transformation and genome editing approaches required delivery of various DNA vectors coding for different "helper" components, including double-strand break reagents (for example, meganucleases, ZFNs, TALENs, or Cas9 nuclease and guide RNA (gRNA)), a selectable marker, morphogenic factors (e.g., ODP2 and WUS), in addition to the "donor" DNA—single-stranded or double-stranded oligonucleotides in gene editing experiments or plasmid DNA containing parts or entire genes with regulatory elements (promoters and terminators) for insertions as the result of double-strand break (DSB) through homology directed repair (HDR) pathway.

Multiple, co-delivered DNA molecules tend to co-integrate into a DSB site through the non-homologous end joining (NHEJ) repair pathway, significantly reducing the frequency of usable events. Moreover, stable integration of CRISPR components may lead to plant chimerism and increase chances of off-site mutagenesis. Minimizing the introduction of the described above "helper" DNA molecules into the target cell, and limiting delivery to the donor DNA, may be beneficial and lead to higher frequencies of quality events (QEs).

Previously, we have described a method for Cas9-gRNA delivery in the form of ribonucleoproteins (RNPs) using gold microparticles. We also described a method for activation of broken pre-integrated selectable marker gene through non-homologous end joining (NHEJ) mechanism upon Cas9-gRNA delivery as DNA vectors or RNP complex (WO 2017/070029 A1).

Morphogenic factor genes (also referred to as "developmental genes", for example but not limited to: ODP2 and WUS) are desired components of the transformation process: their delivery into plant cells facilitates cell division and significantly increases transformation frequencies. Moreover, these genes allow successful transformation of many elite genotypes, which transformation, otherwise, cannot be effectively accomplished. However, stable integration of morphogenic factor genes (e.g., ODP2 and WUS) into the target cell genome may have deleterious effect on plant regenerability and fertility.

Here we describe an approach allowing prevention of morphogenic factor (developmental genes, or "dev genes") integration into the genomes of regenerated plants. First, we demonstrated that delivery of only one of the two morphogenic factor genes (WUS) under a strong promoter (for example, PLTP) was sufficient to stimulate embryogenesis in most tested genotypes. Second, WUS protein has a cell-penetrating peptide (CPP) and therefore has an ability to penetrate cell walls. Thus, the delivery of vector DNA encoding for WUS into a cell led to protein expression and its migration to the neighboring cells stimulating their division. Moreover, overexpression of the protein in the targeted cell is usually toxic preventing the call division, embryogenesis and plant regeneration. Based on these observations, we conducted biolistic delivery of RNP and donor DNA on the first set of gold particles (first shot) followed by delivery of vector DNA containing WUS expression cassette on a separate set of gold particles (second shot). This allowed plant regeneration from cells receiving the DSB and editing components and stimulated to division and embryogenesis by WUS protein molecules coming from adjacent cells.

Gene Deletion

Figure 1A:
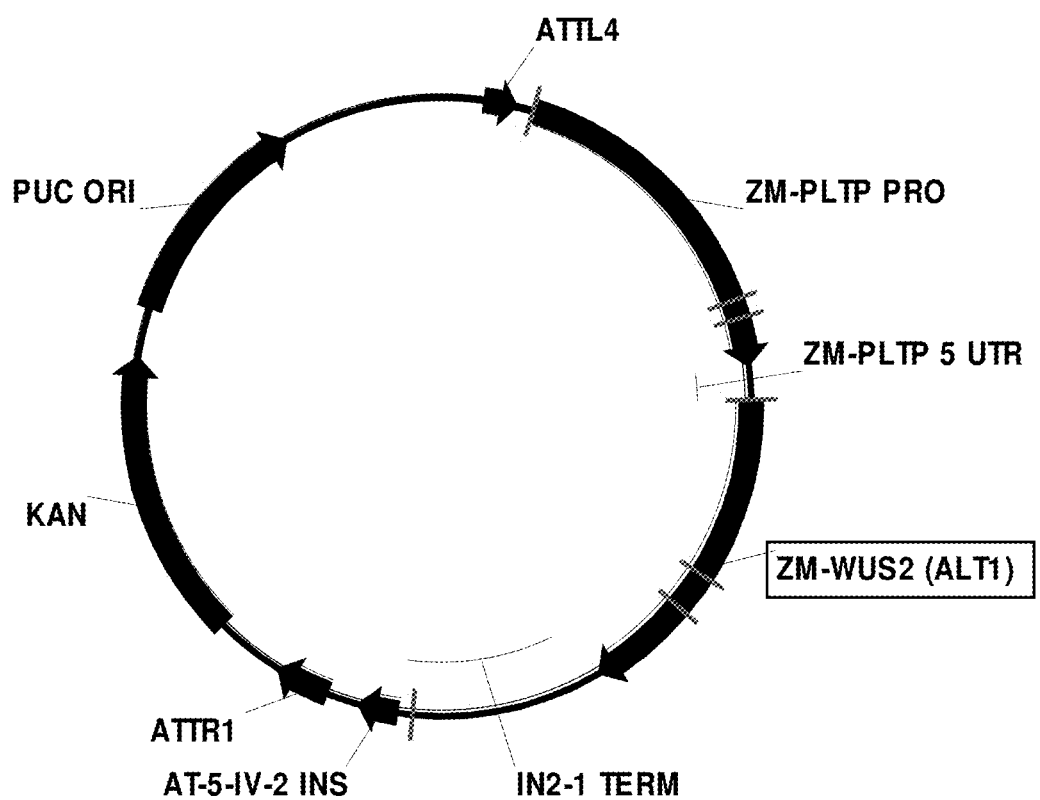
FIG. 1A depicts a DNA vector encoding for WUS (polynucleotide SEQID NO: 23 encoding polypeptide SEQID NO:48) operably linked to a PLTP promoter (SEQID NO:74).
Figure 1B:
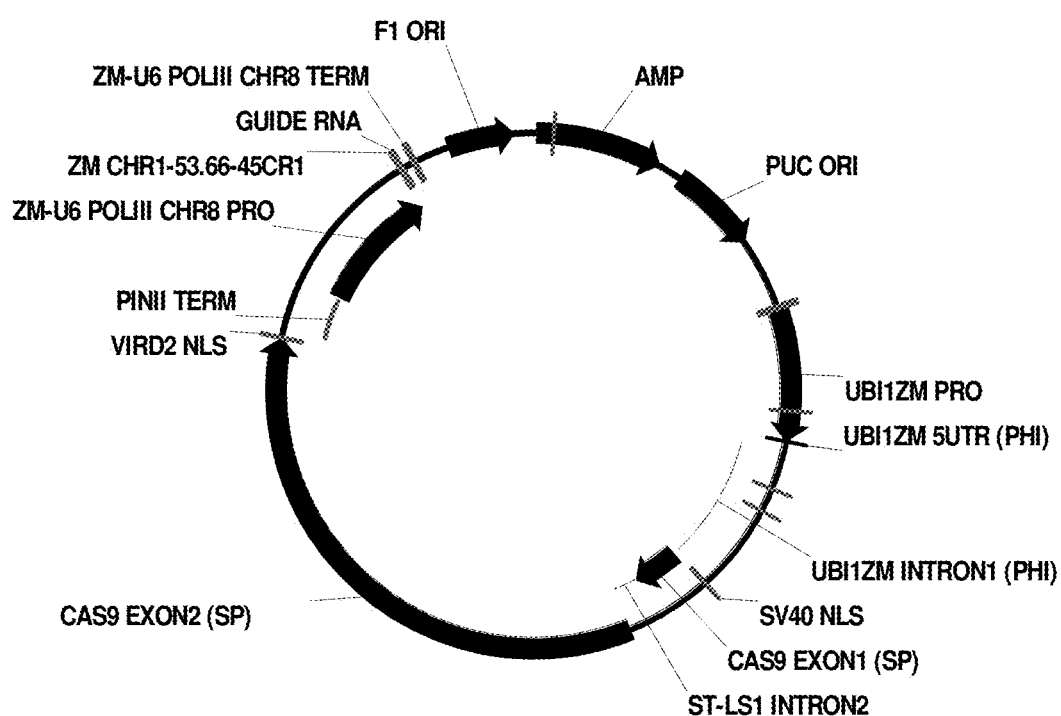
FIG. 1B depicts a maize-optimized *S. pyogenes* Cas9 protein (polynucleotide SEQID NOs: 103-104 encoding polypeptide SEQID NOs: 108-109) and an appropriate gRNA (SEQID NO: 82).

A gene deletion of approximately 21 kb in size was generated. Maize immature embryos were bombarded using gold particles coated with 2 RNP complexes targeting two sites:

```
site 1
                                   SEQ ID NO: 80
   GGATTCCGCGGAAATGGGTG (PAM: CGG)

site 2
                                   SEQ ID NO: 81
   GTCAAGGACATACGAGACC (PAM: AGG)
``` to generate the deletion and then immediately bombarded embryos with the second set of gold particles coated with a DNA vector encoding for WUS (polynucleotide SEQ ID NO: 23 encoding polypeptide SEQ ID NO:48) operably linked to a PLTP promoter (SEQ ID NO:74) (FIG. 1A). Plants were regenerated without selection and analyzed by PCR and sequencing, and qPCR for the presence of deletions and WUS integration, respectively. Results of this experiment are presented in Table 2.

TABLE 2

Frequency of RecQ4 gene deletion

| Embryos bombarded | Plants sampled | Plants with deletion | Plants with WUS integration | Plants with deletion No WUS integration |
|---|---|---|---|---|
| 385 | 1128 | 54 (5%) | 34 (3%) | 51 |

These results demonstrate efficient, "DNA-free" gene deletion with high efficiency.

Site-Specific Gene Insertion

Figure 1C:
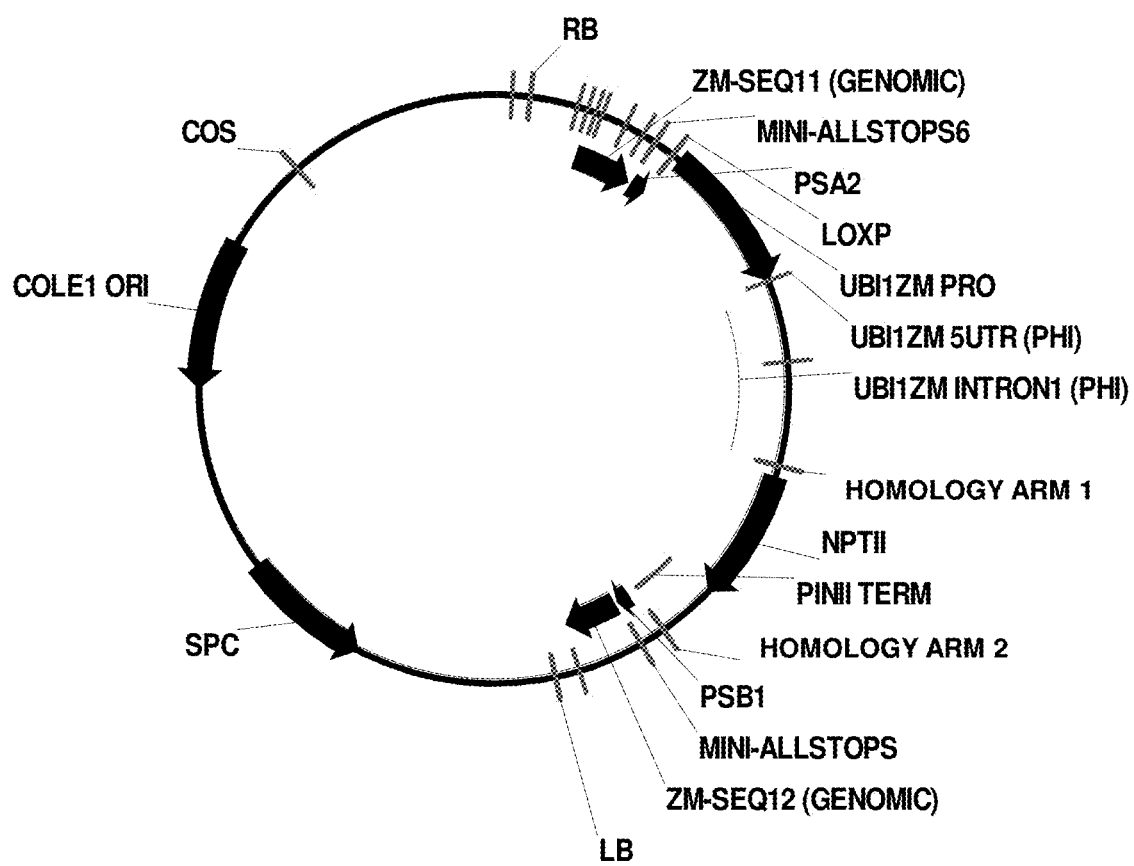
FIG. 1C depicts a DNA vector comprising a selectable marker gene (NPTII, polynucleotide SEQID NO: 77 encoding polypeptide SEQID NO:100) flanked with homology arms (SEQID NOs: 78 and 79) as donor DNA.

Separate WUS delivery was used to generated a gene insertion of approximately 3.5 kb in size to a specific genomic target site. Maize immature embryos were bombarded using gold particles co-coated with a DNA vector comprising polynucleotides encoding an optimized *S. pyogenes* Cas9 protein (exons 1 and 2 given as polynucleotide SEQID NOs: 103-104 encoding polypeptide SEQID NOs: 108-109, with a potato LS1 intron inserted between the two exons, and further comprising SV40 and VIRD2 NLS sequences) and an appropriate gRNA (SEQID NO: 82) (FIG. 1B), and a DNA vector comprising a selectable marker gene (NPTII, polynucleotide SEQID NO: 77 encoding polypeptide SEQID NO:100) flanked with homology arms (SEQID NOs: 78 and 79) as donor DNA (FIG. 1C). The donor DNA comprised a gene of interest flanked with sequences homologous to the genomic sequences on both sides of the DSB (homology arms). The same embryos were then bombarded a second time, delivering a DNA vector encoding for WUS under the PLTP promoter (FIG. 1A). Plants were regenerated on media containing a selective agent (G418), which is toxic to cells that have not integrated and express the NPTII gene. Plants were analyzed by junction PCR for integration of the gene of interest into the targeted genomic site. Regenerants were also tested by qPCR for the presence of WUS. Results of the experiment are presented in Table 3.

TABLE 3

Frequency of NPTII targeted gene integration generated

| Embryos bombarded | Plants sampled | Plants with targeted integration | Plants with NPTII insertion, WUS integration | Plants with NPTII insertion, No WUS integration |
|---|---|---|---|---|
| 305 | 115 | 10 (8.7%) | 6 (60%) | 4 (40%) |

Separate delivery of WUS was sufficient to promote plant regeneration from cells with targeted mutations/deletions, gene edits or gene insertions and, therefore, replaced co-delivery of morphogenic factor genes (ODP2 and/or WUS) along with other components. Thus, plants regenerated in these experiments didn't contain morphogenic factor genes randomly integrated into the genome, thus improving regenerability and fertility of the plants.

This method of separate delivery of a morphogenic factor gene facilitated a "DNA-free" approach to gene knockout, targeted gene editing, and gene insertion in plant cells of agronomically important crop plants including but not limited to maize, soybean, wheat, rice, millet, *Sorghum*, cotton, and canola.

Example 4: Activation of Endogenous Morphogenic Factors Improves CRISPR-Cas Mediated Polynucleotide Modification of Target Cells In this example, a method is provided for enabling plant transformation using the targeted overexpression of a developmental gene using an RNA programmable homing endonuclease-transcriptional activator complex. The basic platform this is built upon is the CRISPR/Cas9 system (specifically *S. pyogenes*, abbreviated Spy Cas9) which is capable of being directed to any target sequence with the modifications of removing its endonuclease activity and combining it with a known transcriptional activator motif. In this case, the D10A and H840A mutations in Spy Cas9 were made (polynucleotide SEQID NO:105 encoding polypeptide SEQID NO:110) and the transcriptional activator component of *Arabidopsis* CBF1 protein (referred to as AT-CBF1A, polynucleotide SEQID NO:83 encoding polypeptide SEQID NO:101) was fused. This method is a novel advancement to the method of plant transformation and creation of polynucleotide modifications in cell genomes via a double-strand-break-inducing agent, in which manipulation of the endogenous gene's expression is enhanced.

Figure 2A:
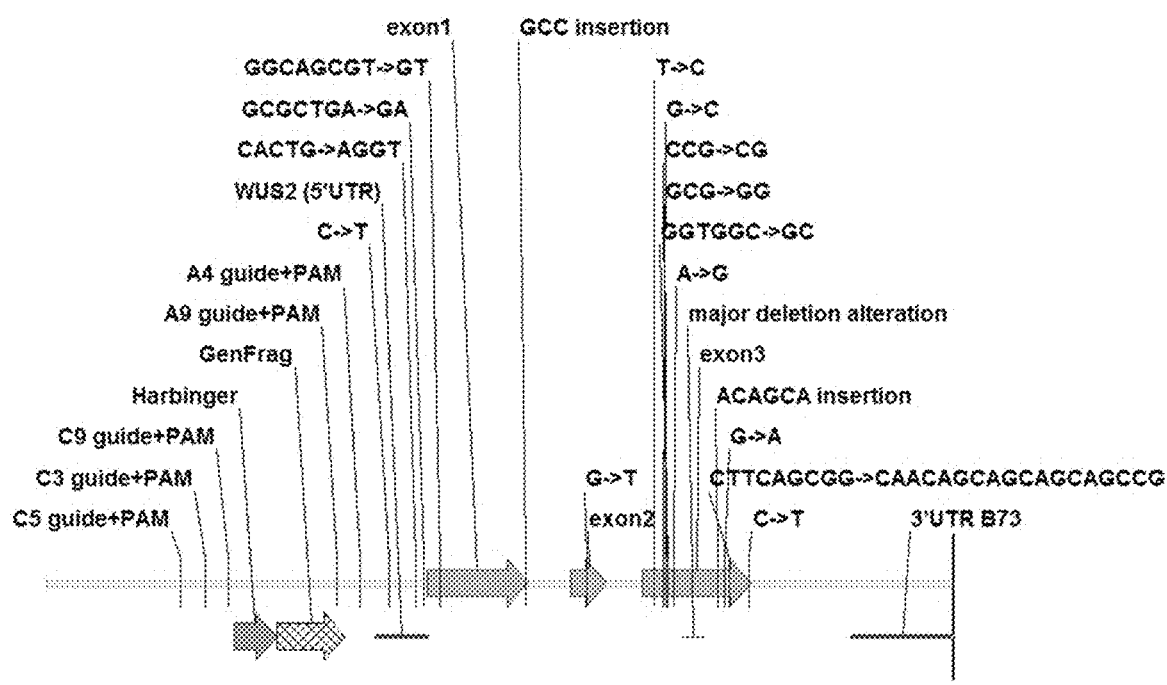
FIG. 2A depicts the general location of the designed guides (UTRs and exon/intron structures based on the maize B73 version of the gene, using genomic maize Variety 1 contig sequences.

To test the ability of a dSpy-Cas9 and guides expressed from bombarded plasmids, pol III (promoter polynucleotide SEQID NO:84) expression cassettes with guides targeting the Variety 1 promoter region of WUS2 were developed. FIG. 2A shows the general location of the 5 effective guides (UTRs and exon/intron structures based on the maize B73 version of the gene, using genomic maize Variety 1 contig sequences, with markups representing the allele differences.

guide sequences used in expression cassette construction:

```
C5
                              (SEQ ID NO: 86)
GCCTTTGCAGTTTGCACC

C3
                              (SEQ ID NO: 87)
GTTGCCACAAGGGGAGCC

C9
                              (SEQ ID NO: 88)
GCAAATGACTTCTGTCTCTA

A9
                              (SEQ ID NO: 89)
GACTCTTCCAAATTTCGAAG

A4
                              (SEQ ID NO: 90)
GTCGTATCACCCATGGGCAA
```

Figure 2B:
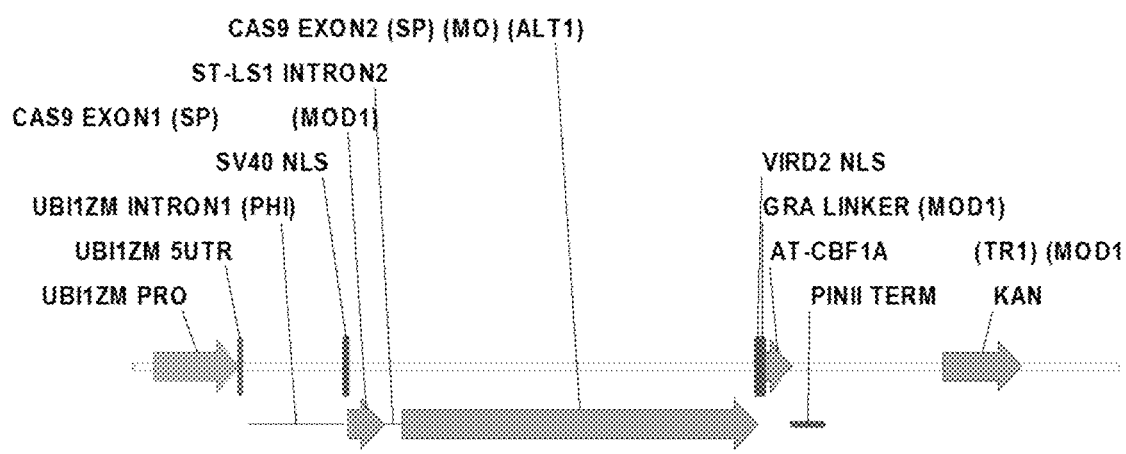
FIG. 2B depicts the map of a dCas9-GRA-CBF1A vector.

The map of the dCas9-GRA-CBF1A vector is shown in FIG. 2B. The GRA sequence was: GGCAGGGCT.

Figure 2C:
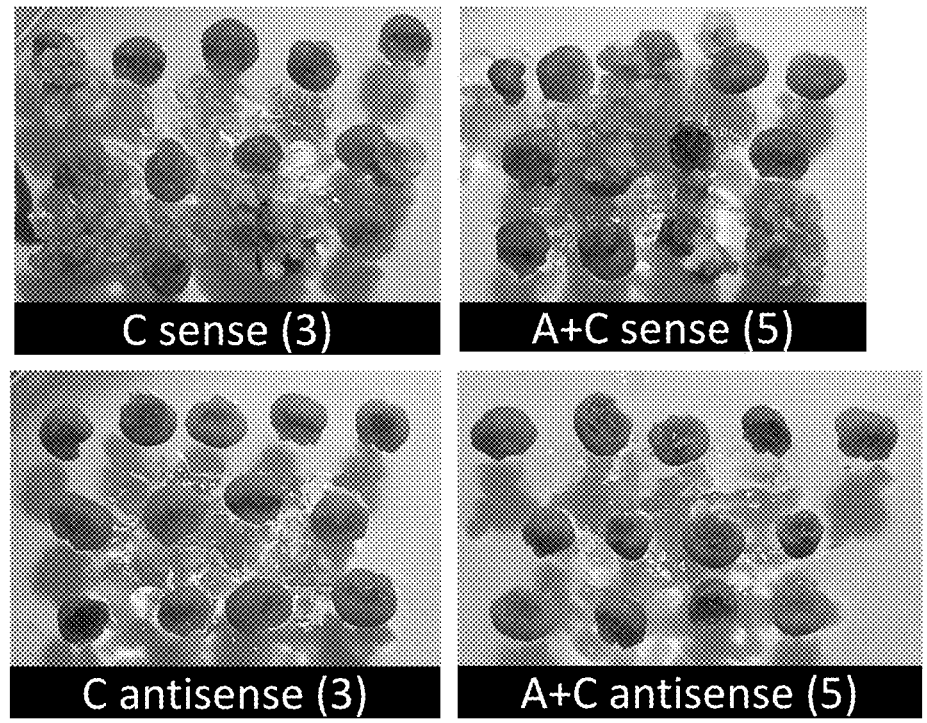
FIG. 2C shows transformation enhancement in embryos bombarded with the sense guide RNAs.

Different combinations of guides were delivered into Variety 1 along with NPT II selection marker and dCas9-GRA-CBF1A and were monitored for embryonic stem cell growths. At 4 weeks post bombardment the embryos were analyzed. Notably, the 3 sense C guides and all 5 of the A and C sense guides gave strong responses. The antisense guides did not provide transformation enhancement (FIG. 2C).

Figure 2D:
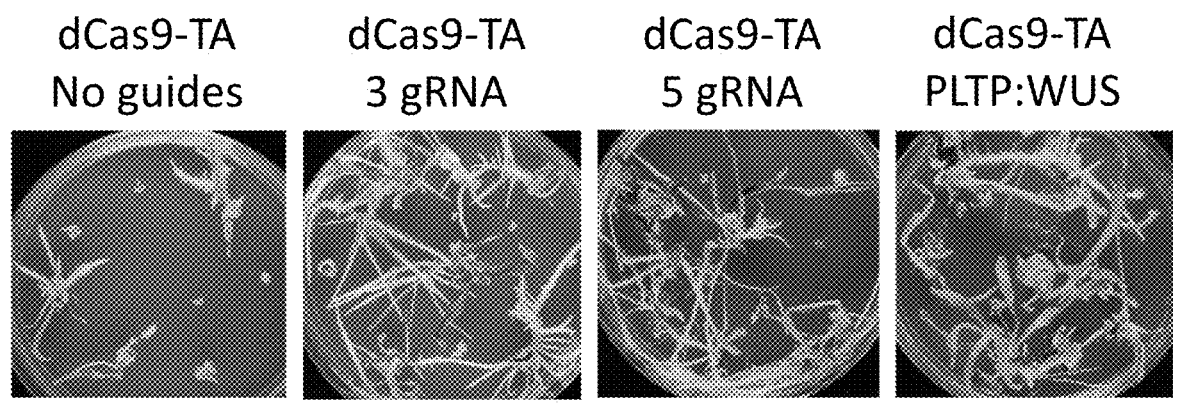
FIG. 2D shows plants after 5-7 weeks of outgrowth.

The experiment was repeated with full growth with NPTII selection until plants developed using only the 3 sense C guides and the 5 sense A+C guides. FIG. 2D shows plants after 5-7 weeks of outgrowth.

FIG. 2E shows the protein sequence differences between the WUS2 from a recombinant vector (polynucleotide SEQID NOs: 73 (exon 1) and 24 (exon 2) encoding polypeptide SEQID NO:49), from a native B73 maize plant (polynucleotide SEQID NO:25 encoding polypeptide SEQID NO:50), and from a native Variety 1 maize plant (polynucleotide SEQID NO:26 encoding polypeptide SEQID NO:51).

As shown in Table 4, fertile TO plants were recovered from the plants. "Total recovered" was the number of plantlets successfully generated in the transformation lab through NPTII selection and sent to greenhouse. "Number discarded" refers to those that were observed from the greenhouse to be off phenotype, runts, sterile, or died. "Pollinated" refers to the number of plants that either via carry-in or carry-out gave >10 seed number.

TABLE 4

Recovery of Fertile TOs from Endogenous Morphogenic Factor Activation

|  | 3 guides | 5 guides | PLTP:wus | no DevGenes |
| --- | --- | --- | --- | --- |
| total recovered | 30 | 31 | 48 | 12 |
| number discarded | 8 | 11 | 24 | 6 |
| pollinated | 22 | 20 | 24 | 6 |
| % pollinated/recovered | 73.3% | 64.5% | 50% | 50% |

Example 5: Morphogenic Factor Gene Placement Outside of the Transformation Cassette Borders Improves CRISPR-Cas Mediated Polynucleotide Modification of Target Cells Three plasmids are prepared for *Agrobacterium*-mediated transformation as described above, each comprising the same T-DNA:

RB+Promoter::SelectableMarker::Terminator+Promoter::DSBagent::Terminator+LB but differing in the placement of the morphogenic factor expression cassettes beyond the left border.

Plasmid A comprises two expression cassettes immediately outside the Left Border:
Promoter::MorphogenicFactor1::Terminator
Promoter::MorphogenicFactor2::Terminator
Plasmid B comprises a single expression cassette:
Promoter::MorphogenicFactor::Terminator
Plasmid C comprises a single expression cassette outside the Left Border:
Promoter::MorphogenicFactor1+MorphogenicFactor2::Terminator One example of a vector comprising two morphogenic factor genes (WUS2 given as polynucleotide SEQID NO:27 encoding polypeptide SEQID NO:52, and ODP2 given as polynucleotide SEQID NO:22 encoding polypeptide SEQID NO:17) outside of the left T-DNA border is shown in FIG. 3.

After *Agrobacterium*-mediated transformation with these respective T-DNAs and selection during somatic embryo maturation and regeneration, TO plants are analyzed by qPCR. Based on qPCR analysis, using Plasmid A results in 10.2% of the recovered TO plants being single copy for the DSB agent gene within the T-DNA, while the values for Plasmid B and Plasmid C were 12.2% and 12.3%, respectively, while lacking integrated morphogenic factor gene, with no additional indications of plasmid backbone contamination.

A cell transformed with any of these plasmids exhibit modifications of its genomic polynucleotide sequence as a result of the presence of the introduced DSB agent, without the heterologous morphogenic factor gene integrated into the genomic DNA.

These results demonstrate that positioning the morphogenic factor expression cassettes outside the T-DNA Left Border provides the necessary stimulation of transformation without the concomitant integration of these morphogenic factors into the genome of the target cell.

Example 6: Enabling Morphogenic Factor Mobility Improves CRISPR-Cas Mediated Polynucleotide Modification of Target Cells For this experiment, the maize WUS2 gene is modified through either replacing the WUS Cell Penetrating Peptide (CPP) motif with a KN1 CPP motif, or by leaving the WUS CPP unaltered and adding a KN1 CPP to the amino terminus of the protein. In both cases, when an expression cassette is used that expresses the wild-type WUS protein (e.g. PLTP PRO::WUS2::IN2-1 TERM) along with UBLCAS9::PINII TERM+U6-POL PRO::gRNA::U6 TERM cassette where the gRNA is designed to guide the dCAS9 protein to bind and cut the endogenous maize ALS gene, edits of the ALS gene to confer chlorsulfuron resistance to the cells are readily recovered. However, when either the KN1-CPP is substituted for the WUS-CPP or the KN1-CPP is added to the WUS protein, more diffusion of the modified WUS proteins results in increased growth and a higher rate of recovering chlorsulfuron-resistant plants.

Example 7: Using a Combination of WUS and REPA Results in Higher Rates of Cell Division and Concomitant CRISPR-Cas Mediated Polynucleotide Modification of Target Cells For these experiments, two treatments are compared. In the first treatment, an *Agrobacterium* containing a T-DNA with the following components is used; In the first treatment, a single *Agrobacterium* is used containing a single T-DNA comprising the following components: RB+U6-POL PRO::gRNA::U6 TERM cassette where the gRNA is designed to guide the dCAS9 protein to bind and cut the endogenous maize ALS gene, ii) a UBI PRO::CAS9::PINII TERM, iii) an expression cassette containing a PLTP PRO::ZM-WUS2:: IN2-1 TERM expression cassette (the Control Plasmid). In the second treatment, a mixture of two Agrobacteria are used; in the first *Agrobacterium*, a plasmid contains a binary vector with the following components within the T-DNA; i) a) a U6-POL PRO::gRNA::U6 TERM cassette where the gRNA is designed to guide the dCAS9 protein to bind and cut the endogenous maize ALS gene, ii) an expression cassette containing a PLTP PRO::ZM-WUS2:: IN2-1 TERM expression cassette and a PLTP PRO::CAMV-REPA::IN2-1 TERM expression cassette. The second *Agrobacterium* contains a T-DNA with a sequence (not in an expression cassette) that will be used as the editing template for modifying the ALS gene (the Test Plasmid). The first and second Agrobacteria are mixed in a ratio of 9:1 and used for transformation.

After *Agrobacterium*-mediated transformation with *Agrobacterium* strain LBA4404 THY-containing the control plasmid, during somatic embryo maturation and regeneration, TO plants are analyzed by qPCR. Using the control plasmid in the *Agrobacterium*, it is expected that the frequency of recovering TO plants (relative to the number of *Agrobacterium*-infected immature embryos) that contain a modified endogenous ALS locus in addition to the integrated T-DNA (with CAS9, WUS and gRNA expression cassettes at a 5-10% frequency. When the second treatment with the *Agrobacterium* is tested, it is expected that transformation frequencies will be higher than the control, the growth of transgenic somatic embryos will be accelerated and the frequency of recovering TO plants that TO plants containing the modified ALS gene with no additional integrations of the second T-DNA will be recovered at a higher frequency. It is expected that positioning the dCAS9, REPA and the WUS2 expression cassettes in the second T-DNA (within the lower titer *Agrobacterium* will provide an improved stimulation of ALs gene editing without the concomitant integration of the morphogenic gene expression cassettes.

Example 8: Use of a Morphogenic Factor Expression Cassette and a Constitutively-Expressed dCas-Repressor Fusion Cassette Outside the T-DNA Borders Stimulates Transformation and Selection of Single-Copy TO Maize Plants that Contain No Morphogenic Factor or RepA Expression Cassettes A "Dead-CAS9" (dCAS9) as used herein, is used to supply a transcriptional repressor domain. The dCAS9 has been mutated so that can no longer cut DNA. The dCAS0 can still bind when guided to a sequence by the gRNA and can also be fused to repressor elements (see Gilbert et al., *Cell* 2013 Jul. 18; 154(2): 442-451, Kiani et al., 2015 November *Nature Methods* Vol. 12 No. 11: 1051-1054). The dCAS9 fused to the repressor element, as described herein, is abbreviated to dCAS9-REP, where the repressor element (REP) can be any of the known repressor motifs that have been characterized in plants (see Kagale and Rozxadowski, 20010 *Plant Signaling & Behavior* 5:6, 691-694 for review). An expressed guide RNA (gRNA) binds to the dCAS9-REP protein and targets the binding of the dCAS9-REP fusion protein to a specific predetermined nucleotide sequence within a promoter (a promoter within the T-DNA). For example, if this is expressed Beyond-the Border using a ZM-UBI PRO::dCAS9-REP::PINII TERM cassette along with a U6-POL PRO::gRNA::U6 TERM cassette and the gRNA is designed to guide the dCAS9-REP protein to bind the SB-UBI promoter in the expression cassette SB-UBI PRO::moPAT::PINII TERM within the T-DNA, any event that has integrated the Beyond-the-Border sequence would be bialaphos sensitive. Transgenic events that integrate only the T-DNA would express moPAT and be bialaphos resistant. The advantage of using a dCAS9 protein fused to a repressor (as opposed to a TETR or ESR) is the ability to target these repressors to any promoter within the T-DNA. TETR and ESR are restricted to cognate operator binding sequences. Alternatively, a synthetic Zinc-Finger Nuclease fused to a repressor domain can be used in place of the gRNA and dCAS9-REP (Urritia et al., 2003, Genome Biol. 4:231) as described above.

For these experiments, two plasmids are compared. The first contains a T-DNA comprising the following components: RB+SI-UBI3 PRO::ZS-GREEN1::PINII TERM+SB-ALS PRO::ZM-HRA::SB-PEPC1 TERM+LB (the Control Plasmid). The second plasmid contains the same components within the T-DNA (RB+SI-UBI3 PRO::ZS-GREEN1:: PINII TERM+SB-ALS PRO::ZM-HRA::SB-PEPC1 TERM+LB) plus three additional expression cassette immediately beyond the left border: i) an expression cassette containing ZM-U6 PRO::gRNA::ZM-U6 TERM; ii) ZM-UBI PRO::dCAS9~REP::PINII TERM expression cassette; and iii) a PLTP PRO::ZM-WUS2:: IN2-1 TERM expression cassette (the Test Plasmid). The gRNA within the first expression cassette has been designed to target the dCAS9~REP to the SB-ALS PRO sequence which transcriptionally silences HRA expression and renders the cell sensitive to imazapyr.

After *Agrobacterium*-mediated transformation with *Agrobacterium* strain LBA4404 THY-containing the control plasmid, during somatic embryo maturation and regeneration, TO plants are analyzed by qPCR. Using the control plasmid in the *Agrobacterium*, it is expected that the frequency of recovering TO plants (relative to the number of *Agrobacterium*-infected immature embryos) that are single copy for the Trait genes within the T-DNA with no vector (plasmid) backbone will be approximately 5%. When the Test plasmid is used in the *Agrobacterium*, it is expected that transformation frequencies will be higher than the control, the growth of transgenic somatic embryos will be accelerated and the frequency of recovering TO plants that are single copy for the Trait genes within the T-DNA while lacking integrated WUS and dCAS9~REP and no vector (plasmid) backbone will be increased relative to the control treatment. It is expected that positioning the dCAS9~REP and the WUS2 expression cassettes outside the T-DNA Left Border will provide an improved stimulation of transformation without the concomitant integration of these morphogenic gene expression cassettes.

Alternatively, a synthetic Zinc-Finger Nuclease fused to a repressor domain can be used in place of the gRNA and dCAS9~REP (Urritia et al., 2003, Genome Biol. 4:231) in the above example.

We claim:

1. A method of editing a target polynucleotide in the genome of a target cell, comprising:
   (a) providing a Cas endonuclease to the target cell, wherein the Cas endonuclease is provided as a polynucleotide molecule on a first vector that further comprises, outside of the T-DNA borders, a repressor fused to a polynucleotide encoding a second Cas endonuclease that lacks nuclease activity, wherein said repressor is capable of binding to a regulatory element operably linked to the polynucleotide encoding the Cas endonuclease;
   (b) providing at least one heterologous morphogenic factor to a cell, and
   (c) incubating the target cell to allow for the Cas endonuclease and a guide RNA toform a complex that recognizes, binds to, and nicks or cleaves the target polynucleotide;
wherein the editing is selected from the group consisting of: insertion of at least one polynucleotide, deletion of at least one polynucleotide, molecular alteration of at least one polynucleotide, substitution of at least one polynucleotide, and a combination of at least two of the preceding.

2. The method of claim 1, wherein the composition of (a) is provided as a polynucleotide on a different construct than the composition of (b).

3. The method of claim 1, wherein the composition of (a) is provided as a polynucleotide on the same construct as the composition of (b).

4. The method of claim 1, wherein the morphogenic factor is provided as a polypeptide.

5. The method of claim 1, wherein the morphogenic factor is provided via upregulation of an endogenous morphogenic factor gene.

6. The method of claim 1, wherein a polynucleotide sequence encoding the Cas endonuclease or the guide RNA or both is provided as a recombinant construct on a T DNA vector between the left and right borders, wherein the T-DNA vector further comprises the at least one morphogenic factor outside of the left and right borders.

7. A method of editing a polynucleotide in the genome of a target cell, comprising:
   (a) providing a Cas endonuclease to a cell, wherein the Cas endonuclease is provided as a polynucleotide molecule on a first vector that further comprises, outside of the T-DNA borders, a repressor fused to a polynucleotide encoding a second Cas endonuclease that lacks nuclease activity, wherein said repressor is capable of binding to a regulatory element operably linked to the polynucleotide encoding the Cas endonuclease,
   (b) providing at least one morphogenic factor to the cell, wherein the morphogenic factor is provided via stimulation or upregulation of an endogenous morphogenic factor gene, and
   (c) incubating the target cell to allow for the Cas endonuclease and a guide RNA to form a complex that recognizes, binds to, and nicks or cleaves the target polynucleotide;

wherein the editing is selected from the group consisting of: insertion of at least one polynucleotide, deletion of at least one polynucleotide, molecular alteration of at least one polynucleotide, substitution of at least one polynucleotide, and a combination of at least two of the preceding.

8. The method of claim 1 wherein themorphogenic factor is selected from the group consisting of: Wuschel, Ovule Development Protein, and Babyboom.

9. The method of claim 1 further comprising introducing a polynucleotide modification template into the target cell.

10. The method of claim 1 further comprising introducing a heterologous polynucleotide donor DNA molecule into said target cell.

11. The method of claim 1 wherein the cell is a plant cell; wherein said benefit is selected from the group consisting of: improved health, improved growth, improved fertility, improved fecundity, improved environmental tolerance, improved vigor, improved disease resistance, improved disease tolerance, improved tolerance to a heterologous molecule, improved fitness, improved physical characteristic, greater mass, increased production of a biochemical molecule, decreased production of a biochemical molecule, upregulation of a gene, downregulation of a gene, upregulation of a biochemical pathway, downregulation of a biochemical pathway, stimulation of cell reproduction, and suppression of cell reproduction.

12. The method of claim 1 further comprising regenerating an organism or tissue from the cell.

13. The method of claim 1 wherein the editing of a polynucleotide in the genome of the cell modulates a trait of agronomic importance in a plant obtained or derived from the cell, wherein the trait of agronomic importance is selected from the group consisting of: disease resistance, drought tolerance, heat tolerance, cold tolerance, salinity tolerance, metal tolerance, herbicide tolerance, improved water use efficiency, improved nitrogen utilization, improved nitrogen fixation, pest resistance, herbivore resistance, pathogen resistance, yield improvement, health enhancement, vigor improvement, growth improvement, photosynthetic capability improvement, nutrition enhancement, altered protein composition, altered oil composition, increased biomass, increased shoot length, increased root length, improved root architecture, modulation of a metabolite, modulation of the proteome, increased seed weight, altered seed carbohydrate composition, altered seed oil composition, altered seed protein composition, and altered seed nutrient composition; as compared to an isoline plant not comprising or derived from a cell whose genome was edited with said RNA-guided Cas endonuclease.

* * * * *